US011166994B2

(12) United States Patent
Lichtenstein et al.

(10) Patent No.: US 11,166,994 B2
(45) Date of Patent: Nov. 9, 2021

(54) DELIVERY VEHICLE

(71) Applicant: NEMESIS BIOSCIENCE LTD, Norfolk (GB)

(72) Inventors: Conrad Paul Lichtenstein, Norfolk (GB); Yoshikazu Gi Mikawa, Norfolk (GB)

(73) Assignee: NEMESIS BIOSCIENCE LTD, Norfolk (GB)

( * ) Notice: Subject to any disclaimer, the term of this patent is extended or adjusted under 35 U.S.C. 154(b) by 0 days.

(21) Appl. No.: 15/752,753

(22) PCT Filed: Aug. 12, 2016

(86) PCT No.: PCT/GB2016/052524
§ 371 (c)(1),
(2) Date: Feb. 14, 2018

(87) PCT Pub. No.: WO2017/029485
PCT Pub. Date: Feb. 23, 2017

(65) Prior Publication Data

US 2019/0000896 A1 Jan. 3, 2019

(30) Foreign Application Priority Data

Aug. 14, 2015 (GB) .................................. 1514510.5

(51) Int. Cl.
*A61K 35/76* (2015.01)
*A61P 31/04* (2006.01)
*A61K 45/06* (2006.01)

(52) U.S. Cl.
CPC .............. *A61K 35/76* (2013.01); *A61K 45/06* (2013.01); *A61P 31/04* (2018.01)

(58) Field of Classification Search
CPC ..................................................... A61K 35/76
See application file for complete search history.

(56) References Cited

U.S. PATENT DOCUMENTS

| | | | | |
|---|---|---|---|---|
| 5,399,496 A | 3/1995 | Fujiwara et al. | | |
| 2006/0003454 A1 | 1/2006 | Suzuki et al. | | |
| 2013/0224865 A1* | 8/2013 | Filutowicz | C12N 15/64 | 435/488 |
| 2015/0064138 A1* | 3/2015 | Lu | C12N 15/74 | 424/93.2 |

FOREIGN PATENT DOCUMENTS

| | | | | |
|---|---|---|---|---|
| CN | 102027107 A | 4/2011 | | |
| EP | 2042602 A1 | 4/2009 | | |
| WO | 99/00517 A2 | 1/1999 | | |
| WO | WO-9900517 A2 * | 1/1999 | C12Q 1/6897 | |
| WO | 02/18605 A2 | 3/2002 | | |
| WO | 2004/033633 A2 | 4/2004 | | |
| WO | 2007/025097 A2 | 3/2007 | | |
| WO | WO-2007025097 A2 * | 3/2007 | C12Q 1/70 | |
| WO | 2007/141540 A2 | 12/2007 | | |
| WO | 2009/114504 A2 | 9/2009 | | |
| WO | 2010/075424 A2 | 7/2010 | | |
| WO | WO-2010075424 A2 * | 7/2010 | C12N 15/113 | |
| WO | 2012/164565 A1 | 12/2012 | | |

OTHER PUBLICATIONS

Bikard et al Nature Biotechnology, 32, 1146-1150 (Year: 2014).*
Ditta et al Proc. Natl. Acad. Sci. USA, 77, 12, 7347-7351 (Year: 1980).*
Bikard et al Nature Biotechnology, 32(11), 1146-1150 (Year: 2014).*
Connell et al Gene, 153, 85-87 (Year: 1995).*
Thomas & Nielsen Nat. Rev. Microbiol. 3, 711-21 (Year: 2006).*
Aakvik et al., FEMS Microbiol. Lett. 296, 149-58 (Year: 2009).*
UKIPO Search Report dated Jun. 8, 2016 issued in GB1514510.5.
PLoS One, vol. 9, 2014, Strand, T.A. et al., "A New and Improved Host-Independent Plasmid System for RK2-Based Conjugal Transfer" article No. e90372, Mar. 2014, vol. 9, issue 3, pp. 1-6.
International Search Report dated Oct. 31, 2016 issued in PCT/GB2016/052524.
PCT Written Opinion of the International Searching Authority dated Oct. 31, 2016 issued in PCT/GB2016/052524.
Aakvik, T. et al. "A Plasmid RK2-based Broad-Host-Range Cloning Vector Useful for Transfer of Metgenomic Libraries to a Variety of Bacterial Species", FEMS Microbiol Lett, May 2009, vol. 296, pp. 149-158.
Bernard, P. et al. "Positive-Selection Vectors Using the F Plasmid ccdB Killer Gene", Gene, Feb. 1994, vol. 148, pp. 71-74.
Bikard, D. et al. "Exploiting CRISPR-Cas Nucleases to Produce Sequence-specific Antimicrobials", Nature Biotechnology, Nov. 2014, vol. 32, No. 11, pp. 1146-1150.
Bingle, L. et al. "Regulatory Circuits for Plasmid Travel", Current Opinion in Microbiology, 2001, vol. 4, pp. 194-200.
Collins, J. et al. "Cosmids: A Type of Plasmid Gene-Cloning Vector That is Packageable in Vitro in Bactriophage λ Heads" Proc. Natl. Acad. Sci. USA, Biochemistry, Sep. 1978, vol. 75, No. 9, pp. 4242-4246.

(Continued)

*Primary Examiner* — Scott Long
(74) *Attorney, Agent, or Firm* — Scully, Scott, Murphy & Presser, P.C.

(57) ABSTRACT

The invention relates in one aspect to a pharmaceutical composition comprising a nucleic acid delivery vehicle for delivering a deliverable nucleic acid into a bacterial cell, wherein the delivery vehicle comprises a deliverable nucleic acid packaged into one or more bacteriophage coat proteins, and wherein the delivery vehicle is capable of infecting the bacterial cell to introduce the deliverable nucleic acid into the cell, following which the deliverable nucleic acid is capable of forming a plasmid in the cell and being transmitted to one or more different bacterial cells by conjugation and not by infection. Compositions including a pharmaceutical composition comprising the delivery vehicle, and methods involving use or manufacture of the delivery vehicle, are also disclosed.

23 Claims, 39 Drawing Sheets

Specification includes a Sequence Listing.

(56) References Cited

OTHER PUBLICATIONS

Cotter, P. et al. "Bacteriocins—A Viable Alternative to Antibiotics? ", Nature Reviews Microbiology, Feb. 2013, vol. 11, pp. 95-105.
Crepin, S. et al. "Chromosomal Complementation Using Tn7 Transposon Vectors in Enterobacteriaceae" Applied and Environmental Microbiology, Sep. 2012, vol. 78, No. 17, pp. 6001-6008.
Ditta, G. et al. "Broad Host Range DNA Cloning System for Gram-Negative Bacteria: Construction of a Gene Bank of Rhizobium Meliloti", Proc. Natl. Acad. Sci., Dec. 1980, vol. 77, No. 12, pp. 7347-7351.
Ferretti, J. et al. "Complete Genome Sequence of an M1 Strain of *Steptococcus pyogenes*", PNAS, Apr. 10, 2001, vol. 98, No. 8, pp. 4658-4663.
Fling, M. et al., "The Nucleotide Sequence of the Trimethoprim-resistant Dihydrofolate Reductase Gene Harbored by Tn7", Nucleic Acids Research, Jun. 1983, vol. 11, No. 15, pp. 5147-5158.
GenBank Acc. No. Y714837, "Cloning Vector pUC57, Complete Sequence", http://www.ncbi.nlm.mih.gov/nuccore/Y14837, Feb. 11, 1999.
GenBank Acc. No. JF8262422, "Cloning vector pUC57-Kan, Complete Sequence", http://www.ncbi.nlm.nih.gov/nuccore/JF826242.2, May 16, 2012.
Gibson, D. et al., "Enzymatic Assembly of DNA Molecules up to Several Hundred Kilobases", Nature Methods, May 2009, vol. 6, No. 5, pp. 343-345.
Goeders, N, et al., "Toxin-Antitoxin Systems as Multilevel Interaction Systems", Toxins, Jan. 2014, vol. 6, pp. 304-324.
Jinek, M. et al., "A Programmable Dual RNA-guided DNA Endonuclease in Adaptive Bacterial Immunity", Science, Aug. 17, 2013, vol. 337, pp. 816-821.
Lichtenstein, C. et al., "Unique Insertion Site of Tn7 in the *E. coli* Chromosome", Nature, Jun. 17, 1982, vol. 297, pp. 601-603.
Lichtenstein, C. et al., "Site Specific Properties of Tn7 Transposition into the *E. coli* Chormosome", Mol. Gen. Genet., Jun. 1981, vol. 183, pp. 380-387.
Nobrega, F. et al., "Revisiting Phage Therapy: New Applications for Old Resources", Trends in Microbiology, Apr. 2015, vol. 23, No. 4, pp. 185-191.
Proudfoot, C. et al., "Zinc Finger Recombinases with Adaptable DNA Sequence Specificity", PLoS One, Apr. 2011, vol. 6, issue 4, pp. 1-9, E19537.
Saka, K. et al., "A Complete Set of *Escherichia coli* Open Reading Frames in Mobile Plasmids Facilitating Genetic Studies", DNA Research, Jan. 2005, vol. 12, No. 1, pp. 63-68.
Schembri, M. et al, "Molecular Characterizationi of the Multidrug Resistant *Escherichia coli* ST131 Clone", Pathogens, Jun. 2015, vol. 4, pp. 422-430.
Thomas, C. et al., "Mechanisms of, and Barriers to, Horizontal Gene Transfer Between Bacteria", Nature Reviews Microbiology, Sep. 2005, vol. 3, pp. 711-721.
Tsai, S. Q. et al., "Dimeric CRISPR RNA-guided FokI Nucleases for Highly Specific Genome Editing", Nature Biotechnology, Jun. 2014, vol. 32, No. 6, pp. 569-576.
Yosef, I. et al., "Temperate and Lytic Bacteriophages Programmed to Sensitize and Kill Antibiotic-Resistant Bacteria", PNAS, Jun. 9, 2015, vol. 112, No. 23, pp. 7267-7272.
GenBank "*Escherichia coli* str. k-12 substr. MG 1655, complete genome", http://www.ncbi.nlm.nih.gov/nucleotide/556503834?report=genbank&log$=nuclalign&blast_rank=1&RID=JUYB76FX014, Oct. 11, 2018.
Connell, T.D. et al., "A new mobilizable cosmid vector for use in Vibrio cholerae and other Gram—bacteria", Gene, vol. 153, pp. 85-87 (1995).
European Office Action dated Aug. 6, 2020 in European Patent Application No. 16 753 448.6.
English-language translation of Chinese Office Action dated Feb. 3, 2021 received in Chinese Application No. 201680058900.9.

* cited by examiner

| F | | RK2 | BP | | pBeloBAC11 | Size | pGRG36::lox | Size | Total |
|---|---|---|---|---|---|---|---|---|---|
| TRA | | Tra1 | 15431 | | | | | | |
| TRA | | Tra2 | 12206 | | | | | | |
| ORI | | *ori*V | | 711 | ***ori2*** | 220 | | | |
| ORI | | ***oriT*** | | 110 | | | | | |
| REP | | *trf*A | | 1149 | ***repE*** | 756 | | | |
| REP | | ***ssb*** | | 68 | | | | | |
| REP | | | | | | | | | |
| MOB | | ***traI*** | | 2178 | | | | | |
| MOB | | ***traJ*** | | 372 | | | | | |
| MOB | | ***traK*** | | 405 | | | | | |
| MOB | | ***traA*** | | 291 | | | | | |
| PAR | | *par*A | | | ***sopA*** | 1176 | | | |
| PAR | | *par*B | | | ***sopB*** | 972 | | | |
| PAR | | *par*C | | | ***sopC*** | 476 | | | |
| PAR | | *par*D | | 310 | ***incC*** | 251 | | | |
| PAR | | *par*E | | | | | | | |
| PM | KilA | *kla*A | | 774 | | | | | |
| PM | | *kla*B | | 1137 | | | | | |
| PM | | *kla*C | | 954 | | | | | |
| PM | KilE | *kle*A | | 234 | | | | | |
| PM | | *kle*B | | 216 | | | | | |
| PM | | *kle*C | | 231 | | | | | |
| PM | | *kle*D | | 219 | | | | | |
| PM | | *kle*E | | 324 | | | | | |
| PM | | *kle*F | | 315 | | | | | |
| RGE | Cti | ***korA*** | | 1122 | | | | | |
| RGE | | ***korB*** | | *1077* | | | | | |
| RGE | | *korC* | | *258* | | | | | |
| RGE | | *korF* | | *522* | | | | | |
| RGE | | *korG* | | *528* | | | | | |
| REC | | | | | | | ***tnsA*** | 822 | |
| REC | | | | | | | ***tnsB*** | 2109 | |
| REC | | | | | | | ***tnsC*** | 1668 | |
| REC | | | | | | | ***tnsD*** | 1527 | |
| REC | | | | | | | ***lox*** | 68 | |
| REC | | | | | | | ***Tn7*** | 444 | |
| PK | | | | | ***cos*** | *399* | | | |
| AM | | ***aphA*** | | 762 | ***cat*** | *660* | | | |
| | | **30598** | | | **4910** | | **6638** | | **42146** |

Fig. 5 bla CTX-M-15

Cm plate

Ap/Cm plate pNB108 VONCKIST pNB100 –ve control

SEQUENCE LISTING

<160> NUMBER OF SEQ ID NOS: 203

<210> SEQ ID NO 1
<211> LENGTH: 80
<212> TYPE: DNA
<213> ORGANISM: Artificial Sequence
<220> FEATURE:
<223> OTHER INFORMATION: DNA cassette sequence

<400> SEQUENCE: 1
ataacttcgt ataaggtatc ctatacgaag ttatgcggcg caagcttacc gttcgtatag 60
catacattat acgaagttat 80

<210> SEQ ID NO 2
<211> LENGTH: 86
<212> TYPE: DNA
<213> ORGANISM: Artificial Sequence
<220> FEATURE:
<223> OTHER INFORMATION: DNA cassette sequence

<400> SEQUENCE: 2
ggccataact tcgtataatg tatgctatac gaacggtaag cttgcgccgc ataacttcgt 60
ataggatacc ttatacgaag ttatat 86

<210> SEQ ID NO 3
<211> LENGTH: 13
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (10)..(13)
<223> OTHER INFORMATION: Residues 10-11, 11-12 and 12-13 linked by phosphorothioate linkage

<400> SEQUENCE: 3
gacatgaggt tgc 13

<210> SEQ ID NO 4
<211> LENGTH: 11
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (8)..(11)
<223> OTHER INFORMATION: Residues 8-9, 9-10 and 10-11 linked by
phosphorothioate linkage

<400> SEQUENCE: 4
atggcgatcg c 11

<210> SEQ ID NO 5
<211> LENGTH: 20
<212> TYPE: DNA
<213> ORGANISM: Artificial Sequence
<220> FEATURE:
<223> OTHER INFORMATION: Spacer sequence

<400> SEQUENCE: 5
ccgcgtaggc atgatagaaa 20

<210> SEQ ID NO 6
<211> LENGTH: 20
<212> TYPE: DNA
<213> ORGANISM: Artificial Sequence
<220> FEATURE:
<223> OTHER INFORMATION: Spacer sequence

<400> SEQUENCE: 6
acgttaaaca ccgccattcc 20

<210> SEQ ID NO 7
<211> LENGTH: 20
<212> TYPE: DNA
<213> ORGANISM: Artificial Sequence
<220> FEATURE:
<223> OTHER INFORMATION: Spacer sequence

<400> SEQUENCE: 7
gcgctggaga aaagcagcgg 20

<210> SEQ ID NO 8
<211> LENGTH: 20
<212> TYPE: DNA
<213> ORGANISM: Artificial Sequence
<220> FEATURE:
<223> OTHER INFORMATION: Spacer sequence

<400> SEQUENCE: 8
aagctgattg cccatctggg 20

<210> SEQ ID NO 9
<211> LENGTH: 20
<212> TYPE: DNA
<213> ORGANISM: Artificial Sequence
<220> FEATURE:
<223> OTHER INFORMATION: Spacer sequence

<400> SEQUENCE: 9
acgctcaaca ccgcgatccc 20

<210> SEQ ID NO 10
<211> LENGTH: 20
<212> TYPE: DNA
<213> ORGANISM: Artificial Sequence
<220> FEATURE:
<223> OTHER INFORMATION: Spacer sequence

<400> SEQUENCE: 10
aactacttac tctagcttcc 20

<210> SEQ ID NO 11
<211> LENGTH: 20
<212> TYPE: DNA
<213> ORGANISM: Artificial Sequence
<220> FEATURE:
<223> OTHER INFORMATION: Spacer sequence

<400> SEQUENCE: 11
ttgttgctga aggagttggg 20

<210> SEQ ID NO 12
<211> LENGTH: 20
<212> TYPE: DNA
<213> ORGANISM: Artificial Sequence
<220> FEATURE:
<223> OTHER INFORMATION: Spacer sequence

<400> SEQUENCE: 12
agcgaaaaac accttgccga 20

<210> SEQ ID NO 13
<211> LENGTH: 20
<212> TYPE: DNA
<213> ORGANISM: Artificial Sequence
<220> FEATURE:
<223> OTHER INFORMATION: Spacer sequence

<400> SEQUENCE: 13
ctgggaaacg gcactgaatg 20

<210> SEQ ID NO 14
<211> LENGTH: 20
<212> TYPE: DNA
<213> ORGANISM: Artificial Sequence
<220> FEATURE:
<223> OTHER INFORMATION: Spacer sequence

<400> SEQUENCE: 14
tgggttgttg gagagaaaac 20

<210> SEQ ID NO 15
<211> LENGTH: 20
<212> TYPE: DNA
<213> ORGANISM: Artificial Sequence
<220> FEATURE:
<223> OTHER INFORMATION: Spacer sequence

<400> SEQUENCE: 15
aaacacagcg gcacttctcg 20

<210> SEQ ID NO 16
<211> LENGTH: 20
<212> TYPE: DNA

<213> ORGANISM: Artificial Sequence
<220> FEATURE:
<223> OTHER INFORMATION: Spacer sequence

<400> SEQUENCE: 16
aaaattgaag ttttttatcc 20

<210> SEQ ID NO 17
<211> LENGTH: 20
<212> TYPE: DNA
<213> ORGANISM: Artificial Sequence
<220> FEATURE:
<223> OTHER INFORMATION: Spacer sequence

<400> SEQUENCE: 17
tggcagccgc agtggaagcc 20

<210> SEQ ID NO 18
<211> LENGTH: 20
<212> TYPE: DNA
<213> ORGANISM: Artificial Sequence
<220> FEATURE:
<223> OTHER INFORMATION: Spacer sequence

<400> SEQUENCE: 18
tcacagctac ttgaaggttc 20

<210> SEQ ID NO 19
<211> LENGTH: 20
<212> TYPE: DNA
<213> ORGANISM: Artificial Sequence
<220> FEATURE:
<223> OTHER INFORMATION: Spacer sequence

<400> SEQUENCE: 19
atcaaaactg gcagccgcaa 20

<210> SEQ ID NO 20
<211> LENGTH: 20
<212> TYPE: DNA
<213> ORGANISM: Artificial Sequence
<220> FEATURE:
<223> OTHER INFORMATION: Spacer sequence

<400> SEQUENCE: 20
cagtactcca accccagcat 20

<210> SEQ ID NO 21
<211> LENGTH: 20
<212> TYPE: DNA
<213> ORGANISM: Artificial Sequence
<220> FEATURE:
<223> OTHER INFORMATION: Spacer sequence

<400> SEQUENCE: 21
tcacctggcc gcaaatagtc 20

<210> SEQ ID NO 22
<211> LENGTH: 20
<212> TYPE: DNA
<213> ORGANISM: Artificial Sequence
<220> FEATURE:
<223> OTHER INFORMATION: Spacer sequence

<400> SEQUENCE: 22
acaacggatt aacagaagca 20

<210> SEQ ID NO 23
<211> LENGTH: 20
<212> TYPE: DNA
<213> ORGANISM: Artificial Sequence
<220> FEATURE:
<223> OTHER INFORMATION: Spacer sequence

<400> SEQUENCE: 23
agaacatcag cgcttggtca 20

<210> SEQ ID NO 24
<211> LENGTH: 20
<212> TYPE: DNA
<213> ORGANISM: Artificial Sequence
<220> FEATURE:
<223> OTHER INFORMATION: Spacer sequence

<400> SEQUENCE: 24
ataacggctt gacccagtca 20

<210> SEQ ID NO 25
<211> LENGTH: 20
<212> TYPE: DNA
<213> ORGANISM: Artificial Sequence
<220> FEATURE:
<223> OTHER INFORMATION: Spacer sequence

<400> SEQUENCE: 25
ggcaaccaga atatcagtgg 20

<210> SEQ ID NO 26
<211> LENGTH: 20
<212> TYPE: DNA
<213> ORGANISM: Artificial Sequence
<220> FEATURE:
<223> OTHER INFORMATION: Spacer sequence

<400> SEQUENCE: 26
ggatgccggt gacgaacagc 20

<210> SEQ ID NO 27
<211> LENGTH: 20
<212> TYPE: DNA
<213> ORGANISM: Artificial Sequence
<220> FEATURE:
<223> OTHER INFORMATION: Spacer sequence

<400> SEQUENCE: 27
gctacagtac agcgataacg 20

<210> SEQ ID NO 28
<211> LENGTH: 20
<212> TYPE: DNA
<213> ORGANISM: Artificial Sequence
<220> FEATURE:
<223> OTHER INFORMATION: Spacer sequence

<400> SEQUENCE: 28
gacgttgcgt cagcttacgc 20

<210> SEQ ID NO 29
<211> LENGTH: 20
<212> TYPE: DNA
<213> ORGANISM: Artificial Sequence
<220> FEATURE:

<223> OTHER INFORMATION: Spacer sequence

<400> SEQUENCE: 29
acctttaaag tgctgctgtg 20

<210> SEQ ID NO 30
<211> LENGTH: 20
<212> TYPE: DNA
<213> ORGANISM: Artificial Sequence
<220> FEATURE:
<223> OTHER INFORMATION: Spacer sequence

<400> SEQUENCE: 30
ggtttgatcg tcagggatgg 20

<210> SEQ ID NO 31
<211> LENGTH: 20
<212> TYPE: DNA
<213> ORGANISM: Artificial Sequence
<220> FEATURE:
<223> OTHER INFORMATION: Spacer sequence

<400> SEQUENCE: 31
gtggattaac gttccgaaag 20

<210> SEQ ID NO 32
<211> LENGTH: 20
<212> TYPE: DNA
<213> ORGANISM: Artificial Sequence
<220> FEATURE:
<223> OTHER INFORMATION: Spacer sequence

<400> SEQUENCE: 32
cagcgacagc aaagtggcat 20

<210> SEQ ID NO 33
<211> LENGTH: 20
<212> TYPE: DNA
<213> ORGANISM: Artificial Sequence
<220> FEATURE:
<223> OTHER INFORMATION: Spacer sequence

<400> SEQUENCE: 33
cttgccacct acagtgcggg 20

<210> SEQ ID NO 34
<211> LENGTH: 20
<212> TYPE: DNA
<213> ORGANISM: Artificial Sequence
<220> FEATURE:
<223> OTHER INFORMATION: Spacer sequence

<400> SEQUENCE: 34
cccccaaagg aatggagatc 20

<210> SEQ ID NO 35
<211> LENGTH: 20
<212> TYPE: DNA
<213> ORGANISM: Artificial Sequence
<220> FEATURE:
<223> OTHER INFORMATION: Spacer sequence

<400> SEQUENCE: 35
caccaagtct ttaagtggga 20

<210> SEQ ID NO 36
<211> LENGTH: 14
<212> TYPE: DNA
<213> ORGANISM: Artificial Sequence
<220> FEATURE:
<223> OTHER INFORMATION: Section of synthetic primer

<400> SEQUENCE: 36
cctcgaggcg cgcc 14

<210> SEQ ID NO 37
<211> LENGTH: 28
<212> TYPE: DNA
<213> ORGANISM: Artificial Sequence
<220> FEATURE:
<223> OTHER INFORMATION: Section of synthetic primer

<400> SEQUENCE: 37
gcgatcgcac gcgtttaatt aacctagg 28

<210> SEQ ID NO 38
<211> LENGTH: 14
<212> TYPE: DNA
<213> ORGANISM: Artificial Sequence
<220> FEATURE:
<223> OTHER INFORMATION: Section of synthetic primer

<400> SEQUENCE: 38
ggcgcgcctc gagg 14

<210> SEQ ID NO 39
<211> LENGTH: 28
<212> TYPE: DNA
<213> ORGANISM: Artificial Sequence
<220> FEATURE:
<223> OTHER INFORMATION: Synthetic primer

<400> SEQUENCE: 39
ttccattgtt cattccacgg acaaaaac 28

<210> SEQ ID NO 40
<211> LENGTH: 25
<212> TYPE: DNA
<213> ORGANISM: Artificial Sequence
<220> FEATURE:
<223> OTHER INFORMATION: Synthetic primer

<400> SEQUENCE: 40
gcctgaaaaa acttcccttg gggtt 25

<210> SEQ ID NO 41
<211> LENGTH: 53
<212> TYPE: DNA
<213> ORGANISM: Artificial Sequence
<220> FEATURE:
<223> OTHER INFORMATION: Synthetic primer

<400> SEQUENCE: 41
accgtcggtt cgagcggtaa cctcgaggcg cgccggcgtt taagggcacc aat 53

<210> SEQ ID NO 42
<211> LENGTH: 70
<212> TYPE: DNA
<213> ORGANISM: Artificial Sequence
<220> FEATURE:
<223> OTHER INFORMATION: Synthetic primer

<400> SEQUENCE: 42
ggataagtgg ataaccccaa gggaagtttt ttcaggcgcg ccatcgtgtg taagcagaat 60
atataagtgc 70

<210> SEQ ID NO 43
<211> LENGTH: 18
<212> TYPE: DNA
<213> ORGANISM: Artificial Sequence
<220> FEATURE:
<223> OTHER INFORMATION: Synthetic primer

<400> SEQUENCE: 43
aggcgtagca accaggcg 18

<210> SEQ ID NO 44
<211> LENGTH: 26
<212> TYPE: DNA
<213> ORGANISM: Artificial Sequence
<220> FEATURE:
<223> OTHER INFORMATION: Synthetic primer

<400> SEQUENCE: 44
ggttacgacg acatgtcaat acttgc 26

<210> SEQ ID NO 45
<211> LENGTH: 76
<212> TYPE: DNA
<213> ORGANISM: Artificial Sequence
<220> FEATURE:
<223> OTHER INFORMATION: Synthetic primer

<400> SEQUENCE: 45
ttttgtccgt ggaatgaaca atggaagcga tcgcacgcgt ttaattaacc taggtcaccc 60
tccttgcggg attgcc 76

<210> SEQ ID NO 46
<211> LENGTH: 39
<212> TYPE: DNA
<213> ORGANISM: Artificial Sequence
<220> FEATURE:
<223> OTHER INFORMATION: Synthetic primer

<400> SEQUENCE: 46
atcagcacga cgacgctggt gtagtagccc acggccacg 39

<210> SEQ ID NO 47
<211> LENGTH: 36
<212> TYPE: DNA
<213> ORGANISM: Artificial Sequence
<220> FEATURE:
<223> OTHER INFORMATION: Synthetic primer

<400> SEQUENCE: 47
tcgtggccgt gggctactac accagcgtcg tcgtgc 36

<210> SEQ ID NO 48
<211> LENGTH: 37
<212> TYPE: DNA
<213> ORGANISM: Artificial Sequence
<220> FEATURE:
<223> OTHER INFORMATION: Synthetic primer

<400> SEQUENCE: 48
gcaacttcgc catgcggatg cggtccaggt cctcgtt 37

<210> SEQ ID NO 49
<211> LENGTH: 38
<212> TYPE: DNA
<213> ORGANISM: Artificial Sequence
<220> FEATURE:
<223> OTHER INFORMATION: Synthetic primer

<400> SEQUENCE: 49
cgcaacgagg acctggaccg catccgcatg gcgaagtt 38

<210> SEQ ID NO 50
<211> LENGTH: 50
<212> TYPE: DNA
<213> ORGANISM: Artificial Sequence
<220> FEATURE:
<223> OTHER INFORMATION: Synthetic primer

<400> SEQUENCE: 50
aacgccggcg cgcctcgagg ttaccgctcg aaccgacggt aggcgtcgct 50

<210> SEQ ID NO 51
<211> LENGTH: 74
<212> TYPE: DNA
<213> ORGANISM: Artificial Sequence
<220> FEATURE:
<223> OTHER INFORMATION: Synthetic primer

<400> SEQUENCE: 51
aatgcctgtc aagggcaagt attgacatgt cgtcgtaacc gcgatcgcca tcgtggcgtt 60
gacaacgtgc ctgg 74

<210> SEQ ID NO 52
<211> LENGTH: 39
<212> TYPE: DNA
<213> ORGANISM: Artificial Sequence
<220> FEATURE:
<223> OTHER INFORMATION: Synthetic primer

<400> SEQUENCE: 52
accatgcgtg gggcggccac caatggcttg ccgacttcg 39

<210> SEQ ID NO 53
<211> LENGTH: 40
<212> TYPE: DNA
<213> ORGANISM: Artificial Sequence
<220> FEATURE:
<223> OTHER INFORMATION: Synthetic primer

<400> SEQUENCE: 53
gcgaagtcgg caagccattg gtggccgccc cacgcatggt 40

<210> SEQ ID NO 54
<211> LENGTH: 69
<212> TYPE: DNA
<213> ORGANISM: Artificial Sequence
<220> FEATURE:
<223> OTHER INFORMATION: Synthetic primer

<400> SEQUENCE: 54
ttattggtgc ccttaaacgc ctggttgcta cgcctacgcg tgggtagggg gatatatgca 60
atttgaacg 69

<210> SEQ ID NO 55

<211> LENGTH: 67
<212> TYPE: DNA
<213> ORGANISM: Artificial Sequence
<220> FEATURE:
<223> OTHER INFORMATION: Synthetic primer

<400> SEQUENCE: 55
aatgcctgtc aagggcaagt attgacatgt cgtcgtaacc acgcgttcac caggtcagaa 60
ccggcct 67

<210> SEQ ID NO 56
<211> LENGTH: 37
<212> TYPE: DNA
<213> ORGANISM: Artificial Sequence
<220> FEATURE:
<223> OTHER INFORMATION: Synthetic primer

<400> SEQUENCE: 56
tgggccgact ggctcaaggc cgaggcgatg aagggcg 37

<210> SEQ ID NO 57
<211> LENGTH: 35
<212> TYPE: DNA
<213> ORGANISM: Artificial Sequence
<220> FEATURE:
<223> OTHER INFORMATION: Synthetic primer

<400> SEQUENCE: 57
cgtcgccctt catcgcctcg gccttgagcc agtcg 35

<210> SEQ ID NO 58
<211> LENGTH: 57
<212> TYPE: DNA
<213> ORGANISM: Artificial Sequence
<220> FEATURE:
<223> OTHER INFORMATION: Synthetic primer

<400> SEQUENCE: 58
gcaaaaacaa gcccggcaac gccgggcttt ttcatctgcg cctctgcgat tcataac 57

<210> SEQ ID NO 59
<211> LENGTH: 40
<212> TYPE: DNA
<213> ORGANISM: Artificial Sequence
<220> FEATURE:
<223> OTHER INFORMATION: Synthetic primer

<400> SEQUENCE: 59
cgcagatgaa aaagcccggc gttgccgggc ttgtttttgc 40

<210> SEQ ID NO 60
<211> LENGTH: 84
<212> TYPE: DNA
<213> ORGANISM: Artificial Sequence
<220> FEATURE:
<223> OTHER INFORMATION: Synthetic primer

<400> SEQUENCE: 60
ggcagttatt ggtgccctta aacgcctggt tgctacgcct ttaattaatt tagcggctaa 60
aggtgttgac gtgcgagaaa tgtt 84

<210> SEQ ID NO 61
<211> LENGTH: 71
<212> TYPE: DNA
<213> ORGANISM: Artificial Sequence
<220> FEATURE:
<223> OTHER INFORMATION: Synthetic primer

<400> SEQUENCE: 61
aatgcctgtc aagggcaagt attgacatgt cgtcgtaacc ttaattaatg tgggcggaca 60
aaatagttgg g 71

<210> SEQ ID NO 62
<211> LENGTH: 47
<212> TYPE: DNA
<213> ORGANISM: Artificial Sequence
<220> FEATURE:
<223> OTHER INFORMATION: Synthetic primer

<400> SEQUENCE: 62
taattcaggc acgtatgtgg gtaggctgta atcttcttga tcatccg 47

<210> SEQ ID NO 63
<211> LENGTH: 47
<212> TYPE: DNA
<213> ORGANISM: Artificial Sequence
<220> FEATURE:
<223> OTHER INFORMATION: Synthetic primer

<400> SEQUENCE: 63
tcaagaagat tacagcctac ccacatacgt gcctgaatta tttcagg 47

<210> SEQ ID NO 64
<211> LENGTH: 67
<212> TYPE: DNA
<213> ORGANISM: Artificial Sequence
<220> FEATURE:
<223> OTHER INFORMATION: Synthetic primer

<400> SEQUENCE: 64
ggcagttatt ggtgccctta aacgcctggt tgctacgcct cctaggagta aatcgagtcc 60
atttccg 67

<210> SEQ ID NO 65
<211> LENGTH: 67
<212> TYPE: DNA
<213> ORGANISM: Artificial Sequence
<220> FEATURE:
<223> OTHER INFORMATION: Synthetic primer

<400> SEQUENCE: 65
aaaaccttta gcggccgccc ggtagagttt taatttaatg ctaaataaat taaaatgtta 60
tgagttc 67

<210> SEQ ID NO 66
<211> LENGTH: 46
<212> TYPE: DNA
<213> ORGANISM: Artificial Sequence
<220> FEATURE:
<223> OTHER INFORMATION: Synthetic primer

<400> SEQUENCE: 66
aaaaccttta gcgatcgctc gaacacttca cgaacaatga aatggt 46

<210> SEQ ID NO 67
<211> LENGTH: 20
<212> TYPE: DNA
<213> ORGANISM: Artificial Sequence
<220> FEATURE:

<223> OTHER INFORMATION: Synthetic primer

<400> SEQUENCE: 67
cgacgaccgg gtcgaatttg 20

<210> SEQ ID NO 68
<211> LENGTH: 33
<212> TYPE: DNA
<213> ORGANISM: Artificial Sequence
<220> FEATURE:
<223> OTHER INFORMATION: Synthetic primer

<400> SEQUENCE: 68
acatgagaat tacaacttat atcgtatggg gct 33

<210> SEQ ID NO 69
<211> LENGTH: 59
<212> TYPE: DNA
<213> ORGANISM: Artificial Sequence
<220> FEATURE:
<223> OTHER INFORMATION: Synthetic primer

<400> SEQUENCE: 69
tgaagtcagc cccatacgat ataagttgta attctcatgt atcgccatct tccagcagg 59

<210> SEQ ID NO 70
<211> LENGTH: 35
<212> TYPE: DNA
<213> ORGANISM: Artificial Sequence
<220> FEATURE:
<223> OTHER INFORMATION: Synthetic primer

<400> SEQUENCE: 70
cggtttgcgt attgggcgct tgccgcaggg ggacg 35

<210> SEQ ID NO 71
<211> LENGTH: 55
<212> TYPE: DNA
<213> ORGANISM: Artificial Sequence
<220> FEATURE:
<223> OTHER INFORMATION: Synthetic primer

<400> SEQUENCE: 71
atttcacaca ggaaacagct atgcagttta aggtttacac ctataaaaga gagag 55

<210> SEQ ID NO 72
<211> LENGTH: 61
<212> TYPE: DNA
<213> ORGANISM: Artificial Sequence
<220> FEATURE:
<223> OTHER INFORMATION: Synthetic primer

<400> SEQUENCE: 72
gaatggcaga aattcgaaag caaattcgac ccggtcgtcg gtagctgaca ttcatccggg 60
g 61

<210> SEQ ID NO 73
<211> LENGTH: 40
<212> TYPE: DNA
<213> ORGANISM: Artificial Sequence
<220> FEATURE:
<223> OTHER INFORMATION: Synthetic primer

<400> SEQUENCE: 73
gcagccgtcc ccctgcggca agcgcccaat acgcaaaccg 40

<210> SEQ ID NO 74
<211> LENGTH: 48
<212> TYPE: DNA
<213> ORGANISM: Artificial Sequence
<220> FEATURE:
<223> OTHER INFORMATION: Synthetic primer

<400> SEQUENCE: 74
gtgtaaacct taaactgcat agctgtttcc tgtgtgaaat tgttatcc 48

<210> SEQ ID NO 75
<211> LENGTH: 4758
<212> TYPE: DNA
<213> ORGANISM: Artificial Sequence
<220> FEATURE:
<223> OTHER INFORMATION: PCR amplicon

<400> SEQUENCE: 75
atgccggtac tgccgggcct cttgcgggat ccagaagtct ttttcttgca ctgtttcctt 60
ttctttatga tagtttacga aatcatcctg tggagcttag taggtttagc aagatggcag 120
cgcctaaatg tagaatgata aaaggattaa gagattaatt tccctaaaaa tgataaaaca 180
agcgttttga aagcgcttgt ttttttggtt tgcagtcaga gtagaataga agtatcaaaa 240
aaagcaccga ctcggtgcca ctttttcaag ttgataacgg actagcctta ttttaacttg 300
ctatgctgtt ttgaatggtt ccaacaagat tattttataa cttttataac aaataatcaa 360
ggagaaattc aaagaaattt atcagccata aaacaatact taatactata gaatgataac 420
aaaataaact actttttaaa agaattttgt gttataatct atttattatt aagtattggg 480
taatattttt tgaagagata ttttgaaaaa gaaaaattaa agcatattaa actaatttcg 540
gaggtcatta aaactattat tgaaatcatc aaactcatta tggatttaat ttaaactttt 600
tattttagga ggcaaaaatg gataagaaat actcaatagg cttagatatc ggcacaaata 660
gcgtcggatg ggcggtgatc actgatgaat ataaggttcc gtctaaaaag ttcaaggttc 720
tgggaaatac agaccgccac agtatcaaaa aaaatcttat aggggctctt ttatttgaca 780
gtggagagac agcggaagcg actcgtctca aacggacagc tcgtagaagg tatacacgtc 840
ggaagaatcg tatttgttat ctacaggaga tttttttcaaa tgagatggcg aaagtagatg 900
atagtttctt tcatcgactt gaagagtctt ttttggtgga agaagacaag aagcatgaac 960
gtcatcctat ttttggaaat atagtagatg aagttgctta tcatgagaaa tatccaacta 1020
tctatcatct gcgaaaaaaa ttggtagatt ctactgataa agcggatttg cgcttaatct 1080
atttggcctt agcgcatatg attaagtttc gtggtcattt tttgattgag ggagatttaa 1140
atcctgataa tagtgatgtg gacaaactat ttatccagtt ggtacaaacc tacaatcaat 1200
tatttgaaga aaaccctatt aacgcaagtg gagtagatgc taaagcgatt ctttctgcac 1260
gattgagtaa atcaagacga ttagaaaatc tcattgctca gctccccggt gagaagaaaa 1320
atggcttatt tgggaatctc attgctttgt cattgggttt gacccctaat tttaaatcaa 1380
attttgattt ggcagaagat gctaaattac agctttcaaa agatacttac gatgatgatt 1440
tagataattt attggcgcaa attggagatc aatatgctga tttgtttttg gcagctaaga 1500
atttatcaga tgctatttta ctttcagata tcctaagagt aaatactgaa ataactaagg 1560
ctcccctatc agcttcaatg attaaacgct acgatgaaca tcatcaagac ttgactcttt 1620
taaaagcttt agttcgacaa caacttccag aaaagtataa agaaatcttt tttgatcaat 1680

-continued

```
caaaaaacgg atatgcaggt tatattgatg ggggagctag ccaagaagaa ttttataaat   1740
ttatcaaacc aattttagaa aaaatggatg gtactgagga attattggtg aaactaaatc   1800
gtgaagattt gctgcgcaag caacggacct ttgacaacgg ctctattccc catcaaattc   1860
acttgggtga gctgcatgct attttgagaa gacaagaaga cttttatcca tttttaaaag   1920
acaatcgtga gaagattgaa aaaatcttga cttttcgaat tccttattat gttggtccat   1980
tggcgcgtgg caatagtcgt tttgcatgga tgactcggaa gtctgaagaa acaattaccc   2040
catggaattt tgaagaagtt gtcgataaag gtgcttcagc tcaatcattt attgaacgca   2100
tgacaaactt tgataaaaat cttccaaatg aaaaagtact accaaaacat agtttgcttt   2160
atgagtattt tacggtttat aacgaattga caaaggtcaa atatgttact gaaggaatgc   2220
gaaaaccagc atttctttca ggtgaacaga agaaagccat tgttgattta ctcttcaaaa   2280
caaatcgaaa agtaaccgtt aagcaattaa aagaagatta tttcaaaaaa atagaatgtt   2340
ttgatagtgt tgaaatttca ggagttgaag atagatttaa tgcttcatta ggtacctacc   2400
atgatttgct aaaaattatt aaagataaag attttttgga taatgaagaa aatgaagata   2460
tcttagagga tattgtttta acattgacct tatttgaaga tagggagatg attgaggaaa   2520
gacttaaaac atatgctcac ctctttgatg ataaggtgat gaaacagctt aaacgtcgcc   2580
gttatactgg ttggggacgt ttgtctcgaa aattgattaa tggtattagg gataagcaat   2640
ctggcaaaac aatattagat tttttgaaat cagatggttt tgccaatcgc aattttatgc   2700
agctgatcca tgatgatagt ttgacattta aagaagacat tcaaaaagca caagtgtctg   2760
gacaaggcga tagtttacat gaacatattg caaatttagc tggtagccct gctattaaaa   2820
aaggtatttt acagactgta aaagttgttg atgaattggt caaagtaatg gggcggcata   2880
agccagaaaa tatcgttatt gaaatggcac gtgaaaatca gacaactcaa aagggccaga   2940
aaaattcgcg agagcgtatg aaacgaatcg aagaaggtat caaagaatta ggaagtcaga   3000
ttcttaaaga gcatcctgtt gaaaatactc aattgcaaaa tgaaaagctc tatctctatt   3060
atctccaaaa tggaagagac atgtatgtgg accaagaatt agatattaat cgtttaagtg   3120
attatgatgt cgatcacatt gttccacaaa gtttccttaa agacgattca atagacaata   3180
aggtcttaac gcgttctgat aaaaatcgtg gtaaatcgga taacgttcca agtgaagaag   3240
tagtcaaaaa gatgaaaaac tattggagac aacttctaaa cgccaagtta atcactcaac   3300
gtaagtttga taatttaacg aaagctgaac gtggaggttt gagtgaactt gataaagctg   3360
gttttatcaa acgccaattg gttgaaactc gccaaatcac taagcatgtg gcacaaattt   3420
tggatagtcg catgaatact aaatacgatg aaaatgataa acttattcga gaggttaaag   3480
tgattacctt aaaatctaaa ttagtttctg acttccgaaa agatttccaa ttctataaag   3540
tacgtgagat taacaattac catcatgccc atgatgcgta tctaaatgcc gtcgttggaa   3600
ctgctttgat taagaaatat ccaaaacttg aatcggagtt tgtctatggt gattataaag   3660
tttatgatgt tcgtaaaatg attgctaagt ctgagcaaga aataggcaaa gcaaccgcaa   3720
aatatttctt ttactctaat atcatgaact tcttcaaaac agaaattaca cttgcaaatg   3780
gagagattcg caaacgccct ctaatcgaaa ctaatgggga aactggagaa attgtctggg   3840
ataaagggcg agattttgcc acagtgcgca aagtattgtc catgccccaa gtcaatattg   3900
tcaagaaaac agaagtacag acaggcggat tctccaagga gtcaatttta ccaaaaagaa   3960
attcggacaa gcttattgct cgtaaaaaag actgggatcc aaaaaaatat ggtggttttg   4020
atagtccaac ggtagcttat tcagtcctag tggttgctaa ggtggaaaaa gggaaatcga   4080
```

agaagttaaa atccgttaaa gagttactag ggatcacaat tatggaaaga agttcctttg 4140
aaaaaaatcc gattgacttt ttagaagcta aaggatataa ggaagttaaa aaagacttaa 4200
tcattaaact acctaaatat agtctttttg agttagaaaa cggtcgtaaa cggatgctgg 4260
ctagtgccgg agaattacaa aaaggaaatg agctggctct gccaagcaaa tatgtgaatt 4320
ttttatattt agctagtcat tatgaaaagt tgaagggtag tccagaagat aacgaacaaa 4380
aacaattgtt tgtggagcag cataagcatt atttagatga gattattgag caaatcagtg 4440
aattttctaa gcgtgttatt ttagcagatg ccaatttaga taaagttctt agtgcatata 4500
acaaacatag agacaaacca atacgtgaac aagcagaaaa tattattcat ttatttacgt 4560
tgacgaatct tggagctccc gctgctttta aatattttga tacaacaatt gatcgtaaac 4620
gatatacgtc tacaaaagaa gttttagatg ccactcttat ccatcaatcc atcactggtc 4680
tttatgaaac acgcattgat ttgagtcagc taggaggtga ctgatggcca cgtgaactat 4740
atgattttcc gcagtata 4758

<210> SEQ ID NO 76
<211> LENGTH: 276
<212> TYPE: DNA
<213> ORGANISM: Artificial Sequence
<220> FEATURE:
<223> OTHER INFORMATION: PCR amplicon

<400> SEQUENCE: 76
attgatttga gtcagctagg aggtgactga tggccacgtg aactatatga ttttccgcag 60
tatattttag atgaagatta tttcttaata actaaaaata tggtataata ctcttaataa 120
atgcagtaat acaggggctt ttcaagactg aagtctagct gagacaaata gtgcgattac 180
gaaatttttt agacaaaaat agtctacgag gttttagagc tatgctgttt tgaatggtcc 240
caaaactgag accagtctcg gacgtccaaa ggtctc 276

<210> SEQ ID NO 77
<211> LENGTH: 452
<212> TYPE: DNA
<213> ORGANISM: Artificial Sequence
<220> FEATURE:
<223> OTHER INFORMATION: PCR amplicon

<400> SEQUENCE: 77
gagaccagtc tcggacgtcc aaaggtctcg ttttagagct atgctgtttt gaatggtccc 60
aaaacaacat tgccgatgat aacttgagaa agagggttaa taccagcagt cggatacctt 120
cctattcttt ctgttaaagc gttttcatgt tataataggc aaaagaagag tagtgtgatg 180
gaacaaacat tttttatgat taagccatat ggggttaagc aaggggaggt agttggagag 240
gttttacggt ggattgaacg cctaagattt acgtttaagc gattcgagct aagacaagct 300
agttcgaaat acttggctaa gcacgacgag gccttggtga taaacctttt gatcctaaac 360
ttaaagctta catgacaagt ggtcctgttt taattgggat aattcttggg gactaaggtg 420
gtatcgtcca ttccgacagc atcgccagtc ac 452

<210> SEQ ID NO 78
<211> LENGTH: 9578
<212> TYPE: DNA
<213> ORGANISM: Artificial Sequence
<220> FEATURE:
<223> OTHER INFORMATION: pNB100 construct

<400> SEQUENCE: 78

```
gaattccgga tgagcattca tcaggcgggc aagaatgtga ataaaggccg gataaaactt     60
gtgcttattt ttctttacgg tctttaaaaa ggccgtaata tccagctgaa cggtctggtt    120
ataggtacat tgagcaactg actgaaatgc ctcaaaatgt tctttacgat gccattggga    180
tatatcaacg gtggtatatc cagtgatttt tttctccatt ttagcttcct tagctcctga    240
aaatctcgat aactcaaaaa atacgcccgg tagtgatctt atttcattat ggtgaaagtt    300
ggaacctctt acgtgccgat caacgtctca ttttcgccaa aagttggccc agggcttccc    360
ggtatcaaca gggacaccag gatttattta ttctgcgaag tgatcttccg tcacaggtat    420
ttattcggcg caaagtgcgt cgggtgatgc tgccaactta ctgatttagt gtatgatggt    480
gtttttgagg tgctccagtg gcttctgttt ctatcagctg tccctcctgt tcagctactg    540
acggggtggt gcgtaacggc aaaagcaccg ccggacatca gcgctagcgg agtgtatact    600
ggcttactat gttggcactg atgagggtgt cagtgaagtg cttcatgtgg caggagaaaa    660
aaggctgcac cggtgcgtca gcagaatatg tgatacagga tatattccgc ttcctcgctc    720
actgactcgc tacgctcggt cgttcgactg cggcgagcgg aaatggctta cgaacggggc    780
ggagatttcc tggaagatgc caggaagata cttaacaggg aagtgagagg gccgcggcaa    840
agccgttttt ccataggctc cgcccccctg acaagcatca cgaaatctga cgctcaaatc    900
agtggtggcg aaacccgaca ggactataaa gataccaggc gtttccccct ggcggctccc    960
tcgtgcgctc tcctgttcct gcctttcggt ttaccggtgt cattccgctg ttatggccgc   1020
gtttgtctca ttccacgcct gacactcagt tccgggtagg cagttcgctc caagctggac   1080
tgtatgcacg aaccccccgt tcagtccgac cgctgcgcct tatccggtaa ctatcgtctt   1140
gagtccaacc cggaaagaca tgcaaaagca ccactggcag cagccactgg taattgattt   1200
agaggagtta gtcttgaagt catgcgccgg ttaaggctaa actgaaagga caagttttgg   1260
tgactgcgct cctccaagcc agttacctcg gttcaaagag ttggtagctc agagaacctt   1320
cgaaaaaccg ccctgcaagg cggttttttc gttttcagag caagagatta cgcgcagacc   1380
aaaacgatct caagaagatc atcttattaa tcagataaaa tatttctaga tttcagtgca   1440
atttatctct tcaaatgtag cacctgaagt cagccccata cgatataagt tgtaattctc   1500
atgtttgaca gcttatcatc gataagcttt aatgcggtag tttatcacag ttaaattgct   1560
aacgcagtca ggcaccgtgt atgaaatcta acaatgcgct catcgtcatc ctcggcaccg   1620
tcaccctgga tgctgtaggc ataggcttgg ttatgccggt actgccgggc ctcttgcggg   1680
atccagaagt ctttttcttg cactgtttcc ttttctttat gatagtttac gaaatcatcc   1740
tgtggagctt agtaggttta gcaagatggc agcgcctaaa tgtagaatga taaaaggatt   1800
aagagattaa tttccctaaa aatgataaaa caagcgtttt gaaagcgctt gtttttttgg   1860
tttgcagtca gagtagaata gaagtatcaa aaaaagcacc gactcggtgc cactttttca   1920
agttgataac ggactagcct tattttaact tgctatgctg ttttgaatgg ttccaacaag   1980
attattttat aacttttata acaaataatc aaggagaaat tcaaagaaat ttatcagcca   2040
taaaacaata cttaatacta tagaatgata acaaaataaa ctacttttta aaagaatttt   2100
gtgttataat ctatttatta ttaagtattg ggtaatattt tttgaagaga tattttgaaa   2160
aagaaaaatt aaagcatatt aaactaattt cggaggtcat taaaactatt attgaaatca   2220
tcaaactcat tatggattta atttaaactt tttattttag gaggcaaaaa tggataagaa   2280
atactcaata ggcttagata tcggcacaaa tagcgtcgga tgggcggtga tcactgatga   2340
```

```
atataaggtt ccgtctaaaa agttcaaggt tctgggaaat acagaccgcc acagtatcaa   2400
aaaaaatctt ataggggctc ttttatttga cagtggagag acagcggaag cgactcgtct   2460
caaacggaca gctcgtagaa ggtatacacg tcggaagaat cgtatttgtt atctacagga   2520
gatttttca aatgagatgg cgaaagtaga tgatagtttc tttcatcgac ttgaagagtc    2580
tttttggtg gaagaagaca agaagcatga acgtcatcct atttttggaa atatagtaga    2640
tgaagttgct tatcatgaga aatatccaac tatctatcat ctgcgaaaaa aattggtaga   2700
ttctactgat aaagcggatt tgcgcttaat ctatttggcc ttagcgcata tgattaagtt   2760
tcgtggtcat tttttgattg agggagattt aaatcctgat aatagtgatg tggacaaact   2820
atttatccag ttggtacaaa cctacaatca attatttgaa gaaaacccta ttaacgcaag   2880
tggagtagat gctaaagcga ttctttctgc acgattgagt aaatcaagac gattagaaaa   2940
tctcattgct cagctccccg gtgagaagaa aaatggctta tttgggaatc tcattgcttt   3000
gtcattgggt ttgaccccta attttaaatc aaattttgat ttggcagaag atgctaaatt   3060
acagctttca aaagatactt acgatgatga tttagataat ttattggcgc aaattggaga   3120
tcaatatgct gatttgtttt tggcagctaa gaatttatca gatgctattt tactttcaga   3180
tatcctaaga gtaaatactg aaataactaa ggctccccta tcagcttcaa tgattaaacg   3240
ctacgatgaa catcatcaag acttgactct tttaaaagct ttagttcgac aacaacttcc   3300
agaaaagtat aaagaaatct tttttgatca atcaaaaaac ggatatgcag gttatattga   3360
tggggggagct agccaagaag aattttataa atttatcaaa ccaattttag aaaaaatgga  3420
tggtactgag gaattattgg tgaaactaaa tcgtgaagat ttgctgcgca agcaacggac   3480
ctttgacaac ggctctattc cccatcaaat tcacttgggt gagctgcatg ctattttgag   3540
aagacaagaa gacttttatc cattttttaaa agacaatcgt gagaagattg aaaaaatctt  3600
gacttttcga attccttatt atgttggtcc attggcgcgt ggcaatagtc gttttgcatg   3660
gatgactcgg aagtctgaag aaacaattac cccatggaat tttgaagaag ttgtcgataa   3720
aggtgcttca gctcaatcat ttattgaacg catgacaaac tttgataaaa atcttccaaa   3780
tgaaaaagta ctaccaaaac atagtttgct ttatgagtat tttacggttt ataacgaatt   3840
gacaaaggtc aaatatgtta ctgaaggaat gcgaaaacca gcatttcttt caggtgaaca   3900
gaagaaagcc attgttgatt tactcttcaa aacaaatcga aaagtaaccg ttaagcaatt   3960
aaaagaagat tatttcaaaa aaatagaatg ttttgatagt gttgaaattt caggagttga   4020
agatagattt aatgcttcat taggtaccta ccatgatttg ctaaaaatta ttaaagataa   4080
agattttttg gataatgaag aaaatgaaga tatcttagag gatattgttt taacattgac   4140
cttatttgaa gatagggaga tgattgagga aagacttaaa acatatgctc acctctttga   4200
tgataaggtg atgaaacagc ttaaacgtcg ccgttatact ggttggggac gtttgtctcg   4260
aaaattgatt aatggtatta gggataagca atctggcaaa acaatattag atttttttgaa  4320
atcagatggt tttgccaatc gcaattttat gcagctgatc catgatgata gtttgacatt   4380
taaagaagac attcaaaaag cacaagtgtc tggacaaggc gatagtttac atgaacatat   4440
tgcaaattta gctggtagcc ctgctattaa aaaaggtatt ttacagactg taaaagttgt   4500
tgatgaattg gtcaaagtaa tggggcggca taagccagaa aatatcgtta ttgaaatggc   4560
acgtgaaaat cagacaactc aaaagggcca gaaaaattcg cgagagcgta tgaaacgaat   4620
cgaagaaggt atcaaagaat taggaagtca gattcttaaa gagcatcctg ttgaaaatac   4680
```

```
tcaattgcaa aatgaaaagc tctatctcta ttatctccaa aatggaagag acatgtatgt   4740
ggaccaagaa ttagatatta atcgtttaag tgattatgat gtcgatcaca ttgttccaca   4800
aagtttcctt aaagacgatt caatagacaa taaggtctta acgcgttctg ataaaaatcg   4860
tggtaaatcg gataacgttc caagtgaaga agtagtcaaa aagatgaaaa actattggag   4920
acaacttcta aacgccaagt taatcactca acgtaagttt gataatttaa cgaaagctga   4980
acgtggaggt ttgagtgaac ttgataaagc tggttttatc aaacgccaat tggttgaaac   5040
tcgccaaatc actaagcatg tggcacaaat tttggatagt cgcatgaata ctaaatacga   5100
tgaaaatgat aaacttattc gagaggttaa agtgattacc ttaaaatcta aattagtttc   5160
tgacttccga aaagatttcc aattctataa agtacgtgag attaacaatt accatcatgc   5220
ccatgatgcg tatctaaatg ccgtcgttgg aactgctttg attaagaaat atccaaaact   5280
tgaatcggag tttgtctatg gtgattataa agtttatgat gttcgtaaaa tgattgctaa   5340
gtctgagcaa gaaataggca aagcaaccgc aaaatatttc ttttactcta atatcatgaa   5400
cttcttcaaa acagaaatta cacttgcaaa tggagagatt cgcaaacgcc ctctaatcga   5460
aactaatggg gaaactggag aaattgtctg ggataaaggg cgagattttg ccacagtgcg   5520
caaagtattg tccatgcccc aagtcaatat tgtcaagaaa acagaagtac agacaggcgg   5580
attctccaag gagtcaattt taccaaaaag aaattcggac aagcttattg ctcgtaaaaa   5640
agactgggat ccaaaaaaat atggtggttt tgatagtcca acggtagctt attcagtcct   5700
agtggttgct aaggtggaaa aagggaaatc gaagaagtta aaatccgtta aagagttact   5760
agggatcaca attatggaaa gaagttcctt tgaaaaaaat ccgattgact tttagaagc    5820
taaaggatat aaggaagtta aaaaagactt aatcattaaa ctacctaaat atagtctttt   5880
tgagttagaa aacggtcgta aacggatgct ggctagtgcc ggagaattac aaaaaggaaa   5940
tgagctggct ctgccaagca aatatgtgaa tttttttatat ttagctagtc attatgaaaa   6000
gttgaagggt agtccagaag ataacgaaca aaaacaattg tttgtggagc agcataagca   6060
ttatttagat gagattattg agcaaatcag tgaattttct aagcgtgtta ttttagcaga   6120
tgccaattta gataaagttc ttagtgcata taacaaacat agagacaaac caatacgtga   6180
acaagcagaa aatattattc atttatttac gttgacgaat cttggagctc ccgctgcttt   6240
taaatatttt gatacaacaa ttgatcgtaa acgatatacg tctacaaaag aagttttaga   6300
tgccactctt atccatcaat ccatcactgg tctttatgaa acacgcattg atttgagtca   6360
gctaggaggt gactgatggc cacgtgaact atatgatttt ccgcagtata ttttagatga   6420
agattatttc ttaataacta aaaatatggt ataatactct taataaatgc agtaatacag   6480
gggcttttca agactgaagt ctagctgaga caaatagtgc gattacgaaa tttttttagac   6540
aaaaatagtc tacgaggttt tagagctatg ctattttgaa tggtcccaaa actgagacca   6600
gtctcggacg tccaaaggtc tcgttttaga gctatgctgt tttgaatggt cccaaaacaa   6660
cattgccgat gataacttga gaaagagggt taataccagc agtcggatac cttcctattc   6720
tttctgttaa agcgttttca tgttataata ggcaaaagaa gagtagtgtg atggaacata   6780
catttttat gattaagcca tatggggtta agcaagggga ggtagttgga gaggttttac    6840
ggtggattga acgcctaaga tttacgttta agcgattcga gctaagacaa gctagttcga   6900
aatacttggc taagcacgac gaggccttgg tgataaacct tttgatccta aacttaaagc   6960
ttacatgaca agtggtcctg ttttaattgg gataattctt ggggactaag gtggtatcgt   7020
ccattccgac agcatcgcca gtcactatgg cgtgctgcta gcgctatatg cgttgatgca   7080
```

atttctatgc gcacccgttc tcggagcact gtccgaccgc tttggccgcc gcccagtcct 7140
gctcgcttcg ctacttggag ccactatcga ctacgcgatc atggcgacca cacccgtcct 7200
gtggatcctc tacgccggac gcatcgtggc cggcatcacc ggcgccacag gtgcggttgc 7260
tggcgcctat atcgccgaca tcaccgatgg ggaagatcgg gctcgccact tcgggctcat 7320
gagcgcttgt ttcggcgtgg gtatggtggc aggccccgtg gccgggggac tgttgggcgc 7380
catctccttg catgcaccat tccttgcggc ggcggtgctc aacggcctca acctactact 7440
gggctgcttc ctaatgcagg agtcgcataa gggagagcgt cgaccgatgc ccttgagagc 7500
cttcaaccca gtcagctcct tccggtgggc gcggggcatg actatcgtcg ccgcacttat 7560
gactgtcttc tttatcatgc aactcgtagg acaggtgccg gcagcgctct gggtcatttt 7620
cggcgaggac cgctttcgct ggagcgcgac gatgatcggc ctgtcgcttg cggtattcgg 7680
aatcttgcac gccctcgctc aagccttcgt cactggtccc gccaccaaac gtttcggcga 7740
gaagcaggcc attatcgccg gcatggcggc cgacgcgctg ggctacgtct tgctggcgtt 7800
cgcgacgcga ggctggatgg ccttccccat tatgattctt ctcgcttccg gcggcatcgg 7860
gatgcccgcg ttgcaggcca tgctgtccag gcaggtagat gacgaccatc agggacagct 7920
tcaaggatcg ctcgcggctc ttaccagcct aacttcgatc attggaccgc tgatcgtcac 7980
ggcgatttat gccgcctcgg cgagcacatg gaacgggttg gcatggattg taggcgccgc 8040
cctatacctt gtctgcctcc ccgcgttgcg tcgcggtgca tggagccggg ccacctcgac 8100
ctgaatggaa gccggcggca cctcgctaac ggattcacca ctccaagaat tggagccaat 8160
caattcttgc ggagaactgt gaatgcgcaa accaaccctt ggcagaacat atccatcgcg 8220
tccgccatct ccagcagccg cacgcggcgc atctcgggca gcgttgggtc ctggccacgg 8280
gtgcgcatga tcgtgctcct gtcgttgagg acccggctag gctggcgggg ttgccttact 8340
ggttagcaga atgaatcacc gatacgcgag cgaacgtgaa gcgactgctg ctgcaaaacg 8400
tctgcgacct gagcaacaac atgaatggtc ttcggtttcc gtgtttcgta aagtctggaa 8460
acgcggaagt cccctacgtg ctgctgaagt tgcccgcaac agagagtgga accaaccggt 8520
gataccacga tactatgact gagagtcaac gccatgagcg gcctcatttc ttattctgag 8580
ttacaacagt ccgcaccgct gtccggtagc tccttccggt gggcgcgggg catgactatc 8640
gtcgccgcac ttatgactgt cttctttatc atgcaactcg taggacaggt gccggcagcg 8700
cccaacagtc ccccggccac ggggcctgcc accataccca cgccgaaaca agcgccctgc 8760
accattatgt tccggatctg catcgcagga tgctgctggc taccctgtgg aacacctaca 8820
tctgtattaa cgaagcgcta accgttttta tcaggctctg ggaggcagaa taaatgatca 8880
tatcgtcaat tattacctcc acggggagag cctgagcaaa ctggcctcag gcatttgaga 8940
agcacacggt cacactgctt ccggtagtca ataaaccggt aaaccagcaa tagacataag 9000
cggctattta acgaccctgc cctgaaccga cgaccgggtc gaatttgctt tcgaatttct 9060
gccattcatc cgcttattat cacttattca ggcgtagcac caggcgttta agggcaccaa 9120
taactgcctt aaaaaaatta cgccccgccc tgccactcat cgcagtactg ttgtaattca 9180
ttaagcattc tgccgacatg gaagccatca cagacggcat gatgaacctg aatcgccagc 9240
ggcatcagca ccttgtcgcc ttgcgtataa tatttgccca tggtgaaaac gggggcgaag 9300
aagttgtcca tattggccac gtttaaatca aaactggtga aactcaccca gggattggct 9360
gagacgaaaa acatattctc aataaaccct ttagggaaat aggccaggtt ttcaccgtaa 9420

```
cacgccacat cttgcgaata tatgtgtaga aactgccgga aatcgtcgtg gtattcactc   9480

cagagcgatg aaaacgtttc agtttgctca tggaaaacgg tgtaacaagg gtgaacacta   9540

tcccatatca ccagctcacc gtctttcatt gccatacg                           9578


<210> SEQ ID NO 79
<211> LENGTH: 20
<212> TYPE: DNA
<213> ORGANISM: Artificial Sequence
<220> FEATURE:
<223> OTHER INFORMATION: Candidate anti-protospacer sequence

<400> SEQUENCE: 79

tagataacta cgatacggga                                                 20


<210> SEQ ID NO 80
<211> LENGTH: 20
<212> TYPE: DNA
<213> ORGANISM: Artificial Sequence
<220> FEATURE:
<223> OTHER INFORMATION: Candidate anti-protospacer sequence

<400> SEQUENCE: 80

gatcgttgtc agaagtaagt                                                 20


<210> SEQ ID NO 81
<211> LENGTH: 20
<212> TYPE: DNA
<213> ORGANISM: Artificial Sequence
<220> FEATURE:
<223> OTHER INFORMATION: Candidate anti-protospacer sequence

<400> SEQUENCE: 81

actttaaaag tgctcatcat                                                 20


<210> SEQ ID NO 82
<211> LENGTH: 20
<212> TYPE: DNA
<213> ORGANISM: Artificial Sequence
<220> FEATURE:
<223> OTHER INFORMATION: Candidate anti-protospacer sequence

<400> SEQUENCE: 82

tttactttca ccagcgtttc                                                 20


<210> SEQ ID NO 83
<211> LENGTH: 20
<212> TYPE: DNA
<213> ORGANISM: Artificial Sequence
<220> FEATURE:
<223> OTHER INFORMATION: Candidate anti-protospacer sequence

<400> SEQUENCE: 83

attaatagac tggatggagg                                                 20


<210> SEQ ID NO 84
<211> LENGTH: 20
<212> TYPE: DNA
<213> ORGANISM: Artificial Sequence
<220> FEATURE:
<223> OTHER INFORMATION: Candidate anti-protospacer sequence

<400> SEQUENCE: 84

acaattaata gactggatgg                                                 20
```

<210> SEQ ID NO 85
<211> LENGTH: 20
<212> TYPE: DNA
<213> ORGANISM: Artificial Sequence
<220> FEATURE:
<223> OTHER INFORMATION: Candidate anti-protospacer sequence

<400> SEQUENCE: 85
gcaacaatta atagactgga 20

<210> SEQ ID NO 86
<211> LENGTH: 20
<212> TYPE: DNA
<213> ORGANISM: Artificial Sequence
<220> FEATURE:
<223> OTHER INFORMATION: Candidate anti-protospacer sequence

<400> SEQUENCE: 86
cccggcaaca attaatagac 20

<210> SEQ ID NO 87
<211> LENGTH: 20
<212> TYPE: DNA
<213> ORGANISM: Artificial Sequence
<220> FEATURE:
<223> OTHER INFORMATION: Candidate anti-protospacer sequence

<400> SEQUENCE: 87
acgttgcgca aactattaac 20

<210> SEQ ID NO 88
<211> LENGTH: 20
<212> TYPE: DNA
<213> ORGANISM: Artificial Sequence
<220> FEATURE:
<223> OTHER INFORMATION: Candidate anti-protospacer sequence

<400> SEQUENCE: 88
tgtaactcgc cttgatcgtt 20

<210> SEQ ID NO 89
<211> LENGTH: 20
<212> TYPE: DNA
<213> ORGANISM: Artificial Sequence
<220> FEATURE:
<223> OTHER INFORMATION: Candidate anti-protospacer sequence

<400> SEQUENCE: 89
atgtaactcg ccttgatcgt 20

<210> SEQ ID NO 90
<211> LENGTH: 20
<212> TYPE: DNA
<213> ORGANISM: Artificial Sequence
<220> FEATURE:
<223> OTHER INFORMATION: Candidate anti-protospacer sequence

<400> SEQUENCE: 90
aacttacttc tgacaacgat 20

<210> SEQ ID NO 91
<211> LENGTH: 20
<212> TYPE: DNA
<213> ORGANISM: Artificial Sequence
<220> FEATURE:
<223> OTHER INFORMATION: Candidate anti-protospacer sequence

<400> SEQUENCE: 91
agtcacagaa aagcatctta 20

<210> SEQ ID NO 92
<211> LENGTH: 20
<212> TYPE: DNA
<213> ORGANISM: Artificial Sequence
<220> FEATURE:
<223> OTHER INFORMATION: Candidate anti-protospacer sequence

<400> SEQUENCE: 92
acttttaaag ttctgctatg 20

<210> SEQ ID NO 93
<211> LENGTH: 25
<212> TYPE: DNA
<213> ORGANISM: Artificial Sequence
<220> FEATURE:
<223> OTHER INFORMATION: Spacer sequence

<400> SEQUENCE: 93
aaactagata actacgatac gggag 25

<210> SEQ ID NO 94
<211> LENGTH: 25
<212> TYPE: DNA
<213> ORGANISM: Artificial Sequence
<220> FEATURE:
<223> OTHER INFORMATION: Spacer sequence

<400> SEQUENCE: 94
aaaactcccg tatcgtagtt atcta 25

<210> SEQ ID NO 95
<211> LENGTH: 25
<212> TYPE: DNA
<213> ORGANISM: Artificial Sequence
<220> FEATURE:
<223> OTHER INFORMATION: Spacer sequence

<400> SEQUENCE: 95
aaacacttta aaagtgctca tcatg 25

<210> SEQ ID NO 96
<211> LENGTH: 25
<212> TYPE: DNA
<213> ORGANISM: Artificial Sequence
<220> FEATURE:
<223> OTHER INFORMATION: Spacer sequence

<400> SEQUENCE: 96
aaaacatgat gagcactttt aaagt 25

<210> SEQ ID NO 97
<211> LENGTH: 25
<212> TYPE: DNA
<213> ORGANISM: Artificial Sequence
<220> FEATURE:
<223> OTHER INFORMATION: Spacer sequence

<400> SEQUENCE: 97
aaacacgttg cgcaaactat taacg 25

<210> SEQ ID NO 98
<211> LENGTH: 25

<212> TYPE: DNA
<213> ORGANISM: Artificial Sequence
<220> FEATURE:
<223> OTHER INFORMATION: Spacer sequence

<400> SEQUENCE: 98
aaaacgttaa tagtttgcgc aacgt 25

<210> SEQ ID NO 99
<211> LENGTH: 25
<212> TYPE: DNA
<213> ORGANISM: Artificial Sequence
<220> FEATURE:
<223> OTHER INFORMATION: Spacer sequence

<400> SEQUENCE: 99
aaacactttt aaagttctgc tatgg 25

<210> SEQ ID NO 100
<211> LENGTH: 25
<212> TYPE: DNA
<213> ORGANISM: Artificial Sequence
<220> FEATURE:
<223> OTHER INFORMATION: Spacer sequence

<400> SEQUENCE: 100
aaaaccatag cagaacttta aaagt 25

<210> SEQ ID NO 101
<211> LENGTH: 81
<212> TYPE: DNA
<213> ORGANISM: Artificial Sequence
<220> FEATURE:
<223> OTHER INFORMATION: Adaptor sequence

<400> SEQUENCE: 101
aaacacttta aaagtgctca tcatgtttta gagctatgct gttttgaatg gtcccaaaac 60
acttttaaag ttctgctatg g 81

<210> SEQ ID NO 102
<211> LENGTH: 81
<212> TYPE: DNA
<213> ORGANISM: Artificial Sequence
<220> FEATURE:
<223> OTHER INFORMATION: Adaptor sequence

<400> SEQUENCE: 102
aaaaccatag cagaacttta aaagtgtttt gggaccattc aaaacagcat agctctaaaa 60
catgatgagc acttttaaag t 81

<210> SEQ ID NO 103
<211> LENGTH: 20
<212> TYPE: DNA
<213> ORGANISM: Artificial Sequence
<220> FEATURE:
<223> OTHER INFORMATION: Spacer sequence

<400> SEQUENCE: 103
ctgggaaacg gaactgaatg 20

<210> SEQ ID NO 104
<211> LENGTH: 34
<212> TYPE: DNA
<213> ORGANISM: Artificial Sequence
<220> FEATURE:

<223> OTHER INFORMATION: Spacer sequence

<400> SEQUENCE: 104
ggctagttaa aaataaaatt gaagtttttt atcc 34

<210> SEQ ID NO 105
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 105
gggctggcaa gccacgtttg gtgggtctcg aaacggtttg atcgtcaggg atgg 54

<210> SEQ ID NO 106
<211> LENGTH: 90
<212> TYPE: DNA
<213> ORGANISM: Artificial Sequence
<220> FEATURE:
<223> OTHER INFORMATION: Synthetic oligonucleotide

<400> SEQUENCE: 106
ggataaaaaa cttcaatttt atttttaact agccgttttg ggaccattca aaacagcata 60
gctctaaaac ccatccctga cgatcaaacc 90

<210> SEQ ID NO 107
<211> LENGTH: 90
<212> TYPE: DNA
<213> ORGANISM: Artificial Sequence
<220> FEATURE:
<223> OTHER INFORMATION: Synthetic oligonucleotide

<400> SEQUENCE: 107
ggctagttaa aaataaaatt gaagtttttt atccgtttta gagctatgct gttttgaatg 60
gtcccaaaac aaacacagcg gcacttctcg 90

<210> SEQ ID NO 108
<211> LENGTH: 76
<212> TYPE: DNA
<213> ORGANISM: Artificial Sequence
<220> FEATURE:
<223> OTHER INFORMATION: Synthetic oligonucleotide

<400> SEQUENCE: 108
cccaactcct tcagcaacaa gttttgggac cattcaaaac agcatagctc taaaaccgag 60
aagtgccgct gtgttt 76

<210> SEQ ID NO 109
<211> LENGTH: 76
<212> TYPE: DNA
<213> ORGANISM: Artificial Sequence
<220> FEATURE:
<223> OTHER INFORMATION: Synthetic oligonucleotide

<400> SEQUENCE: 109
ttgttgctga aggagttggg gttttagagc tatgctgttt tgaatggtcc caaaacgtcc 60
atcccactta aagact 76

<210> SEQ ID NO 110
<211> LENGTH: 76
<212> TYPE: DNA
<213> ORGANISM: Artificial Sequence
<220> FEATURE:
<223> OTHER INFORMATION: Synthetic oligonucleotide

<400> SEQUENCE: 110
cattcagttc cgtttcccag gttttgggac cattcaaaac agcatagctc taaaacagtc 60
tttaagtggg atggac 76

<210> SEQ ID NO 111
<211> LENGTH: 76
<212> TYPE: DNA
<213> ORGANISM: Artificial Sequence
<220> FEATURE:
<223> OTHER INFORMATION: Synthetic oligonucleotide

<400> SEQUENCE: 111
ctgggaaacg gaactgaatg gttttagagc tatgctgttt tgaatggtcc caaaacaact 60
acttactcta gcttcc 76

<210> SEQ ID NO 112
<211> LENGTH: 111
<212> TYPE: DNA
<213> ORGANISM: Artificial Sequence
<220> FEATURE:
<223> OTHER INFORMATION: Synthetic oligonucleotide

<400> SEQUENCE: 112
ccgggagctg catgtgtcag aggggtctcc aaaacggaat ggcggtgttt aacgtgtttt 60
gggaccattc aaaacagcat agctctaaaa cggaagctag agtaagtagt t 111

<210> SEQ ID NO 113
<211> LENGTH: 111
<212> TYPE: DNA
<213> ORGANISM: Artificial Sequence
<220> FEATURE:
<223> OTHER INFORMATION: Synthetic oligonucleotide

<400> SEQUENCE: 113
ccgggagctg catgtgtcag aggggtctcc aaaaccccaa ctccttcagc aacaagtttt 60
gggaccattc aaaacagcat agctctaaaa ccgagaagtg ccgctgtgtt t 111

<210> SEQ ID NO 114
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 114
gggctggcaa gccacgtttg gtggctcttc aaacgtccat cccacttaaa gact 54

<210> SEQ ID NO 115
<211> LENGTH: 111
<212> TYPE: DNA
<213> ORGANISM: Artificial Sequence
<220> FEATURE:
<223> OTHER INFORMATION: Synthetic oligonucleotide

<400> SEQUENCE: 115
ccgggagctg catgtgtcag agggctcttc aaaacggaat ggcggtgttt aacgtgtttt 60
gggaccattc aaaacagcat agctctaaaa cggaagctag agtaagtagt t 111

<210> SEQ ID NO 116

<211> LENGTH: 23
<212> TYPE: DNA
<213> ORGANISM: Artificial Sequence
<220> FEATURE:
<223> OTHER INFORMATION: Synthetic primer

<400> SEQUENCE: 116
gggctggcaa gccacgtttg gtg 23

<210> SEQ ID NO 117
<211> LENGTH: 23
<212> TYPE: DNA
<213> ORGANISM: Artificial Sequence
<220> FEATURE:
<223> OTHER INFORMATION: Synthetic primer

<400> SEQUENCE: 117
ccgggagctg catgtgtcag agg 23

<210> SEQ ID NO 118
<211> LENGTH: 18
<212> TYPE: DNA
<213> ORGANISM: Artificial Sequence
<220> FEATURE:
<223> OTHER INFORMATION: Synthetic primer

<400> SEQUENCE: 118
ggtgactgat ggccacgt 18

<210> SEQ ID NO 119
<211> LENGTH: 23
<212> TYPE: DNA
<213> ORGANISM: Artificial Sequence
<220> FEATURE:
<223> OTHER INFORMATION: Synthetic primer

<400> SEQUENCE: 119
ccaactacct ccccttgctt aac 23

<210> SEQ ID NO 120
<211> LENGTH: 43
<212> TYPE: DNA
<213> ORGANISM: Artificial Sequence
<220> FEATURE:
<223> OTHER INFORMATION: Synthetic primer

<400> SEQUENCE: 120
attgaaaaag gaagagtatg gaattgccca atattatgca ccc 43

<210> SEQ ID NO 121
<211> LENGTH: 38
<212> TYPE: DNA
<213> ORGANISM: Artificial Sequence
<220> FEATURE:
<223> OTHER INFORMATION: Synthetic primer

<400> SEQUENCE: 121
agtcccgcta ggtctcaacc gtcagcgcag cttgtcgg 38

<210> SEQ ID NO 122
<211> LENGTH: 42
<212> TYPE: DNA
<213> ORGANISM: Artificial Sequence
<220> FEATURE:
<223> OTHER INFORMATION: Synthetic primer

<400> SEQUENCE: 122
attgaaaaag gaagagtatg cgtgtattag ccttatcggc tg 42

<210> SEQ ID NO 123
<211> LENGTH: 55
<212> TYPE: DNA
<213> ORGANISM: Artificial Sequence
<220> FEATURE:
<223> OTHER INFORMATION: Synthetic primer

<400> SEQUENCE: 123
agtcccgcta ggtctcaacc gctagggaat aattttttcc tgtttgagca cttct 55

<210> SEQ ID NO 124
<211> LENGTH: 47
<212> TYPE: DNA
<213> ORGANISM: Artificial Sequence
<220> FEATURE:
<223> OTHER INFORMATION: Synthetic primer

<400> SEQUENCE: 124
attgaaaaag gaagagtatg cgttattttc gcctgtgtat tatctcc 47

<210> SEQ ID NO 125
<211> LENGTH: 41
<212> TYPE: DNA
<213> ORGANISM: Artificial Sequence
<220> FEATURE:
<223> OTHER INFORMATION: Synthetic primer

<400> SEQUENCE: 125
agtcccgcta ggtctcaacc gttagcgttg ccagtgctcg a 41

<210> SEQ ID NO 126
<211> LENGTH: 59
<212> TYPE: DNA
<213> ORGANISM: Artificial Sequence
<220> FEATURE:
<223> OTHER INFORMATION: Synthetic primer

<400> SEQUENCE: 126
aatattgaaa aaggaagagt ggaagagcgg cttgttatga ctgttttttt gtacagtct 59

<210> SEQ ID NO 127
<211> LENGTH: 48
<212> TYPE: DNA
<213> ORGANISM: Artificial Sequence
<220> FEATURE:
<223> OTHER INFORMATION: Synthetic primer

<400> SEQUENCE: 127
gagtaaactt ggtctgacag cgaagagcct actcggcgac tgagcgat 48

<210> SEQ ID NO 128
<211> LENGTH: 43
<212> TYPE: DNA
<213> ORGANISM: Artificial Sequence
<220> FEATURE:
<223> OTHER INFORMATION: Synthetic primer

<400> SEQUENCE: 128
attgaaaaag gaagagtatg tcactgtatc gccgtctagt tct 43

<210> SEQ ID NO 129
<211> LENGTH: 39
<212> TYPE: DNA

<213> ORGANISM: Artificial Sequence
<220> FEATURE:
<223> OTHER INFORMATION: Synthetic primer

<400> SEQUENCE: 129
agtcccgcta ggtctcaacc gttactgccc gttgacgcc 39

<210> SEQ ID NO 130
<211> LENGTH: 60
<212> TYPE: DNA
<213> ORGANISM: Artificial Sequence
<220> FEATURE:
<223> OTHER INFORMATION: Synthetic primer

<400> SEQUENCE: 130
attgaaaaag gaagagtatg agcaagttat ctgtattctt tatatttttg ttttgtagca 60

<210> SEQ ID NO 131
<211> LENGTH: 61
<212> TYPE: DNA
<213> ORGANISM: Artificial Sequence
<220> FEATURE:
<223> OTHER INFORMATION: Synthetic primer

<400> SEQUENCE: 131
agtcccgcta ggtctcaacc gttagttgct tagttttgat ggttttttac tttcgtttaa 60
c 61

<210> SEQ ID NO 132
<211> LENGTH: 44
<212> TYPE: DNA
<213> ORGANISM: Artificial Sequence
<220> FEATURE:
<223> OTHER INFORMATION: Synthetic primer

<400> SEQUENCE: 132
attgaaaaag gaagagtatg gttaaaaaat cactgcgcca gttc 44

<210> SEQ ID NO 133
<211> LENGTH: 47
<212> TYPE: DNA
<213> ORGANISM: Artificial Sequence
<220> FEATURE:
<223> OTHER INFORMATION: Synthetic primer

<400> SEQUENCE: 133
agtcccgcta ggtctcaacc gttacaaacc gtcggtgacg attttag 47

<210> SEQ ID NO 134
<211> LENGTH: 58
<212> TYPE: DNA
<213> ORGANISM: Artificial Sequence
<220> FEATURE:
<223> OTHER INFORMATION: Synthetic primer

<400> SEQUENCE: 134
tcataacaag ccgctcttcc actcttcctt tttcaatatt attgaagcat ttatcagg 58

<210> SEQ ID NO 135
<211> LENGTH: 32
<212> TYPE: DNA
<213> ORGANISM: Artificial Sequence
<220> FEATURE:
<223> OTHER INFORMATION: Synthetic primer

<400> SEQUENCE: 135
acgggctgtc tgattcaggt tatttccgat gg 32

<210> SEQ ID NO 136
<211> LENGTH: 38
<212> TYPE: DNA
<213> ORGANISM: Artificial Sequence
<220> FEATURE:
<223> OTHER INFORMATION: Synthetic primer

<400> SEQUENCE: 136
acctgaatca gacagcccgt aaggtgaaca gcgggcag 38

<210> SEQ ID NO 137
<211> LENGTH: 61
<212> TYPE: DNA
<213> ORGANISM: Artificial Sequence
<220> FEATURE:
<223> OTHER INFORMATION: Synthetic primer

<400> SEQUENCE: 137
gtcgccgagt aggctcttcg ctgtcagacc aagtttactc atatatactt tagattgatt 60
t 61

<210> SEQ ID NO 138
<211> LENGTH: 834
<212> TYPE: DNA
<213> ORGANISM: Artificial Sequence
<220> FEATURE:
<223> OTHER INFORMATION: Amplified gene

<400> SEQUENCE: 138
accgtcagcg cagcttgtcg gccatgcggg ccgtatgagt gattgcggcg cggctatcgg 60
gggcggaatg gctcatcacg atcatgctgg ccttggggaa cgccgcacca aacgcgcgcg 120
ctgacgcggc gtagtgctca gtgtcggcat caccgagatt gccgagcgac ttggccttgc 180
tgtccttgat caggcagcca ccaaaagcga tgtcggtgcc gtcgatccca acggtgatat 240
tgtcactggt gtggccgggg ccggggtaaa ataccttgag cgggccaaag ttgggcgcgg 300
ttgctggttc gacccagcca ttggcggcga aagtcaggct gtgttgcgcc gcaaccatcc 360
cctcttgcgg ggcaagctgg ttcgacaacg cattggcata agtcgcaatc cccgccgcat 420
gcagcgcgtc cataccgccc atcttgtcct gatgcgcgtg agtcaccacc gccagcgcga 480
ccggcaggtt gatctcctgc ttgatccagt tgaggatctg ggcggtctgg tcatcggtcc 540
aggcggtatc gaccaccagc acgcggccgc catccctgac gatcaaaccg ttggaagcga 600
ctgccccgaa acccggcatg tcgagatagg aagtgtgctg ccagacattc ggtgcgagct 660
ggcggaaaac cagatcgcca aaccgttggt cgccagtttc catttgctgg ccaatcgtcg 720
ggcggatttc accgggcatg cacccgctca gcatcaatgc agcggctaat gcggtgctca 780
gcttcgcgac cgggtgcata atattgggca attccatact cttccttttt caat 834

<210> SEQ ID NO 139
<211> LENGTH: 819
<212> TYPE: DNA
<213> ORGANISM: Artificial Sequence
<220> FEATURE:
<223> OTHER INFORMATION: Amplified gene

<400> SEQUENCE: 139
accgctaggg aataattttt tcctgtttga gcacttcttt tgtgatggct tggcgcagcc 60

```
ctaaaccatc cgatgtgggc atatccatat tcatcgcaaa aaaccacaca ttatcatcaa    120

gttcaaccca accgacccac cagccaatct taggttcgat tctagtcgag tatccagttt    180

tagcccgaat aatatagtca ccattggctt cggtcagcat ggcttgtttg acaatacgct    240

ggctgcgctc cgatacgtgt aacttattgt gatacagctt tcttaaaaag ctgatttgct    300

ccgtggccga aattcgaata ccaccgtcga gccagaaact gtctacattg cccgaaatgt    360

cctcattacc ataatcgaaa gcatgtagca tcttgctcat acgtgcctcg ccaatttggc    420

gggcaaattc ttgataaaca ggcacaactg aatatttcat cgcggtgatt agattatgat    480

cgcgattcca agtggcgata tcgcgcgtct gtccatccca cttaaagact tggtgttcat    540

ccttaaccac gcccaaatcg agggcgatca agctattggg aattttaaag gtagatgcgg    600

gtaaaaatgc ttggttcgcc cgtttaagat tattggtaaa tccttgctgc ttattctcat    660

tccagagcac aactacgccc tgtgatttat gttcagtaaa gtgagcattc caacttttgt    720

tttcttgcca ttcctttgct accgcaggca ttccgataat cgatgccacc aaaaacacag    780

ccgataaggc taatacacgc atactcttcc tttttcaat                           819
```

<210> SEQ ID NO 140
<211> LENGTH: 882
<212> TYPE: DNA
<213> ORGANISM: Artificial Sequence
<220> FEATURE:
<223> OTHER INFORMATION: Amplified gene

<400> SEQUENCE: 140

```
accgttagcg ttgccagtgc tcgatcagcg ccgcgccgat cccggcgatt tgctgatttc     60

gctcggccat gctcgccggc gtatcccgca gataaatcac cacaatccgc tctgctttgt    120

tattcgggcc aagcagggcg acaatcccgc gcgcaccccg tttggcagct ccggtcttat    180

cggcgataaa ccagcccgcc ggcagcacgg agcggatcaa cggtccggcg acccgatcgt    240

ccaccatcca ctgcagcagc tgccgttgcg aacgggcgct cagacgctgg ctggtcagca    300

gcttgcgcag ggtcgcggcc atgctggccg gggtagtggt gtcgcgggcg tcgccgggaa    360

gcgcctcatt cagttccgtt tcccagcggt caaggcgggt gacgttgtcg ccgatctggc    420

gcaaaaaggc agtcaatcct gcggggccgc cgacggtggc cagcagcaga ttggcggcgc    480

tgttatcgct catggtaatg gcggcggcac agagttcgcc gaccgtcatg ccgtcggcaa    540

ggtgtttttc gctgaccggc gagtagtcca ccagatcctg ctggcgatag tggatctttc    600

gctccagctg ttcgtcaccg gcatccaccc gcgccagcac tgcgccgcag agcactactt    660

taaaggtgct catcatggga aagcgttcat cggcgcgcca ggcggtcagc gtgcggccgc    720

tggccagatc catttctatc atgcctacgc tgcccgacag ctggctttcg cttagtttaa    780

tttgctcaag cggctgcggg ctggcgtgta ccgccagcgg cagggtggct aacagggaga    840

taatacacag gcgaaaataa cgcatactct tcctttttca at                       882
```

<210> SEQ ID NO 141
<211> LENGTH: 822
<212> TYPE: DNA
<213> ORGANISM: Artificial Sequence
<220> FEATURE:
<223> OTHER INFORMATION: Amplified gene

<400> SEQUENCE: 141

```
accgctactc ggcgactgag cgatttttgt gtgctttgac aacgttcgct gtgtgctgga     60

gcaagtctag accgcccggt agaccgtgcc cgggaatgac gacctctgct tccgggtagt    120
```

gtttttgaat ccgctcaacg gaggtgggcc attcagccag atcggcatcg gccacgttcc 180
ccgcagacgt gcttgacaac tcatgaacgg cacaaccacc gtatagcacg ttcgctgacg 240
ggacgtatac aaccagattg tcggtcgaat gcgcagcacc aggatagaag agctctactg 300
gaccgaagcg cactgcgtcc ccgctcgatg agagtccttc tagagaatgc gtgggaatct 360
cgttcccctc tgcctcggct agccggcgtg tcgacggtga tgcgtacgtt gccaccccag 420
ccgcccgaag gacatcaacg ccgccgacgc ggtcgtcatg aaagtgcgtg gagactgcac 480
gcgttacggg aagtccaatt tgcttttcaa tctccgcgag aagtgccgct gtgtttttcg 540
caccccacgc tgtatcaatc aaaagcaact catcaccatc acggacaatg agaccattgg 600
acgggtagac cgcgccatca aacgactgcg ttgcgatatg cgaccaaaca ccatcggcaa 660
tctggtaaag tcggacctct ccgaccggaa tttcgttgac tgtcggatac tcaccactcg 720
gctccccgga atgggctaac ggacttgcga cagccatgac agacgcggtc atgtagacca 780
ataaactact aataactttt aacatactct tcctttttca at 822

<210> SEQ ID NO 142
<211> LENGTH: 903
<212> TYPE: DNA
<213> ORGANISM: Artificial Sequence
<220> FEATURE:
<223> OTHER INFORMATION: Amplified gene

<400> SEQUENCE: 142
accgttactg cccgttgacg cccaatccct cgagcgcgag tctagccgca gcggcgatga 60
cggcctcgct gtacttgtca tccttgttag gcgcccgggt gtagacggcc aacacaatag 120
gtgcgcgccc agtgggccag acgacggcat agtcatttgc cgtgccatac actccgcagg 180
ttccggtttt gtctccgact gcccagtctg ccggcaccgc cgcgcggatg cggtggttgc 240
cggtcgtgtt tccctttagc caatcaacaa actgctgccg ctgcggcgca gccagtgcag 300
agcccagtgt cagtttttgt aagctttccg tcacggcgcg cggcgatgag gtatcgcgcg 360
catcgcctgg gatggcggag ttcagctcca gctcccagcg gtccagacgg aacgtggtat 420
cgccgataga gcgcatgaag gccgtcagcc cggccgggcc gcccaactcc ttcagcaaca 480
aattggcggc ggcgttatca ctgtattgca cggcggccgc ggacagctcc gccaccgtca 540
tgcctgttgt cagatatttt tccgagatgg gtgaccacgg aaccagcgca tttttgccgt 600
aacggatggg tgtgtccagc aagccggcct gctgctggct gcgagccagc acagcggcag 660
caagaaagcc cttgaatgag ctgcacagtg ggaagcgctc ctcagcgcgg taacttacag 720
ttgcgcctga gccggtatcc atcgcgtaca caccgatgga gccgccaaag tcctgttcga 780
gtttagcgaa tggttccgcg acgaggttgg tcagcgcggt ggcagaaaag ccagccagcg 840
gccatgagag acaagacagc agaactagac ggcgatacag tgacatactc ttcctttttc 900
aat 903

<210> SEQ ID NO 143
<211> LENGTH: 762
<212> TYPE: DNA
<213> ORGANISM: Artificial Sequence
<220> FEATURE:
<223> OTHER INFORMATION: Amplified gene

<400> SEQUENCE: 143
accgttagtt gcttggtttt gatggttttt tactttcgtt taacccttta accgcctgct 60

-continued

```
ctaatgtaag tttcaagagt gatgcgtctc caacttcact gtgacttgga acaaccagtt    120

ttgccttacc atatttggac tttaataatt tggcggactt tggccaagct tctatatttg    180

cgtcacccaa attgcctaaa ccgtacggtt taataaaaca accaccgaat aatattttcc    240

tttcaggcag ccaaaccact acgttatctg gagtgtgtcc cgggcctgga taaaaaactt    300

caattttatt tttaactagc caatagttaa ctccgctaaa tgaatttgta gcttgaacct    360

tgccgtcttt tttaagcagt tcatttgtta attcagatgc atacgtgggg atagatcgag    420

aattaagcca ctctattccg cccgtgctgt cgctatgaaa atgagaggaa atactgcctt    480

ttattttata gccacgctcc acaaaccaag tgactaactt ttcagtatct ttagccgtaa    540

atggagtgtc aattagataa gcctcagcat ttacaagaac caccaaacca tgtttaggaa    600

caacgcccca cccgttaact tcttcaaacg aagtatgaac ataaacgcct tcatcaagct    660

tttcaatttt taaatctggt aaagactctg ctgcggtagc aatgctacaa aacaaaaata    720

taaagaatac agataacttg ctcatactct tcctttttca at                        762
```

<210> SEQ ID NO 144
<211> LENGTH: 897
<212> TYPE: DNA
<213> ORGANISM: Artificial Sequence
<220> FEATURE:
<223> OTHER INFORMATION: Amplified gene

<400> SEQUENCE: 144

```
accgttacaa accgtcggtg acgattttag ccgccgacgc taatacatcg cgacggcttt     60

ctgccttagg ttgaggctgg gtgaagtaag tgaccagaat cagcggcgca cgatcttttg    120

gccagatcac cgcgatatcg ttggtggtgc catagccacc gctgccggtt ttatccccca    180

caacccagga agcaggcagt ccagcctgaa tgctcgctgc accggtggta ttgcctttca    240

tccatgtcac cagctgcgcc cgttggctgt cgcccaatgc tttacccagc gtcagattcc    300

gcagagtttg cgccattgcc cgaggtgaag tggtatcacg cggatcgccc ggaatggcgg    360

tgtttaacgt cggctcggta cggtcgagac ggaacgtttc gtctcccagc tgtcgggcga    420

acgcggtgac gctagccggg ccgccaacgt gagcaatcag cttattcatc gccacgttat    480

cgctgtactg tagcgcggcc gcgctaagct cagccagtga catcgtccca ttgacgtgct    540

tttccgcaat cggattatag ttaacaaggt cagatttttt gatctcaact cgctgattta    600

acagattcgg ttcgctttca cttttcttca gcaccgcggc cgcggccatc actttactgg    660

tgctgcacat cgcaaagcgc tcatcagcac gataaagtat ttgcgaatta tctgctgtgt    720

taatcaatgc cacacccagt ctgcctcccg actgccgctc taattcggca agtttttgct    780

gtacgtccgc cgtttgcgca tacagcggca cacttcctaa caacagcgtg acggttgccg    840

tcgccatcag cgtgaactgg cgcagtgatt ttttaaccat actcttcctt tttcaat       897
```

<210> SEQ ID NO 145
<211> LENGTH: 20
<212> TYPE: DNA
<213> ORGANISM: Artificial Sequence
<220> FEATURE:
<223> OTHER INFORMATION: Cos site sequence
<220> FEATURE:
<221> NAME/KEY: misc_feature
<222> LOCATION: (12)..(13)
<223> OTHER INFORMATION: Cos site L and R ends terminate here

<400> SEQUENCE: 145

```
gggcggcgac ctgggcggcg                                                  20
```

<210> SEQ ID NO 146
<211> LENGTH: 21
<212> TYPE: DNA
<213> ORGANISM: Artificial Sequence
<220> FEATURE:
<223> OTHER INFORMATION: Cos site sequence
<220> FEATURE:
<221> NAME/KEY: misc_feature
<222> LOCATION: (12)..(13)
<223> OTHER INFORMATION: Cos site L and R ends terminate here

<400> SEQUENCE: 146
aggtcgccgc ccaggtcgcc g 21

<210> SEQ ID NO 147
<211> LENGTH: 48
<212> TYPE: DNA
<213> ORGANISM: Artificial Sequence
<220> FEATURE:
<223> OTHER INFORMATION: Synthetic primer

<400> SEQUENCE: 147
taccgggaag ggtctcgacc tacttttggc gaaaatgaga cgttgatc 48

<210> SEQ ID NO 148
<211> LENGTH: 41
<212> TYPE: DNA
<213> ORGANISM: Artificial Sequence
<220> FEATURE:
<223> OTHER INFORMATION: Synthetic primer

<400> SEQUENCE: 148
ttaacgaccc gctcttcacc cgacgaccgg gtcgaatttg c 41

<210> SEQ ID NO 149
<211> LENGTH: 48
<212> TYPE: DNA
<213> ORGANISM: Artificial Sequence
<220> FEATURE:
<223> OTHER INFORMATION: Synthetic primer

<400> SEQUENCE: 149
attttttcgg accgcctagg tgatcttctt gagatcgttt tggtctgc 48

<210> SEQ ID NO 150
<211> LENGTH: 40
<212> TYPE: DNA
<213> ORGANISM: Artificial Sequence
<220> FEATURE:
<223> OTHER INFORMATION: Synthetic primer

<400> SEQUENCE: 150
ggcaacctca tgtcgaattc tgtgaatgcg caaaccaacc 40

<210> SEQ ID NO 151
<211> LENGTH: 50
<212> TYPE: DNA
<213> ORGANISM: Artificial Sequence
<220> FEATURE:
<223> OTHER INFORMATION: Synthetic primer

<400> SEQUENCE: 151
ggttggtttg cgcattcaca gaattcgaca tgaggttgcc ccgtattcag 50

<210> SEQ ID NO 152

<211> LENGTH: 43
<212> TYPE: DNA
<213> ORGANISM: Artificial Sequence
<220> FEATURE:
<223> OTHER INFORMATION: Synthetic primer

<400> SEQUENCE: 152
cctcacccca aaaatggcag tagcgatgag ctcggacttc cat 43

<210> SEQ ID NO 153
<211> LENGTH: 40
<212> TYPE: DNA
<213> ORGANISM: Artificial Sequence
<220> FEATURE:
<223> OTHER INFORMATION: Synthetic primer

<400> SEQUENCE: 153
gaagtccgag ctcatcgcta ctgccatttt tggggtgagg 40

<210> SEQ ID NO 154
<211> LENGTH: 41
<212> TYPE: DNA
<213> ORGANISM: Artificial Sequence
<220> FEATURE:
<223> OTHER INFORMATION: Synthetic primer

<400> SEQUENCE: 154
gatacttcta ttctactctg agatctagcg tggactcaag g 41

<210> SEQ ID NO 155
<211> LENGTH: 53
<212> TYPE: DNA
<213> ORGANISM: Artificial Sequence
<220> FEATURE:
<223> OTHER INFORMATION: Synthetic primer

<400> SEQUENCE: 155
cttgagtcca cgctagatct cagagtagaa tagaagtatc aaaaaaagca ccg 53

<210> SEQ ID NO 156
<211> LENGTH: 36
<212> TYPE: DNA
<213> ORGANISM: Artificial Sequence
<220> FEATURE:
<223> OTHER INFORMATION: Synthetic primer

<400> SEQUENCE: 156
ggaccaacat aataagggat tcgaaaagtc aagatt 36

<210> SEQ ID NO 157
<211> LENGTH: 31
<212> TYPE: DNA
<213> ORGANISM: Artificial Sequence
<220> FEATURE:
<223> OTHER INFORMATION: Synthetic primer

<400> SEQUENCE: 157
cgaatccctt attatgttgg tccattggcg c 31

<210> SEQ ID NO 158
<211> LENGTH: 48
<212> TYPE: DNA
<213> ORGANISM: Artificial Sequence
<220> FEATURE:
<223> OTHER INFORMATION: Synthetic primer

<400> SEQUENCE: 158
atactgcgga aaatcatata gtcggaccgg ccatcagtca cctcctag 48

<210> SEQ ID NO 159
<211> LENGTH: 44
<212> TYPE: DNA
<213> ORGANISM: Artificial Sequence
<220> FEATURE:
<223> OTHER INFORMATION: Synthetic primer

<400> SEQUENCE: 159
aggaggtgac tgatggccgg tccgactata tgattttccg cagt 44

<210> SEQ ID NO 160
<211> LENGTH: 65
<212> TYPE: DNA
<213> ORGANISM: Artificial Sequence
<220> FEATURE:
<223> OTHER INFORMATION: Synthetic primer

<400> SEQUENCE: 160
aaacgatctc aagaagatca cctaggcggt ccgaaaaaat gtatgttcca tcacactact 60
cttct 65

<210> SEQ ID NO 161
<211> LENGTH: 23
<212> TYPE: DNA
<213> ORGANISM: Artificial Sequence
<220> FEATURE:
<223> OTHER INFORMATION: Synthetic primer

<400> SEQUENCE: 161
gacatgaggt tgccccgtat tca 23

<210> SEQ ID NO 162
<211> LENGTH: 28
<212> TYPE: DNA
<213> ORGANISM: Artificial Sequence
<220> FEATURE:
<223> OTHER INFORMATION: Synthetic primer

<400> SEQUENCE: 162
ctcaatcgtg cagaaagaat cgctttag 28

<210> SEQ ID NO 163
<211> LENGTH: 31
<212> TYPE: DNA
<213> ORGANISM: Artificial Sequence
<220> FEATURE:
<223> OTHER INFORMATION: Synthetic primer

<400> SEQUENCE: 163
ccagtgagtc ggccgcagtc cagttacgct g 31

<210> SEQ ID NO 164
<211> LENGTH: 40
<212> TYPE: DNA
<213> ORGANISM: Artificial Sequence
<220> FEATURE:
<223> OTHER INFORMATION: Synthetic primer

<400> SEQUENCE: 164
ctgctatgga gtcgacgtat gatttaaatg gtcagtgatg 40

<210> SEQ ID NO 165

<211> LENGTH: 28
<212> TYPE: DNA
<213> ORGANISM: Artificial Sequence
<220> FEATURE:
<223> OTHER INFORMATION: Synthetic primer
<220> FEATURE:
<221> NAME/KEY: modified_base
<222> LOCATION: (1)..(1)
<223> OTHER INFORMATION: p
<220> FEATURE:
<221> NAME/KEY: misc_feature
<222> LOCATION: (1)..(1)
<223> OTHER INFORMATION: n is a, c, g, or t

<400> SEQUENCE: 165
nacttttggc gaaaatgaga cgttgatc 28

<210> SEQ ID NO 166
<211> LENGTH: 21
<212> TYPE: DNA
<213> ORGANISM: Artificial Sequence
<220> FEATURE:
<223> OTHER INFORMATION: Synthetic primer
<220> FEATURE:
<221> NAME/KEY: modified_base
<222> LOCATION: (1)..(1)
<223> OTHER INFORMATION: p
<220> FEATURE:
<221> NAME/KEY: misc_feature
<222> LOCATION: (1)..(1)
<223> OTHER INFORMATION: n is a, c, g, or t

<400> SEQUENCE: 166
ngacgaccgg gtcgaatttg c 21

<210> SEQ ID NO 167
<211> LENGTH: 27
<212> TYPE: DNA
<213> ORGANISM: Artificial Sequence
<220> FEATURE:
<223> OTHER INFORMATION: Synthetic primer

<400> SEQUENCE: 167
tcagaataag aaatgaggcc gctcatg 27

<210> SEQ ID NO 168
<211> LENGTH: 20
<212> TYPE: DNA
<213> ORGANISM: Artificial Sequence
<220> FEATURE:
<223> OTHER INFORMATION: Synthetic primer

<400> SEQUENCE: 168
ggatcaccgg aaaggacccg 20

<210> SEQ ID NO 169
<211> LENGTH: 25
<212> TYPE: DNA
<213> ORGANISM: Artificial Sequence
<220> FEATURE:
<223> OTHER INFORMATION: Synthetic primer

<400> SEQUENCE: 169
ttatttgacg tggtttgatg gcctc 25

<210> SEQ ID NO 170
<211> LENGTH: 17
<212> TYPE: DNA
<213> ORGANISM: Artificial Sequence
<220> FEATURE:
<223> OTHER INFORMATION: Synthetic primer

<400> SEQUENCE: 170
ggctcgattt cggccgg 17

<210> SEQ ID NO 171
<211> LENGTH: 22
<212> TYPE: DNA
<213> ORGANISM: Artificial Sequence
<220> FEATURE:
<223> OTHER INFORMATION: Synthetic primer

<400> SEQUENCE: 171
gcccctcaag tgtcaaggat cg 22

<210> SEQ ID NO 172
<211> LENGTH: 29
<212> TYPE: DNA
<213> ORGANISM: Artificial Sequence
<220> FEATURE:
<223> OTHER INFORMATION: Synthetic primer

<400> SEQUENCE: 172
cggacaagct tattgctcgt aaaaaagac 29

<210> SEQ ID NO 173
<211> LENGTH: 31
<212> TYPE: DNA
<213> ORGANISM: Artificial Sequence
<220> FEATURE:
<223> OTHER INFORMATION: Synthetic primer

<400> SEQUENCE: 173
cgctttaaca gaaagaatag gaaggtatcc g 31

<210> SEQ ID NO 174
<211> LENGTH: 28
<212> TYPE: DNA
<213> ORGANISM: Artificial Sequence
<220> FEATURE:
<223> OTHER INFORMATION: Synthetic primer

<400> SEQUENCE: 174
cagcagtcgg ataccttcct attctttc 28

<210> SEQ ID NO 175
<211> LENGTH: 21
<212> TYPE: DNA
<213> ORGANISM: Artificial Sequence
<220> FEATURE:
<223> OTHER INFORMATION: Synthetic primer

<400> SEQUENCE: 175
cctgttcctg cctttcggtt t 21

<210> SEQ ID NO 176
<211> LENGTH: 51012
<212> TYPE: DNA
<213> ORGANISM: Artificial Sequence
<220> FEATURE:
<223> OTHER INFORMATION: Sequence of Transmid cTNB001-X

<400> SEQUENCE: 176
aattcgacat gaggttgccc cgtattcagt gtcgctgatt tgtattgtct gaagttgttt 60

-continued

```
ttacgttaag ttgatgcaga tcaattaata cgatacctgc gtcataattg attatttgac    120
gtggtttgat ggcctccacg cacgttgtga tatgtagatg ataatcatta tcactttacg    180
ggtcctttcc ggtgatccga caggttacgg ggcggcgacc tcgcgggttt tcgctattta    240
tgaaaatttt ccggtttaag gcgtttccgt tcttcttcgt cataacttaa tgtttttatt    300
taaaataccc tctgaaaaga aaggaaacga caggtgctga aagcgagctt tttggcctct    360
gtcgtttcct ttctctgttt ttgtccgtgg aatgaacaat ggaagtccga gctcatcgct    420
actgccattt ttggggtgag gccgttcgcg gccgaggggc gcagcccctg gggggatggg    480
aggcccgcgt tagcgggccg ggagggttcg agaagggggg gcacccccct tcggcgtgcg    540
cggtcacgcg ccagggcgca gccctggtta aaaacaaggt ttataaatat tggtttaaaa    600
gcaggttaaa agacaggtta gcggtggccg aaaaacgggc ggaaaccctt gcaaatgctg    660
gattttctgc ctgtggacag cccctcaaat gtcaataggt gcgcccctca tctgtcatca    720
ctctgcccct caagtgtcaa ggatcgcgcc cctcatctgt cagtagtcgc gcccctcaag    780
tgtcaatacc gcagggcact tatccccagg cttgtccaca tcatctgtgg gaaactcgcg    840
taaaatcagg cgttttcgcc gatttgcgag gctggccagc tccacgtcgc cggccgaaat    900
cgagcctgcc cctcatctgt caacgccgcg ccgggtgagt cggcccctca agtgtcaacg    960
tccgcccctc atctgtcagt gagggccaag ttttccgcgt ggtatccaca acgccggcgg   1020
ccgcggtgtc tcgcacacgg cttcgacggc gtttctggcg cgtttgcagg gccatagacg   1080
gccgccagcc cagcggcgag ggcaaccagc ccggtgagcg tcggaaaggc gctggaagcc   1140
ccgtagcgac gcggagaggg gcgagacaag ccaagggcgc aggctcgatg cgcagcacga   1200
catagccggt tctcgcaagg acgagaattt ccctgcggtg cccctcaagt gtcaatgaaa   1260
gtttccaacg cgagccattc gcgagagcct tgagtccacg ctagatctca gagtagaata   1320
gaagtatcaa aaaaagcacc gactcggtgc cactttttca agttgataac ggactagcct   1380
tattttaact tgctatgctg ttttgaatgg ttccaacaag attattttat aacttttata   1440
acaaataatc aaggagaaat tcaaagaaat ttatcagcca taaaacaata cttaatacta   1500
tagaatgata acaaaataaa ctacttttta aaagaatttt gtgttataat ctatttatta   1560
ttaagtattg ggtaatattt tttgaagaga tattttgaaa aagaaaaatt aaagcatatt   1620
aaactaattt cggaggtcat taaaactatt attgaaatca tcaaactcat tatggattta   1680
atttaaactt tttattttag gaggcaaaaa tggataagaa atactcaata ggcttagata   1740
tcggcacaaa tagcgtcgga tgggcggtga tcactgatga atataaggtt ccgtctaaaa   1800
agttcaaggt tctgggaaat acagaccgcc acagtatcaa aaaaaatctt ataggggctc   1860
ttttatttga cagtggagag acagcggaag cgactcgtct caaacggaca gctcgtagaa   1920
ggtatacacg tcggaagaat cgtatttgtt atctacagga gatttttca aatgagatgg    1980
cgaaagtaga tgatagtttc tttcatcgac ttgaagagtc ttttttggtg gaagaagaca   2040
agaagcatga acgtcatcct atttttggaa atatagtaga tgaagttgct tatcatgaga   2100
aatatccaac tatctatcat ctgcgaaaaa aattggtaga ttctactgat aaagcggatt   2160
tgcgcttaat ctatttggcc ttagcgcata tgattaagtt tcgtggtcat tttttgattg   2220
agggagattt aaatcctgat aatagtgatg tggacaaact atttatccag ttggtacaaa   2280
cctacaatca attatttgaa gaaaacccta ttaacgcaag tggagtagat gctaaagcga   2340
ttctttctgc acgattgagt aaatcaagac gattagaaaa tctcattgct cagctccccg   2400
gtgagaagaa aaatggctta tttgggaatc tcattgcttt gtcattgggt ttgaccccta   2460
```

```
attttaaatc aaattttgat ttggcagaag atgctaaatt acagctttca aaagatactt   2520
acgatgatga tttagataat ttattggcgc aaattggaga tcaatatgct gatttgtttt   2580
tggcagctaa gaatttatca gatgctattt tactttcaga tatcctaaga gtaaatactg   2640
aaataactaa ggctccccta tcagcttcaa tgattaaacg ctacgatgaa catcatcaag   2700
acttgactct tttaaaagct ttagttcgac aacaacttcc agaaaagtat aaagaaatct   2760
tttttgatca atcaaaaaac ggatatgcag gttatattga tgggggagct agccaagaag   2820
aattttataa atttatcaaa ccaattttag aaaaaatgga tggtactgag gaattattgg   2880
tgaaactaaa tcgtgaagat ttgctgcgca agcaacggac ctttgacaac ggctctattc   2940
cccatcaaat tcacttgggt gagctgcatg ctattttgag aagacaagaa gacttttatc   3000
catttttaaa agacaatcgt gagaagattg aaaaaatctt gacttttcga atcccttatt   3060
atgttggtcc attggcgcgt ggcaatagtc gttttgcatg gatgactcgg aagtctgaag   3120
aaacaattac cccatggaat tttgaagaag ttgtcgataa aggtgcttca gctcaatcat   3180
ttattgaacg catgacaaac tttgataaaa atcttccaaa tgaaaaagta ctaccaaaac   3240
atagtttgct ttatgagtat tttacggttt ataacgaatt gacaaaggtc aaatatgtta   3300
ctgaaggaat gcgaaaacca gcatttcttt caggtgaaca gaagaaagcc attgttgatt   3360
tactcttcaa aacaaatcga aaagtaaccg ttaagcaatt aaaagaagat tatttcaaaa   3420
aaatagaatg ttttgatagt gttgaaattt caggagttga agatagattt aatgcttcat   3480
taggtaccta ccatgatttg ctaaaaatta ttaaagataa agattttttg gataatgaag   3540
aaaatgaaga tatcttagag gatattgttt taacattgac cttatttgaa gatagggaga   3600
tgattgagga aagacttaaa acatatgctc acctctttga tgataaggtg atgaaacagc   3660
ttaaacgtcg ccgttatact ggttggggac gtttgtctcg aaaattgatt aatggtatta   3720
gggataagca atctggcaaa acaatattag atttttttgaa atcagatggt tttgccaatc   3780
gcaattttat gcagctgatc catgatgata gtttgacatt taaagaagac attcaaaaag   3840
cacaagtgtc tggacaaggc gatagtttac atgaacatat tgcaaattta gctggtagcc   3900
ctgctattaa aaaaggtatt ttacagactg taaaagttgt tgatgaattg gtcaaagtaa   3960
tggggcggca taagccagaa aatatcgtta ttgaaatggc acgtgaaaat cagacaactc   4020
aaaagggcca gaaaaattcg cgagagcgta tgaaacgaat cgaagaaggt atcaaagaat   4080
taggaagtca gattcttaaa gagcatcctg ttgaaaatac tcaattgcaa aatgaaaagc   4140
tctatctcta ttatctccaa aatggaagag acatgtatgt ggaccaagaa ttagatatta   4200
atcgtttaag tgattatgat gtcgatcaca ttgttccaca aagtttcctt aaagacgatt   4260
caatagacaa taaggtctta acgcgttctg ataaaaatcg tggtaaatcg gataacgttc   4320
caagtgaaga agtagtcaaa aagatgaaaa actattggag acaacttcta aacgccaagt   4380
taatcactca acgtaagttt gataatttaa cgaaagctga acgtggaggt ttgagtgaac   4440
ttgataaagc tggttttatc aaacgccaat tggttgaaac tcgccaaatc actaagcatg   4500
tggcacaaat tttggatagt cgcatgaata ctaaatacga tgaaaatgat aaacttattc   4560
gagaggttaa agtgattacc ttaaaatcta aattagtttc tgacttccga aaagatttcc   4620
aattctataa agtacgtgag attaacaatt accatcatgc ccatgatgcg tatctaaatg   4680
ccgtcgttgg aactgctttg attaagaaat atccaaaact tgaatcggag tttgtctatg   4740
gtgattataa agtttatgat gttcgtaaaa tgattgctaa gtctgagcaa gaaataggca   4800
```

```
aagcaaccgc aaaatatttc ttttactcta atatcatgaa cttcttcaaa acagaaatta    4860

cacttgcaaa tggagagatt cgcaaacgcc ctctaatcga aactaatggg gaaactggag    4920

aaattgtctg ggataaaggg cgagattttg ccacagtgcg caaagtattg tccatgcccc    4980

aagtcaatat tgtcaagaaa acagaagtac agacaggcgg attctccaag gagtcaattt    5040

taccaaaaag aaattcggac aagcttattg ctcgtaaaaa agactgggat ccaaaaaaat    5100

atggtggttt tgatagtcca acggtagctt attcagtcct agtggttgct aaggtggaaa    5160

aagggaaatc gaagaagtta aaatccgtta aagagttact agggatcaca attatggaaa    5220

gaagttcctt tgaaaaaaat ccgattgact ttttagaagc taaaggatat aaggaagtta    5280

aaaaagactt aatcattaaa ctacctaaat atagtctttt tgagttagaa acggtcgta    5340

aacggatgct ggctagtgcc ggagaattac aaaaaggaaa tgagctggct ctgccaagca    5400

aatatgtgaa tttttatat ttagctagtc attatgaaaa gttgaagggt agtccagaag    5460

ataacgaaca aaaacaattg tttgtggagc agcataagca ttatttagat gagattattg    5520

agcaaatcag tgaattttct aagcgtgtta ttttagcaga tgccaattta gataaagttc    5580

ttagtgcata taacaaacat agagacaaac caatacgtga acaagcagaa aatattattc    5640

atttatttac gttgacgaat cttggagctc ccgctgcttt taaatatttt gatacaacaa    5700

ttgatcgtaa acgatatacg tctacaaaag aagttttaga tgccactctt atccatcaat    5760

ccatcactgg tctttatgaa acacgcattg atttgagtca gctaggaggt gactgatggc    5820

cggtccgact atatgatttt ccgcagtata ttttagatga agattatttc ttaataacta    5880

aaaatatggt ataatactct taataaatgc agtaatacag gggcttttca agactgaagt    5940

ctagctgaga caaatagtgc gattacgaaa ttttttagac aaaaatagtc tacgaggttt    6000

tagagctatg ctattttgaa tggtcccaaa acactttaaa agtgctcatc atgttttaga    6060

gctatgctgt tttgaatggt cccaaaacaa cattgccgat gataacttga gaaagagggt    6120

taataccagc agtcggatac cttcctattc tttctgttaa agcgttttca tgttataata    6180

ggcaaaagaa gagtagtgtg atggaacata cattttttcg gaccgcctag gagtgcggtt    6240

ggaacgttgg cccagccaga tactcccgat cacgagcagg acgccgatga tttgaagcgc    6300

actcagcgtc tgatccaaga acaaccatcc tagcaacacg gcggtccccg ggctgagaaa    6360

gcccagtaag gaaacaactg taggttcgag tcgcgagatc ccccggaacc aaaggaagta    6420

ggttaaaccc gctccgatca ggccgagcca cgccaggccg agaacattgg ttccttgtag    6480

gcatcgggat tggcggatca aacactaaag ctactggaac gagcagaagt cctccggccg    6540

ccagttgcca ggccgtaaag gtgagcagag gcacgggagg ttgccacttg cgggtcagca    6600

cggttccgaa cgccatggaa accgcccccg ccaggcccgc tgcgacgccg acaggatcta    6660

gcgctgcgtt tggtgtcaac accaacagcg ccacgcccgc agttccgcaa atagccccca    6720

ggaccgccat caatcgtatc gggctaccta gcagagcggc agagatgaac acgaccatca    6780

gcggctgcac agcgcctacc gtcgccgcga cccgcccggc aggcggtaga ccgaaataaa    6840

caacaagctc cagaatagcg aaatattaag tgcgccgagg atgaagatgc gcatccacca    6900

gattcccgtt ggaatctgtc ggacgatcat cacgagcaat aaaccgccg gcaacgcccg    6960

cagcagcata ccggcgaccc ctcggcctcg ctgttcgggc tccacgaaaa cgccggacag    7020

atgcgccttg tgagcgtcct tgggccgtc ctcctgtttg aagaccgaca gcccaatgat    7080

ctcgccgtcg atgtaggcgc cgaatgccac ggcatctcgc aaccgttcag cgaacgcctc    7140

catgggcttt ttctcctcgt gctcgtaaac ggacccgaac atctctggag ctttcttcag    7200
```

ggccgacaat cggatctcgc ggaaatcctg cacgtcggcc gctccaagcc gtcgaatctg 7260
agccttaatc acaattgtca attttaatcc tctgtttatc ggcagttcgt agagcgcgcc 7320
gtgcgcccga gcgatactga gcgaagcaag tgcgtcgagc agtgcccgct tgttcctgaa 7380
atgccagtaa agcgctggct gctgaacccc cagccggaac tgaccccaca aggccctagc 7440
gtttgcaatg caccaggtca tcattgaccc aggcgtgttc caccaggccg ctgcctcgca 7500
actcttcgca ggcttcgccg acctgctcgc gccacttctt cacgcgggtg gaatccgatc 7560
cgcacatgag gcggaaggtt tccagcttga gcgggtacgg ctcccggtgc gagctgaaat 7620
agtcgaacat ccgtcgggcc gtcggcgaca gcttgcggta cttctcccat atgaatttcg 7680
tgtagtggtc gccagcaaac agcacgacga tttcctcgtc gatcaggacc tggcaacggg 7740
acgttttctt gccacggtcc aggacgcgga agcggtgcag cagcgacacc gattccaggt 7800
gcccaacgcg gtcggacgtg aagcccatcg ccgtcgcctg taggcgcgac aggcattcct 7860
cggccttcgt gtaataccgg ccattgatcg accagcccag gtcctggcaa agctcgtaga 7920
acgtgaaggt gatcggctcg ccgatagggg tgcgcttcgc gtactccaac acctgctgcc 7980
acaccagttc gtcatcgtcg gcccgcagct cgacgccggt gtaggtgatc ttcacgtcct 8040
tgttgacgtg gaaaatgacc ttgttttgca gcgcctcgcg cgggattttc ttgttgcgcg 8100
tggtgaacag ggcagagcgg gccgtgtcgt ttggcatcgc tcgcatcgtg tccggccacg 8160
gcgcaatatc gaacaaggaa agctgcattt ccttgatctg ctgcttcgtg tgtttcagca 8220
acgcggcctg cttggcctcg ctgacctgtt ttgccaggtc ctcgccggcg gtttttcgct 8280
tcttggtcgt catagttcct cgcgtgtcga tggtcatcga cttcgccaaa cctgccgcct 8340
cctgttcgag acgacgcgaa cgctccacgg cggccgatgg cgcgggcagg gcagggggag 8400
ccagttgcac gctgtcgcgc tcgatcttgg ccgtagcttg ctggaccatc gagccgacgg 8460
actggaaggt ttcgcggggc gcacgcatga cggtgcggct tgcgatggtt tcggcatcct 8520
cggcggaaaa ccccgcgtcg atcagttctt gcctgtatgc cttccggtca aacgtccgat 8580
tcattcaccc tccttgcggg attgccccga ctcacgccgg ggcaatgtgc ccttattcct 8640
gatttgaccc gcctggtgcc ttggtgtcca gataatccac cttatcggca atgaagtcgg 8700
tcccgtagac cgtctggccg tccttctcgt acttggtatt ccgaatcttg ccctgcacga 8760
ataccagcga ccccttgccc aaatacttgc cgtgggcctc ggcctgagag ccaaaacact 8820
tgatgcggaa gaagtcggtg cgctcctgct tgtcgccggc atcgttgcgc cactcttcat 8880
taaccgctat atcgaaaatt gcttgcggct tgttagaatt gccatgacgt acctcggtgt 8940
cacgggtaag attaccgata aactggaact gattatggct catatcgaaa gtctccttga 9000
gaaaggagac tctagtttag ctaaacattg gttccgctgt caagaacttt agcggctaaa 9060
attttgcggg ccgcgaccaa aggtgcgagg ggcggcttcc gctgtgtaca accagatatt 9120
tttcaccaac atccttcgtc tgctcgatga gcggggcatg acgaaacatg agctgtcgga 9180
gagggcaggg gtttcaattt cgtttttatc agacttaacc aacggtaagg ccaacccctc 9240
gttgaaggtg atggaggcca ttgccgacgc cctggaaact cccctacctc ttctcctgga 9300
gtccaccgac cttgaccgcg aggcactcgc ggagattgcg ggtcatcctt tcaagagcag 9360
cgtgccgccc ggatacgaac gcatcagtgt ggttttgccg tcacataagg cgtttatcgt 9420
aaagaaatgg ggcgacgaca cccgaaaaaa gctgcgtgga aggctctgac gccaagggtt 9480
agggcttgca cttccttctt tagccgctaa aacggcccct tctctgcggg ccgtcggctc 9540

-continued

```
gcgcatcata tcgacatcct caacggaagc cgtgccgcga atggcatcgg gcgggtgcgc   9600
tttgacagtt gttttctatc agaacccccta cgtcgtgcgg ttcgattagc tgtttgtctt   9660
gcaggctaaa cactttcggt atatcgtttg cctgtgcgat aatgttgcta atgatttgtt   9720
gcgtaggggt tactgaaaag tgagcgggaa agaagagttt cagaccatca aggagcgggc   9780
caagcgcaag ctggaacgcg acatgggtgc ggacctgttg gccgcgctca acgacccgaa   9840
aaccgttgaa gtcatgctca acgcggacgg caaggtgtgg cacgaacgcc ttggcgagcc   9900
gatgcggtac atctgcgaca tgcggcccag ccagtcgcag gcgattatag aaacggtggc   9960
cggattccac ggcaaagagg tcacgcggca ttcgcccatc ctggaaggcg agttcccctt  10020
ggatggcagc cgctttgccg gccaattgcc gccggtcgtg gccgcgccaa cctttgcgat  10080
ccgcaagcgc gcggtcgcca tcttcacgct ggaacagtac gtcgaggcgg gcatcatgac  10140
ccgcgagcaa tacgaggtca ttaaaagcgc cgtcgcggcg catcgaaaca tcctcgtcat  10200
tggcggtact ggctcgggca agaccacgct cgtcaacgcg atcatcaatg aaatggtcgc  10260
cttcaacccg tctgagcgcg tcgtcatcat cgaggacacc ggcgaaatcc agtgcgccgc  10320
agagaacgcc gtccaatacc acaccagcat cgacgtctcg atgacgctgc tgctcaagac  10380
aacgctgcgt atgcgccccg accgcatcct ggtcggtgag gtacgtggcc ccgaagccct  10440
tgatctgttg atggcctgga acaccgggca tgaaggaggt gccgccaccc tgcacgcaaa  10500
caaccccaaa gcgggcctga gccggctcgc catgcttatc agcatgcacc cggattcacc  10560
gaaacccatt gagccgctga ttggcgaggc ggttcatgtg gtcgtccata tcgccaggac  10620
ccctagcggc cgtcgagtgc aagaaattct cgaagttctt ggttacgaga acggccagta  10680
catcaccaaa accctgtaag gagtatttcc aatgacaacg gctgttccgt tccgtctgac  10740
catgaatcgc ggcattttgt tctaccttgc cgtgttcttc gttctcgctc tcgcgttatc  10800
cgcgcatccg gcgatggcct cggaaggcac cggcggcagc ttgccatatg agagctggct  10860
gacgaacctg cgcaactccg taaccggccc ggtggccttc gcgctgtcca tcatcggcat  10920
cgtcgtcgcc ggcggcgtgc tgatcttcgg cggcgaactc aacgccttct tccgaaccct  10980
gatcttcctg gttctggtga tggcgctgct ggtcggcgcg cagaacgtga tgagcacctt  11040
cttcggtcgt ggtgccgaaa tcgcggccct cggcaacggg gcgctgcacc aggtgcaagt  11100
cgcggcggcg gatgccgtgc gtgcggtagc ggctggacgg ctcgcctaat catggctctg  11160
cgcacgatcc ccatccgtcg cgcaggcaac cgagaaaacc tgttcatggg tggtgatcgt  11220
gaactggtga tgttctcggg cctgatggcg tttgcgctga ttttcagcgc ccaagagctg  11280
cgggccaccg tggtcggtct gatcctgtgg ttcggggcgc tctatgcgtt ccgaatcatg  11340
gcgaaggccg atccgaagat gcggttcgtg tacctgcgtc accgccggta caagccgtat  11400
tacccggccc gctcgacccc gttccgcgag aacaccaata gccaagggaa gcaataccga  11460
tgatccaagc aattgcgatt gcaatcgcgg gcctcggcgc gcttctgttg ttcatcctct  11520
ttgcccgcat ccgcgcggtc gatgccgaac tgaaactgaa aaagcatcgt tccaaggacg  11580
ccggcctggc cgatctgctc aactacgccg ctgtcgtcga tgacggcgta atcgtgggca  11640
agaacggcag ctttatggct gcctggctgt acaagggcga tgacaacgca agcagcaccg  11700
accagcagcg cgaagtagtg tccgcccgca tcaaccaggc cctcgcgggc ctgggaagtg  11760
ggtggatgat ccatgtggac gccgtgcggc gtcctgctcc gaactacgcg gagcggggcc  11820
tgtcggcgtt ccctgaccgt ctgacggcag cgattgaaga agagcgccgg cggcatttcg  11880
agagcctggg aacgatgtac gagggctatt tcgtcctcac cttgacctgg ttcccgccgc  11940
```

```
tgctcgccca gcgcaagttc gtcgagctga tgtttgacga cgacgcgacc gcaccggatc  12000
gcaaggcgcg cacgcggggc ctcatcgacc aattcaagcg tgacgtgcgc agcatcgagt  12060
cgcgcctgtc gtcggccgtg tcgctcactc gcttgaaggg gcacaagatc gtcaacgagg  12120
acggcacgac cgtcacgcat gacgacttcc tgcgctggct gcaattctgc gtgacgggcc  12180
tgcaccatcc ggtgcagctc cccagcaacc cgatgtacct ggacgccctg gtcggcggac  12240
aggaaatgtg gggcggggta gtgcccaagg tcggccgcaa gttcgtccag gtggtcgctc  12300
tcgaaggctt ccccttggag tcctatcccg gcatcctgac ggcgctcggc gagctgccct  12360
gcgagtatcg gtggtcgagc cggttcatct tcatggacca gcacgaagcc gtgaagcacc  12420
tcgacaagtt ccgcaagaag tggcggcaga agattcgcgg cttcttcgac caggtgttca  12480
acacgaacac cggcccggtc gatcaggacg cgctttcgat ggtggccgat gctgaggcgg  12540
ccattgccga agtcaacagc ggcatcgtgg ccgtgggcta ctacaccagc gtcgtcgtgc  12600
tgatggatga ggaccgcacg cgcctggaag ctgcggcccg cgatgttgaa aaggccgtca  12660
accggttggg ctttgccgcg cgcatcgagt ccatcaacac cctggacgcc ttccttggta  12720
gtttgccggg ccacggcgtg gaaaacgtcc gccggccgct catcaacacg atgaacctgg  12780
ccgacctgct gccgaccagc accatctgga ccggcaacgc gaacgcgcca tgcccgatgt  12840
acccgccgct gtcgccggcg ctcatgcact gcgtcacgca aggatcaacg ccgttccggc  12900
tgaacctgca cgtgcgcgac ctcggccaca cctttatgtt cgggccgacc ggcgcaggta  12960
aatcgacgca cctggcgatc ctcgccgcgc agctccgtcg ctatgccggc atgtcgatct  13020
tcgcctttga caagggcatg tcgatgtacc cgctggccgc cggcatccgt gcggccacga  13080
agggcaccag cggcctgcac ttcaccgtgg cggccgacga cgaacgcctg gcgttctgcc  13140
cgttgcagtt cctgagcacc aagggcgacc gtgcttgggc gatggagtgg atcgacacca  13200
tcctggcgtt gaacggcgtc gaaacgaccc cggcccagcg caacgaaatc ggcaacgcga  13260
tcatgagcat gcacgccagc ggcgcgcgca cgctctccga gttcagcgtg acgattcagg  13320
atgaggcgat ccgcgaggcg atccgccagt acaccgtcga tggcgcaatg ggccatctgc  13380
tcgacgccga agaggacggc ttggcgctgt ccgactttac agtgttcgag atcgaagagc  13440
tgatgaacct cggcgagaaa ttcgccctgc ctgtgttgct ctacctgttc cgccgtatcg  13500
agcgcgccct gacgggccag ccggccgtca tcatcctgga cgaagcctgg ttgatgctcg  13560
gccacccggc attccgcgcg aagatcaggg aatggctcaa ggtgctgcgt aaggccaact  13620
gccttgtgct gatggcaacg cagagcctgt ccgacgccgc caacagcggc atcctggacg  13680
tgatcgtgga atcgaccgcg accaagattt tcctgccgaa tatttacgcc agggatgagg  13740
acacggcggc cctgtaccgc cgcatgggcc tgaacgctcg ccagatcgag attctggccc  13800
aggccgttcc caagcgtcag tactactacg tgtcggaaaa cggccgccgt ctctacgacc  13860
tggcacttgg cccgctcgcg ctcgcgttcg tcggcgcatc cgacaaggaa tccgtcgcca  13920
tcatcaagaa cctggaagcc aagttcggcg accagtgggt ggatgaatgg ctgcgtggcc  13980
ggggcctcgc ccttgatgaa tacctggagg cagcatgagt tttgcagaca cgatcaaggg  14040
cttgatcttc aagaagaagc ccgcaacggc cgcagcagcg gcgacgccgg ccgcgaccgg  14100
cccgcaaacc gacaacccgt acctgacggc gcggcgcacc tggaacgacc acgttggttc  14160
cgttgtgtcg caaaagcaga cctggcaggt tgtcggcatc ctttcgctga tgatcgtcct  14220
cgcggcggtc ggcggcatca tccacatcgg cagccagtcg aagttcgtgc cctatgtcta  14280
```

-continued

```
cgaggtagac aagctcgggc agacggccgc cgtggggccg atgaccaggg cgtcgaaagc  14340
cgatccgcgt gtcattcacg cctcggtggc tgagttcgtc ggcgatgctc gcctggtgac  14400
gccggacgta gctttgcagc gcaaggccgt ctaccgcctc tatgccaagc tcgggccgaa  14460
tgacccggcc accgccaaga tgaacgaatg gctcaacggc accgccgacg ccagcccgtt  14520
cgctcgcgcg gccgtcgaaa cggtcagcac cgaaatcact tccgtaatcc cgcagacgcc  14580
cgacacctgg caggtcgatt gggtcgagac gacgcgcgac aggcaaggcg tggtgaaagg  14640
ccagcccgtg cgcatgcggg ccttggtgac ggtctacgtc gtcgagccga cggcggacac  14700
caaggaagaa caactgcgaa acaacccggc cgggatctac gtccgggact tctcctggtc  14760
gagacttctg tgaggcactg aattatgaaa aaggaactgt ttgctttggt cctggccgcg  14820
tccgttagcg tgcctgcatt tgccgccgat cccggcgcgg acctgactga cctctatttt  14880
tccggcaaga acccggagct gaccgcgcaa gagcgggcgg ccatcgccat cgccaagaag  14940
tgggaggcgg gtaccgccgg catgcggccg gtggccggcc ccggtggttc ggtgcgcttc  15000
ctgttcggcg cgcagcagcc gagcatcgta tgcgccgtgc tgcaagtgtg cgacgtggcc  15060
ctgcaacccg gcgagcaagt caactcgatc aacctgggcg acaccgcccg ttggacggtc  15120
gagccggcca ttaccggcag cggcgcgaac gaaacccagc acctcatcat caagccgatg  15180
gatgtgggcc tggaaaccag cctggtcgtg accacggacc gccgcagcta ccacatgcgc  15240
ctgcgctcgc atcgcacgca gtacatgccg caggtgtcgt tcacctaccc ggaagatgcc  15300
cttgcgaagt gggacgccat caagaaccgc gaacagcggg atcgcgtcga gaaaaccatt  15360
ccgcagaccg gcgagtacct gggcaacctg agcttcaact actccgtcag cgggtccacg  15420
tcgtggaagc cggtgcgcgt ctacaacgac ggcaagaaaa ccatcatcca gatgccgcac  15480
tcgatggaac agaccgaagc gccgacgctc ctggtcgttc gcagggaggg cggcctgttc  15540
tccgacgatg aaacggtgat ggtcaactac cgggtccagg gcgaccgcta catcgtcgat  15600
acgattttcg acaaggccat cctcatcgcg ggcgtgggca gcagccagga ccgcgtgacc  15660
atttcaaggg ggaactaaac catgcgtaag attctgaccg tcatcgcact cgcggccacg  15720
ttggccggct gcgcgacctc caagtacggc agcttcgtcc aggacgcgcc ggccgcctac  15780
aaccagacca ttgcgaccga cgcggtgaag cagctcgtca agctctaccc gccggcgcaa  15840
accaagctgg aattgcagca ggctacgccc gatccgttcg gcattgccct ggtcactgac  15900
cttcgcgccc agggctatgc tgtcatggag tacaagcccg acggcaacgc ggccgcagct  15960
ccggctgctg cgtcctcggc cgctgcgaag ccggcaacgc cgcaagccca gggcggctat  16020
ccgctgcgct acgtgctgga ccaattcagc gacagcaacc tgtatcgcct gaccgtcatg  16080
gtcggctctc aatcgctcac gcgcgcctac ctcgcccaaa acaacacgat ggtcccggcc  16140
ggcgcatggg ttcggaagga gtaagccaat gagcgaagat caaatggcac cggacgcatc  16200
gccagatgcg gtcaagccga aaagcggggt tcgccgcgtc aacaacatgc cgatgtacct  16260
catcggcggt gtgctcggca tcttcctgct ggtgatggcc ctggttgctg cggatcgcgc  16320
tgcgcagcag aaccagccgg gagctgcgaa ggctgagaag gccggcagca ccagcatgtt  16380
tgccgacgaa attgccggca aacagcagga cggcatcatc aaggccaagc cgctggagat  16440
tccgccggaa caaaccgccc agcaaccgac gacggagctg acgccagccc cggcgcaggg  16500
aacgactatc acggtcgcac ggcccgagaa cctggaccag cccccgacgc cgccgcaggg  16560
tgcgcgcaac gaggacctgg accgcatccg catggcgaag ttgcagatgc tggaagaggc  16620
gatcaaggcc aagacgacgg tgcgcatcga cgcgccgcgc agccagggca gcgccggcgg  16680
```

cggtgctccg cagggccgcg aggaaaccct tgcgcgcatc caggagctgc gtcggcaggc 16740
tgagaacgcc cgcgccaccg atccgaccgc cgcctatcag gccgcgcttg cgcaggctcg 16800
cacgatgggc ggcgcggcag ggggtggcgg tatgggcggc tcgggtgcgc cgaccctcgt 16860
gcagacctcg aaccgcagtg gtggcggcgc tggctatggg tcgttcgaca accgcagcga 16920
gggcgaccgt tggcggctcg actcccagcc ggaagcacct gcaacgccct atgtgctgcg 16980
cgctggcttc gtcgttccgg ctacgcttat ctcgggcatc aactccgatc tgccaggcca 17040
aatcatggcc caggtatcgc agtcggtgta cgacacggcg accggcaagc acatgctcat 17100
cccccaaggc tcgcgcctgg tgggcagcta ctcgaacgat gtggcctacg ggcagaagcg 17160
cgttctggtg gcatggcagc gcatcatctt ccccgacggc aaggcaatgg acattggggc 17220
catgccgggc ggcgatagcg ctgggtatgc aggcttcaac gacaaggtca acaaccacta 17280
cttccgcacc ttcgcatcgg cattcctcat gtcgggcgtc gttgcgggca tcagcttgag 17340
tcaggaccgt ggcaacagca acagcggtta cggacgacaa gacgcgggtt ccgcgatgag 17400
tgaagcgttg ggtcaacagc tcggccaagt aacggcgcag atgatcgcca aaaacttgaa 17460
tatcgcgccg acgctggaaa tccgtccggg ctatcgcttc aacgtcattg tcacgaaaga 17520
catgacgttt tctaagccct accaggcgtt tgactattaa ctccaaggag taacttatga 17580
agaagctcgc taagaatgtt ttagccgcta aagtagctct ggtgctggcc ctctcggtcg 17640
gcaccttggc ggtcacgcct gcgcaagcgg gcattccggt catcgacggc accaacctgt 17700
cacaaaccac tgtcaccgcg attcagcagg ttgcgcaggt ccagaagcaa atcgaggaat 17760
accggacgca gttgcagcag tacgaaaaca tgctgcaaaa cacggtggcc ccggccgcct 17820
acgtgtggga ccaggcgcag tccaccatca acggcctgat gagcgccgtt gataccctga 17880
actactacaa gaaccaggcg ggcagcatcg acgcttacct gggcaagttc aaggacgtgt 17940
cctactacaa ggggtcgccg tgcttctccc tgtcgggctg ctcggaaagc gagcgcaagg 18000
cgatggaaga gaaccgccgc ctggcgtccg aatcgcagaa aaaggccaac gatgcgctgt 18060
tccgtggcct cgatcagcag cagagcaacc tcaagtccga cgccgccacg ctggagcaat 18120
tgaagggcaa ggcgacgacg gcgcagggcc agttggaagc cctcggctac gccaaccagt 18180
tcgccagcca gcaggccaac cagctcatgc aaatccgtgg ccttctgctt gcgcagcaga 18240
acgccatcgc cacgcagatg caggcccagc aggaccggca ggcccagcag gacgctgcgg 18300
gcgcgaagct gcgcgagggt tcgtaccgcg caagcccgtc taagacctgg tgaggggagg 18360
cgcgatgaag aaatccaact tcatcgcagt tgccgcgctg gccgccgtca tggcggccag 18420
cctggcaggc tgcgacaaca agcccgacac cgacaagctg acctgcgccg atctgccgaa 18480
ggtcacggat gccgctcaac gcgcggagct gttgaagaag tgcccgcgcg gagaaccggg 18540
aggcttcaag cccagcgaaa agaaagagtg gtgatgacgt atgaaaatcc agactagagc 18600
tgccgcgctc gcggtcctga tgctggcctt gatgccggta gcggcatacg cccaaatcga 18660
caattcgggc atcctcgaca acgtattgca gcgctaccag aacgccgcga gcggctgggc 18720
cactgtcgtc cagaacgccg caacctggct gttctggacc ttgaccgtga ttagcatggt 18780
ctggaccttc ggcatgatgg cactgcgcaa ggccgacatt ggcgagttct tcgccgagtt 18840
cgtgcggttc accatcttca ccggcttctt ctggtggctg ctgaccaacg gcccgaattt 18900
cgcgtcgtcc atctatgcgt ccctgcggca gattgcaggc caggcaacgg ggttggggca 18960
ggggctttcg ccgtccggca tcgtcgatgt tggcttcgag attttcttca aggtgatgga 19020

-continued cgaaacctcg tactggtcgc cggtcgatag cttcgtcggt gcctcgttgg cggccgccat 19080
cctctgcatc ctggccctgg tcggcgtgaa tatgcttctg ctcctggcgt ccggatggat 19140
tcttgcctac ggcggtgtgt tcttcctggg cttcggcggc tcgcgctgga cctcggacat 19200
ggcgatcaac tactacaaga ccgtcctcgg ggtcgccgcg cagctcttcg caatggtgct 19260
gctcgtaggc atcggcaaga ccttcctcga tgactactac agccgcatga gcgaaggcat 19320
caacttcaag gaacttggag tgatgctgat cgtcggcctg atcctgctcg ttctggtcaa 19380
caaggtgccg cagctcatcg ccggcatcat caccggcgcg agcgtcggcg gtgctggtat 19440
cggccagttc ggcgctggca cgctcgtcgg tgcggccgcg acggccggcg cggcaatcgc 19500
aactggcggc gcatctatcg cggccggcgc tgcggcggcg gccggtggcg cgcaggccat 19560
catggcggcc gcgtcgaagg ccagcgataa cgtctctgcc ggcactgaca ttctgtcgag 19620
catgatgggc ggcggcggtg gcggcggcgg tggtagcgcc ggcaccagcg gcggcgacgg 19680
cggcggctcg ggtggcggcg gtggctcggg cggcggtgaa accccgatgg cctcggccgc 19740
cggcgacaac agcagcggcg cacgcggcgg cagttcgggc ggcggctcgg gtggtggccg 19800
ttcgtctggc ggtatcggtg ccacggcggc caagggcggc cggatcgcgg ccgataccgt 19860
cgccaacctg gcgaaaggtg ccggctcgat tgccaaggcc aaggccggcg aaatgcgcgc 19920
atcggcccag gaacgcatcg gcgataccgt aggcggcaag atcgcgcagg caattcgcgg 19980
cgcgggtgcg gcggcgcaga ccgctgcaac cgtcgccgat agcaacagcc aggcgcagga 20040
acaacctgca ccggcacccg caccgtcgtt cgacgacaac agcctttccg caagcaacaa 20100
cagggaagcg gccgccgacg cggattccga agtggcgagc ttcgtcaaca agcccgccca 20160
atcctgaaac gactcttagg agctacgacc atgcaactga aaaaagcgtt ctcgtcggcc 20220
gccctggtgg tggccttggg cctcggcgca actggctcgg ccagcgcgca agacgtgctg 20280
acgggcgata cccgcctggc ctgcgaggcc attctgtgcc tgtccacggg cagccggccc 20340
agcgagtgca gcccgtcgct ctcgcggtac ttcggcatcc acaagcgcaa gctgtcggac 20400
acgctcaagg cgcggctgaa cttcctcaac ctctgcccgg tatcgaacca gacgccggaa 20460
atgcagacgc tcgtttcctc gatttcgcgc ggggccgggc gctgcgatgc gtcctcgctg 20520
aactccgtgc tgcgtgagtg gcggagctgg gacgaccagt tctacatcgg caaccgcctg 20580
ccggactact gcgcggccta caccggccat gcctataccg acttcaacac gaccgcgccg 20640
cgctacgtcg gcacgccgga agagggcggc tattggatcg aggcggccga ctacgaccgc 20700
gcgctcaagg agtacgaggc gaagctgaaa gagcggcagc agcagtacgg tcgctatggc 20760
agcgacgcct accgtcggtt cgagcggtaa ggggagggga tagcgatgcc gtttgccaag 20820
ctgctggcac ggaacgctct gccggtggtc gccctggtgg cggccactgg cttcggtgcg 20880
gcggatgcga ccgccgcacg gctcttcccc gatctgtcgg aacagatgga agagcgcgtt 20940
gtgtgctcgg tgtctgcggc cgcgaagtac gagattccgg ccaacattct tctcgccatt 21000
cgggaaaagg agggcggcaa gccgggccag tgggtcaaga acaccaatgg cacctatgac 21060
gtgggcgagc tgcaattcaa caccgcctac ctgggcgacc tggcgaagta tgggatcacg 21120
gcccaggacg ttgctgcggc aggctgctat ccctatgacc tggcggcctg gcggttgcgc 21180
gggcacattc gcaacgacag gggcgatctg tggacacgcg ccgctaacta tcactcgcgc 21240
acgccgtcga agaacgcgat ctatcgcgcc gatctgatgg tgaaggccga caagtgggcg 21300
aagtggctgg atgcgcgttt cgtcaccgtc aactatggcc ccagctcgcc ggcgcagccg 21360
gcagggaagg ggaccacact tgcggccgct gatacgtcgg cagcagcgcc ggccgaagcg 21420
cagccgatga agcaaggccg gatcacccgc accagcctcc gcagctcggg ttacgtaccc 21480
cggcagctca tcatcaacaa cacgccataa ggaggaacgg ccgtttagcg gctaaagcct 21540
atgggcattc gcaacctgac gcagcgatac atgaacgggg ccagggccta cgcggcctgg 21600
gcggcatcgc aggcgaaagc gccgtttgat cttctggtac tgggcatcgg gcctgtcatc 21660
gtctttggcc tggtcgcgca tacgctgctc gcgttcctgc ccacatgggc catgtacgcc 21720
gccggcgctc tgctggtcct cgcggccctg cctttggcgc tgcacgtcct ccgggaatac 21780
gcgctgcgct atgggcgcaa atagcgccct gcagggcgtt cttactccaa gggggagggc 21840
atgaatacac gcgccatgaa cgacgccagc ggccgggcct cgctgcctgc catggtgatc 21900
gccgacggca ccattgaagc cttgaagtgg ctcgccttgc ttcccatgac cggggatcac 21960
gtcaacaagt acctgttcaa cggtacgctg ccatatctgt tcgaggcggg gcgcttggcc 22020
ctgcctcttt tcgttttcgt cctggcgtac aacctcgccc gcccgggcgc gctcgagcgc 22080
ggtttgtacg ggcgagcgat gaaacgcctg ttggccttcg gcctggtcgc ctcggtcccg 22140
ttcattgcgt tgggtggagt ggtgggcgga tggtggccgc tgaacgtcat gttcacgctg 22200
ttggccgcaa ccgcgatgct ctacctggtc gagcgcggcc gctcggtcgc tcctatagcg 22260
ctgttcgtcg tggccggcgg cctggtcgag ttctgttggc cggcgctgct gctggccgcg 22320
tctgtctggt tgtacctcaa gcgcccgacg tgggcggccg cgttgatggc gctgctgtct 22380
tgcgcgtccc tgtggtacat caatggcaac ctttgggcgc ttgctgttgt gcccctggtg 22440
atcgtcgccg ccggcgtcga tcttcgtgtc ccgcgcctgc gctgggcctt ttacacgtac 22500
tacccgctgc atcttgccgc tctttggctg atccgcattc cgatgcgcga ggcgggctac 22560
ttgtttttca cctgaccttt gagattccaa tatgcaattg ctcaagaaat gcaccatcgc 22620
ggccctgccg ctgctcgccc tgtccggctg cgcactgctg aacatcccca tgccgacgcc 22680
gcccggttcg accccgccgg aaatgctgac cgtgccagtg gcgcaaatct gccgcgacgc 22740
tgacaagaac cctgttcggg caacggagct gtacggcaag aaagggttgt cggccaccgg 22800
caaggtgcag gtgatttccg aaggcttcaa gcctcgctat cgggtgctgc tgccgcctgg 22860
cagcgcctcg gtccatgctg ggaccgataa ccagctcgcc atcaagtcgg tttccaccgg 22920
ccagaccacg cgcgtcactg gcaccgtgaa ggacgtgtcc tacgaccata acggctgctc 22980
gatctcgctt gacgatgcga agttctactg aggggagggc ggcggatgct gacacggttg 23040
aagggcttcc ttgctcgtcg ccgcgagttg aaggaactgg atgtgtccgt ggtgagccgg 23100
ccccggccgg ctccggcgga attggtccag gttgatgcac gcgaggccgt ttggcgcgtg 23160
ccggtgcccg gccaggccga ccgcttcatg tcggccaagc ctggcgcgat caacgatgaa 23220
atgttcgtgg ttcgggtgga caccgaagcg ttctatcggg cttggctgcg cagcagctcg 23280
acgggccgcg aaacgcggtc ggacaactgc ccgctgcgct cggaaatgcc gcaggactac 23340
aagttcaagc acgccgtcca gggcttcgcg cacggcaggg aaaatcctgt gccgctggcc 23400
ttcgccggcg cgcaccagga gcgccaccgg gtggacattg gtttcagcaa cggggtcacg 23460
cgctcgttct ggctgattgc caacaaggct ccgtcgttcc cgatccaggt ccacggccgg 23520
gagtcggccg agctgctgaa caaggtttgc ggcctcgatc ctgcgccgct gtcgttcacg 23580
gaactgttcg cgcaggccca acgccaggct ccgcaggtcg ccacaccggc ccggcctgcg 23640
ccggcagcgg ccacccggcc agctcccaag gtgcagccac gccccggccg aagcggcccg 23700
cgcaaaggcc gcggactctg actacaaccg tgcgcaaggc gcattaggga ggatgtatgt 23760
atgtaatcgc ctgcggcatc gttgccggct tggcggctgc ggtggccctg ttgggcttca 23820
cgccgatgat ggaggcgctt gccgccggcg aacgccgcaa ggcactcgcg caatggacgc 23880
ggacgatgtt cctggtgctg ctgcctgtcg tgctgatgtg cgcgcccatc gggtccagca 23940
tttacgacgc cgtgcaagcg gacgctggca agcccatcgc tttccacaac ggccggatca 24000
cggtcgtcat ggccctggtc ggcagcttgg ccgttgtcct ggtcgcggct gcgcgtgcgg 24060
tggtcaaccg caagcatgcc agcttctggt tcgtcggctg ggtgatggcg tcggttttgg 24120
ccggcggcgt cggcgcgatc gccagcgcga agcaactggc gttcctcggc gaacatagcg 24180
gcatggtggc cttcggcttc ttccgcgacc aggtgaagga catgcactgc gatgcggacg 24240
tgatcctggc ccggtgggat gaaaaggcga actcgccggt ggtctaccgc tgcccgaagg 24300
cgtacctgct caacaggttc gcatccgcgc ccttcgtgcc ctggccggac tacaccgagg 24360
gggaaagcga ggatctaggt agggcgctcg cagcggccct gcgggacgcg aaaaggtgag 24420
aaaagccggg cactgcccgg ctttattttt gctgctgcgc gttccaggcc gcccacactc 24480
gtttgacctg gctcgggctg catccgacca gcttggccgt cttggcaatg ctcgatccgc 24540
cggagcgaag cgtgatgatg cggtcgtgca tgccggcgtc acgtttgcgg ccggtgtagc 24600
ggccggcggc cttcgccaac tggacaccct gacgttgacg ctcgcgccga tcctcgtagt 24660
cgtcgcgggc catctgcaag gcgagcttca aaagcatgtc ctggacggat tccagaacga 24720
ttttcgccac tccgttcgcc tcggcggcca gctccgacag gtccaccacg ccaggcacgg 24780
ccagcttggc ccctttggcc cggatcgacg caaccaggcg ctcggcctcg gccaacggca 24840
agcggctgat gcggtcgatc ttctccgcaa cgacgacttc accaggttgc aggtccgcga 24900
tcatgcgcag cagctcgggc cggtcggcgc gtgcgccgga cgccttctcg cggtagatgc 24960
cggcgacgta gtacccggcg gcccgcgtgg ccgctacaag gctctcctgg cgttcaagat 25020
tctgctcgtc cgtactggcg cgcaggtaga tgcgggcgac cttcaacctt cgtccctccg 25080
gttgttgctc tcgcgtcgcc atttccacgg ctcgacggcg tgcggatcgg accagaggcc 25140
gacgcgcttg cctcgcgcct cctgttcgag ccgcagcatt tcagggtcgg ccgcgcggcc 25200
gtggaagcga taggcccacg ccatgccctg gtgaaccatc gcggcgttga cgttgcgcgg 25260
ctgcggcggc cggctggcca gctccatgtt gacccacacg gtgcccagcg tgcggccgta 25320
acggtcggtg tccttctcgt cgaccaggac gtgccggcgg aacaccatgc cggccagcgc 25380
ctggcgcgca cgttcgccga aggcttgccg cttttccggc gcgtcaatgt ccaccaggcg 25440
cacgcgcacc ggctgcttgt ctaccagcac gtcgatggtg tcgccgtcga tgatgcgcac 25500
gacctcgccg cgcagctcgg cccatgccgg cgaggcaacg accaggacgg ccagcgcggc 25560
agcggcgcgc agcatggcgt agcttcggcg cttcatgcgt ggccccattg ctgatgatcg 25620
gggtacgcca ggtgcagcac tgcatcgaaa ttggccttgc agtagccgtc cagcgccacc 25680
cgcgagccga acgccggcga aaggtactcg accaggccgg gccggtcgcg gacctcgcgc 25740
cccaggacgt ggatgcgccg gccgcgtgtg ccgtcgggtc caggcacgaa ggccagcgcc 25800
tcgatgttga agtcgatgga tagaagttgt cggtagtgct tggccgccct catcgcgtcc 25860
cccttggtca aattgggtat acccatttgg gcctagtcta gccggcatgg cgcattacag 25920
caatacgcaa tttaaatgcg cctagcgcat tttcccgacc ttaatgcgcc tcgcgctgta 25980
gcctcacgcc cacatatgtg ctaatgtggt tacgtgtatt ttatggaggt tatccaatga 26040
gccgcctgac aatcgacatg acggaccagc agcaccagag cctgaaagcc ctggccgcct 26100
tgcagggcaa gaccattaag caatacgccc tcgaacgtct gttccccggt gacgctgatg 26160

```
ccgatcaggc atggcaggaa ctgaaaacca tgctggggaa ccgcatcaac gatgggcttg  26220
ccggcaaggt gtccaccaag agcgtcggcg aaattcttga tgaagaactc agcggggatc  26280
gcgcttgacg gcctacatcc tcacggctga ggccgaagcc gatctacgcg gcatcatccg  26340
ctacacgcgc cgggagtggg gcgcggcgca ggtgcgccgc tatatcgcta agctggaaca  26400
gggcatagcc aggcttgccg ccggcgaagg cccgtttaag gacatgagcg aactctttcc  26460
cgcgctgcgg atggcccgct gcgaacacca ctacgttttt tgcctgccgc gtgcgggcga  26520
acccgcgttg gtcgtggcga tcctgcatga gcgcatggac ctcatgacgc gacttgccga  26580
caggctcaag ggctgatttc agccgctaaa aatcgcgcca ctcacaacgt cctgatggcg  26640
tacttaccca aagaacagct aggagaatca tttatgctca gcacacttcc acaagctcat  26700
gcaactttct tgaaccgcat ccgcgatgcg gtcgcttccg atgttcgctt ccgcgctctt  26760
ctgatcggcg gctcttacgt tcacggagga ctcgatgagc actccgattt ggatttcgac  26820
atcgttgttg aggacaactg ctacgcagat gtcttgtcta cacgcaagga ttttgccgag  26880
gcactgcccg gcttcctcaa cgcgttcacc ggcgaacatg taggagaacc gcgccttctg  26940
atctgcctat atggtccgcc actgctacac atcgatttga agttttctct tgcttccgat  27000
ctcgaccagc aaatcgagcg gcgggcggtt ctgtttgctc gtgatccggc agagatcgag  27060
aagcgcattg aggcggcagc ggtggcatgg ccaaaccgtc cctccgagtg gttcgaagca  27120
cgttgtcagc gccagtgata taagacggta attcaccatt tggattgtcc gctccaccca  27180
acatgttgtt tccttaaggt tctcacacca gaaaggacat caacatgctg agcagagagg  27240
acttttacat gataaagcaa atgcgccagc agggcgcgta cattgtcgat attgcgactc  27300
agattggttg ctctgaacgg acggtcagac gctacctcaa ataccctgaa ccgccagcca  27360
gaaagacccg ccacaaaatg gttaagctga aaccgtttat ggattacatc gacatgcgcc  27420
tggcagagaa tgtctggaat agtgaggtta tctttgcgga gattaaggca atgggttata  27480
cgggcggacg ttccatgctg cgttactaca tccagcccaa acgtaaaatg cgtccgtcaa  27540
aaagaacagt tcgcttcgaa actcagccta gataccagct ccagcacgac tggggcgaag  27600
ttgaggtgga ggttgccggg caacggtgca aagttaactt tgcggttaat acgctggggt  27660
tctcccgccg cttccatgtc ttcgccgcac caaaacagga tgctgagcat acctacgaat  27720
cactggttcg cgccttccgc tacttcggtg gttgtgtgaa aacggtgctg gttgataacc  27780
agaaggctgc ggtgctgaag aataacaacg ggaaagtcgt gttcaactcc ggattcctgt  27840
tgctggccga ccactataac ttcctgccac gggcatgccg tccacgcagg gccagaacaa  27900
aaggtaaggt tgagcggatg gtgaaatacc tcaaggagaa cttcttcgtt cggtaccgca  27960
ggttcgacag cttcactcat gttaatcaac aactggagca atggatagcc gatgtggctg  28020
acaaacggga acttcgccag ttcaaagaaa cgccggaaca gcgcttcgcg ctggagcagg  28080
aacatctgca gccgttaccg gatacggact tcgataccag ttacttcgac atccgccatg  28140
tgtcctggga cagctatatc gaggttggtg gtaatcgtta cagcgttccc gaagcgctgt  28200
gtggtcagcc ggtatcgata cgaatatcgc tggatgacga gttgcggatc tacagtaatg  28260
agaaactggt ggcctcacat cgcctctgtt cggcatcgtc tggctggcag acagtgccgg  28320
agcatcacgc cccgctctgg cagcaggtca gtcaggtgga acatcgacca ctgagtgcct  28380
atgaggagct gttgtgatgc atgagctgga agtcctgctg agtcgcctga aaatggagca  28440
tctgagttat cacgttgaaa gcctgctgga acaggcagct aaaaaagagc tgaactaccg  28500
```

```
ggagttcctg tgcatggcgc tacagcagga atggaacggc aggcatcagc gcggtatgga  28560
gtccaggctg aagcaggctc gtctgccgtg ggtcaaaacg ctggagcagt tcgactttac  28620
cttccagccg ggcatcgacc gtaaggttgt ccgggaactg gctggtctgg cgttcgtgga  28680
gcgcagcgaa aacgtgatcc tgctgggacc tcctggtgtc ggaaaaactc atctggccat  28740
agctcttggc gtgaaagcgg tggatgcggg acatcgggta ctgtttatgc cactggacag  28800
actgatcgcg acactgatga aagcgaaaca ggaaaaccgg ctggagcgtc agctgcagca  28860
actgagttat gcccgggtgt tgatcctgga tgaaataggc tatctgccga tgaacagaga  28920
ggaagccagc ctgttcttcc ggctactgaa ccgtcgatat gaaaaagcga gcatcatact  28980
gacgtcaaac aaagggttcg cagactgggg agaaatgttc ggagatcacg tgctggcaac  29040
agcgatactg gatcggttgc tacatcactc aaccacgctg aatatcaaag gagagagtta  29100
ccggttaaaa gagaaacgta aagctggagt gctgaccaaa aacacaacgc caatcagtga  29160
tgatgaaatg gtgaaaagcg gacagcatca gtaacgaaag tatcttagcg ggcatgaaaa  29220
tggcaaataa cggtcaaaca tcgtggcgtt gacaacgtgc ctggatctgg ctacactatg  29280
cggccaccaa gctcgcccgt ggagtctcta cgaagcgatc ggcatgctcg gtttccttcc  29340
gtgagcaagt gttaggacct ttgctctacc gtcgcgctgg aaaggaccag cgcggagtga  29400
ggcgattgga aacccttcga ctgggatgaa gagcgcagac ctagccacca ccattgcgct  29460
gcacgatgcg ttgtctgtca gggatgccat caaagcatct gcctccatct atctcgacct  29520
ccgagccgcc gatccgtcgt tggaaccgac aacgcatatg ccaggtcttc tgtacgactt  29580
aatagaacgt gcggtaccag gcacgcctaa ccgtcagtga gattggatga gtgaacgata  29640
ttgatcgaga agagccctgc gcagccgctg ccgtgcccga gagcatggcg gctcacgtga  29700
tgggatacaa atgggcgcgt gataaggttg gtcagtccgg ctgcgcggtc tatcggctgc  29760
atagcaagtc aggcggctcc gacttgtttc tgaagcacgg caaagatgct tttgccgacg  29820
acgtgactga tgaaatggtg agattgcgtt ggctggcggg gcacatttct gtgccctccg  29880
ttgtaagctt cgttcgcacg cccaatcagg catggctcct gacaacagca atacatggaa  29940
aaacggcata tcaagtgctg aaatcggatt tcggagcccg tctcgttgtt gttgacgcat  30000
tggcggcgtt catgcgccga ctgcatgcga tcccagtgag cgaatgctcc gttcaacagt  30060
ggaccacgca tgcaggcttg cccgagcgcg ggagtatcga ggcgggggtt gttgatgtcg  30120
atgacttcga taaggagcgc gaagggtgga cggccgaaca ggtttgggag gcgatgcatc  30180
gcctcctacc gctcgcgccg gacccagtcg tgacgcacgg cgatttttca ctcgataatc  30240
tacttatcgt cgaaggtaag gtagtcggct gcatcgacgt tgggcgggct ggtattgctg  30300
atcgatacca agaccttgcc gtgttatgga actgtcttga ggagttcgaa ccttcgcttc  30360
aggagaggct tgttgcgcaa tatggcattg ccgatccgga taggcgcaag ctgcaatttc  30420
atctcctgct ggacgaactt ttctaaggcg atgccccctc gacctcgatc agggaggcgt  30480
tcaggacgac tcacaaagaa agccgggcaa tgcccggctt tttctgctgc tacctccgta  30540
gtcgtaaggt cgttgcaggt gctcgggtgc ggtacaactc gccggtcgcc agctcaagcg  30600
cgatcacgtc gttgccgtcg tagttgacga tgatgctgtt gggccgactg tcctcacgct  30660
tcgcagggag aggccagcct tcaatcgaag ccggcgcaag ctcgtagtgc ttcccggttt  30720
cgacgctgcg cagcgtccag gtcctgcaac cggccacgcc ggtcgcagaa accacggcga  30780
gcgagccgcg aaaatcgtgc gggtacgcct cgatgttcat acgcctccta gatcgagcgc  30840
gagcgtttct gctcggcctt ggccgcctgt tcctgggaca cctcgccgat gaccttgccc  30900
```

-continued

```
tggccccggc tgtaggcgat ttcgtagttc ttgccgacaa ccggcggctt ctcaaagatg  30960
ccccggctgt gtttcacgat cccgccttcg ctgaactggt agacgttgcg cccatcgtcg  31020
tgcagcacct ggccgacgtg cttgtgcggg tggacgtttt tgcttgcgtc cttcgcatcg  31080
ctcaactggt gaatgccttt cggtagcccc gcctcgggca acaccttcat ggtcagccat  31140
tcgccgttca ctacctggtc cacctggcgg ctgccgttca tgacggcgat cttgacgctg  31200
ccctcgggtt tcatgatgac gccagggctt gccgatgtgc gtggtgcccc gatctgtact  31260
ttgttcatac gctctagttc tccttagtag gttctcgcgc ggcgttgccg ctgttcttgc  31320
tgctcgatgt cttgctgctt gagctgctgc accttctgcc gctggccctc gtcgagaagc  31380
accttgccga cagcacttct cacctggcgt tcaaccccgt ccttgcccag gctgctgcgc  31440
tcggacaggt cgttgaaatc ggtgtgcttc ttcatgttcg acagggcggc gagctggcca  31500
tcgttcaaca gcgattcctt gagcttggcc gtgtcggcct cgctcaactg gaccttgccg  31560
gccgccgcgt ccgcgaggcg cttttcagcg tgcaaatggt tgcggtagtt ctccggggtg  31620
atcggcggca gctccttcgg gtaggcgttc tcgcccggcg cgaagattgg gaagatggcc  31680
ttgccgccga ccgccttggc ggcctcctgt gccttcgtcc tgccgggatt cacgccctgg  31740
gtgatctgca cctggcggtc gtcgtcgccg gcgatcacaa cgggcttgtc cgggaatttc  31800
gcgtgcaggg cctcggcaac agcctgtagg ttgccggaat cgaacgcggc gacagtcgcg  31860
tgccccagcg cttcggccac tgtggcggcg gtggcatagc cttcgccgat caccagcgcc  31920
ggcgcggccg cgagcgcatc catgccaccg acgacatgga agcatccttc cttgcggctg  31980
tccttggcga agcgcttggt gccgtcctcc tggatgtact gcatggtcca ttgcttgccg  32040
tcggcgtcgt aggccgggat gtaggttttc tggccctcct ggtcggtaag gacgccggcg  32100
tgcacctgta gacccttgtc gcgcaggtac ggcgtcggtt ccgtgatggg aaccaggctt  32160
tgcgcctggc ggccgatgcg ctgcgccgtg gcttcgtgct ggcgttcttg ttcctcggca  32220
cgcgcggcca gcttggccgc cgcctcggcc tgcatcttgg ccttctcggc ggggtccagg  32280
gcgtagccct tggccttcca cttcatttcg acgccggtgc ggttgttttt gatgtaaccg  32340
gccgggtggc cgtcgaggtg gccgacgtag aagcccgact tctcgccctt cttgtcgccc  32400
tcggtctcga tgcggtgctt cttgccgtcc atgatggggt gctcgccgcc tggggtgacg  32460
acgcagccca tgcttttcag ggcctccgcg aactcatctt cgggggtgac ggccggggat  32520
tgctgggtgg gcacgttgtc cggcagccag cgttgcagct tgcccatgtc ggcgttcggt  32580
ccggcgtacc aggacttggc caccttgtcc cactgcgcgc cggccgcctt ggcaacctgg  32640
cgctcgccgt agggcacggc caggtagacg cgctcctggg ccgcgttggg gcgctcggcc  32700
gtgggttggg taggctgggc ctcggcgcgg gcctctacgg ccgctgtagc gccctcgcgc  32760
gcccatttgg cgaacggggc agggtcaacc cctgccggaa cgtaccaggc gcgttcctgg  32820
cggtcccagc gcgctccaag ggccttcacc tcgtctttct ccttgaacgg cacgttcaag  32880
taggcgcgct cgggcttggc gggggcttga gcggccgccg gctgctcggc ggcgttcatg  32940
gcctgggcca tttcctgctg ctcgcgctcg tagtcggcga tccggcgctg taggtcctcg  33000
tcgtgcagca tggccgtgcc ctcggcggcc ttgcgcgcct ccttggcggc aacgcggtcc  33060
tcgtcggtgc tgttgggatc gcggcgaact cgctcttcat ggatgcgggc gaacttcgcg  33120
gcctgctcgt actcgttggc cgtcgcgtaa gcgtcgatca cggccaggcg gtcggcgagc  33180
gcttcggcat tggtctgcgc gtcggggccg gcgaagtcgg caagccattg gtggccgccc  33240
```

```
cacgcatggt tcgcatagac gccccaaaac tccggctctc ggtcgccggc cggcaccacg  33300
gaccgttcgc cgtcgtgctc gacctcgacg ttggcctgga cctggacgcg gccggtccaa  33360
tcggcaggca gctcaaagcc cagcgtggtt tcggtcagcg cggccagcga ttggttgcct  33420
tccgccggct ccgcgccggc gcggtacatg cgcagggtct gcgcgatcag ctcgtcggcc  33480
ggcgcaatgg ccggtcgtgc cacctggtct tgctgttgct ccatagttgc cccctgcgca  33540
ggctcgatgg cctgctgggt cgtttgttct tgaatttgct tctgctcgaa cgccaggacg  33600
aaatcctgga tcttctccgc gtcggcggcc gcgcggaaaa tctctagcgg gtcctcttgt  33660
agcgccttga tccacgatcc gacataggcc gcgtgctggc cggggtcgtg gccgatgccc  33720
agctcgtcgc ccaggatcat gctggcaatc tcggcccgca gctcttcctt ggcgtacccc  33780
tcgctcccga agggatgcgc caggtcgcgg tccagccgcg acgggtggcc ggtccagtgc  33840
cccagctcat ggagcgcggt tgcgtagtag ttgtcggcgc tcgggaactg gcctttgtcg  33900
ggcagatgga tgctgtccgt ggacggccga taaaacgcgc ggtcgtgctc gccgtggcgg  33960
atggtggcac ctgacgccgc aaggatgtgc tcggcccgct cgacggcgct ccaagtctgt  34020
tccttgcgtt ccaacggcgg caggccgtcg atctgctccg cattgaacac ggtggcgaag  34080
aacacgcgcg ggcgttcgag ctgcaccgtc accttgaccg gatcgccgtt ggcatcgagg  34140
accggcttgc cggtctgctc gtcggtcttg gtctgctctt cgctgaactt ccaatactgg  34200
atcggcgtgc ctttctcgcc gcgacgcacc tgtgcgccgg cggcagcggc ctgcttgtag  34260
gtcatccagc gcgggtccgc atggccctgg gccatgagct gaatcgcgtt gatgcccttg  34320
taacgcttcc cggtagtcgg gttgagcggg atgaaggagc cgggcatgcc cggttcccac  34380
ggtttttgcc acggcgcagt gccggctttc agttgctcaa tgaggcgttc ggcaacctgc  34440
tcgtggaacg gctttttgac ctctgccata gccaattacc tcccgtcatt ggcggccgcg  34500
gtcgtcgtgt cctcgggcac ggtcgcgtcc accaggtcaa tgtcgctctc ggcggcgtcc  34560
tgctcgctca aggcgtcctc ggggaaggcc ccggccttct ccgcttcttc cgggtcgaac  34620
tcgacctgga agccgggcgt catcgcatcg gcgagctttt cacgcagggc ggcggcggcg  34680
ttcgcggtat cgtcgaacgg cgcaaagtcg tcctgctgca cggtcttggg atcattcatc  34740
gctttcactc ctggttggtg ccgttacggc ctttgctgta gtccggcctg cctttcaggt  34800
cggggtatgt ctgcttgcac gtcgggaagt tgctgcaccc ccaccagaac atgccgcgct  34860
tcttgccagg ccgacgggaa aggccgtggc cgcaggccat gcacttgtgc agctcggaga  34920
ctttcggggc ctcgcgcggg acgggcttgc cgcccttgtc gtcgcacgcg aacttgcagc  34980
cgtcggcaaa gccggtgcag ccccaaaagt attcgttctt gtccttcttc ttgaggcgtc  35040
gcagcggctt gccgcaggac gggcaagggt gcgtgtcgat cttcatgttg aggccgttgt  35100
ctttgatgtt ggcgacctcg gcgccgatgt attccatcag ctcgttgacg aacgacagcg  35160
tgtcgcgctc gccggcctgg atggccttct gctgctcatg ccagagcgcg gtcatgtcgg  35220
ggaatctggc cgtgtcgggc agtgcgtcgt acagctcttc gccggtcggc gtggacacga  35280
tgtgcttgcc cttctccacc aggtagccgc gctcgaaaag cgtggcgatg atggagtctc  35340
gcgttgccgg cgtgccgatc ccgccgtgct cgccttgctt gcccttgtcc ttttcgatca  35400
agattttccg caggcggtca tcgcggatgt atttcgcaac gcgggtaagg tccgacagca  35460
gagattccat cgtgtacagc ggctgcggtt tcgtctcctg ctgctcggcc ttcgcatcgg  35520
tgcaggtgcc ggcctggccg tcacgcagct tgcgcaggtc ctgttcaatg tcgtcggcat  35580
tgccttccag gtcctcgttg ccggcgtcgt tcttgtagag aatcttccag cccggcgacg  35640
```

tggtgacgtt cgagcgcacg ccgaaacgat gatcgccgac ctgggcaagc acgtcggtct 35700
ggtcatacag atgcttcggc cagaactgcg cgacgtaggc gcgcgcgatc agcaggtaaa 35760
tcttctgctc ggcatcggtg agcttcgaca ggtcggccgt gctttcggtc gggatgatcg 35820
cgtggtgcgc ggaaaccttg gacgagttga aggcgcggct cttgatcgtc ggattggcgc 35880
gctgcgcagc agcggccagc atgggggccg tctgtgcgat ggccgccagc acgcccggcg 35940
catcgccgtg ctgttcctcg ctcaagtatt cgcagtcgga acggttgtag gtgatgagct 36000
tgtgcttctc gcgcagggcc tgcgtaatgt ccttcacctg gtccggcttg aagccgaact 36060
tgcgcgaggc gtccatttgc agtttcagca ggttgtaggg cagcggcgca gccgcttcct 36120
tcgccttggt ggtcacggac acgatgcggg cgggttggcc gctcacggcg gccgcgatgc 36180
cctcggcgtg ctccttgttg ctgaggcggc ctttctcgtc caccggatcg ccgtcggcga 36240
cctggtaacg ggccgggaac tgaatgccct cgacctcgaa ctggccgttc accaggtagt 36300
agtaggtttt ctggtgggcc gcgttctcgc ggcaacggcg cacgacaagg cccaggatcg 36360
gagtctgcac gcgccccacg ctcaacagcc cctgatagcc cttcgcgcgt gccgcaagcg 36420
tgtacaggcg cgtgatgttg aagccgtata gctggtcgcc gacgctgcgg gcctcggccg 36480
cagcggacag gccggcgaac tcgcggttgt cgcgcatcgc ggcgagctgc cggcgcacga 36540
tcttcacgtt gttgtcgttg ataagcagcc gctgcaccgg cagacggcag ttggcgtatt 36600
ccaggatttc atcgaccaga agctggcctt cgtcgtccgg gtcgccggcg tgaaccacgc 36660
ttttcgcctg cttcaacagg ctgaggatgg tcttgaactg agctttcgca ccggcatcgc 36720
cggacggttt cttgcgccag ggaatatgga cgatgggcag gtcggccatg ttccagttgg 36780
cgtagcgctc gtcgtagtcc tccgggtcta gcaaggccag catgtgaccg tagcaccagg 36840
tcacgcggtc ggagccgcat tcgtaatagc cgtccttgcg gctgccgccg cccaggccct 36900
cgacgatggc ttttgccagc tccggttttt cagcgattac aaggcgttca aattgcatat 36960
atccccctac cctcaccagg tcagaaccgg cctgatgacg gtgatgattt gcgaacgatt 37020
gacaggcccg aagtagcggc cgtcgaaaga cgtgtcgctt acgtcggaca taagcagaac 37080
ctcggcggtc cccagggtgt agctgtcgga ctgataacga ggcagcggcc gtcctgatgg 37140
atcggccttg atgagcgcgc tgtgaggcag cagcccgcca ttcacgcgca cgccggcgtc 37200
ggtgatggca acctcgtcgc ctttagcggc taaaactcgc ttcatcatgt agccgtagtc 37260
gccggggcag aaaccgccgg cgatgtagcc ccgctccttg gcgtccgaaa acacgccgac 37320
ttgcggcggg cagaacatga cgtaagcccc cttctccacc ggcgcattcg atttccagta 37380
caggccgacc ggaatgcttt tggtggtgtt gaccttcgcg ccggcgagat aggccgcgcc 37440
ggcgagcaac aaggccgcgc cgcctccgat ggcgacgtac ttggtgaggc gctggaagcg 37500
gctcatatcg tgatcccctc cccttcctcg acggtggccg tctggatcag cttgtcgctg 37560
accttcggag ccggtacggc cgcgcgggcc tggaatatcg ggtctttgaa gtagagcggc 37620
tgcttgccgt agatcgcggg atagccggcg acgtacacaa ccatgtcgcc cgcctcttca 37680
atgctgccgt cggcgctctt cttcggcccc ggcatgcgca ggcattcatc gggggtcagc 37740
aatggccgct gcacttcctg gaaggtccgc gagacgttgc ccaacagcgc cgacgtgcgg 37800
cggccgctcg tcgtgatctg ctccttcacg atggtcgtgg tgcctgtcag ttttgacagg 37860
tgctcggccg tctccacgcg gttcggcggg taggcgttct gcacgtggca gttcgacgtg 37920
atgctttcgt cgtggccgta gccggtttcg cggctcttga gctggttaat gtcctggcag 37980

-continued

```
atgaggtagc acttgatgcc gtagccggcg acgaaggcaa gggactcttg caggatttcg  38040
agcttgccca ggctggggaa ctcgtcgagc atcatcagca gacgatgctt gtagtgcgcg  38100
acaggacggc cgttctcgaa gtccatcttg tcggccagca gccggacgat catgttgacc  38160
atgacgcgca ccagaggccg cagacgggcc ttgtcgttgg gctgcgtcac gatgaacagg  38220
cttaccgggt cgtcgtggtg catcagttgc ttgatgcgga agtcggactt gctgacgttg  38280
cgggccacaa ccgggtcgcg gtacagggcc aggtaggact tggcggtgga cagcacggaa  38340
ccggattctt cctccgggcg gtccatcatg tcgcgggccg cagagccgac cgcagggtgg  38400
ttctgcccgt caacgtggcc gtaggtggtc atttccatcc aaagctcgcc cacgtcgcgg  38460
ttcgggtcgg caagcatgcc gtccaccgac ggcagggtgg ccggcgtacc ctcgttctta  38520
gccttgtaga gcgcgtgcag gatgacgccg acaagcagcg cctggctggt tttctgccag  38580
tgcgattcca ggcccttgcc gtccggatcg acgatcaggg tggcaaggtt ctgcacgtcg  38640
ccaacctcgt actcggtccc caagcggatt tcatcgagcg ggttccagca cgcgctaccc  38700
tgcgcggatg ccggctcaaa gcgcacgacc ttgttgcggg catgcttctt ccgccagccg  38760
gcggtcagcg cccacaactc gcctttcagg tcggtgatga cggcgctgtg cgcccaggaa  38820
agcagcgtcg gaacgaccag gccgacgccc ttgccggagc gcgtcggcgc gtaggtcaag  38880
acgtgctcgg ggccgttgtg ccgcaggtag tggaacttgc cgtccttgtc ctgccagccg  38940
cccacataga cgccgctgga agtgggcggg tgtttgcctg acaccagctc gacgacggtg  39000
cgcggccggg gcagcaggcc ggcggcctgt atgtccttct tgtcggccca gcgggccgaa  39060
ccgtgcagat agtcgttcgc cttgccggtg ttcgccttga ccatctgcgt gacggccgtg  39120
cccagcaggc ccacggtcga aacgaccata cccatgctgg ccgcgcgcat gaaatcgtcg  39180
ggatattggc cgtaccactt gccggcccat tgaaggatcg accagggcgt gtagacgtgg  39240
ttgatattcc agccaagtcc ggcctgatac tggaaggaat gggcgaaata ttgcgtcgcg  39300
gtctgcaagc ctgccccaag ggacaggccg gcgaggatgg gaacggtctt gctggccttc  39360
ggtttttttcg cccgtatctg tggccccacg gcgttgtttc ggttcttcat ctactcctac  39420
ctcgggtagt tttaagggag cctcgcgggg tcacggtgac gggatcaccg atggcgaggc  39480
gcttcatgcg ttgcaccgtg gccttatcga cgggcagcac cagaatctcg tcgttttctt  39540
tcctcaacag ggccagcgcc tggtcctcga cgttccgggt gcctgcatag gacagcgcac  39600
caacataatc agtatatcgt gcatgcttcg gtatatcgaa gccgtttagc cgcttttgct  39660
cgcgctcggc aacatatttc tcggccgccg cgatctgttc gggctttagc cctcttcctg  39720
gcccagaaac tccccgtcgc agtgcgtgag ctggttcggc tccttgctgc tccacgtgac  39780
caggaacatc acgcggcaat agcatttcag ctccgccggc gatgcgaacc acaccgagtt  39840
gggacagcgc tcgcaaacgg ttttggcttt ggggcggcgg ctttcgtcca atgcgtccaa  39900
cgttgggctt gcggagtgcg acggttccgc cggcgctgac ggcgcgagcg tcccgtcggt  39960
cgccgtcgcc gcctgtggcg ttgagggtgg ttctggctgc ggcaggtcga atgcctccat  40020
cgccgccgcg atctcttcgt ccgtcatttc gttcgggttg ctcatgtgct tgctccttcg  40080
tcagtagttc ttgacggcgg cgctcaaggg cggcgtcgtc aaaggtgatt gccagacggc  40140
cagcggcggc cgcctgcgcg atccgctcct tgaactctgc tgtgccgttg acggtgatcc  40200
ggtcgccgaa gcgctccatt gccaggcgca gggcggcgtc caggccgtcc gtggtggcct  40260
cgcgcgagac ttgcaggcgg tcgccgtcgt cgcggacggc gctgctgccg acgcgataga  40320
tgatggttcc cttcttcgtg atgttgtccg tcacggccgc atggcccggc ttggcctcgc  40380
```

cgctgccctg gatggtgttg cccttgaggt cgctgcggcc ctcgcgtgcg cgcagcgcgg 40440
ccagggcctt gtcgtcgccc ttcatcgcct cggccttgag ccagtcggcc cacgcgcggc 40500
gctgcgtgcg ctcctggacc gcctgacggc cctgccggta ctcgcggttg atcttgtcca 40560
ggtcggcgcg cagagccttg tgcgcctgcg cgtacatcag tcgctttgca atgcgcccct 40620
cgcccagcag cttgatagcg gcgcggcgca gccggttgct gcgcatcgcg gcttcaatca 40680
ggcggtcacg acgccggcgc agcgtgtcca gctcgccctt gcgcacggcc cccatttcct 40740
ggcgttcaga ctgataccgg gcgtatagct cggtggtgtc gatgcgggtc ttgagcggct 40800
tcgctcgata ctcccgccgc cggggggctt cgccgccctc ggctggcgtg aatgccccga 40860
atcgggcttc gagcttcggc ttggacaggt cgcgcgaaac ggtgctggcc ttgaccgtcg 40920
tgccgtcgcc ggcctcgaag atgaagccgt ttccgcgctc gcgcagctta agcccgtttt 40980
cccgcaggac gcggtgcagg tcctcccagg attgcgccgc ttgcagctcc ggcaggcatt 41040
cgcgcttgat ccagccgacc aggctttcca cgcccgcgtg ccgctccatg tcgttcgcgc 41100
ggttctcgga aacgcgctgc cgcgtttcgt gattgtcacg ctcaagcccg tagtcccgtt 41160
cgagcgtcgc gcagaggtca gcgagggcgc ggtaggcccg atacggctca tggatggtgt 41220
ttcgggtcgg gtgaatcttg ttgatggcga tatggatgtg caggttgtcg gtgtcgtgat 41280
gcacggcact gacgcgctga tgctcggcga agccaagccc agcgcagatg cggtcctcaa 41340
tcgcgcgcaa cgtctccgcg tcgggcttct ctcccgcgcg gaagctaacc agcaggtgat 41400
aggtcttgtc ggcctcggaa cgggtgttgc cgtgctgggt cgccatcacc tcggccatga 41460
cagcgggcag ggtgtttgcc tcgcagttcg tgacgcgcac gtgacccagg cgctcggtct 41520
tgccttgctc gtcggtgatg tacttcacca gctccgcgaa gtcgctcttc ttgatggagc 41580
gcatggggac gtgcttggca atcacgcgca ccccccggcc gttttagcgg ctaaaaaagt 41640
catggctctg ccctcgggcg gaccacgccc atcatgacct tgccaagctc gtcctgcttc 41700
tcttcgatct tcgccagcag ggcgaggatc gtggcatcac cgaaccgcgc cgtgcgcggg 41760
tcgtcggtga gccagagttt cagcaggccg cccaggcggc ccaggtcgcc attgatgcgg 41820
gccagctcgc ggacgtgctc atagtccacg acgcccgtga ttttgtagcc ctggccgacg 41880
gccagcaggt aggccgacag gctcatgccg gccgccgccg ccttttcctc aatcgctctt 41940
cgttcgtctg gaaggcagta caccttgata ggtgggctgc ccttcctggt tggcttggtt 42000
tcatcagcca tccgcttgcc ctcatctgtt acgccggcgg tagccggcca gcctcgcaga 42060
gcaggattcc cgttgagcac cgccaggtgc gaataaggga cagtgaagaa ggaacacccg 42120
ctcgcgggtg ggcctacttc acctatcctg cccggctgac gccgttggat acaccaagga 42180
aagtctacac gaacccttg gcaaaatcct gtatatcgtg cgaaaaagga tggatatacc 42240
gaaaaaatcg ctataatgac cccgaagcag ggttatgcag cggaaaagcg ctgcttccct 42300
gctgttttgt ggaatatcta ccgactggaa acaggcaaat gcaggaaatt actgaactga 42360
ggggacaggc gagagacgat gccaaagagc tacaccgacg agctggccga gtgggttgaa 42420
tcccgcgcgg ccaagaagcg ccggcgtgat gaggctgcgg ttgcgttcct ggcggtgagg 42480
gcggatgtcg aggcggcgtt agcgtccggc tatgcgctcg tcaccatttg ggagcacatg 42540
cgggaaacgg ggaaggtcaa gttctcctac gagacgttcc gctcgcacgc caggcggcac 42600
atcaaggcca agcccgccga tgtgcccgca ccgcaggcca aggctgcgga acccgcgccg 42660
gcacccaaga cgccggagcc acggcggccg aagcaggggg gcaaggctga aaagccggcc 42720
cccgctgcgg ccccgaccgg cttcaccttc aacccaacac cggacaaaaa ggatctactg 42780
taatggcgaa aattcacatg gttttgcagg gcaagggcgg ggtcggcaag tcggccatcg 42840
ccgcgatcat tgcgcagtac aagatggaca aggggcagac acccttgtgc atcgacaccg 42900
acccggtgaa cgcgacgttc gagggctaca aggccctgaa cgtccgccgg ctgaacatca 42960
tggccggcga cgaaattaac tcgcgcaact tcgacaccct ggtcgagctg attgcgccga 43020
ccaaggatga cgtggtgatc gacaacggtg ccagctcgtt cgtgcctctg tcgcattacc 43080
tcatcagcaa ccaggtgccg gctctgctgc aagaaatggg gcatgagctg gtcatccata 43140
ccgtcgtcac cggcggccag gctctcctgg acacggtgag cggcttcgcc cagctcgcca 43200
gccagttccc ggccgaagcg cttttcgtgg tctggctgaa cccgtattgg gggcctatcg 43260
agcatgaggg caagagcttt gagcagatga aggcgtacac ggccaacaag gcccgcgtgt 43320
cgtccatcat ccagattccg gccctcaagg aagaaaccta cggccgcgat ttcagcgaca 43380
tgctgcaaga gcggctgacg ttcgaccagg cgctggccga tgaatcgctc acgatcatga 43440
cgcggcaacg cctcaagatc gtgcggcgcg gcctgtttga acagctcgac gcggcggccg 43500
tgctatgagc gaccagattg aagagctgat ccgggagatt gcggccaagc acggcatcgc 43560
cgtcggccgc gacgacccgg tgctgatcct gcataccatc aacgcccggc tcatggccga 43620
cagtgcggcc aagcaagagg aaatccttgc cgcgttcaag gaagagctgg aagggatcgc 43680
ccatcgttgg ggcgaggacg ccaaggccaa agcggagcgg atgctgaacg cggccctggc 43740
ggccagcaag gacgcaatgg cgaaggtaat gaaggacagc gccgcgcagg cggccgaagc 43800
gatccgcagg gaaatcgacg acggccttgg ccgccagctc gcggccaagg tcgcggacgc 43860
gcggcgcgtg gcgatgatga acatgatcgc cggcggcatg gtgttgttcg cggccgccct 43920
ggtggtgtgg gcctcgttat gaatcgcaga ggcgcagatg aaaaagcccg gcgttgccgg 43980
gcttgttttt gcgttagctg ggcttgtttg acaggcccaa gctctgactg cgcccgcgct 44040
cgcgctcctg ggcctgtttc ttctcctgct cctgcttgcg catcagggcc tggtgccgtc 44100
gggctgcttc acgcatcgaa tcccagtcgc cggccagctc gggatcgtcc gcgcgcatct 44160
tgcgcgtcgc cagttcctcg atcttgggcg cgtgaatgcc catgccttcc ttgatttcgc 44220
gcaccatgtc cagccgcgtg tgcagggtct gcaagcgggc ttgctgttgg gcctgctgct 44280
gctgccaggc ggcctttgta cgcggcaggg acagcaagcc gggggcattg gactgtagct 44340
gctgcaaacg cgcctgctga cggtctacga gctgttctag gcggtcctcg atgcgctcca 44400
cctggtcatg ctttgcctgc acgtagagcg caagggtctg ctggtaggtc tgctcgatgg 44460
gcgcggattc taagagggcc tgctgttccg tctcggcctc ctgggccgcc tgtagcaaat 44520
cctcgccgct gttgccgctg gactgcttta ctgccgggga ctgctgttgc cctgctcgcg 44580
ccgtcgtcgc agttcggctt gcccccactc gattgactgc ttcatttcga gccgcagcga 44640
tgcgatctcg gattgcgtca acggacgggg cagcgcggag gtgtccggct tctccttggg 44700
tgagtcggtc gatgccatag ccaaaggttt ccttccaaaa tgcgtccatt gctggaccgt 44760
gtttctcatt gatgcccgca agcatcttcg gcttgaccgc caggtcaagc gcgccttcat 44820
gggcggtcat gacggacgcc gccatgacct tgccgccgtt gttctcgatg tagccgcgta 44880
atgaggcaat ggtgccgccc atcgtcagcg tgtcatcgac aacgatgtac ttctggccgg 44940
ggatcacctc cccctcgaaa gtcgggttga acgccaggcg atgatctgaa ccggctccgg 45000
ttcgggcgac cttctcccgc tgcacaatgt ccgtttcgac ctcaaggcca aggcggtcgg 45060
ccagaacgac cgccatcatg gccggaatct tgttgttccc cgccgcctcg acggcgagga 45120
ctggaacgat gcggggcttg tcgtcgccga tcagcgtctt gagctgggca acagtgtcgt 45180
ccgaaatcag gcgctcgacc aaattaagcg ccgcttccgc gtcgccctgc ttcgcagcct 45240
ggtattcagg ctcgttggtc aaagaaccaa ggtcgccgtt gcgaaccacc ttcgggaagt 45300
ctccccacgg tgcgcgctcg gctctgctgt agctgctcaa gacgcctccc tttttagccg 45360
ctaaaactct aacgagtgcg cccgcgactc aacttgacgc tttcggcact tacctgtgcc 45420
ttgccacttg cgtcataggt gatgcttttc gcactcccga tttcaggtac tttatcgaaa 45480
tctgaccggg cgtgcattac aaagttcttc cccacctgtt ggtaaatgct gccgctatct 45540
gcgtggacga tgctgccgtc gtggcgctgc gacttatcgg ccttttgggc catatagatg 45600
ttgtaaatgc caggtttcag ggccccggct ttatctacct tcgtggttcg tccatgcgcc 45660
ttggttctcg gtctcggaca attctttcgc ccattcatga ccaggaggcg gtgtttcatt 45720
gggtgactcc tgacggttgc ctctggtgtt caaacgtgtc ctggtcgctt gccggctaaa 45780
aaaaagccga cctcggcagt tcgaggccgg ctttccctag agccgggcgc gtcaaggttg 45840
ttccatctat tttagtgaac tgcgttcgat ttatcagtta ctttcctccc gctttgtgtt 45900
tcctcccact cgtttccgcg tctagccgac ccctcaacat agcggcctct tcttgggctg 45960
cctttgcctc ttgccgcgct tcgtcacgct cggcttgcac cgtcgtaaag cgctcggcct 46020
gcctggccgc ctcttgcgcc gccaacttcc tttgctcctg gtgggcctcg gcgtcggcct 46080
gcgccttcgc tttcaccgct gccaactccg tgcgcaaact ctccgcttcg cgcctggtcg 46140
cgtcgcgctc gccgcgaagc gcctgcattt cctggttggc cgcgtccagg gtcttgcggc 46200
tctcttcttt gaatgcgcgg gcgtcctggt gagcgtagtc cagctcggcg cgcagctcct 46260
gcgctcgacg ctccacctcg tcggcccgct gcgtcgccag cgcggcccgc tgctcggctc 46320
ctgccagggc ggtgcgtgct tcggccaggg cttgccgctg gcgtgcggcc agctcggccg 46380
cctcggcggc ctgctgctct agcaatgtaa cgcgcgcctg ggcttcttcc agctcgcggg 46440
cctgcgcctc gaaggcgtcg gccagctccc cgcgcacggc ttccaactcg ttgcgctcac 46500
gatcccagcc ggcttgcgct gcctgcaacg attcattggc aagggcctgg gcggcttgcc 46560
agagggcggc cacggcctgg ttgccggcct gctgcaccgc gtccggcacc tggactgcca 46620
gcggggcggc ctgcgccgtg cgctggcgtc gccattcgcg catgccggcg ctggcgtcgt 46680
tcatgttgac gcgggcggcc ttacgcactg catccacggt cgggaagttc tcccggtcgc 46740
cttgctcgaa cagctcgtcc gcagccgcaa aaatgcggtc gcgcgtctct ttgttcagtt 46800
ccatgttggc tccggtaatt ggtaagaata ataatactct tacctacctt atcagcgcaa 46860
gagtttagct gaacagttct cgacttaacg gcaggttttt tagcggctga agggcaggca 46920
aaaaaagccc cgcacggtcg gcgggggcaa agggtcagcg ggaaggggat tagcgggcgt 46980
cgggcttctt catgcgtcgg ggccgcgctt cttgggatgg agcacgacga agcgcgcacg 47040
cgcatcgtcc tcggccctat cggcccgcgt cgcggtcagg aacttgtcgc gcgctaggtc 47100
ctccctggtg ggcaccaggg gcatgaactc ggcctgctcg atgtaggtcc actccatgac 47160
cgcatcgcag tcgaggccgc gttccttcac cgtctcttgc aggtcgcggt acgcccgctc 47220
gttgagcggc tggtaacggg ccaattggtc gtaaatggct gtcggccatg agcggccttt 47280
cctgttgagc cagcagccga cgacgaagcc ggcaatgcag gcccctggca caaccaggcc 47340
gacgccgggg gcaggggatg gcagcagctc gccaaccagg aaccccgccg cgatgatgcc 47400
gatgccggtc aaccagccct tgaaactatc cggccccgaa acacccctgc gcattgcctg 47460

-continued gatgctgcgc cggatagctt gcaacatcag gagccgtttc ttttgttcgt cagtcatggt 47520
ccgccctcac cagttgttcg tatcggtgtc ggacgaactg aaatcgcaag agctgccggt 47580
atcggtccag ccgctgtccg tgtcgctgct gccgaagcac ggcgaggggt ccgcgaacgc 47640
cgcagacggc gtatccggcc gcagcgcatc gcccagcatg gccccggtca gcgagccgcc 47700
ggccaggtag cccagcatgg tgctgttggt cgccgccggc caccagggcc gacgtgacga 47760
aatcgccgtc attccctctg gattgttcgc tgctcggcgg ggcagtgcgc cgcgccggcg 47820
gcgtcgtgga tggctcgggt tggctggcct gcgacggccg gcgaaaggtg cgcagcagct 47880
cgttatcgac cggctgcggc gtcggggccg ccgccttgcg ctgcggtcgg tgttccttct 47940
tcggctcgcg cagcttgaac agcatgatcg cggaaaccag cagcaacgcc gcgcctacgc 48000
ctcccgcgat gtagaacagc atcggattca ttcttcggtc ctccttgtag cggaaccgtt 48060
gtctgtgcgg cgcgggtggc ccgcgccgct gtctttgggg atcagccctc gatgagcgcg 48120
accagtttca cgtcggcaag gttcgcctcg aactcctggc cgtcgtcctc gtacttcaac 48180
caggcatagc cttccgccgg cggccgacgg ttgaggataa ggcgggcagg gcgctcgtcg 48240
tgctcgacct ggacgatggc ctttttcagc ttgtccgggt ccggctcctt cgcgcccttt 48300
tccttggcgt ccttaccgtc ctggtcgccg tcctcgccgt cctggccgtc gccggcctcc 48360
gcgtcacgct cggcatcagt ctggccgttg aaggcatcga cggtgttggg atcgcggccc 48420
ttctcgtcca ggaactcgcg cagcagcttg accgtgccgc gcgtgatttc ctgggtgtcg 48480
tcgtcaagcc acgcctcgac ttcctccggg cgcttcttga aggccgtcac cagctcgttc 48540
accacggtca cgtcgcgcac gcggccggtg ttgaacgcat cggcgatctt ctccggcagg 48600
tccagcagcg tgacgtgctg ggtgatgaac gccggcgact tgccgatttc cttggcgata 48660
tcgcctttct tcttgccctt cgccagctcg cggccaatga agtcggcaat ttcgcgcggg 48720
gtcagctcgt tgcgttgcag gttctcgata acctggtcgg cttcgttgta gtcgttgtcg 48780
atgaacgccg ggatggactt cttgccggcc cacttcgagc cacggtagcg gcgggcgccg 48840
tgattgatga tatagcggcc cggctgctcc tggttctcgc gcaccgaaat gggtgacttc 48900
accccgcgct ctttgatcgt ggcaccgatt tccgcgatgc tctccgggga aaagccgggg 48960
ttgtcggccg tccgcggctg atgcggatct tcgtcgatca ggtccaggtc cagctcgata 49020
gggccggaac cgccctgaga cgccgcagga gcgtccagga ggctcgacag gtcgccgatg 49080
ctatccaacc ccaggccgga cggctgcgcc gcgcctgcgg cttcctgagc ggccgcagcg 49140
gtgtttttct tggtggtctt ggcttgagcc gcagtcattg ggaaatctcc atcttcgtga 49200
acacgtaatc agccagggcg cgaacctctt tcgatgcctt gcgcgcggcc gttttcttga 49260
tcttccagac cggcacaccg gatgcgaggg catcggcgat gctgctgcgc aggccaacgg 49320
tggccggaat catcatcttg gggtacgcgg ccagcagctc ggcttggtgg cgcgcgtggc 49380
gcggattccg cgcatcgacc ttgctgggca ccatgccaag gaattgcagc ttggcgttct 49440
tctggcgcac gttcgcaatg gtcgtgacca tcttcttgat gccctggatg ctgtacgcct 49500
caagctcgat gggggacagc acatagtcgg ccgcgaagag ggcggccgcc aggccgacgc 49560
caagggtcgg ggccgtgtcg atcaggcaca cgtcgaagcc ttggttcgcc agggccttga 49620
tgttcgcccc gaacagctcg cgggcgtcgt ccagcgacag ccgttcggcg ttcgccagta 49680
ccgggttgga ctcgatgagg gcgaggcgcg cggcctggcc gtcgccggct gcgggtgcgg 49740
tttcggtcca gccgccggca gggacagcgc cgaacagctt gcttgcatgc aggccggtag 49800
caaagtcctt gagcgtgtag gacgcattgc cctgggggtc caggtcgatc acggcaaccc 49860
gcaagccgcg ctcgaaaaag tcgaaggcaa gatgcacaag ggtcgaagtc ttgccgacgc 49920
cgcctttctg gttggccgtg accaaagttt tcatcgtttg gtttcctgtt ttttcttggc 49980
gtccgcttcc cacttccgga cgatgtacgc ctgatgttcc ggcagaaccg ccgttacccg 50040
cgcgtacccc tcgggcaagt tcttgtcctc gaacgcggcc cacacgcgat gcaccgcttg 50100
cgacactgcg cccctggtca gtcccagcga cgttgcgaac gtcgcctgtg gcttcccatc 50160
gactaagacg ccccgcgcta tctcgatggt ctgctgcccc acttccagcc cctggatcgc 50220
ctcctggaac tggctttcgg taagccgttt cttcatggat aacacccata atttgctccg 50280
cgccttggtt gaacatagcg gtgacagccg ccagcacatg agagaagttt agctaaacat 50340
ttctcgcacg tcaacacctt tagccgctaa aactcgtcct tggcgtaaca aaacaaaagc 50400
ccggaaaccg ggctttcgtc tcttgccgct tatggctctg cacccggctc catcaccaac 50460
aggtcgcgca cgcgcttcac tcggttgcgg atcgacactg ccagcccaac aaagccggtt 50520
gccgccgccg ccaggatcgc gccgatgatg ccggccacac cggccatcgc ccaccaggtc 50580
gccgccttcc ggttccattc ctgctggtac tgcttcgcaa tgctggacct cggctcacca 50640
taggctgacc gctcgatggc gtatgccgct tctccccttg gcgtaaaacc cagcgccgca 50700
ggcggcattg ccatgctgcc cgccgctttc ccgaccacga cgcgcgcacc aggcttgcgg 50760
tccagacctt cggccacggc gagctgcgca aggacataat cagccgccga cttggctcca 50820
cgcgcctcga tcagctcttg cactcgcgcg aaatccttgg cctccacggc cgccatgaat 50880
cgcgcacgcg gcgaaggctc cgcagggccg gcgtcgtgat cgccgccgag aatgcccttc 50940
accaagttcg acgacacgaa aatcatgctg acggctatca ccatcatgca gacggatcgc 51000
acgaacccgc tg 51012

<210> SEQ ID NO 177
<211> LENGTH: 460
<212> TYPE: DNA
<213> ORGANISM: Artificial Sequence
<220> FEATURE:
<223> OTHER INFORMATION: Synthetic sgRNA

<400> SEQUENCE: 177
aggaggtgac tgatggccgg tccgactata tgattttccg cagtattctt tttgatgcaa 60
tccgctttgc ttctgactat aatagtcagg gtaaggggtg cgaaaaacac agcggcactt 120
ctcggtttta gagctagaaa tagcaagtta aaataaggct agtccgttat cacgtcgaaa 180
gacgggcacc gagtcggtgc ttttggactg gcatccgttg ggtgctggtc cgtattcttt 240
agaaaactaa tacttttcta ccgtttgcga ttattccccc gatactggct tttacggcta 300
cttttgcgcg atgtcagact gcgatttccg tttgaactaa gacagcgatg actaatgcca 360
cgacgatagc taccaaagta accactgcaa agtcgatcga gacccttgag agccttcaac 420
ccggtctcta ctgcggaccg atggaaaaac gcctgctacg 460

<210> SEQ ID NO 178
<211> LENGTH: 459
<212> TYPE: DNA
<213> ORGANISM: Artificial Sequence
<220> FEATURE:
<223> OTHER INFORMATION: Synthetic sgRNA

<400> SEQUENCE: 178
aggaggtgac tgatggccgg tccgactata tgatgaagac cacgatcccg tctaatgcgc 60
ttccctgttt ttatgttatt ctctctgtaa aggtcgcgcg tctgtccatc ccacttaaag 120
actgccccag agctagaaat agcaagttgg ggtaaggcta gtccgttatc aacttgaaaa 180
agtggcaccg agtcggtgct ttagccgtgc tgtttgcgcg gttcttcggt ccatccgtga 240
ctggggcaat tttgaataat ggtcatgtga ggacatagta gttttcggta catactgcga 300
atgaccttgc catttaagtc tctgacgcga aaggtaagac cgaaattact cctaaataaa 360
caaacactta tagttccggt tagtcgatcg agacccttga gagccttcaa cccggtctct 420
actgacgtct tccggaccga tggaaaaacg cctgctacg 459

<210> SEQ ID NO 179
<211> LENGTH: 436
<212> TYPE: DNA
<213> ORGANISM: Artificial Sequence
<220> FEATURE:
<223> OTHER INFORMATION: Synthetic sgRNA

<400> SEQUENCE: 179
aggaggtgac tgatggccgg tccgactata tgatgaagac cacgattgta agtttataca 60
taggcgagta ctctgttatg gagctggcgg aaaaccagat cgccaaaccg tgttttagag 120
acaagttaaa ataaggctag tccgttatca acttgaaaaa gtggcaccga gtcggtgctt 180
taggccgcct ggcgcggcct gacatctcca gccggaacga ttaccattac cacgatgacc 240
actaaaacga ccgagattaa gggtttaccg agttcagcca ctgccactat taagtggaaa 300
ttacttatta aaggcagtta taaatggaag ggagggagtt agccaactta cagcgggaaa 360
tcgatcgaga cccttgagag ccttcaaccc ggtctctact gacgtcttcc ggaccgatgg 420
aaaaacgcct gctacg 436

<210> SEQ ID NO 180
<211> LENGTH: 458
<212> TYPE: DNA
<213> ORGANISM: Artificial Sequence
<220> FEATURE:
<223> OTHER INFORMATION: Synthetic sgRNA

<400> SEQUENCE: 180
aggaggtgac tgatggccgg tccgactata tgatgaagac cacgatttga taaattcact 60
attgactctt ctcagcgtct taatctaagc tatcgtaccg agccgacgtt aaacaccgcc 120
attccgtttt agagctagaa atagcaagtt aaaataaggc tagtccgtaa cttgaaaaag 180
tggcaccgag tcggtgcttt aagggctggt attccagccc ttttatctga ggaaatcgtt 240
ttagggtatg tcttttaagt aaatgattgc agacctttct gctgttttga aatctagcaa 300
tgcgattgat actcccgaca gacaccttac gatgtccgca acatcaaaca tgaccactgc 360
tttgagtcac aatgccatgt actcgatcga gacccttgag agccttcaac ccggtctcta 420
ctgacgtctt ccggaccgat ggaaaaacgc ctgctacg 458

<210> SEQ ID NO 181
<211> LENGTH: 465
<212> TYPE: DNA
<213> ORGANISM: Artificial Sequence
<220> FEATURE:
<223> OTHER INFORMATION: Synthetic sgRNA

<400> SEQUENCE: 181
aggaggtgac tgatggccgg tccgactata tgatgaagac cacgatccaa cgtcctgact 60
ggtataatga gccagttctt aaaatcgcat aaggtagcaa aagctggcgg cgctggagaa 120
aagcaggttt tagagctaga aatagcaagt taaaataagg ctagtccgtt atcacgccga 180
aaggcgggca ccgagtcggt gctttttccg gcgtttctca acgccggaac agtgcgctta 240
gacgtaatca acttacacca taaggattta gagttgacta cttagaaaga tggacattat 300
tacaacaagg caatcaagca aaataattgc atctaaaaag aagggttgca ggactgacca 360
tattactcgg tcaagaattt tagcgtattt cgatcgagac ccttgagagc cttcaacccg 420
gtctctactg acgtcttccg gaccgatgga aaaacgcctg ctacg 465

<210> SEQ ID NO 182
<211> LENGTH: 476
<212> TYPE: DNA
<213> ORGANISM: Artificial Sequence
<220> FEATURE:
<223> OTHER INFORMATION: Synthetic sgRNA

<400> SEQUENCE: 182
aggaggtgac tgatggccgg tccgactata tgatgaagac cacgatggta aaccatatga 60
attttctatt gattgtgaca aaataaactt attccgcgcg gccgcgctac agtacagcga 120
taacggtttt agagctagaa atagcaagtt aaaataaggc tagtccgtta tcaacttgag 180
aaatcaagtg gcaccgagtc ggtgctttaa ataaagccct gagtttaacc gctcggggct 240
ttttgcgttt taggtcagat ttgtaaaatg ataatggggg agaacgtttt gaagaaaacg 300
ttttcggaga gcgataaaac caaaaatagc agcagaccat ttgctcccaa tactatcaca 360
acgagaatga tacggagcat taaggaaaac cgcaatacat tcgatcgaga cccttgagag 420
ccttcaaccc ggtctctact gacgtcttcc ggaccgatgg aaaaacgcct gctacg 476

<210> SEQ ID NO 183
<211> LENGTH: 488
<212> TYPE: DNA
<213> ORGANISM: Artificial Sequence
<220> FEATURE:
<223> OTHER INFORMATION: Synthetic sgRNA

<400> SEQUENCE: 183
aggaggtgac tgatggccgg tccgactata tgatgaagac cacgatccgt gacggatcct 60
ggtgcaaaac ctttcgcggt atggcatgat agcgcccgcc gccaatttgt tgctgaagga 120
gttggggttt tagagctaga aatagcaagt taaaataagg ctagtccgtt atcagcggga 180
aaccgcggca ccgagtcggt gcttttctga cgataatgcc cgctgatgat cacccggcgg 240
gcattattca ggctgcttaa accagactgg acggagttgg aggacagtta cgaccgccgc 300
cgagactacc accaagacca ccgccgagac tcccaccacc gagactccca ccgccaagac 360
tcccaccgcc gagactccct ccgccaaggc caccaccgag actaaggcca cttcgatcga 420
gacccttgag agccttcaac ccggtctcta ctgacgtctt ccggaccgat ggaaaaacgc 480
ctgctacg 488

<210> SEQ ID NO 184
<211> LENGTH: 495
<212> TYPE: DNA
<213> ORGANISM: Artificial Sequence
<220> FEATURE:
<223> OTHER INFORMATION: Synthetic sgRNA

<400> SEQUENCE: 184
aggaggtgac tgatggccgg tccgactata tgatgaagac cacgatggca cgtaagaggt 60

```
tccaactttc accataatga aataagatca ctaccgggcg tattttttga gggctagtta    120

aaaataaaat tgaagttttt tatccggggg agagctagaa atagcaagtt cccctaaggc    180

tagtccgtta tcaacttgaa aaagtggcac cgagtcggtg ctttgggcgg gcaaacagca    240

taaacgcgtt tgcccgctta ctgattatta cagaaaccgc gaccatttgg tatacttaaa    300

agataactaa cactgtttta tttgaataag gcaccacaga aacgcaaaga aaatatacaa    360

cggtggaaat acatacataa aagatgcaaa cgattgtatg acgcattatt cctcagaatt    420

cgatcgagac ccttgagagc cttcaacccg gtctctactg acgtcttccg gaccgatgga    480

aaaacgcctg ctacg                                                      495
```

<210> SEQ ID NO 185
<211> LENGTH: 463
<212> TYPE: DNA
<213> ORGANISM: Artificial Sequence
<220> FEATURE:
<223> OTHER INFORMATION: Synthetic sgRNA

<400> SEQUENCE: 185

```
aggaggtgac tgatggccgg tccgactata tgatgaagac cacgattatt aacgtttaca     60

atttaaatat ttgcttatac aatcttcctg ttttgccttg accgctggga aacggaactg    120

aatggtttta gagctagaaa tagcaagtta aaataaggct agtccgttat caacttggaa    180

acaagtggca ccgagtcggt gctttaaggc gactgatgag tcgccttttt tttgtctgcc    240

gtgaataggc ggaccatgac tcgttttggg gcgattagga ttaggaagag aactcctcag    300

agtcggagaa ttatgaaagt acaaagtctt attatccaag gctttatccg tcccccgtaa    360

ttgacaaata tgcccgtgac aatgagttcg atcgagaccc ttgagagcct tcaacccggt    420

ctctactgac gtcttccgga ccgatggaaa aacgcctgct acg                      463
```

<210> SEQ ID NO 186
<211> LENGTH: 463
<212> TYPE: DNA
<213> ORGANISM: Artificial Sequence
<220> FEATURE:
<223> OTHER INFORMATION: Synthetic sgRNA

<400> SEQUENCE: 186

```
aggaggtgac tgatggccgg tccgactata tgatgaagac cacgataatt cacctcgaaa     60

gcaagctgat aaaccgatac aattaaaggc tcctttaact ggcgaactac ttactctagc    120

ttccgtttta gagctagaaa tagcaagtta aaataaggct agtccgttat catgaagaaa    180

ttcaggcacc gagtcggtgc tttcgccgga tgaaaagtca tccggcgtca tattactcca    240

aggataaccc gaacgatagg gacttttact cccaccaccg agactcccac cgccaagact    300

cccaccgcca agactcccac cgccatgatt tggaggactc atgccactat gtggataagg    360

cccgatatga atatagttgg gagagcttcg atcgagaccc ttgagagcct tcaacccggt    420

ctctactgac gtcttccgga ccgatggaaa aacgcctgct acg                      463
```

<210> SEQ ID NO 187
<211> LENGTH: 518
<212> TYPE: DNA
<213> ORGANISM: Artificial Sequence
<220> FEATURE:
<223> OTHER INFORMATION: Synthetic sgRNA

<400> SEQUENCE: 187

```
aggaggtgac tgatggccgg tccgactata tgatgaagac cacgattgat cggcacgtaa     60
```

-continued gaggttccaa ctttcaccat aatgaaataa gatcactacc gggcgtattt tttgagttat 120
cgagattttc aggagctaag gaagctaaag aagttaacgg gtggggcgtt gttcctaaac 180
agggggagag ctagaaatag caagttcccc taaggctagt ccgttatcaa cttgaaaaag 240
tggcaccgag tcggtgcttt agtcaaaagc ctccgaccgg aggcttttga ctacagaaac 300
cgcgaccatt tggtatactt aaaagataac taacactgtt ttatttgaat aaggcaccac 360
agaaacgcaa agaaaatata caacggtgga aatacataca taaaagatgc aaacgattgt 420
atgacgcatt attcctcaga atccgatcga gacccttgag agccttcaac ccggtctcta 480
ctgacgtctt ccggaccgat ggaaaaacgc ctgctacg 518

<210> SEQ ID NO 188
<211> LENGTH: 457
<212> TYPE: DNA
<213> ORGANISM: Artificial Sequence
<220> FEATURE:
<223> OTHER INFORMATION: Synthetic sgRNA

<400> SEQUENCE: 188
aggaggtgac tgatggccgg tccgactata tgatgaagac cacgattgta agtttataca 60
taggcgagta ctctgttatg ggccttgacc gctgggaaac ggaactgaat ggttttagag 120
ctagaaatag caagttaaaa taaggctagt ccgttatcaa cttgaaaaag tgcgtgcgag 180
tcgcacgttt tcacactggc tcaccttcgg gtgggccttt ctgcgtttat agccgtgaat 240
aggcggacca tgactcgttt tggggcgatt aggattagga agagaactcc tcagagtcgg 300
agaattatga aagtacaaag tcttattatc caaggcttta tccgtccccc gtaattgaca 360
aatatgcccg tgacaatgag ttcgatcgag acccttgaga gccttcaacc cggtctctac 420
tgacgtcttc cggaccgatg gaaaaacgcc tgctacg 457

<210> SEQ ID NO 189
<211> LENGTH: 46
<212> TYPE: DNA
<213> ORGANISM: Artificial Sequence
<220> FEATURE:
<223> OTHER INFORMATION: Left arm sequence of synthetic sgRNA

<400> SEQUENCE: 189
aggaggtgac tgatggccgg tccgactata tgattttccg cagtat 46

<210> SEQ ID NO 190
<211> LENGTH: 50
<212> TYPE: DNA
<213> ORGANISM: Artificial Sequence
<220> FEATURE:
<223> OTHER INFORMATION: Right arm sequence of synthetic sgRNA

<400> SEQUENCE: 190
tcgatcgaga cccttgagag ccttcaaccc ggtctctact gcggaccgat 50

<210> SEQ ID NO 191
<211> LENGTH: 46
<212> TYPE: DNA
<213> ORGANISM: Artificial Sequence
<220> FEATURE:
<223> OTHER INFORMATION: Left arm sequence of synthetic sgRNA

<400> SEQUENCE: 191
aggaggtgac tgatggccgg tccgactata tgatgaagac cacgat 46

<210> SEQ ID NO 192
<211> LENGTH: 57
<212> TYPE: DNA
<213> ORGANISM: Artificial Sequence
<220> FEATURE:
<223> OTHER INFORMATION: Right arm sequence of synthetic sgRNA

<400> SEQUENCE: 192
tcgatcgaga cccttgagag ccttcaaccc ggtctctact gacgtcttcg gaccgat 57

<210> SEQ ID NO 193
<211> LENGTH: 22
<212> TYPE: DNA
<213> ORGANISM: Artificial Sequence
<220> FEATURE:
<223> OTHER INFORMATION: Synthetic primer

<400> SEQUENCE: 193
gacgttgtaa aacgacggcc ag 22

<210> SEQ ID NO 194
<211> LENGTH: 26
<212> TYPE: DNA
<213> ORGANISM: Artificial Sequence
<220> FEATURE:
<223> OTHER INFORMATION: Synthetic primer

<400> SEQUENCE: 194
tcacacagga aacagctatg accatg 26

<210> SEQ ID NO 195
<211> LENGTH: 40
<212> TYPE: DNA
<213> ORGANISM: Artificial Sequence
<220> FEATURE:
<223> OTHER INFORMATION: Partial sequence of sgRNA

<400> SEQUENCE: 195
cgatcgagac ccttgagagc cttcaacccg gtctctactg 40

<210> SEQ ID NO 196
<211> LENGTH: 40
<212> TYPE: DNA
<213> ORGANISM: Artificial Sequence
<220> FEATURE:
<223> OTHER INFORMATION: Partial sequence of sgRNA

<400> SEQUENCE: 196
cagtagagac cgggttgaag gctctcaagg gtctcgatcg 40

<210> SEQ ID NO 197
<211> LENGTH: 11
<212> TYPE: DNA
<213> ORGANISM: Artificial Sequence
<220> FEATURE:
<223> OTHER INFORMATION: Partial sequence of sgRNA

<400> SEQUENCE: 197
cgatcgagac c 11

<210> SEQ ID NO 198
<211> LENGTH: 11
<212> TYPE: DNA
<213> ORGANISM: Artificial Sequence
<220> FEATURE:
<223> OTHER INFORMATION: Partial sequence of sgRNA

<400> SEQUENCE: 198
gctagctctg g 11

<210> SEQ ID NO 199
<211> LENGTH: 21
<212> TYPE: DNA
<213> ORGANISM: Artificial Sequence
<220> FEATURE:
<223> OTHER INFORMATION: Synthetic primer

<400> SEQUENCE: 199
catcggtccg gaagacgtca g 21

<210> SEQ ID NO 200
<211> LENGTH: 18
<212> TYPE: DNA
<213> ORGANISM: Artificial Sequence
<220> FEATURE:
<223> OTHER INFORMATION: Synthetic primer

<400> SEQUENCE: 200
gactgatggc cggtccga 18

<210> SEQ ID NO 201
<211> LENGTH: 22
<212> TYPE: DNA
<213> ORGANISM: Artificial Sequence
<220> FEATURE:
<223> OTHER INFORMATION: Synthetic primer

<400> SEQUENCE: 201
gggttgaagg ctctcaaggg tc 22

<210> SEQ ID NO 202
<211> LENGTH: 26
<212> TYPE: DNA
<213> ORGANISM: Artificial Sequence
<220> FEATURE:
<223> OTHER INFORMATION: Synthetic primer

<400> SEQUENCE: 202
ggtccgacta tatgatgaag accacg 26

<210> SEQ ID NO 203
<211> LENGTH: 986
<212> TYPE: DNA
<213> ORGANISM: Artificial Sequence
<220> FEATURE:
<223> OTHER INFORMATION: Part of synthetic plasmid pNB018

<400> SEQUENCE: 203
tggtttctta gacgtcaggt ggcacttttc ggggaaatgt gcgcggaacc cctatttgtt 60
tatttttcta aatacattca aatatgtatc cgctcatgag acaataaccc tgataaatgc 120
ttcaataata ttgaaaaagg aagagtatga tgagacatcg cgttaagcgg atgatgctaa 180
tgacaacggc ctgtatttcg ctgttgctgg ggagtgcgcc gctgtatgcg caggcgaacg 240
acgttcagca aaagctggcg gcgctggaga aaagcagcgg ggggcggttg ggagtggcgc 300
tgattgacac cgccgataac gcacagacgc tctaccgcgc cgatgagcgc tttgccatgt 360
gcagcaccag taaggtgatg gcggcagcgg ctgtgctcaa gcaaagtgaa acgcaaaaga 420
aggtgttgag tcagaaggtt gagattaaat cttcagacct gattaactac aatcccatta 480

-continued

```
ctgaaaaaca cgtcaacggc acgatgacgc tggcggaatt gagcgccgcg gcgttgcagt    540

acagcgacaa tacggccatg aacaagctga ttgcccatct tggggggccg gataaagtga    600

cggcgtttgc ccgtgcgatt ggggataaca ccttccggct cgatcgtact gagccgacgc    660

tcaacaccgc gatccccggc gacccgcgcg ataccaccac gccattagcg atggcgcaga    720

cgcttcgcaa tctgacgttg ggcagtgcct taggtgaaac tcagcgtgcg caactggtaa    780

cgtggctgaa aggcaatacc accggcgctg ccagcattca ggctgggcta cccacatcgt    840

gggttgtcgg ggataaaacc ggcagcggtg attatggtac gacgaatgac atcgccgtta    900

tctggccgga agggcgtgcg ccgcttattc tggtcactta cttcacccag ccagagcaga    960

agtaaggtct cgcggtatca ttgcag                                         986
```

DELIVERY VEHICLE

FIELD OF THE INVENTION

This invention relates inter alia to a nucleic acid delivery vehicle, compositions including a pharmaceutical composition comprising the delivery vehicle, and methods involving use or manufacture of the delivery vehicle.

INCORPORATION BY REFERENCE OF SEQUENCE LISTING

The Sequence Listing in an ASCII text file, named 35868_Sequence_Listing.txt of 140 KB, created on Feb. 1, 2018, and submitted to the United States Patent and Trademark Office via EFS-Web, is incorporated herein by reference.

BACKGROUND OF THE INVENTION

The transfer or exchange of genetic information between bacteria in the microbiome is widespread in nature and can occur by direct DNA transfer, by bacterial conjugation, and by bacteriophage ("phage") infection.

Direct DNA transfer was demonstrated by Frederick Griffith in 1928, in what, with hindsight, was the first genetic engineering experiment. *Streptococcus pneumoniae* smooth (S) forms are virulent, the rough (R) form is avirulent. Griffith showed that a mixture of heat-killed S and live R when injected into mice resulted in conversion of the live avirulent R forms into virulent S forms leading to pneumonia and death. The "transforming principle" responsible for this conversion was later identified to be DNA by Avery, MacLeod and McCarty in 1944. Many bacterial species are naturally competent for such DNA transformation having specialised DNA uptake mechanisms that allow this. Experimentally, bacteria lacking natural competence can be made competent for DNA transformation by chemical or physical treatment (see Sambrook and Russell, "Molecular Cloning: A Laboratory Manual", 3rd Edition, CSHL Press, 2001, which is hereby incorporated by reference in its entirety) and great use has been made of this in laboratory gene cloning experiments.

Bacterial conjugation, the transfer of genetic information between bacteria, was described in *Escherichia coli* by Lederberg and Tatum in 1946. In 1952, Lederberg coined the term "plasmid" to describe the DNA molecules transferred. In bacteria, plasmids are usually circular DNA (sometimes linear, for example in *Streptomyces*) molecules that replicate independently of the bacterial chromosome and may be capable of transmission between bacteria during bacterial conjugation. They are the agents for the spread of, for example, genes encoding antibiotic resistance genes and virulence genes and genes providing increased metabolic versatility to bacteria receiving them. Plasmid transfer of such genes may also be mediated via transposable genetic elements and integrons that by DNA recombination may move both between different plasmids and between plasmids and the bacterial chromosome. Plasmids are used as DNA vectors for the introduction of recombinant polynucleotides to bacterial cells by direct DNA transfer.

Bacteriophage (also called a "phage" or a "bacterial virus", which terms are used synonymously and interchangeably herein with "bacteriophage"), are single- or double-stranded DNA or RNA viruses encapsidated in a phage protein coat. The protein coat allows recognition of a target bacterial cell. This is followed by infection via delivery of the phage nucleic acid. After infection, lytic phages replicate, produce phage coat proteins, and are packaged and released following cell lysis and death. Other DNAs present in the cell, for example chromosomal and plasmid DNAs, may instead sometimes be packaged into the phage capsid and such genes can then spread following infection of new cells; this is known as general transduction. Temperate phage have an alternative lifestyle in addition to the lytic cycle: the establishment of lysogeny. For example the *E. coli* phage lambda can, following infection, integrate into the bacterial chromosome and remain dormant replicating passively with the bacterial chromosome, yet is able to later excise and enter the lytic cycle. Mis-excision can result in the packaging of adjacent bacterial genes that may also be packaged into the phage and spread following infection of new cells; this is known as specialised transduction. Other phage called non-virulent phage, infect, replicate and are packaged into coat proteins releasing new phage without killing the cell. Phage are also used experimentally as DNA vectors for the introduction of recombinant polynucleotides to bacterial cells by phage infection, for example those based upon the *E. coli* phages (coliphages) lambda and M13.

Direct DNA transfer, plasmids and phage delivery are used in experimental systems for gene cloning, analysis of gene function, and DNA sequencing. They are also used for expression of recombinant proteins for applications in biological therapeutics. Lytic phages have also long been used as a biological therapeutic for the treatment of bacterial infection (see review on "phage therapy" by Nobrega et al., *Trends in Microbiology,* 23: 185-191, 2015, which is hereby incorporated by reference in its entirety).

SUMMARY OF THE INVENTION

The present invention provides a novel nucleic acid delivery vehicle with novel applications and advantages over prior art systems.

According to a first aspect of the present invention, there is provided a pharmaceutical composition comprising a nucleic acid (for example DNA) delivery vehicle (also referred to herein as a "Transmid") for delivering a deliverable nucleic acid into a microorganism such as a bacterial cell, wherein the delivery vehicle comprises a deliverable nucleic acid packaged into one or more bacteriophage coat proteins, and the deliverable nucleic acid comprises:

(a) a vegetative replication origin (such as oriV) and one or more genes (such as one or more rep genes) encoding one or more nucleic acid replication proteins that allow vegetative nucleic acid replication of the deliverable nucleic acid (for example, either in a broad or narrow range of bacterial species);

(b) a transmittal nucleic acid sequence comprising an origin of transfer (such as oriT) and one or more relaxasome nucleic acid sequences encoding relaxasome functions required for plasmid mobilisation during conjugation;

(c) one or more bacteriophage packaging signal sequences that allow packaging of the deliverable nucleic acid into the one or more bacteriophage coat proteins (for example, in vitro or in vivo); and (d) a selected nucleic acid of interest;

such that the delivery vehicle is capable of infecting the bacterial cell to introduce the deliverable nucleic acid into the cell, following which the deliverable nucleic acid is capable of forming a plasmid in the cell and being transmitted to one or more different bacterial cells by conjugation (and not by infection).

The delivery vehicle is preferably non-lytic, such that once the bacterial cell has been infected, the deliverable nucleic acid can be transmitted to the one or more different bacterial cells by conjugation and not further infection. The deliverable nucleic acid thus may exclude functions which allow lytic behaviour found in lytic phage.

The pharmaceutical composition may further comprise an insertion site that allows insertion of the selected nucleic acid of interest into the deliverable nucleic acid using site-specific nucleic acid recombination (such as Cre/lox-mediated recombination).

The one or more different bacterial cells into which the plasmid is transmitted by conjugation may comprise one or more conjugation nucleic acid sequences (such as tra genes) encoding conjugation functions required for plasmid conjugation (for example in a broad or a narrow host range).

Additionally or alternatively, the transmittal nucleic acid sequence may further comprise one or more conjugation nucleic acid sequences (such as tra genes) encoding conjugation functions required for plasmid conjugation (for example in a broad or a narrow host range, and either within and between different bacterial species).

As elaborated below, where the one or more different bacterial cells into which the plasmid is transmitted by conjugation have their own conjugation nucleic acid sequences, the deliverable nucleic acid does not require its own conjugation nucleic acid sequences because the one or more different bacterial cells are conjugation-competent.

However, the deliverable nucleic acid further comprising one or more conjugation nucleic acid sequences is capable of forming and transmitting a plasmid itself (i.e. it is self-transmissible), allowing for transmittal of the selected nucleic acid to the one or more different bacterial cells by plasmid conjugation even where the one or more different bacterial cells do not comprise endogenous one or more conjugation nucleic acid sequences such as tra genes. In other words, the deliverable nucleic acid here provides its own conjugation competency.

In another aspect of the invention, a bacterial cell may be transformed with a conjugative plasmid and infected with a nucleic acid delivery vehicle of the invention (in either order), such that the deliverable nucleic acid can be transmitted by conjugation to one or more different bacterial cells. In this aspect of the invention, a deliverable nucleic acid which does not have its own conjugation nucleic acid sequences may be used, as the conjugation nucleic acid sequences encoding functions required for plasmid conjugation are provided in the conjugative plasmid.

The invention described above encompasses in various aspects methods for making the conjugative-component bacterial cell (for example, a probiotic bacterium) as well as the conjugative-component bacterial cell thus formed.

Host-specific conjugation nucleic acid sequences and/or host-specific conjugative plasmids may be used in this invention.

The selected nucleic acid of the pharmaceutical composition may be one or more or all of the group consisting of:

- one or more gene-inactivating or down-regulating nucleic acid sequences capable of inactivating or down-regulating one or more genes (for example using a Cas9/CRISPR system, TALENS or zinc finger nucleases for gene inactivation or down-regulation); and/or
- one or more further nucleic acid sequences conferring a desired trait to the bacterial cell and/or one or more further bacterial cells.

For example, the one or more genes inactivated or down-regulated may be an antibiotic-resistance gene, a virulence gene, or an essential gene (inactivation or down-regulation of which results in death of the bacterial cells).

The deliverable nucleic acid of the pharmaceutical composition may further comprise genetic functions allowing transposition of the deliverable nucleic acid to a bacterial chromosome (for example, the site-specific DNA transposition system of the bacterial transposon Tn7).

The deliverable nucleic acid of the pharmaceutical composition may further comprise a selection nucleic acid sequence that provides a selective advantage to the bacterial cell acquiring the deliverable nucleic acid (for example: toxin/antitoxin genes, bacteriocins, and DNA sequences ensuring inheritance of the deliverable nucleic acid following bacterial cell division).

The deliverable nucleic acid of the pharmaceutical composition may further comprise a selectable marker (conferring a trait suitable for artificial selection).

The pharmaceutical composition may be formulated for administration via parenteral, oral, topical or inhalation (for example, via an aerosol) methods.

In one aspect, the selected nucleic acid of the pharmaceutical composition is an antibiotic resistance gene-inactivating nucleic acid sequences capable of inactivating one or more antibiotic resistance genes using a Cas9/CRISPR system for gene inactivation.

In another aspect of the invention, there is provided a pharmaceutical composition as defined herein, for use as a medicament.

The pharmaceutical composition may be for use in the treatment of an infection caused by an antibiotic-resistant bacterium.

In a further aspect of the invention there is provided a method of treating an infection in a subject caused by an antibiotic-resistant bacterial cell comprising an antibiotic resistance gene, in which the method comprises the step of introducing into the bacterial cell a therapeutically effective amount of the pharmaceutical composition with an antibiotic resistance gene-inactivating nucleic acid sequences capable of inactivating one or more antibiotic resistance genes as defined herein, thereby inactivating the antibiotic resistance gene and sensitising the bacterial cell to the antibiotic.

In the method of treating, the composition may be administered parenterally, topically, orally, or by inhalation (for example, via aerosol delivery).

The subject being treated may be a fish, a bird, a reptile or a mammal (such as a human).

In the method of treating, the deliverable nucleic acid may be transferred from the antibiotic-resistant bacterial cell directly into another bacterial cell (such as a further antibiotic-resistant bacterial cell) by plasmid conjugation.

The method of treating may further comprise a step of simultaneously or subsequently administering to the subject an antibiotic to which the bacterial cell has become sensitised.

In another aspect of the invention there is provided a method for modifying a bacterial cell in an industrial cell culture, comprising the step of infecting the bacterial cell with the nucleic acid delivery vehicle of the invention as defined herein.

The selected nucleic acid for the above method may for example be a biosynthetic gene or a gene encoding a pharmaceutically active protein (such as an antibody).

Also provided according to the invention is a nucleic acid delivery vehicle as defined herein.

Further provided is a deliverable nucleic acid as defined herein.

In another aspect the invention provides a nucleic acid delivery vehicle as defined herein, for use in the manufacture of a medicament for the treatment or prevention of an infection caused by an antibiotic-resistant bacterium.

The invention also provides a method of inactivating antibiotic resistance in an antibiotic-resistant bacterial cell, the method comprising the step of introducing into the bacterial cell the nucleic acid delivery vehicle as defined herein or the deliverable nucleic acid as defined herein.

In another aspect, the invention provides a method of making a nucleic acid delivery vehicle as defined herein, comprising the steps of constructing the deliverable nucleic acid and then packaging the deliverable nucleic acid into the one or more bacteriophage coat proteins.

Also provided is a method of making a probiotic composition for inactivating antibiotic resistance in a population of antibiotic-resistant bacterial cells, the method comprising the step of introducing into a probiotic bacterium the nucleic acid delivery vehicle as defined herein by infection or the deliverable nucleic acid as defined herein by conjugation, thereby producing a probiotic composition comprising a probiotic bacterium with a deliverable nucleic acid capable of inactivating the antibiotic resistance.

A probiotic composition obtained or obtainable according to the above method is also an aspect of the invention.

BRIEF DESCRIPTION OF THE DRAWINGS

Further aspects, features and non-limiting embodiments of the present invention will now be described below with reference to the following drawings:

FIG. 5. Genes employed in the design c-Transmid, c-TNB001

Functional genetic elements from the plasmids RK2, pBeloBAC11 and pGRG36 are used in order to exemplify a conjugative Transmid, c-Transmid: Function (F) Transfer (TRA), Origin (ORI), Replication (REP), Mobilisation (MOB, Partitioning (PAR), Plasmid maintenance (PM), Regulation of gene expression (RGE), Recombination (REC), Packaging (PK), Antibiotic marker, (AM) Base pair (BP), Size (S), Total (T). The operons and genes in bold letters in the boxes are collected from the corresponding plasmids and assembled to generate a Transmid.

Figure 6:
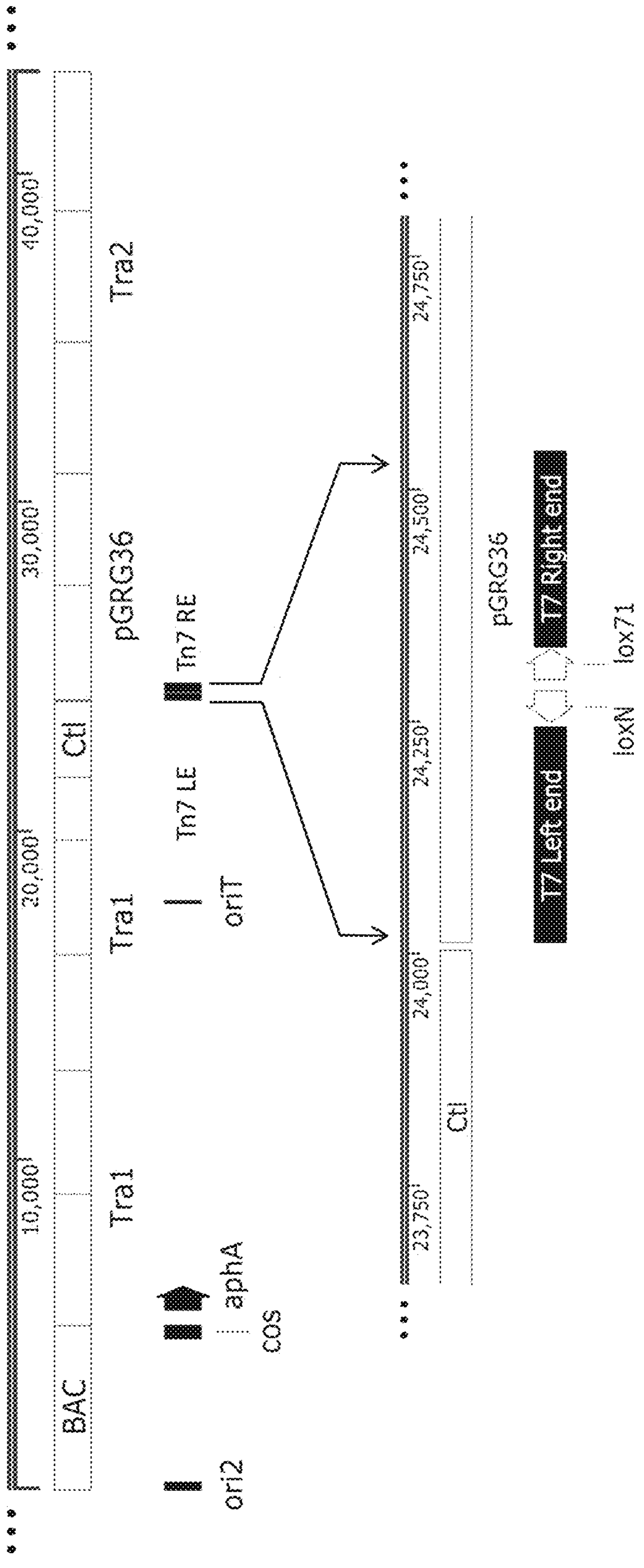

FIG. 6. A structure of c-TNB001 The c-Transmid is circular, this figure shows the linear map of the Transmid. The total size of this Transmid is 43,137 bp. It replicates from the ori2 is taken from pBeloBAC11 (BAC) and is stably maintained following cell division using sopABC of pBeloBAC11. It contains the cos site for lambda packaging from pBeloBAC11; aphA, the antibiotic marker encoding kanamycin resistance (KmR), the Tra1, Tra2 and Ctl operons are taken from RK2. The c-Transmid is transferred from oriT using traIJKA. Transposon Tn7 genes are taken from pGRG36. The inverted lox sites, loxN and lox71 are embedded between Tn7 terminal inverted repeats (TIRs)—the left end (LE) right end (RE); the transposase complex left and right recognition sites, and are shown enlarged in the 23645-24792 region, under the linear map.

Figure 7:
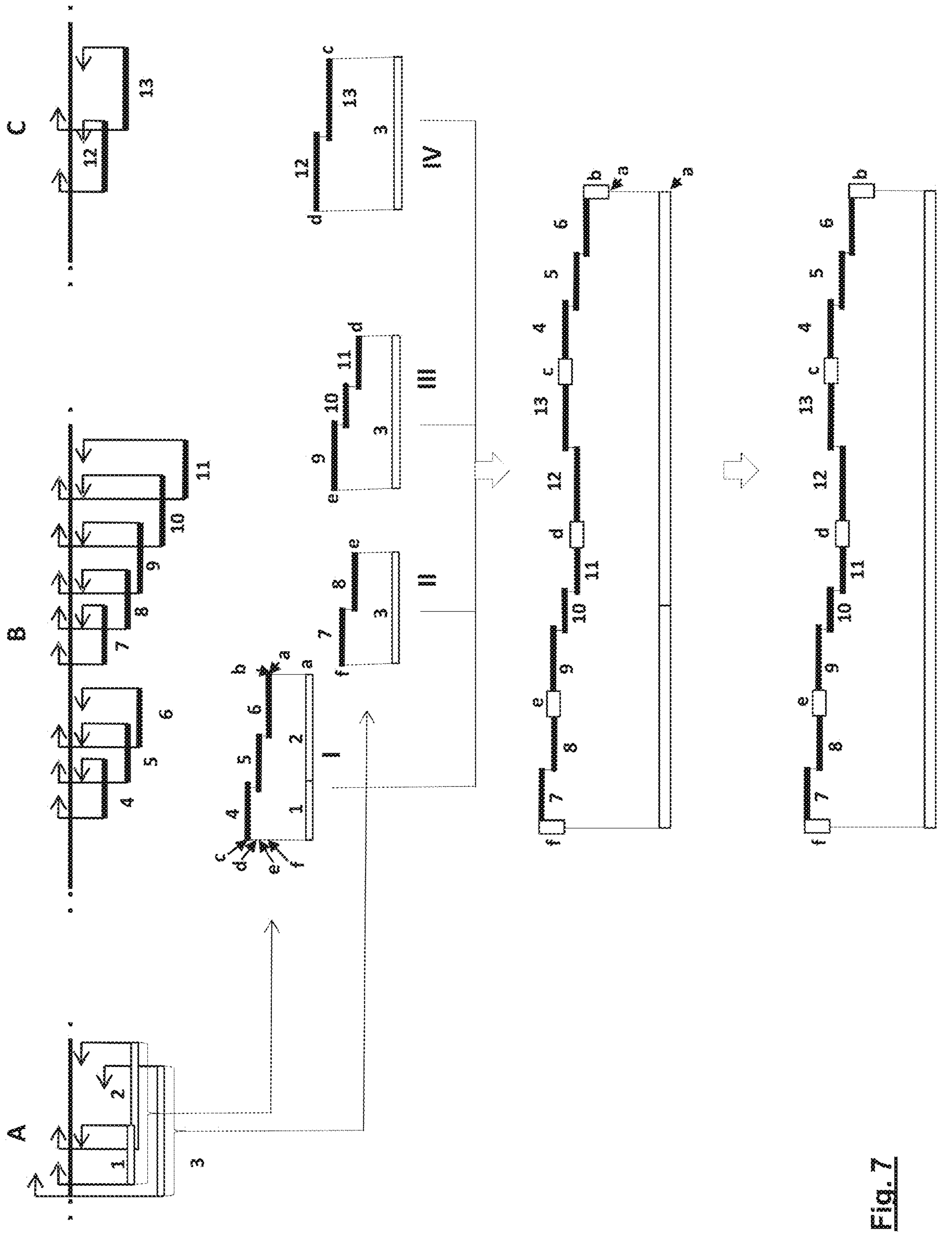

FIG. 7. The c-TNB001 construction scheme

Figure 8:
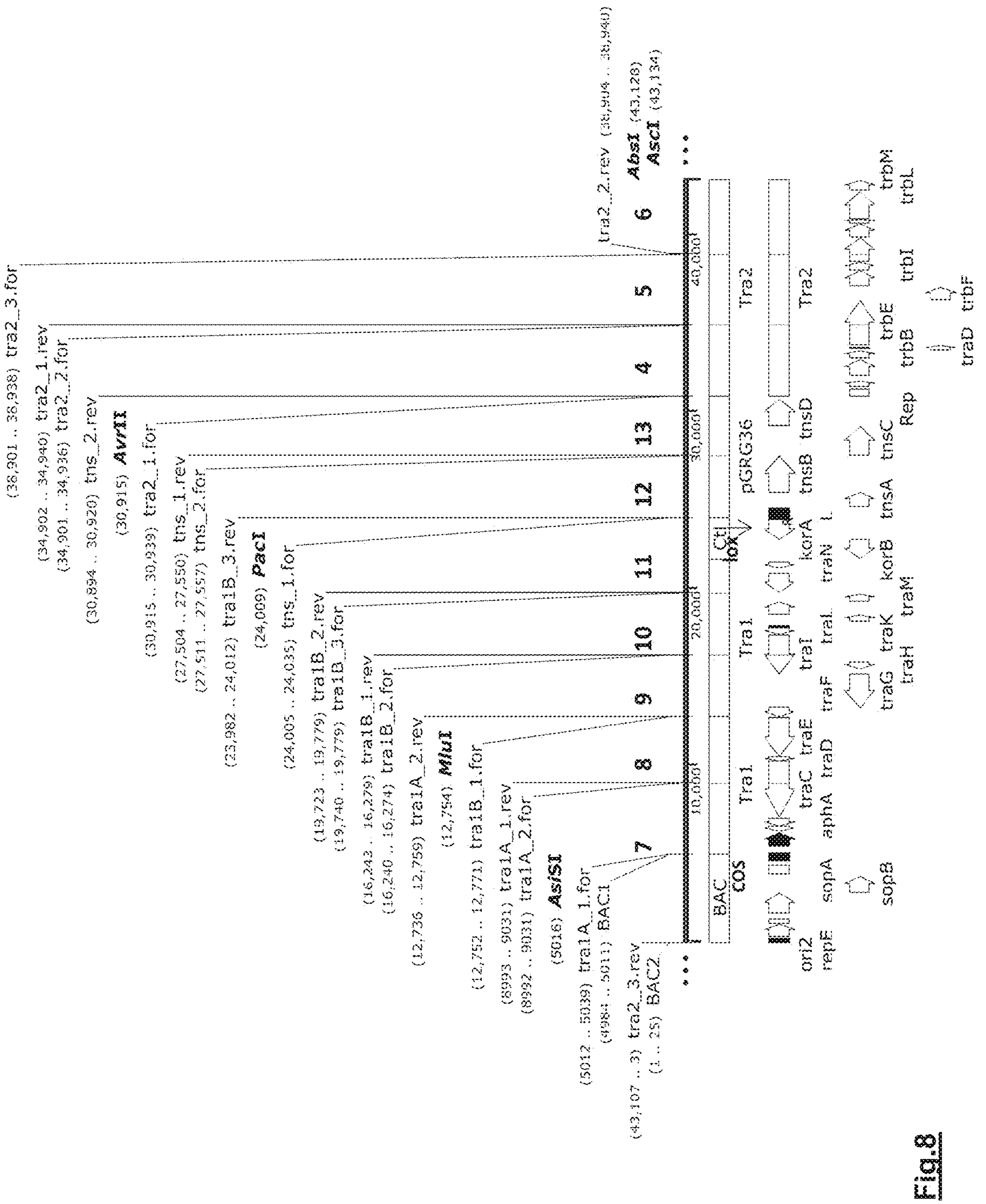

PCR template A: pBeloBAC11, B: RK2, C: pGRG36::lox. The DNA cassette containing two inverted lox sites loxN and lox71 is inserted at PacI and EagI sites on pGR36 and designated pGR36::lox. The sequence of this lox cassette, top and bottom strand are: 5'-ATAACTTCGTATAAgGTATcCTATACGAAGT-TATgcggcgcaagcttaccgTTCGTATAGCATAC ATTATACGAAGTTAT (SEQ ID NO: 1) and 5'-ggccATAACTTCGTATAATGTATGC-TATACGAAcggtaagcttgcgccgcATAACTTCGTATAGgATACcTTATACGAAGTTATat (SEQ ID NO: 2), respectively. Amplicons 1 and 2, 3 are from template A. Amplicons 4, 5, 6, 7, 8, 9, 10 and 11 are separately amplified from template B, Amplicons 12 and 13 are amplified from template C. The genes contained in each amplicon are shown in FIG. 8. Amplicon 1+2 and 3+4+5 are assembled to give construct I, amplicon 3 and 7+8, 9+10+11, 12+13 are assembled to give construct II, III and IV, respectively. The letters a, b, c, d, e, f represent the following restriction enzyme recognition sites: a=AscI, b=AbsI, c=AvrII, d=PacI, e=MluI, f=AsiSI. 4+5+6 is cloned between b and c followed by cloning 12+13 between d and c, 9+10+11 between e and d, 7+8 between f and e. In the final step, the construct is cleaved with AscI (a) to remove the unneeded region of pBeloBac11 including chloramphenicol resistant gene (CmR).

FIG. 8. A genetic map and the primer annealing sites of c-TNB001

The location of the primer annealing regions are mapped along the final construct of the Transmid. The unique restriction enzymes used to ligate the assembled fragments are also shown. The numbers on the linear map correspond to the amplicons indicated in FIG. 7. The gene organisations are shown below the linear map.

Figure 9:
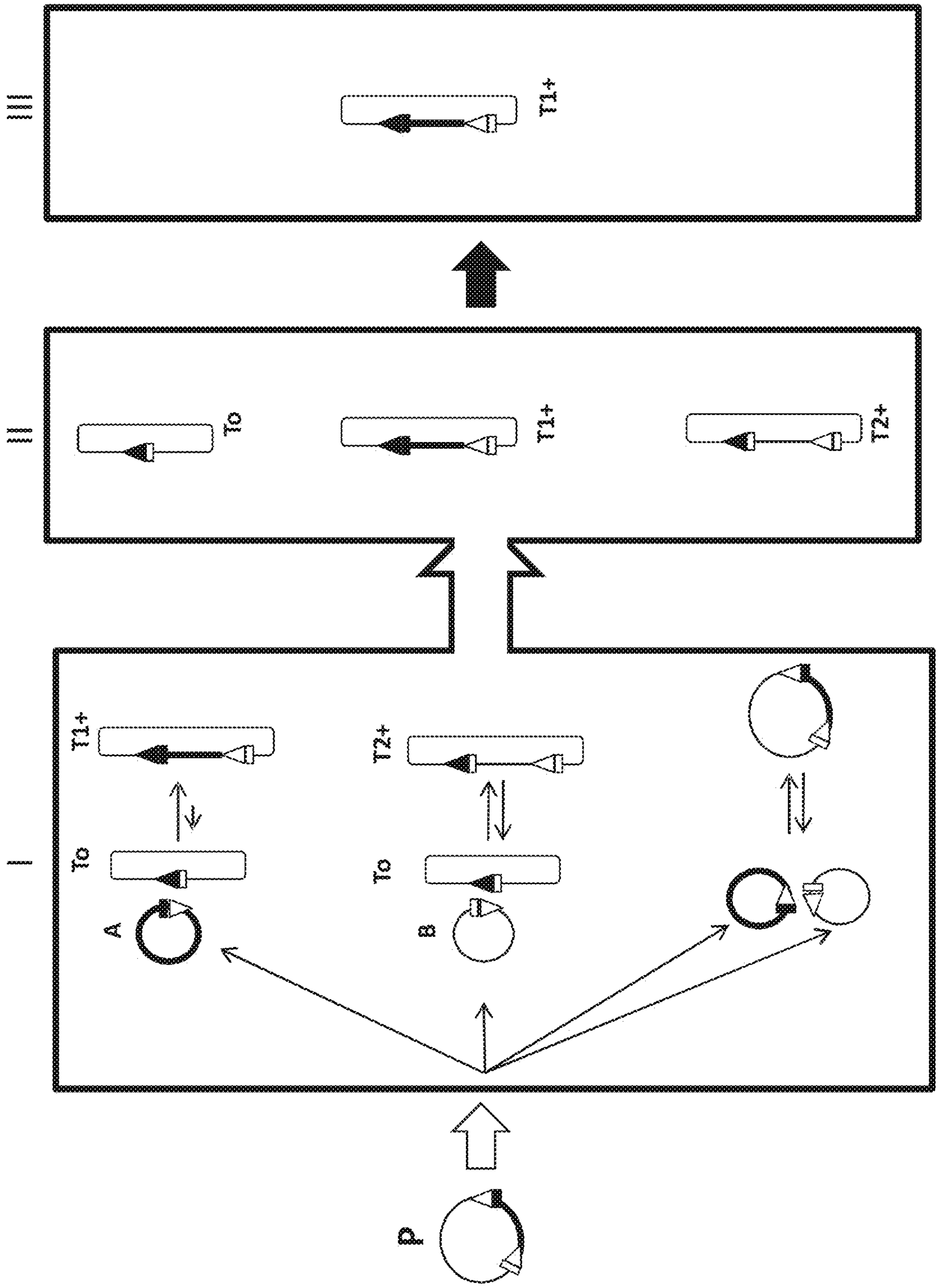

FIG. 9. Cargo docking reaction: recombination pathway 1 excision reaction

The Cargo docking reaction contains two steps: (i) the recombination events between the Transmid and the plasmid donating the Cargo (I) and the selection steps for the cell containing the Cargo integrated into the Transmid (II and III). Plasmid (P) containing Cargo is transformed into the *E. coli* harbouring Transmid. The Cargo is flanked by loxP on one end and by lox71 (a left arm mutant) on the other end, indicated by black rectangle. Following Cre expression, the Cargo is excised to yield two circularised molecules, one containing Cargo with one single lox71 (A), the other, the vector backbone without Cargo and with wild type loxP (B). The Transmid (To) contains a single lox66 site (a right arm mutant), indicated by black triangle, which can recombine either with A or B. When A recombines with lox66 on the Transmid, one end contains a double mutant lox site on one arm (T1+), thus the reverse excision reaction is reduced (I). When B recombines with lox66 on the Transmid, one end contains single mutant on the right (T2+), which still allows the reverse excision reaction to reduce the amount of Transmid loaded with Cargo (I). In the selection step brought about by conjugation, T0, T1+, T2+ are transferred to the recipient (II), the Transmid containing the Cargo can then be selected by using a combination of the antibiotic marker and negative-selectable marker carried by the Cargo and the recipient cells (III).

Figure 10:
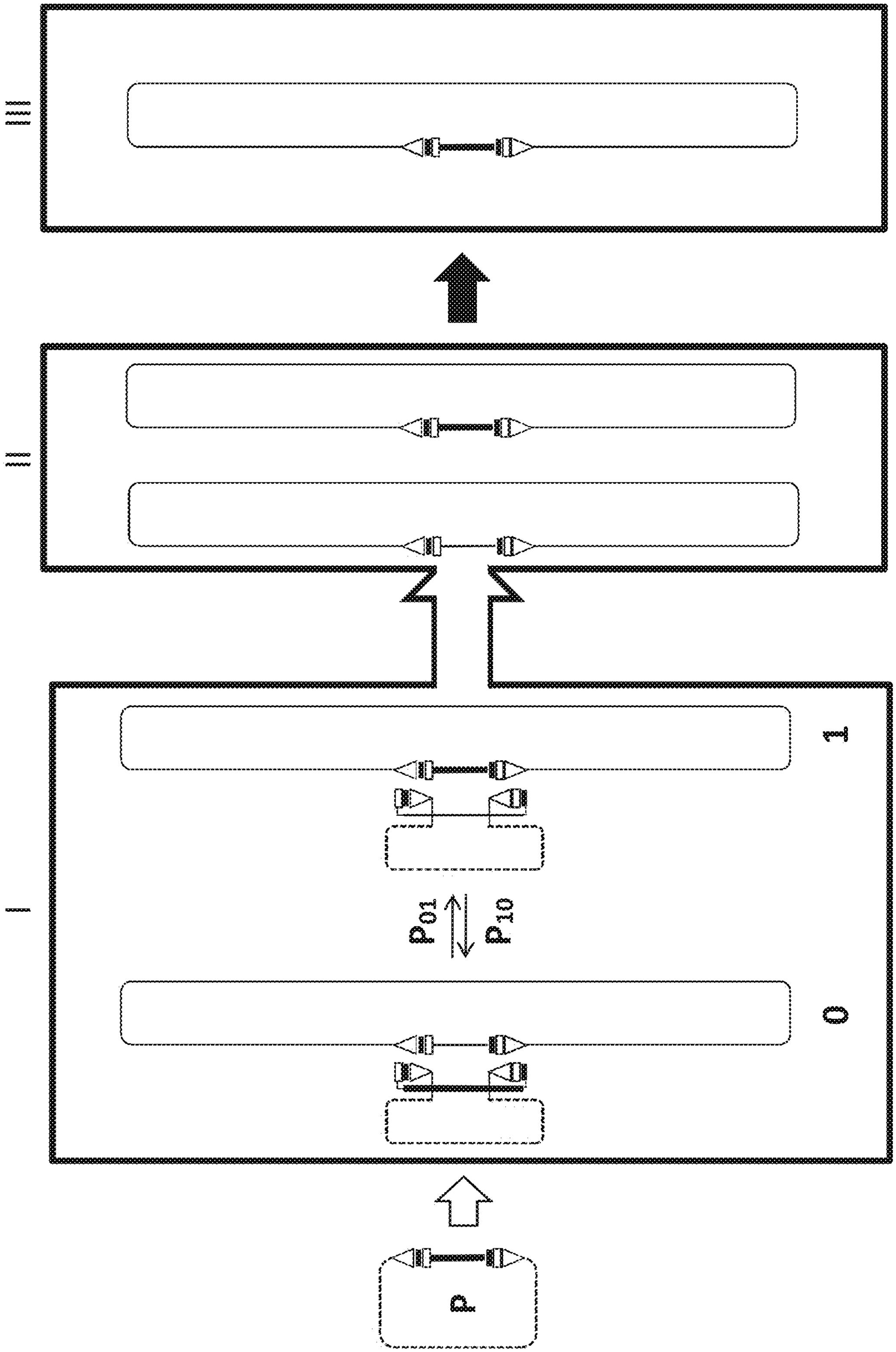

FIG. 10. Cargo docking reaction: recombination pathway 2 by exchange reaction Plasmid (P) containing Cargo is transformed into the *E. coli* carrying the Transmid. Cargo is truncated by loxN (a mutation in 8 bp core region) on one end and by lox71 (a left arm mutant) on the other end. Cargo is not excised between two lox sites, because the recombination requires the identical 8 bp core sequence between the lox sites. With Cre expression, the Cargo is exchanged between plasmid and the Transmid, which also contains inverted loxN and lox71. The loxN core sequence is indicated by the black rectangle, which is sandwiched with white triangle and white rectangle. The lox71 left arm is indicated by black rectangle. 0 indicates the empty Transmid, 1 is indicates the loaded Transmid. P01 and P10 is a state transition probability from state 0 to 1 and vice versa. In the conjugation step, Transmids with or without Cargo are transferred to the recipient (II), where only the Transmid containing the Cargo can be selected using a combination of the antibiotic marker and negative-selectable marker carried by the Cargo and the recipient cells (III).

Figure 11:
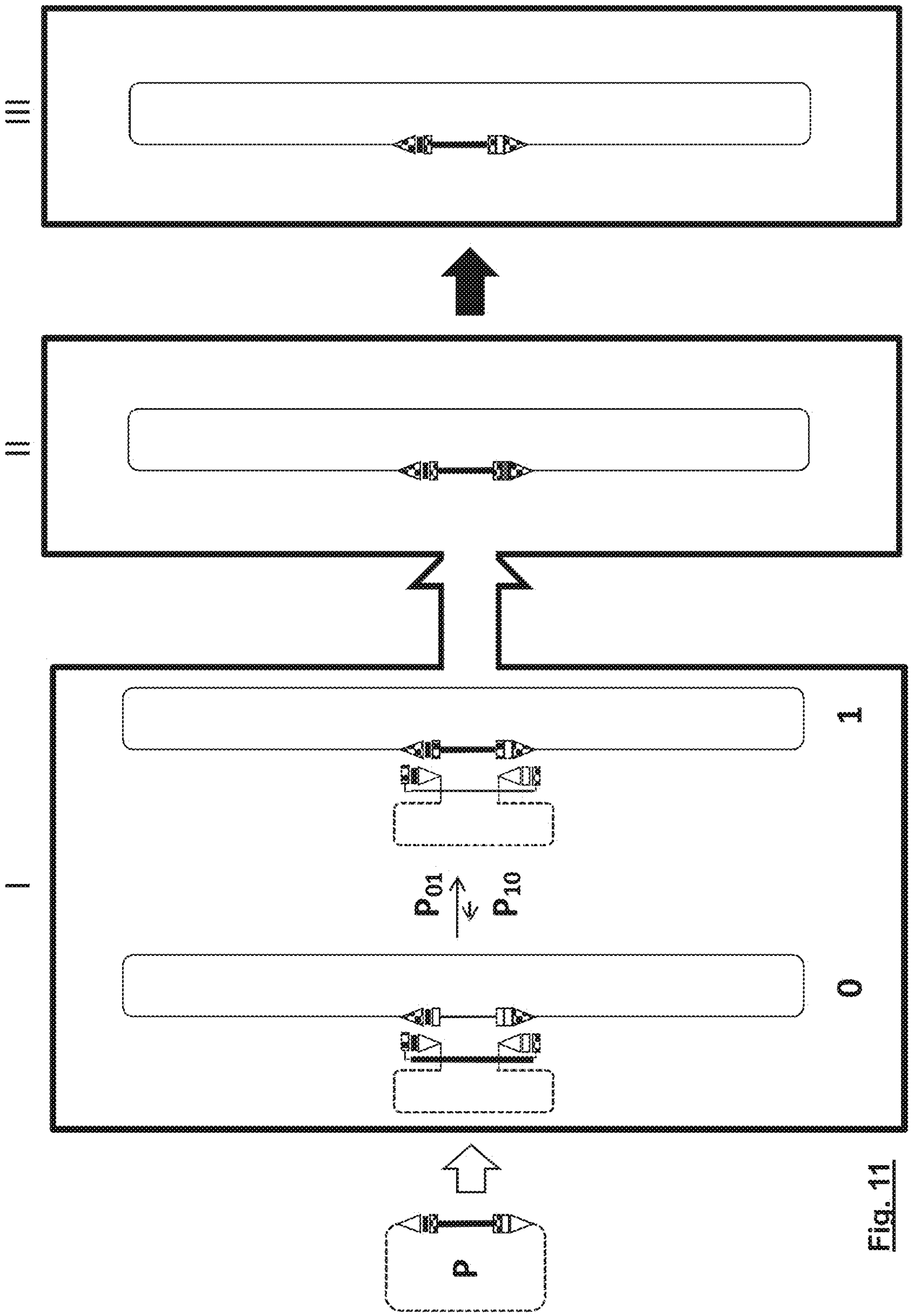

FIG. 11. Cargo docking reaction: recombination pathway 3 by an exchange & locking reaction Plasmid P containing Cargo is transformed into the *E. coli* carrying the Transmid. Cargo is truncated by inverted loxN+71 (mutation in 8 bp core region and the left arm) on one end and by lox71 (left arm mutant) on the other end. Cargo is not excised between two lox sites, because the recombination requires the identical 8 bp core sequence between the lox sites. The Cargo is exchanged between plasmid and the Transmid, which also contains inverted loxN+66 (mutant in 8 bp core region and the right arm) and lox66 (right arm mutant). lox71 left arm is indicated by rectangle filled with black check marks. Recombination occurs between loxN+71 and loxN+66, lox66 and lox71, respectively to gain the double mutant arms on both ends, which reduces the reverse Cargo unloading reaction. lox66 right arm is indicated by triangle filled with black check marks. loxN+71 is indicated with black rectangle sandwiched with white triangle and rectangle with black check marks. loxN+66 is indicated with black rectangle sandwiched with white rectangle and triangle with black check marks. 0 indicates the empty Transmid, 1 indicates the loaded Transmid. P01 and P10 is a state transition probability from state 0 to 1 and vice versa. In the conjugation step, Transmids with or without Cargo are transferred to the recipient (II), where only the Transmid containing the Cargo can be selected using a combination of the antibiotic markers and negative-selectable marker carried by the Cargo and the recipient cells (III).

Figure 12:
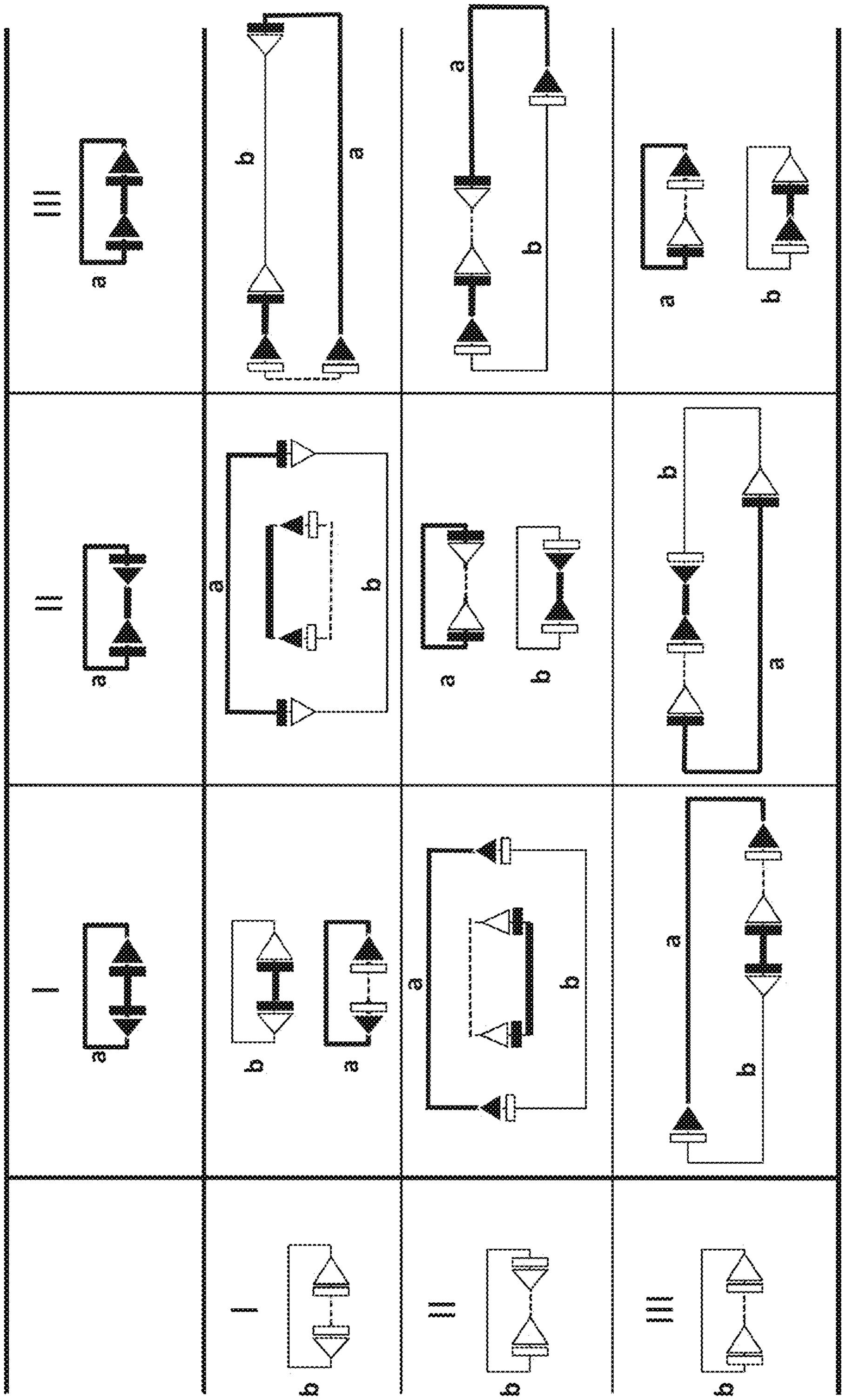

FIG. 12. Recombination patterns between two lox sites pair

Nine recombination pathways are shown. The triangle represents the direction of lox, and right arm. Rectangle represents the lox left arm. And a and b designate different DNA, thick solid lines and dotted lines show regions truncated by lox sites on a and b, respectively. (I, I) and (II, II) and (III, III) combinations lead to the exchange reaction.

Figure 13:
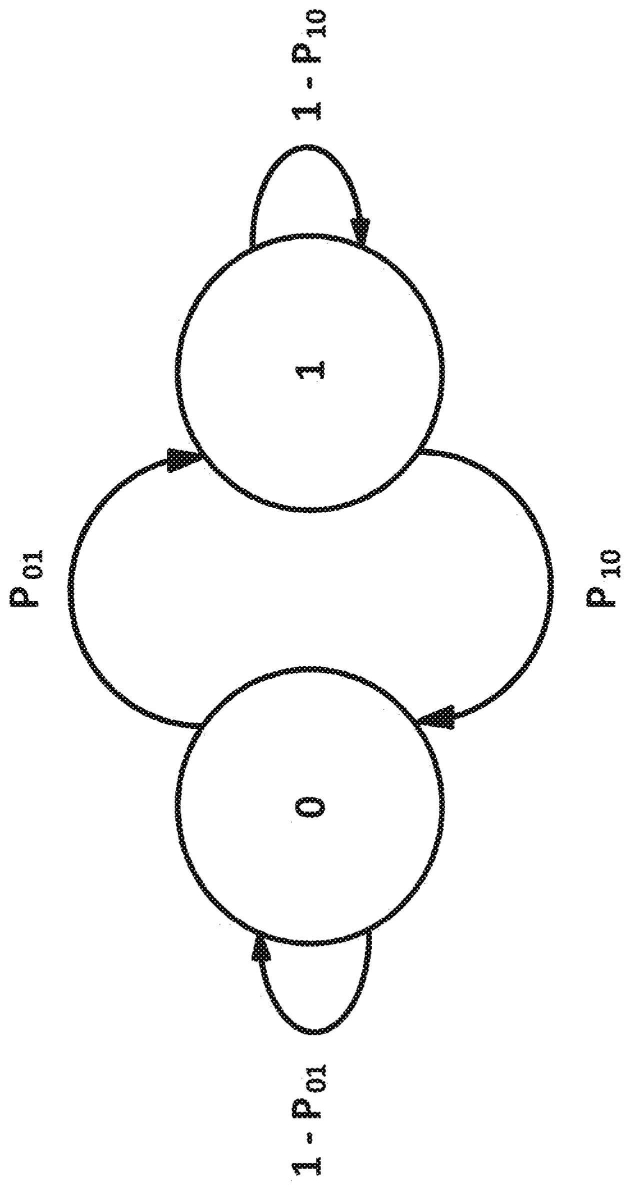

FIG. 13. Transition probability graph of Cargo loaded and unloaded state of Transmid P01=docking probability is the probability to integrate the desired region from pNB300::Cargo to Transmid, P10=undocking probability is the probability to disintegrate the desired integrated region from Transmid and return to the initial state (i.e. empty Transmid), 1−P10=State 1 maintenance probability, 1−P01=State 0 maintenance probability. Steady state probability of state 1=P01/(P10+P01), which is intuitively correct as the P01 is increased more, the more the loaded state of the Transmid is increased.

Figure 14:
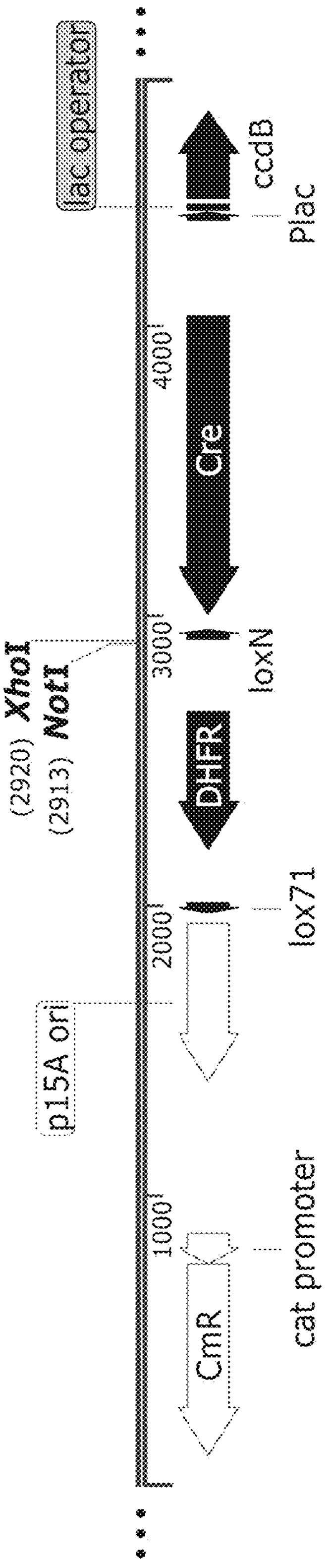

FIG. 14. The structure of Cargo vector, pNB300

The Cargo vector, pNB300 is a circular plasmid, this figure shows the linear map of the vector. The total size of this Cargo vector is 4851 bp. It replicates from the p15A oriV employed from pACYC184. It employs the Cargo docking reaction recombination pathway 2 (FIG. 10) contains two inverted lox sites, lox71 and loxN, between which dihydrofolate reductase gene is located, which will be utilised as a selectable marker for Cre-mediated recombination events. The Cargo can be cloned at unique restriction sites NotI and XhoI. Cre is constitutively expressed from this Cargo vector. The ccdB gene is under the regulation of lac operator, and is used as a negative selection against Cre-mediated recombination events where the vector backbone is transferred to the Transmid rather than just the desired Cargo alone.

Figure 15:
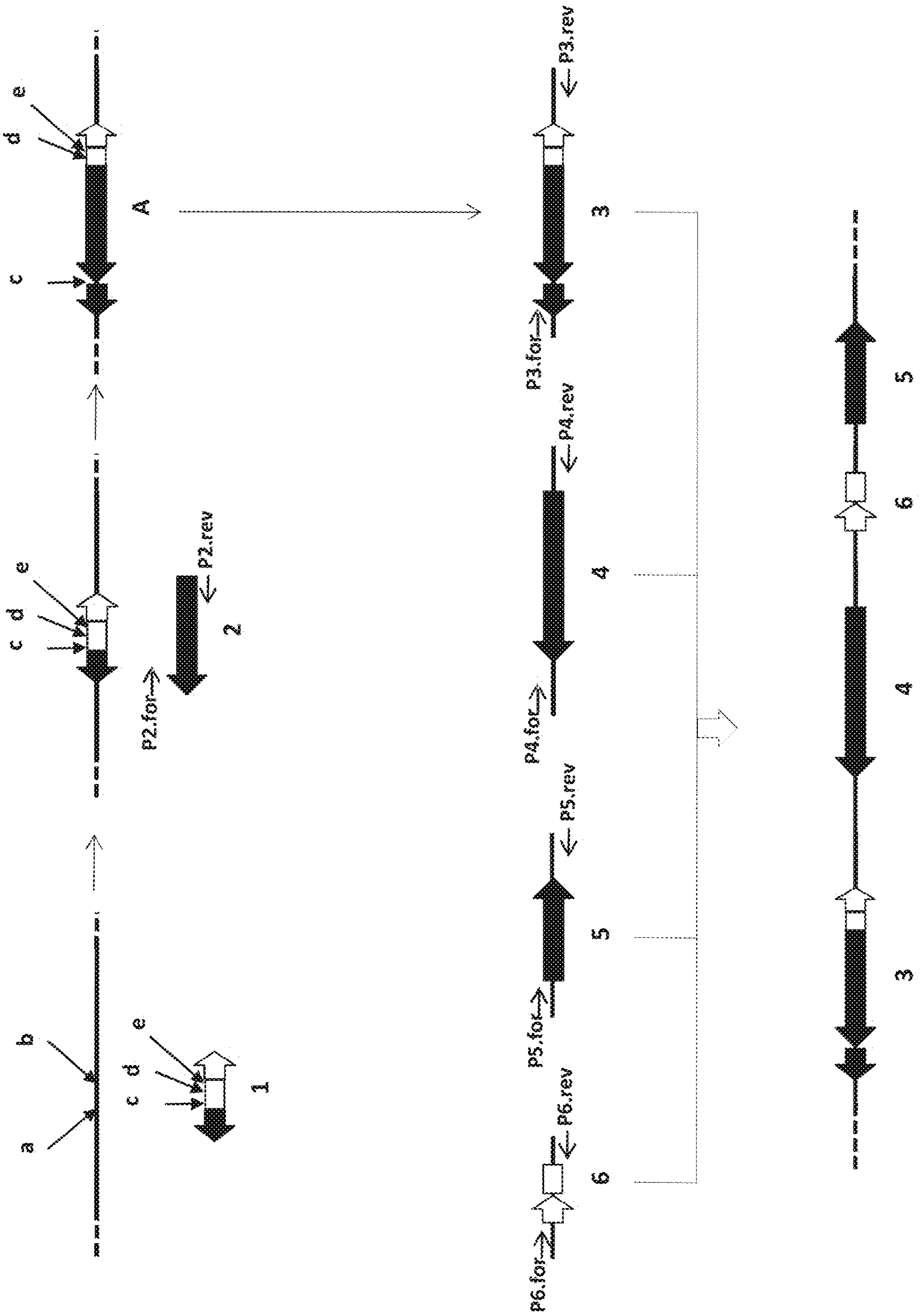

FIG. 15. The pNB300 Cargo vector construction scheme a, b, c, d, e denote the unique restriction enzyme recognition sites: a=XbaI, b=EarI, c=AsiSi, d=NotI, e=XhoI. A synthetic double-stranded cassette 1 containing inverted lox71 and loxN sites (coloured black and white, respectively) flanking a stuffer region with cloning sites (designated lox71-loxN), is cloned into the XbaI and EarI sites of the plasmid pACYC184 to give pACYC184::lox71-loxN. Fragment 2 is an amplicon containing the dihydrofolate reductase gene, dhfr, amplified from the plasmid pFE872 with P2.for and P2.rev primers. AsiSI and NotI sites are incorporated in the ends of amplicon 2, which is digested with AsiSI and NotI and cloned into the AsiSI and NotI of pACYC184::lox71-loxN to give construct A (pACYC184::lox71-dhfr-loxN). Fragment 3 is amplified from construct A with P3.for and P3.rev primers. Fragment 4 containing the cre gene is amplified from the plasmid pCAG-Cre_GFP with P4.for and P4.rev primers. Fragments 5 and 6 are amplified from the plasmid pCR BluntII-TOPO (available from New England Biolabs) with primer set P5.for, P5.rev and P6.for, P6.rev, respectively. Fragments 3, 4, 5 and 6 are assembled by Gibson assembly to give the Cargo vector, pNB300. Primer sequences are shown in Example 1.

Figure 16:
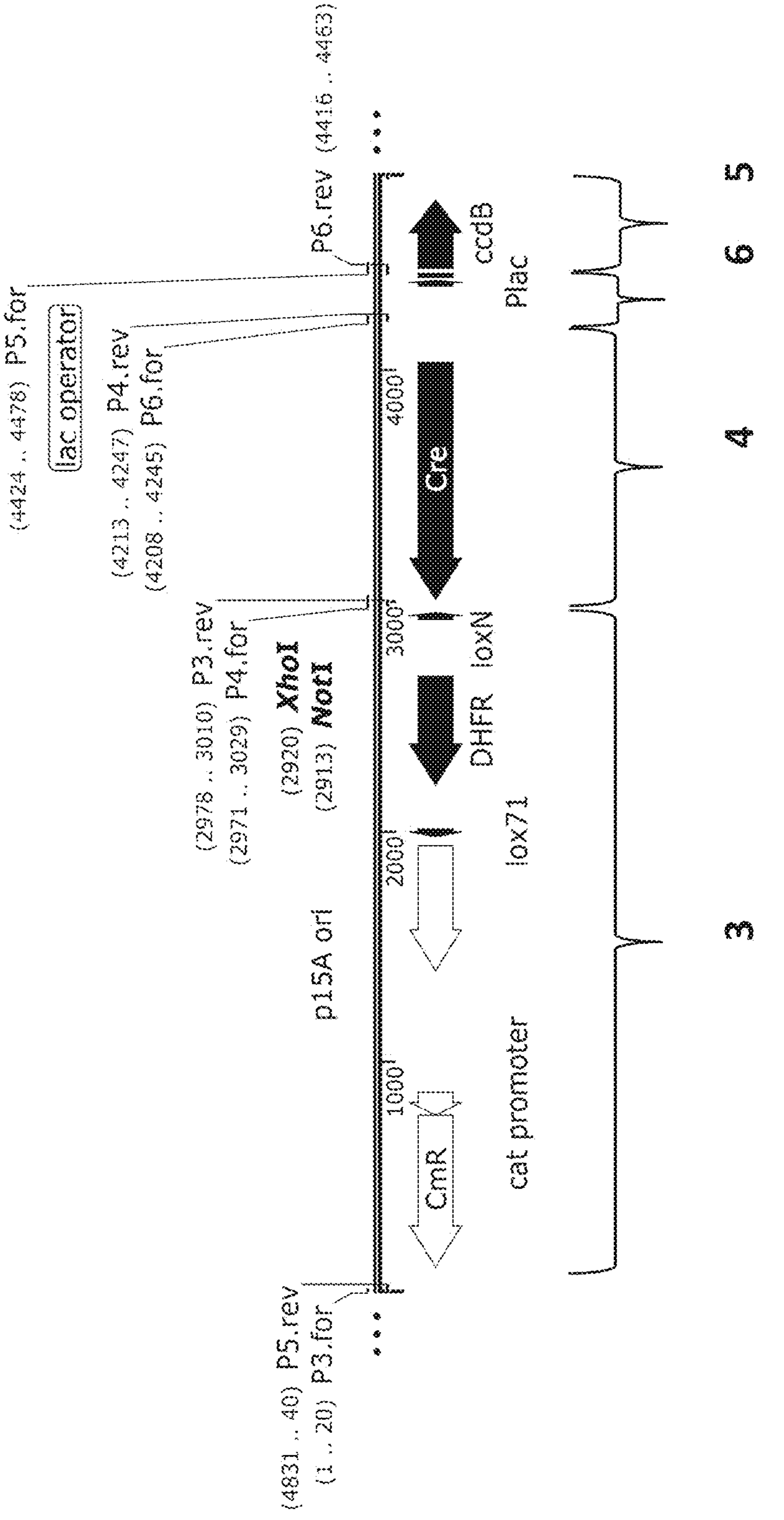

FIG. 16. A genetic map and the primer annealing sites of the Cargo vector pNB300 The location of the primer annealing regions are mapped along the final construct of the Cargo vector. The unique restriction enzymes NotI and XhoI used to ligate the Cargo fragment are also shown. The numbers on the linear map correspond to the amplicons indicated in FIG. 15.

Figure 17:
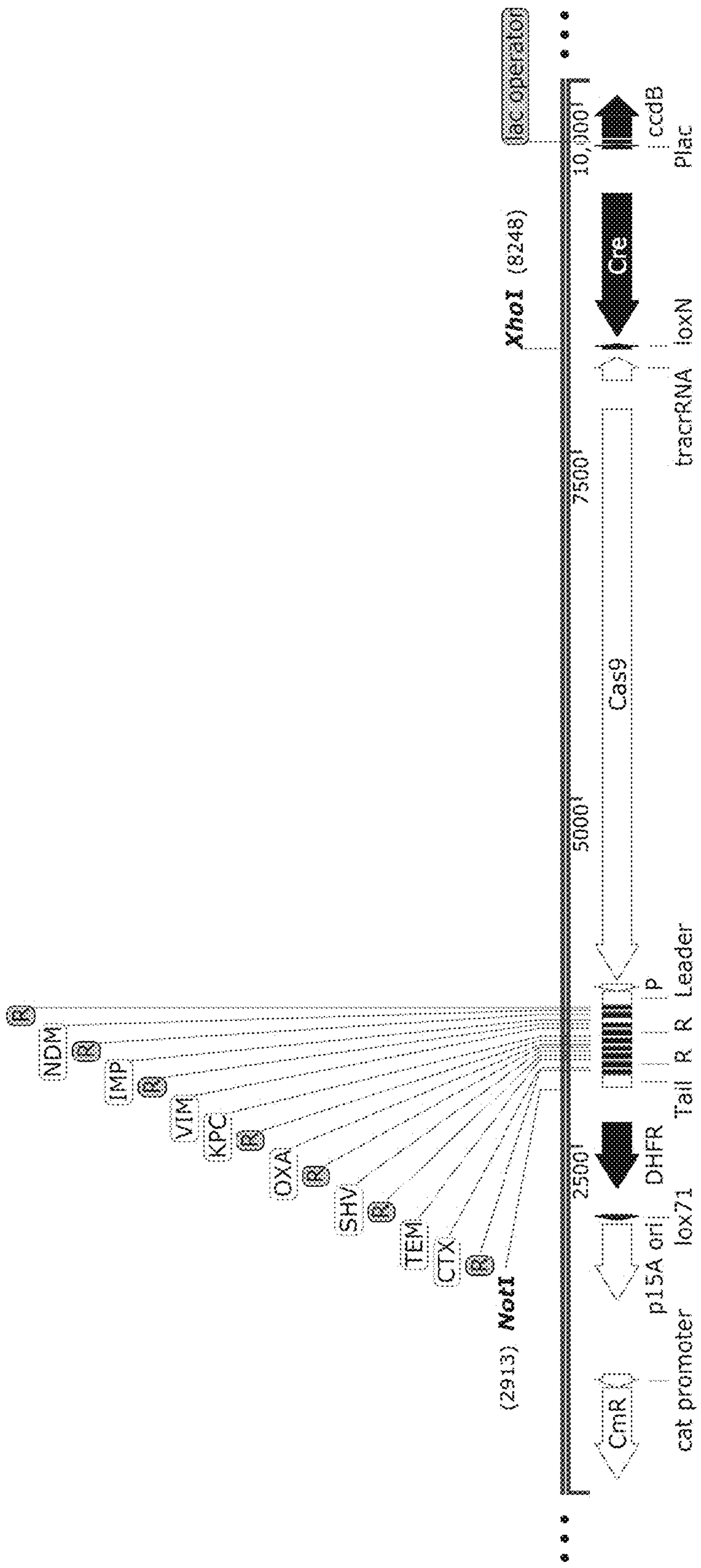

FIG. 17. Linear genetic map of pNB300 carrying Cargo with CRISPRICas9 system plus VONCKIST spacers derived from pNB108

An amplicon encoding tracrRNA Cas9 and VONCKIST CRISPR spacers from the plasmid pNB108 is digested with NotI and XhoI and the 5,335 bp fragment is cloned into the NotI and XhoI site on pNB300 giving pNB301. The total size of pNB301 is 10,179 bp. FIGS. 29-31 describe the construction of the exemplified Cargo.

Figure 18:
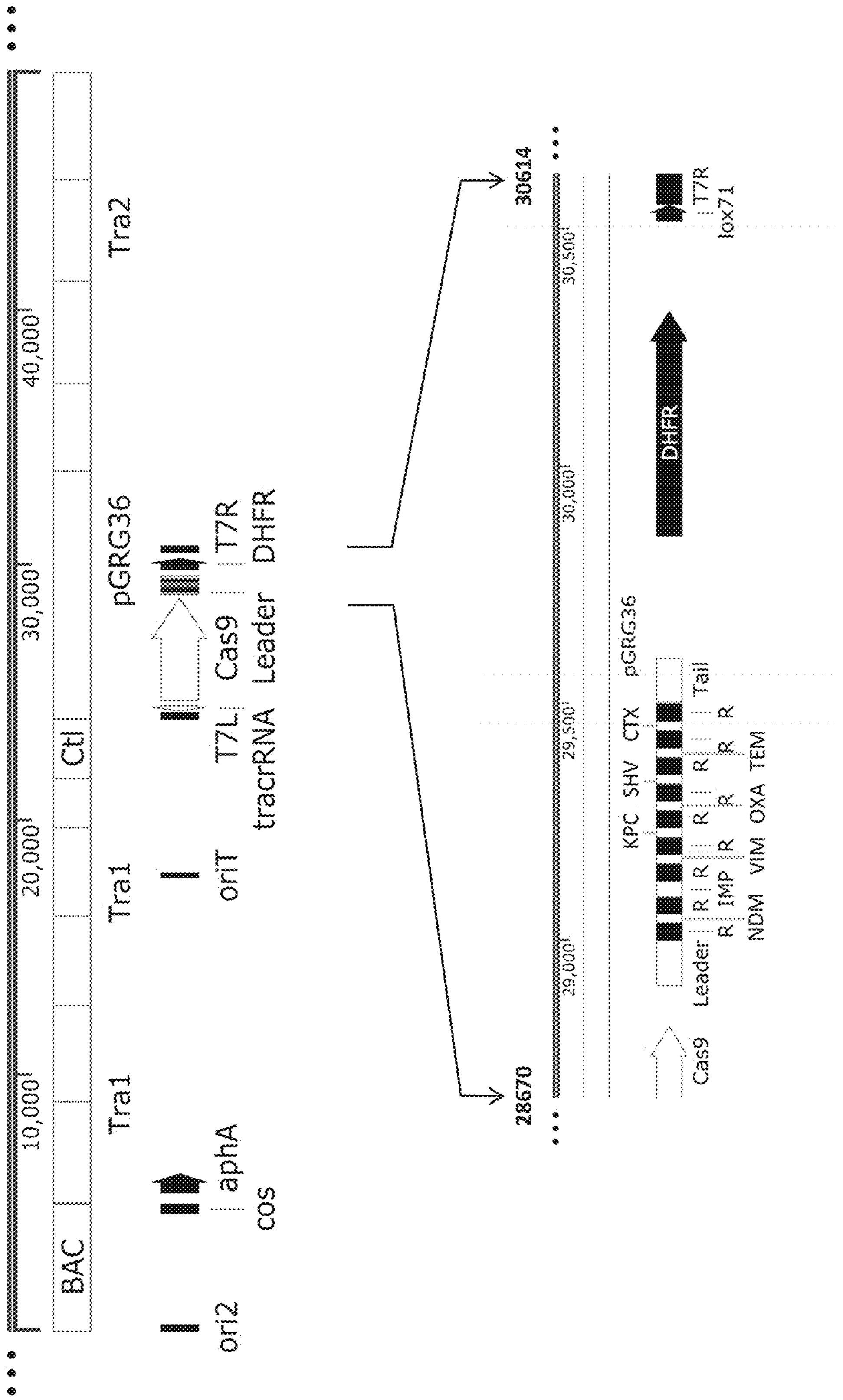

FIG. 18. Linear genetic map of the c-Transmid, c-TNB001, CRISPRICas9 system plus VONCKIST spacers derived from pNB108 following Cre-lox recombination The Cargo tracrRNA Cas9 and VONCKIST CRISPR spacers plus dhfr gene is specifically recombined into cTNB001 by Cre-lox recombination in vivo. This 6,307 bp region is inserted between Tn7 left and right TIRs sites. The Cargo region is enlarged below the linear map and shows the eight VONCKIST spacers. The total size is 49,358 bp.

Figure 19:
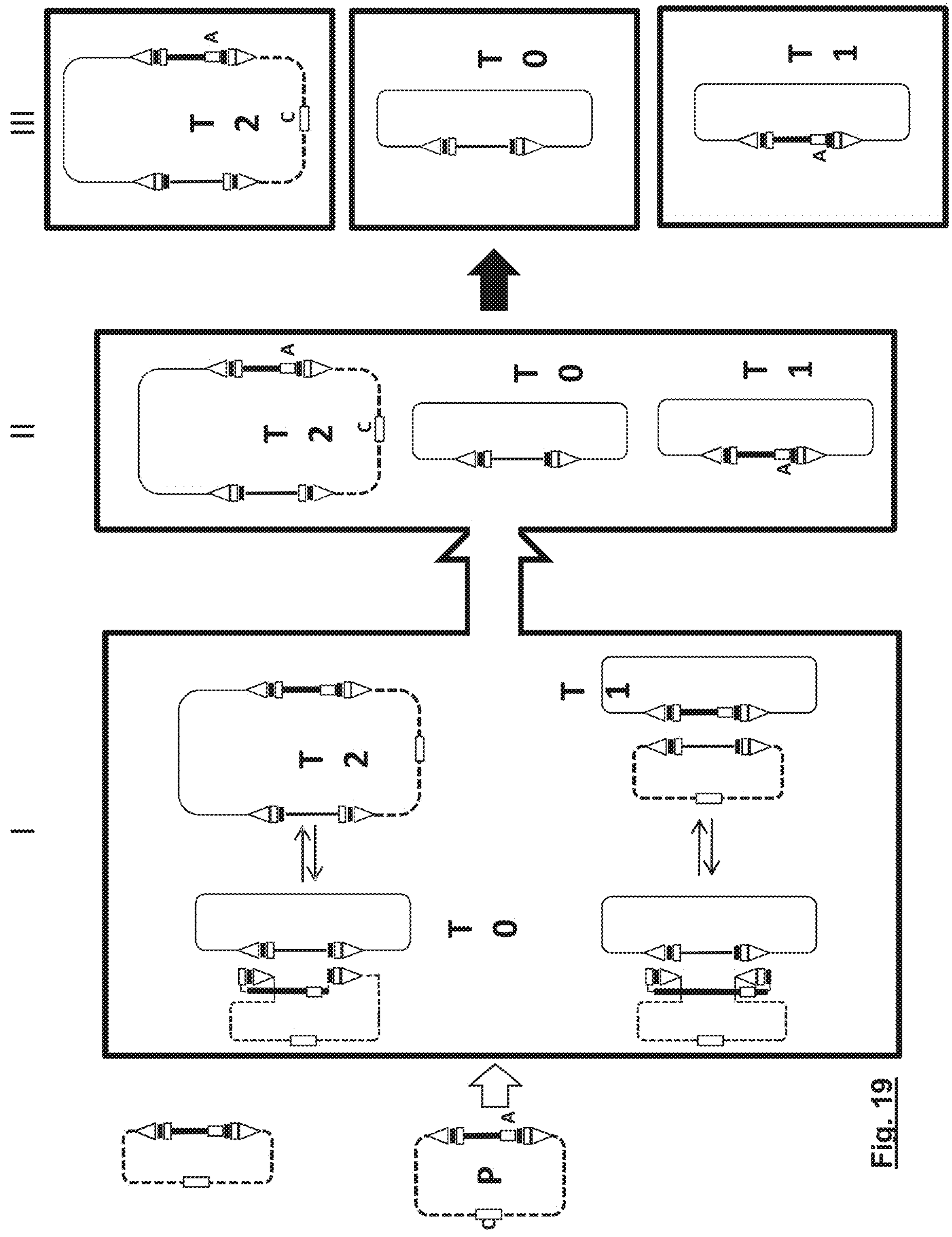

FIG. 19. Selection of c-Transmid loaded with Cargo

The Cargo plasmid (P) denoted by dotted circle line carries genetic elements shown in FIG. 14. c: the ccdB gene regulated by the lac operon for negative-selection, A: dihydrofolate reductase gene, dhfr, for positive selection. P is transformed to the an F+, laclq strain harbouring the c-Transmid, cTNB001, (T0 denoted by solid circle line). Two recombination pathways are shown in step I via the Cargo docking recombination pathway 2 by exchange, shown in FIG. 11. One pathway is recombination at the single lox site to yield an event where the whole plasmid P recombined into the Transmid (T2); the other pathway is recombination at the double lox sites to yield the desired recombinant (T1). In the conjugation step (II), either T0, T1 or T2 are be transferred to the recipient cell with selection for exconjugants. In step 3, ccdB gene is expressed to kill the cell harbouring T2 in the presence of trimethoprim (TpR encoded by the Cargo) and streptomycin (SmR encoded by the bacterial recipient). This selection for recipient cells harbouring only the desired T1 Transmid.

Figure 20:
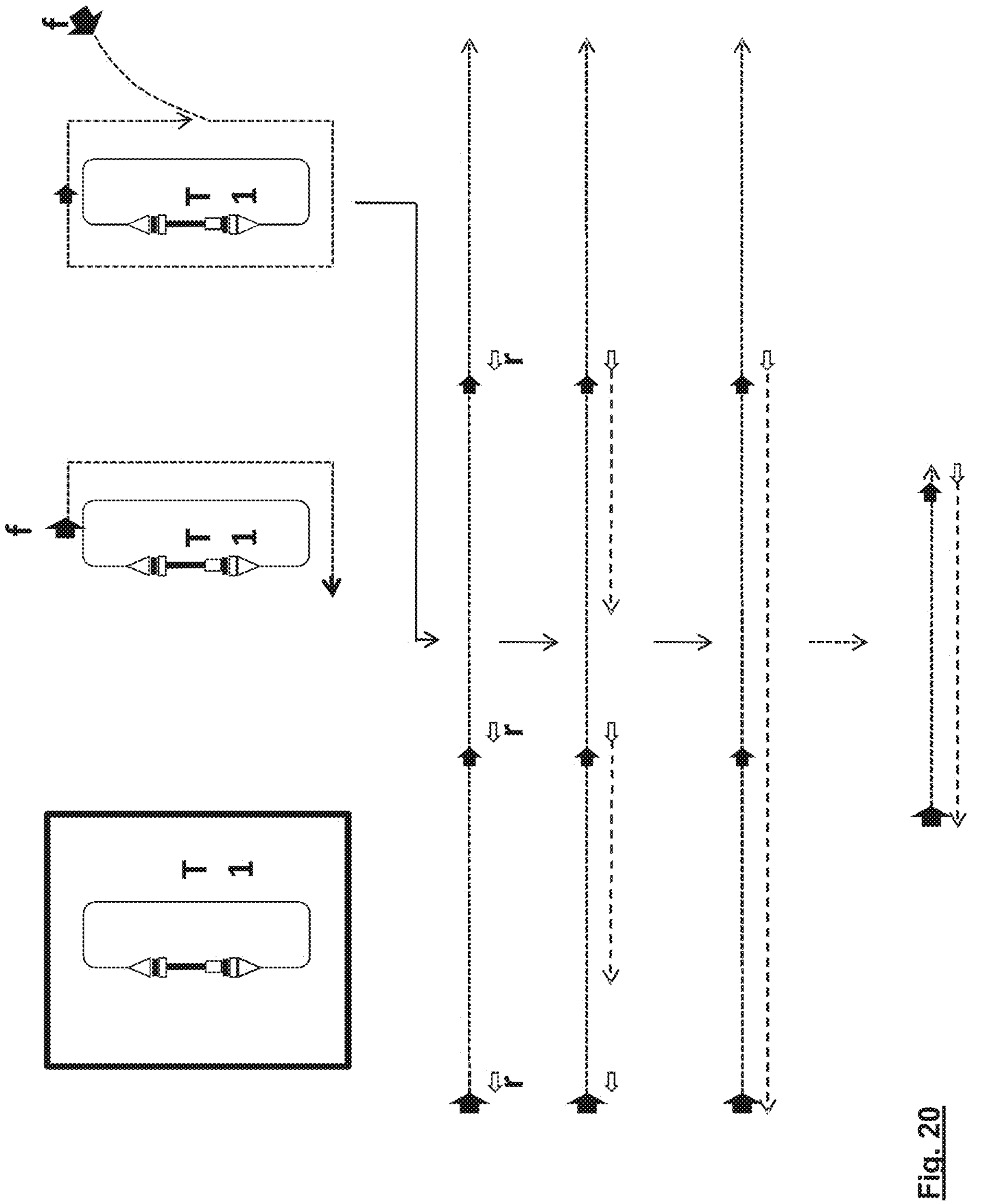

FIG. 20. T1 isolation and RCA amplification to prepare packaging DNA substrate T1 Transmid is isolated from the cells selected in FIG. 19 using a large construct plasmid preparation kit such as QIAGEN large construct kit (cat No. 12462). T1 is a template for rolling circle amplification (RCA) by phi21 DNA polymerase from the primer f (5'-gacatgaggt*t*g*c (SEQ ID NO: 3), where asterisks indicate phosphorothioate linkages) annealing at cos site. In the presence of r primer (5'-atgGCGAT*C*G*C (SEQ ID NO: 4), where asterisks indicate phosphorothioate linkages), which anneals downstream of cos site on the polymerized DNA, concatemeric or mature double stranded DNA is accumulated in the RCA reaction. The reaction can be cleaned by membrane dialysis such as Genomic Tube-O-dialyzer (G-Biosciences, cat No. 786-142-45MC). This dialysed double stranded DNA can be utilised as a substrate for in vitro packaging and package Transmid into the lambda phage using a packaging kit such as MaxPlax Lambda Packaging Extracts (epicentre Cat. No. MP5105).

Figure 21:
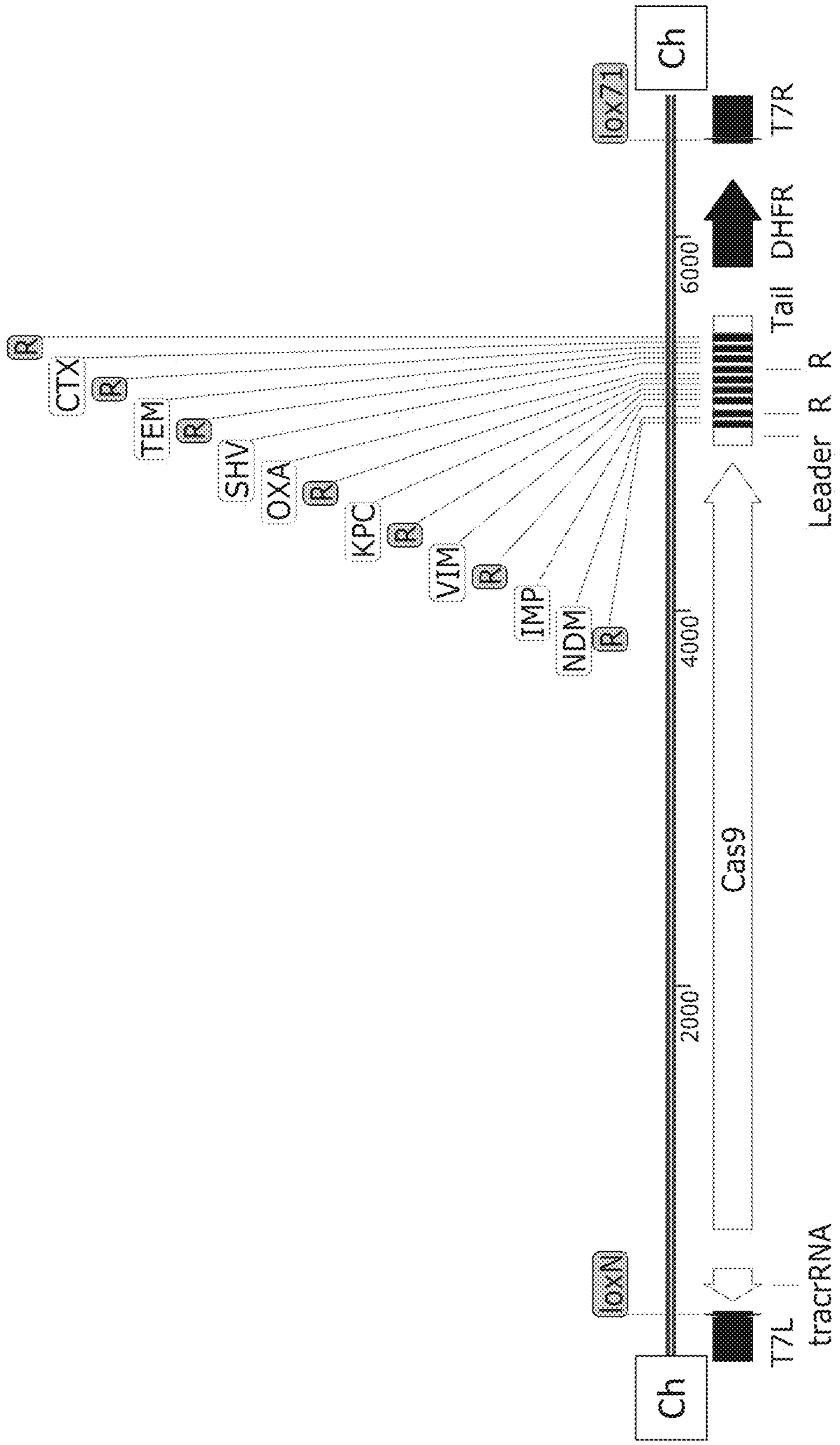

FIG. 21. Structure of Cargo integrated at attTn7 sites on the host chromosome The CRISPR/Cas9 system plus VONCKIST spacers targeting 8 different beta lactamase genes are integrated at attTn7 on host chromosome (Ch) following TnsABCD-mediated transposition from the c-Transmid vector.

Figure 22:
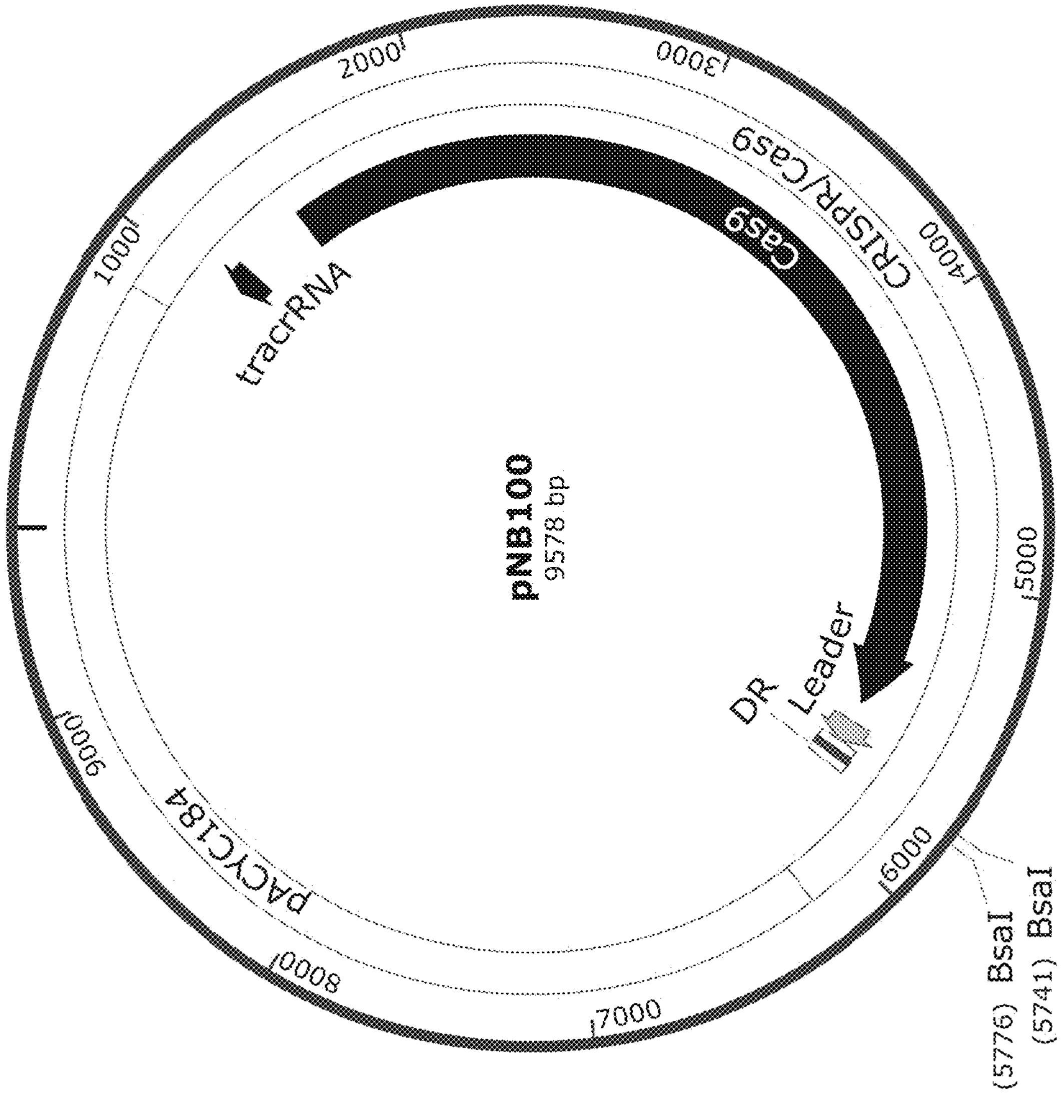

FIG. 22. Plasmid map of pNB100 constructed in Example 2. The plasmid map was drawn by SnapGene viewer ver. 2.4.3 free version (http://www.snapgene.com). Two direct repeats (DR) are shown as narrow white rectangular boxes adjacent to the 3' end of leader sequence.

Figure 23:
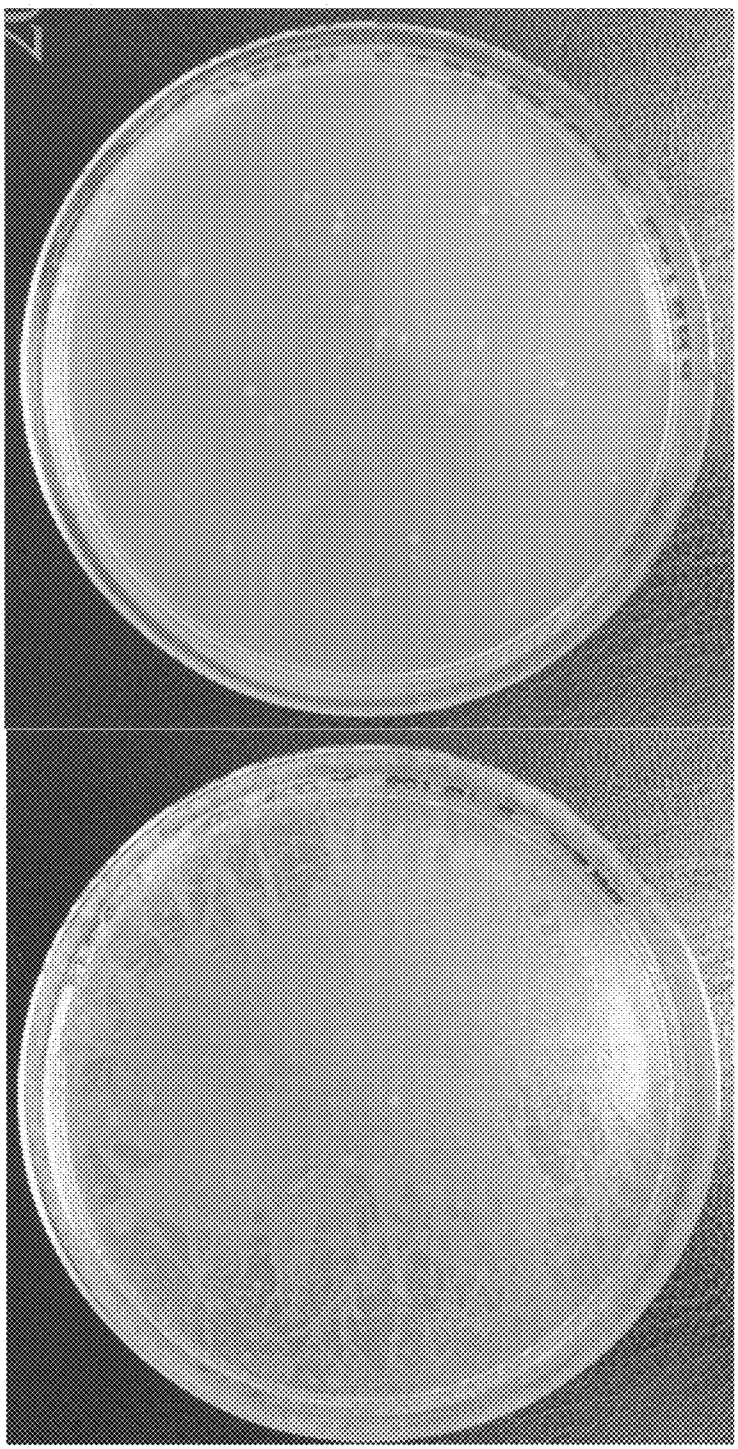

FIG. 23. Photographs show results of "Nemesis Symbiotic activity" (NSA) according to an embodiment of the invention by bacterial cell mating (see Example 2). The left plate shows JA200 pNT3×DH5α pNB100 in Ap100Cm35, while the right plate shows JA200 pNT3×DH5α pNB102 in Ap100Cm35, both plated at $5\times10^7$ cells/ml.

Figure 24:
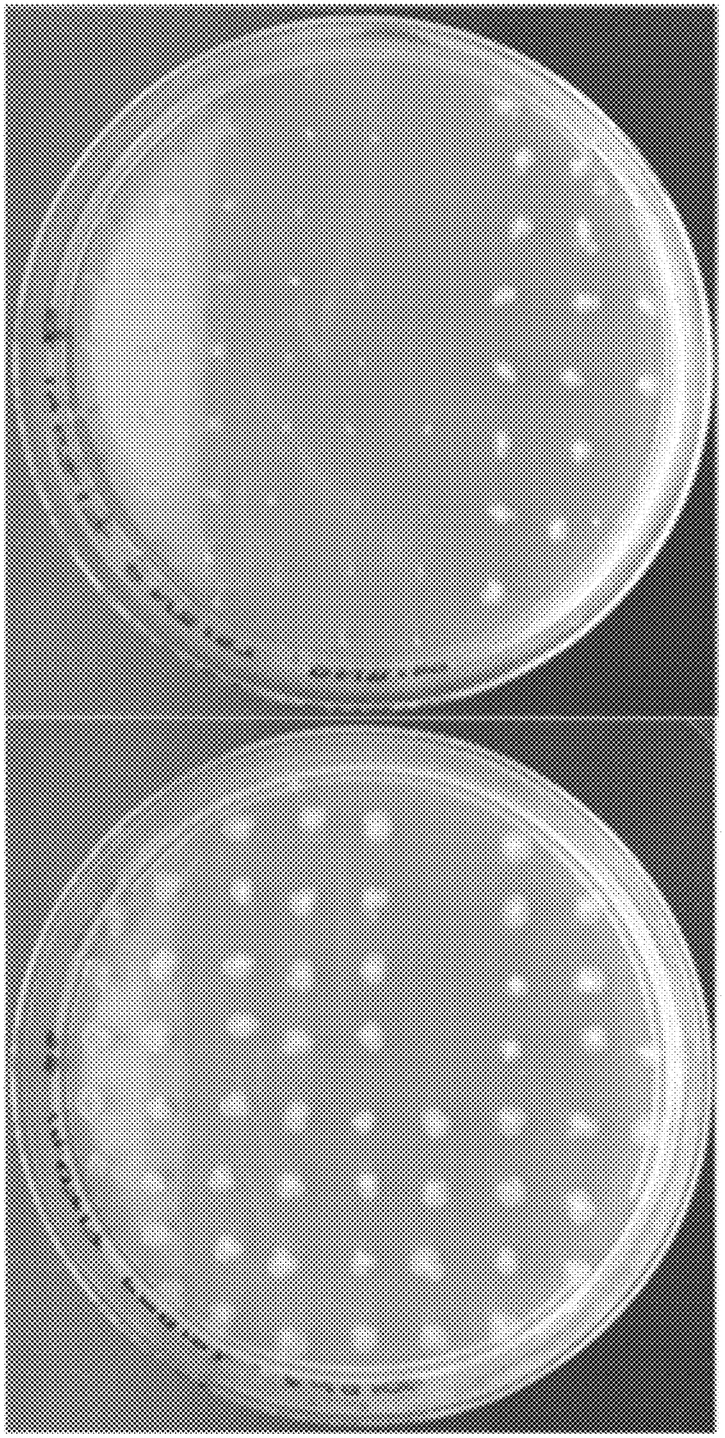

FIG. 24. Photographs show results of NSA according to another embodiment of the invention by plasmid transformation (see Example 2). Left: LB Cm35 plate. Colonies 1-40 are DH5α pBR322 transformed with pNB102; Colonies 45-60 are DH5α pBR322 transformed with pNB100. All colonies show resistance to Cm carried on plasmids pNB100 and pNB102; Right: LB Ap100 plate. Note that colonies 1-40 have lost ApR following transformation with pNB102 carrying the spacer region targeted against the beta-lactamase gene carried on the plasmid pBR322 in strain NBEc001, thereby demonstrating Nemesis Symbiotic activity. pNB100 lacking this spacer region but carrying the Cas9 gene is unable to inactivate the beta-lactamase gene.

Figure 25:
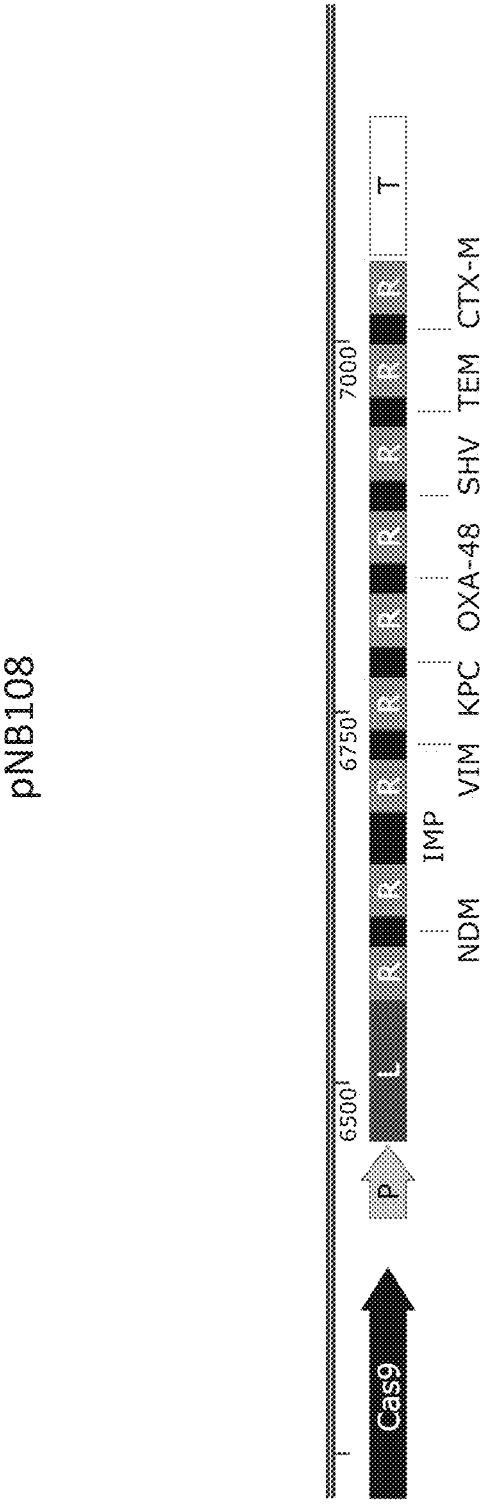

FIG. 25. Plasmid map of pNB108 constructed in Example 2. The plasmid map was drawn by SnapGene viewer ver. 2.4.3 free version (http://www.snapgene.com). The octamer spacer concatemer (see FIG. 26B) was digested with BsaI, whose restriction site is located in A1 and A2, and ligated to BsaI spacer cloning sites on pNB100 to give pNB108. The single promoter and spacer region (6221-7225) on pNB108 is shown. P=Promoter, L=Leader, R=Direct repeat, S=Spacer, T=Tail. The concatenated spacers (targeted against NDM, IMP, VIM, KPC, OXA-48, SHV, TEM and CTX-M) are located under the single promoter.

Figure 26A:
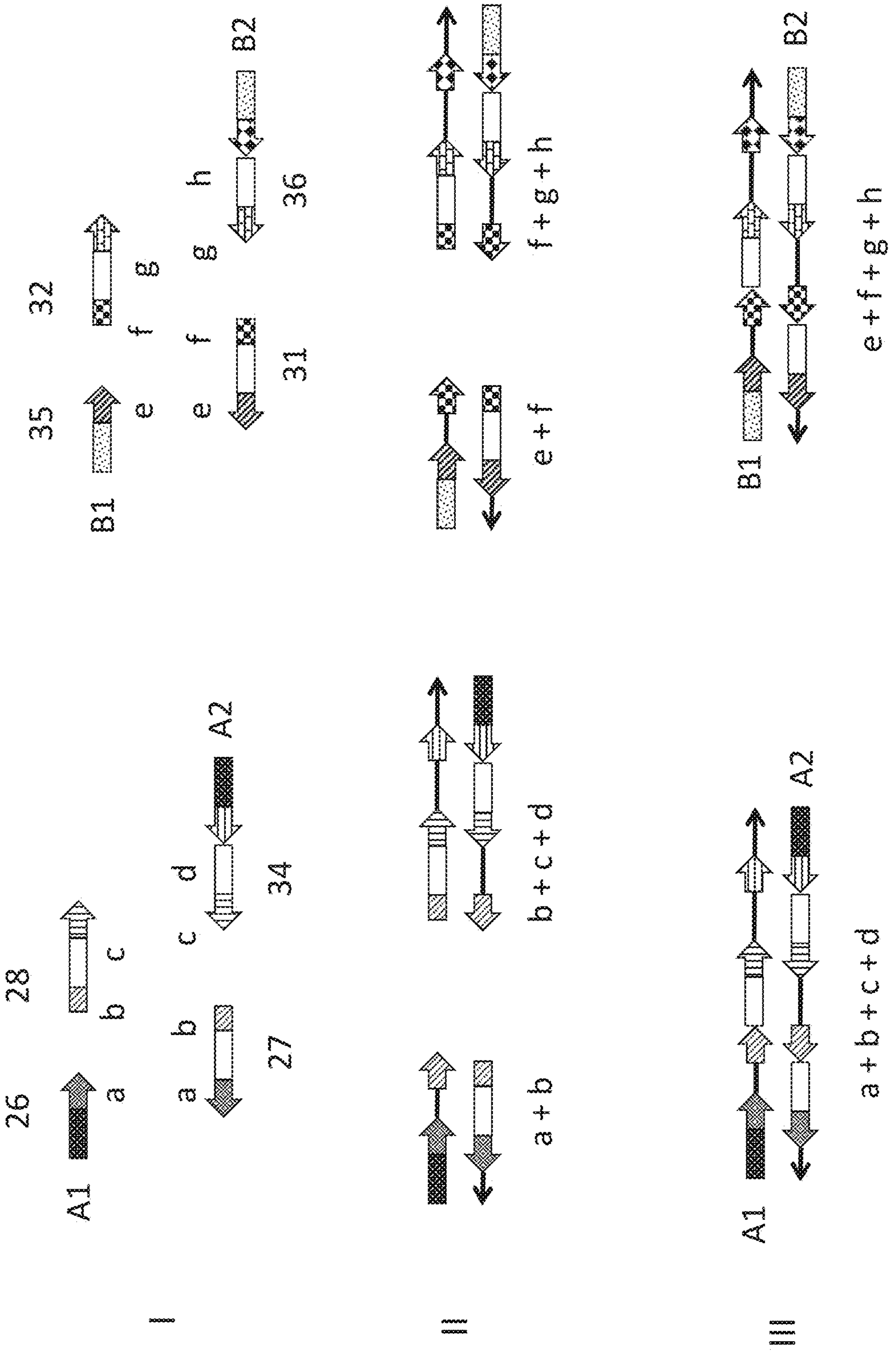

FIG. 26A. Tetramer spacer concatenation in Example 2. The numbers associating oligos are corresponding to the primer numbers listed in FIG. 15. Oligos are pairwise annealed between 26 and 27, 28 and 34, 35 and 31, 32 and 36 via a, c, e and g unique spacer region (I), respectively and extended in individual tubes (II). Dimer concatemer from 26 and 27 concatenate spacer a and b. Dimer concatemer from 28 and 34 concatenate spacer b, c and d. Dimer concatemer from 35 and 31 concatenate spacer e and f. Dimer concatemer from 32 and 36 concatenate spacer f, g and h (II). Concatenated dimmers a+b and b+c+d, e+f and f+g+h are further hybridised via b and f spacer region, respectively and extended to concatenate four spacers a, b, c and d or e, f, g and h (III). The tetramer spacer concatemer e+f+g+h was digested with SapI, whose restriction site is located in B1 and B2, and ligated to SapI spacer cloning sites on pNB200 to give pNB202. Tetra spacer concatemer a+b+c+d was digested with BsaI, whose restriction site is located in A1 and A2, and ligated to BsaI spacer cloning sites on pNB202 to give pNB203.

a=20 mer spacer for NDM, b=20 mer spacer for IMP, c=20 mer spacer for VIM, d=20 mer spacer for KPC, e=20 mer spacer for OXA-48, f=20 mer spacer for SHV, g=20 mer spacer for TEM, h=20 mer spacer for CTX-M.

Figure 26B:
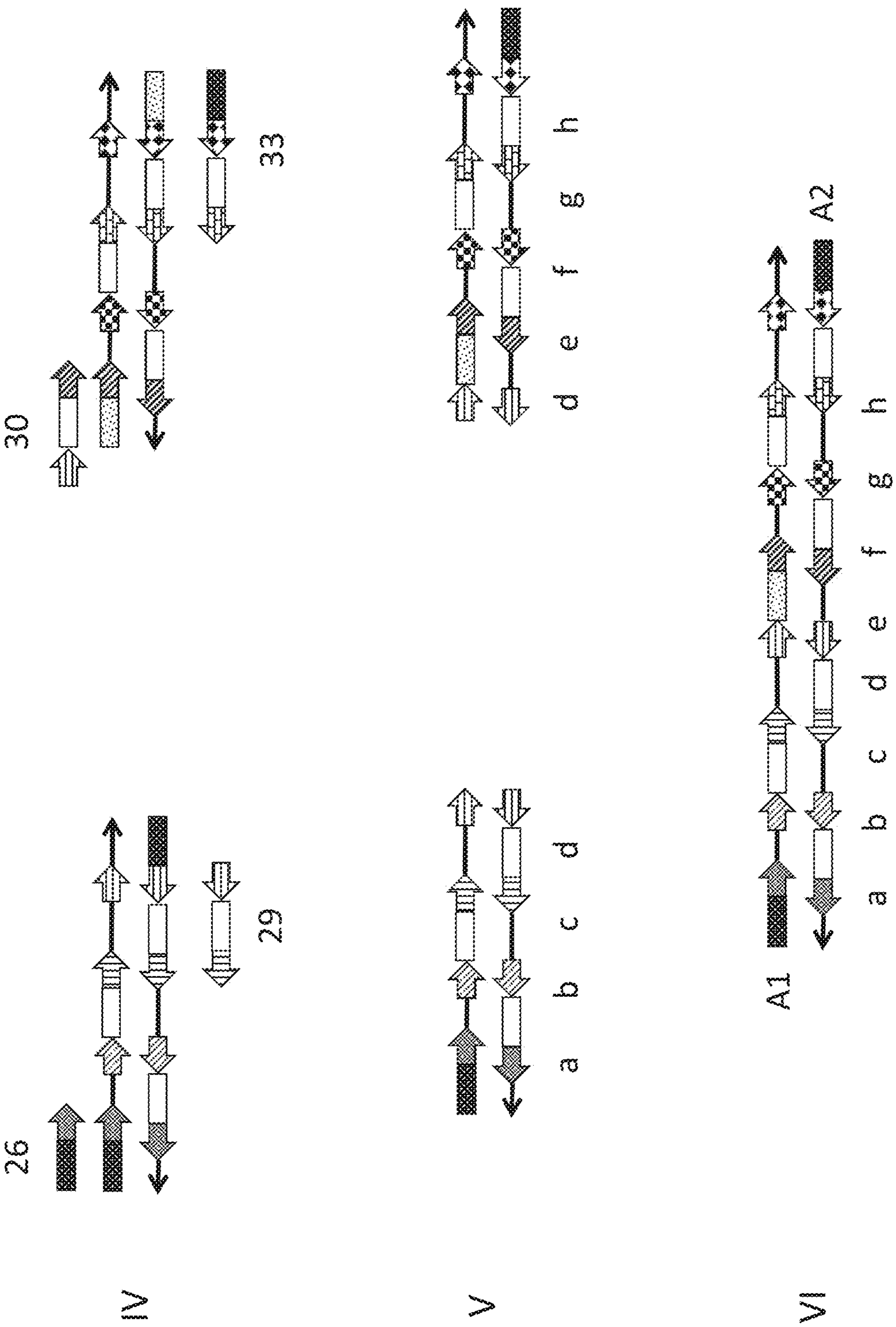
Figure 27A:
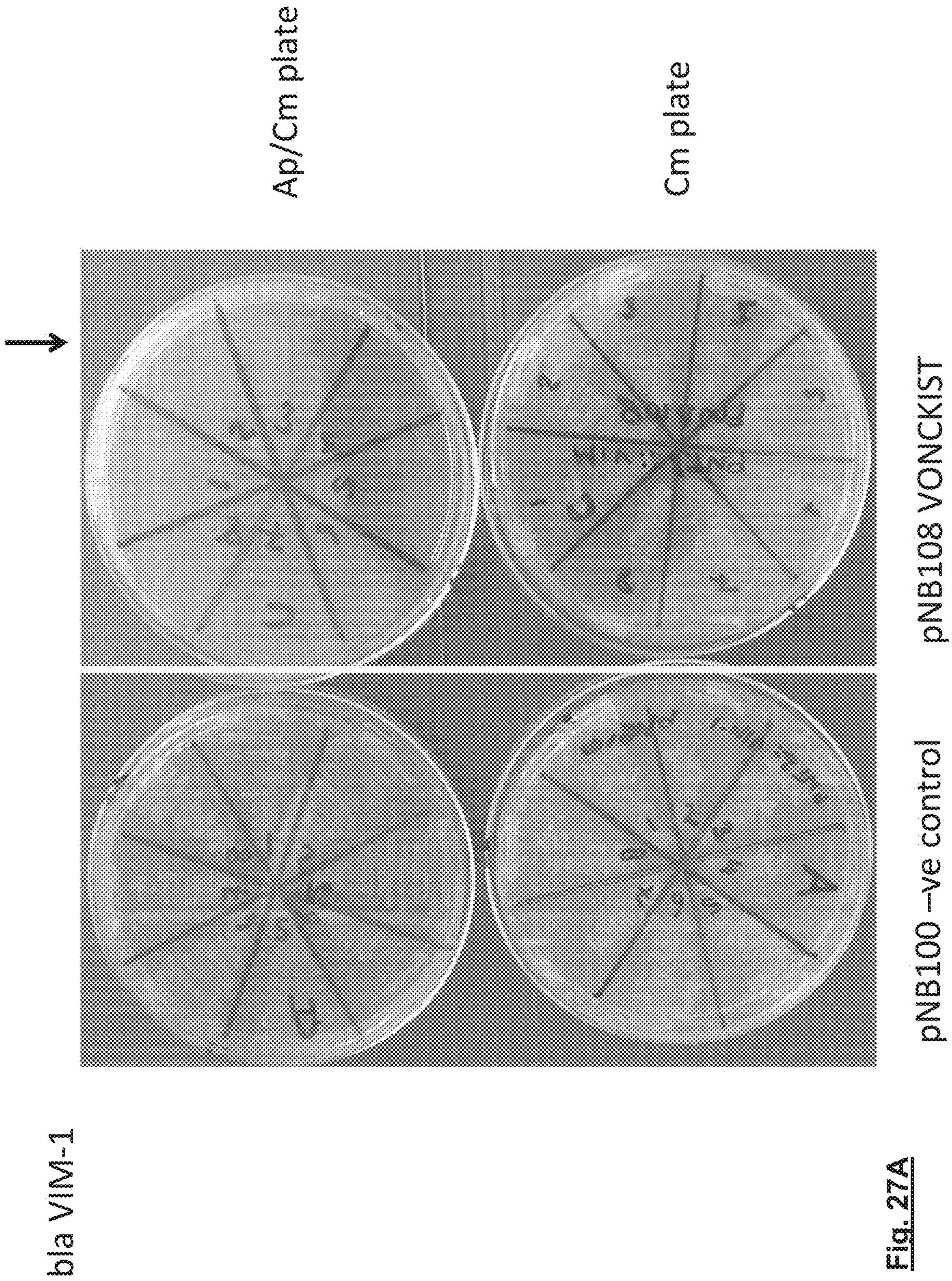
Figure 27B:
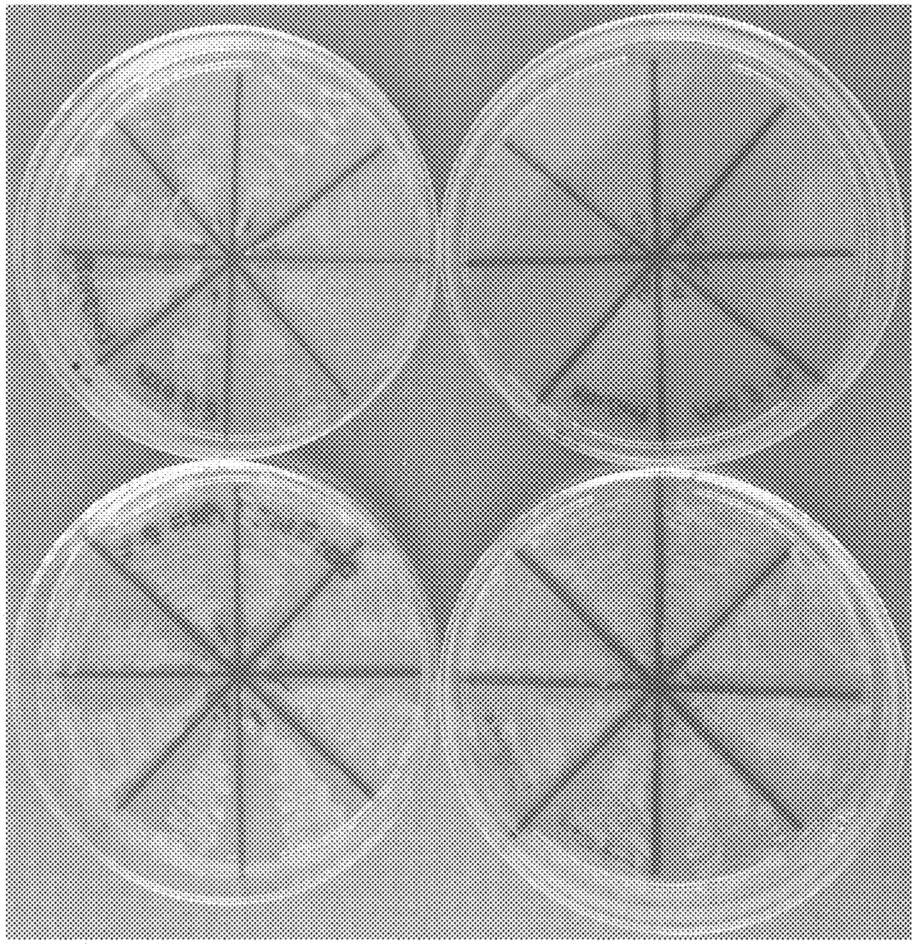
Figure 27C:
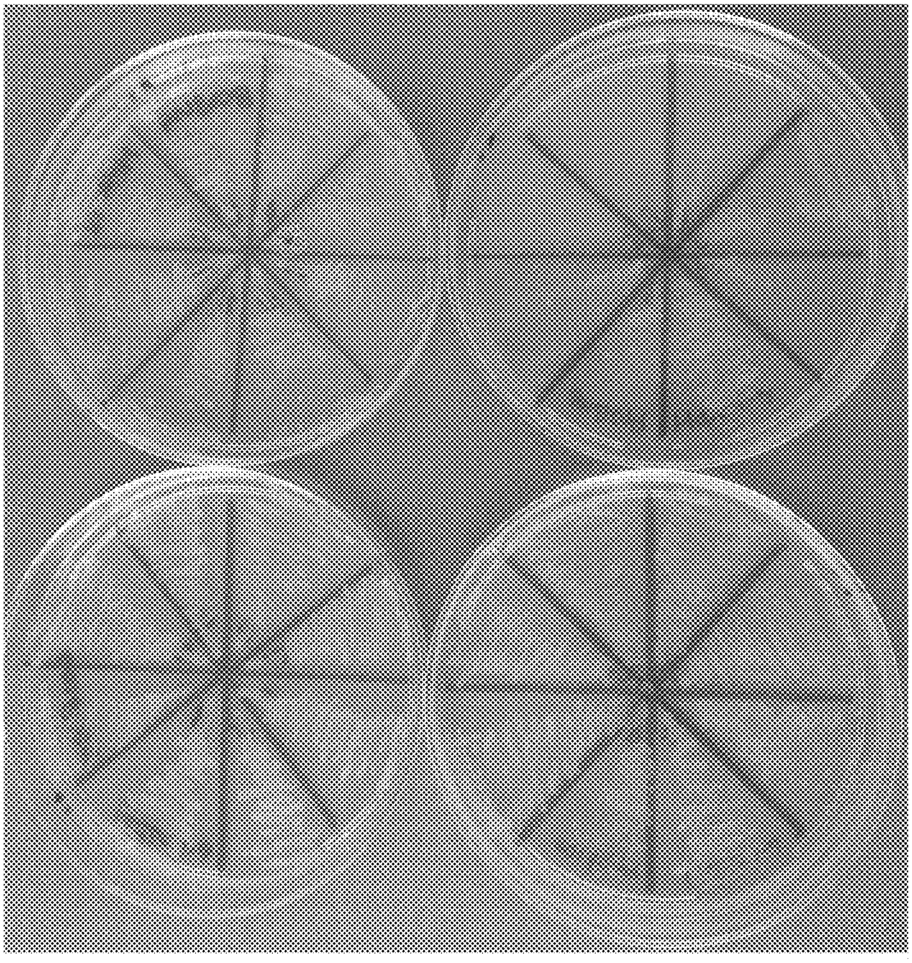
Figure 27D:
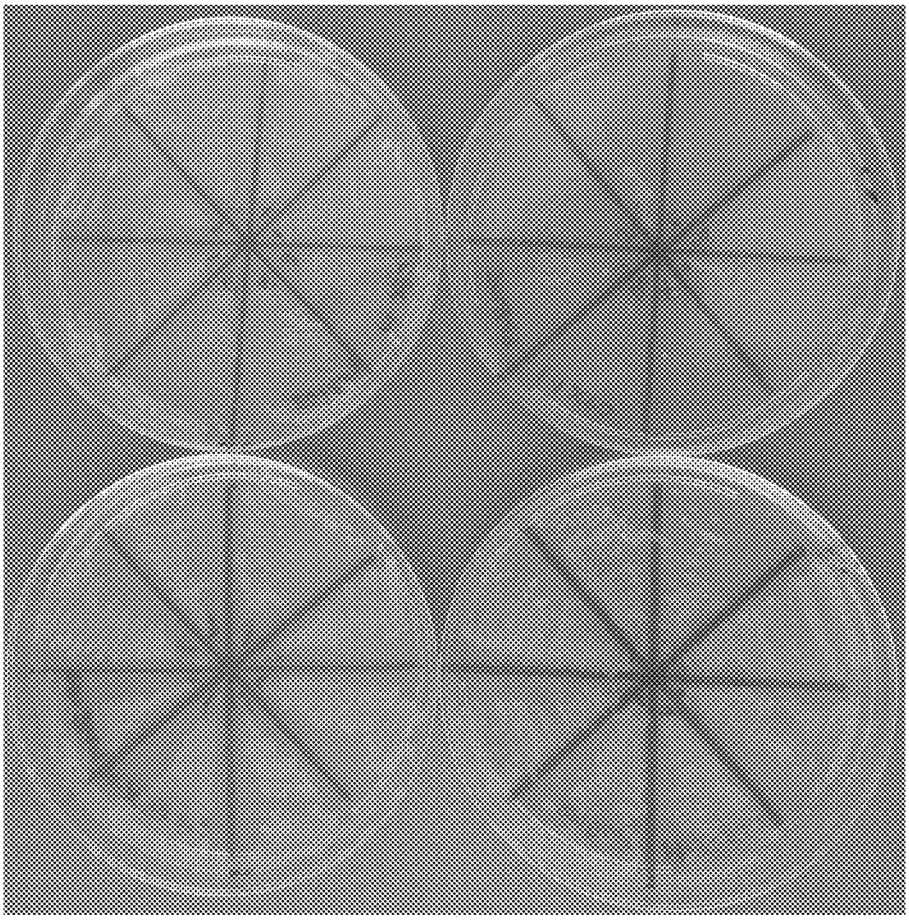
Figure 27E:
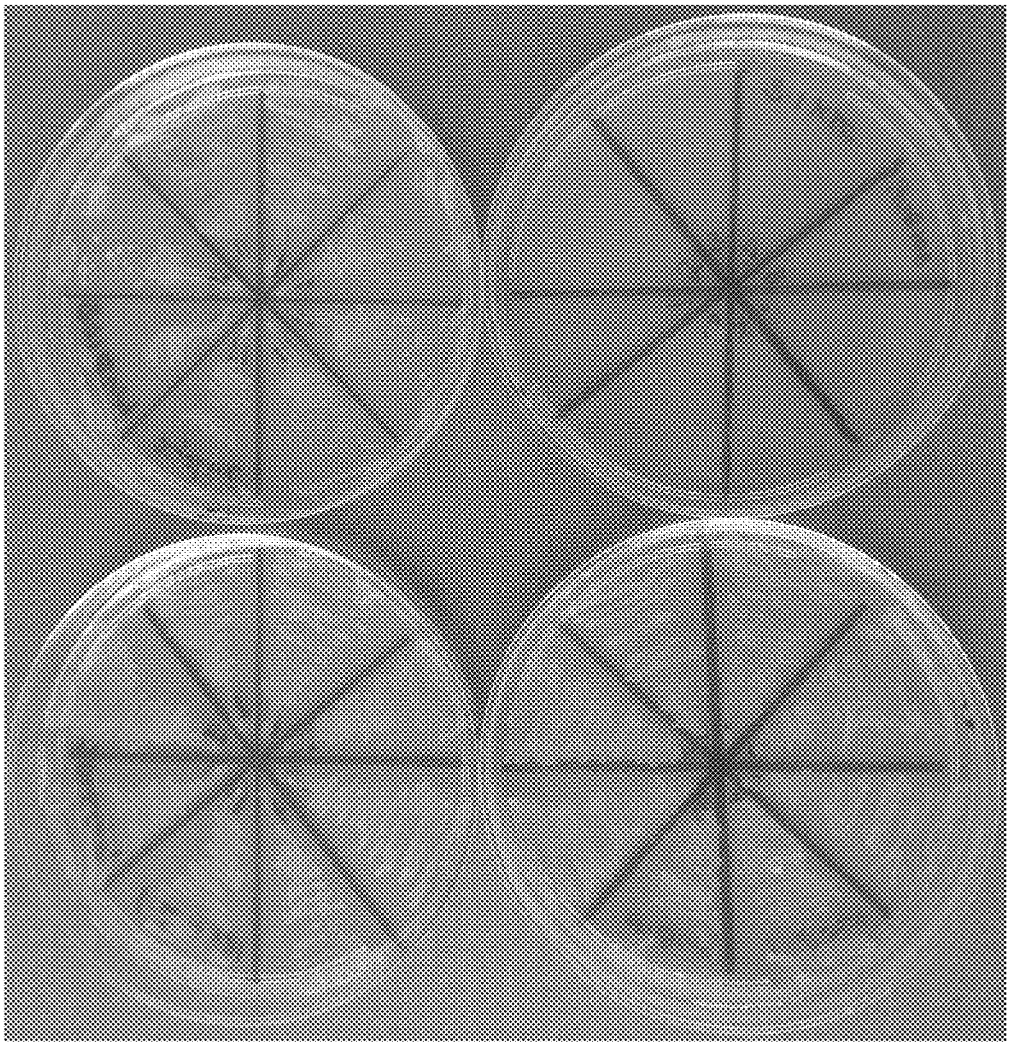
Figure 27F:
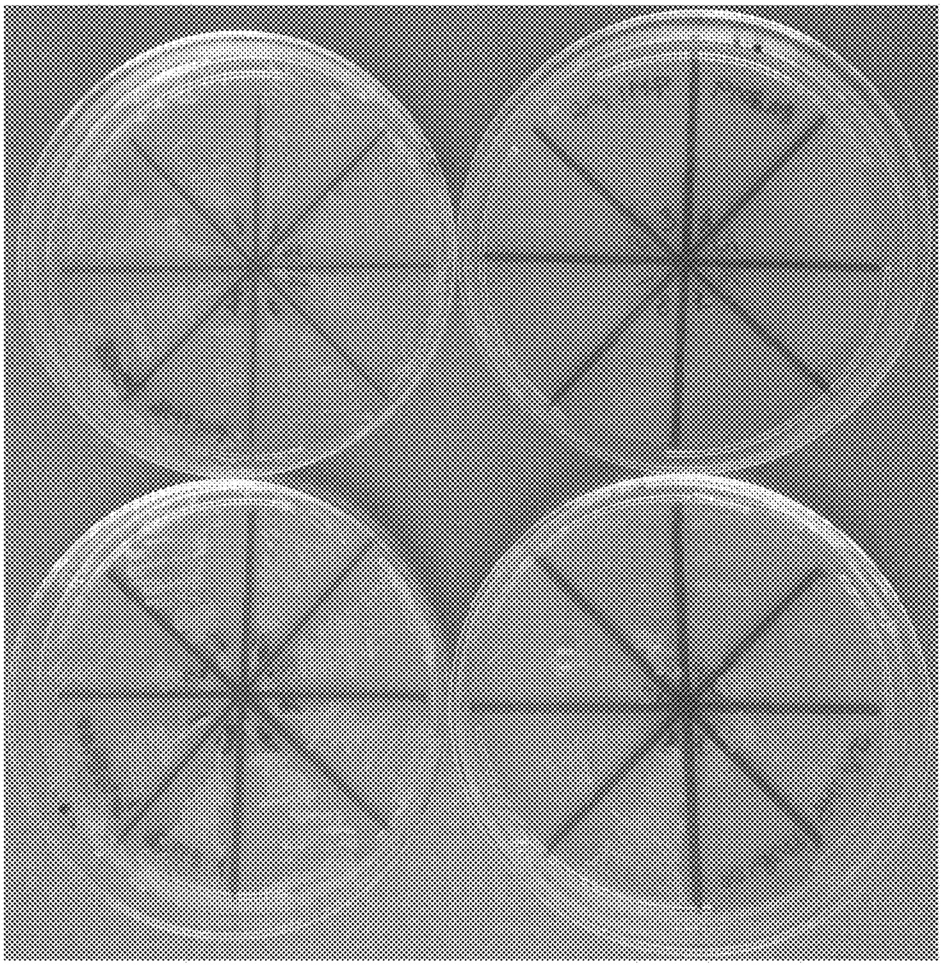
Figure 27G:
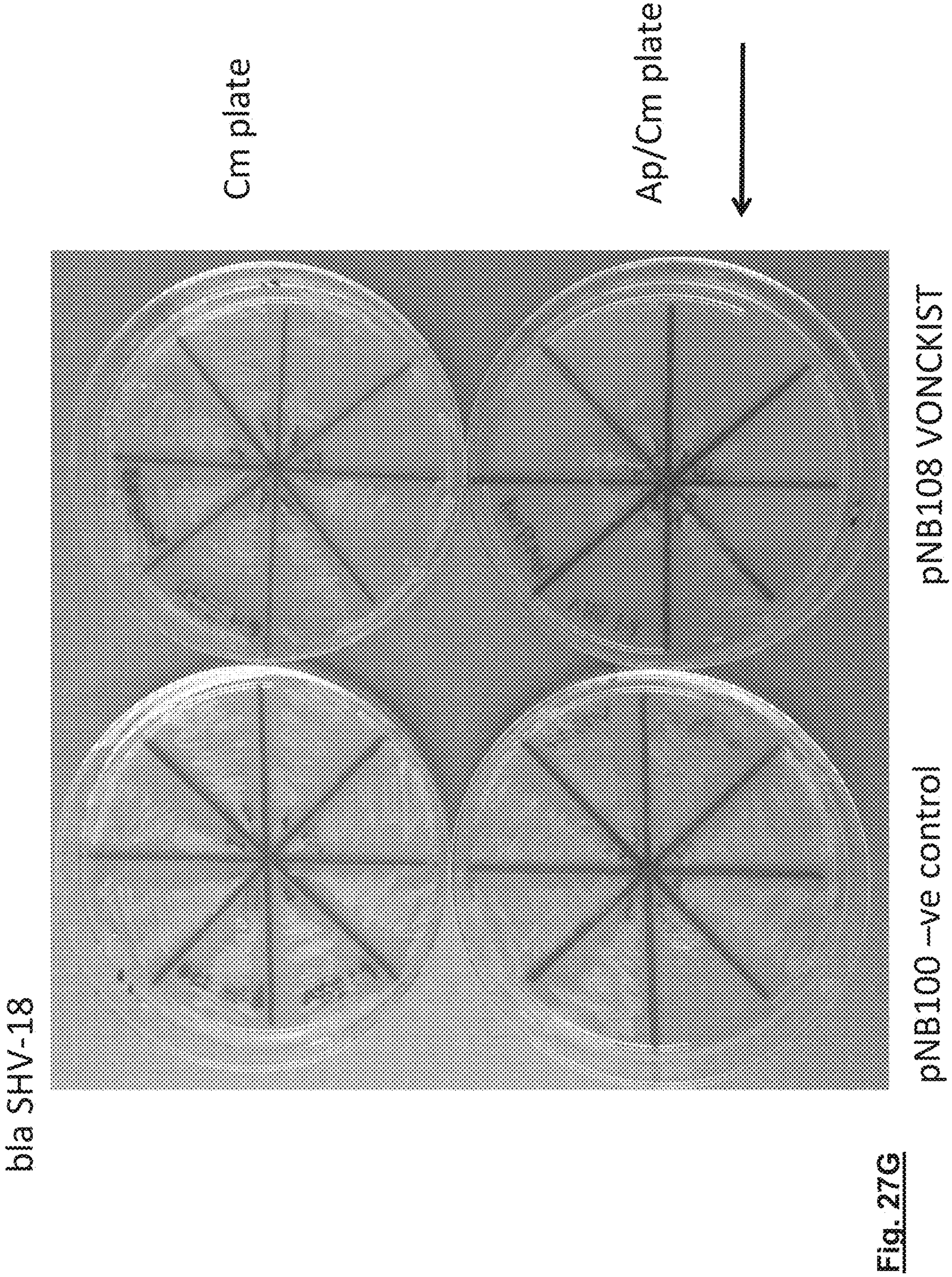
Figure 27H:
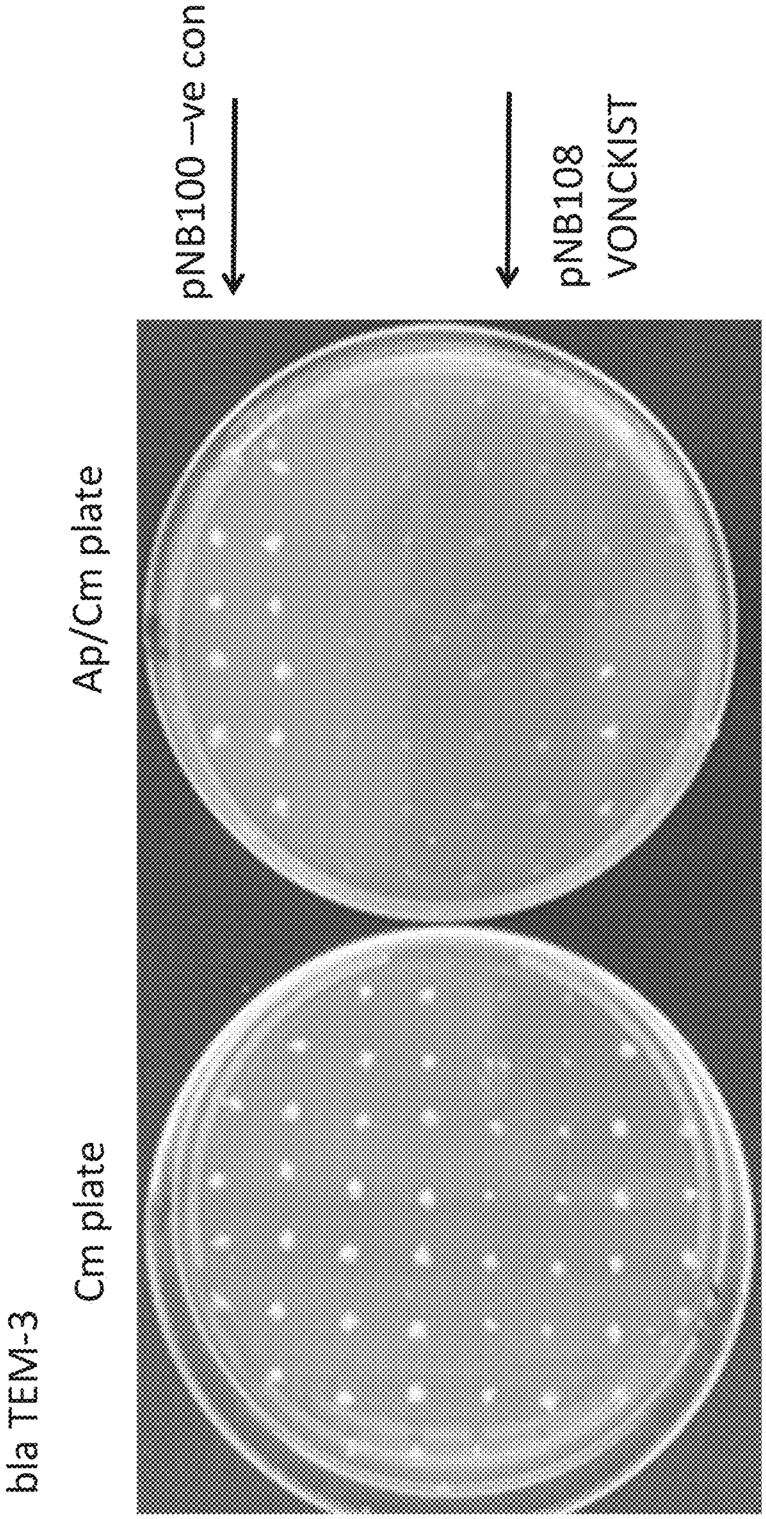

FIG. 26B. Octamer spacer concatenation in Example 2. The tetramer spacer concatemer a+b+c+d and e+f+g+h were amplified with primer pair NB026 and NB029, NB030 and NB033, respectively (V), and hybridise tetra concatemer via spacer d region followed by extension to yield octamer spacer a+b+c+d+e+f+g+h. This octamer was digested with BsaI and ligated to BsaI, whose restriction site is located in A1 and A2, sand ligated to BsaI spacer cloning sites on pNB100 to give pNB108. a=20 mer spacer for NDM, b=20 mer spacer for IMP, c=20 mer spacer for VIM, d=20 mer spacer for KPC, e=20 mer spacer for OXA-48, f=20 mer spacer for SHV, g=20 mer spacer for TEM, h=20 mer spacer for CTX-M.

FIG. 27. Photographs show results of NSA by plasmid transformation (see Example 2). DH5α with plasmids carrying blaVIM-1 (A); blaOXA-48 (B); blaNDM-1 (C) blaCTX-M-15 (D); blaKPC-3 (E); blaIMP-1 (F) blaSHV-18 (G); and blaTEM-3 ((H) were transformed with pNB108 and with pNB100 and selected on LB plates supplemented with chloramphenicol (Cm) 16 μg/mL. In (A-G), six single colonies were picked and streaked on LBCm16 plates and on plates carrying both Cm and ampicillin (Ap), LBCm16Ap100 plates (Cm, 16 μg/mL Ap, 100 μg/mL). As expected all colonies retain resistance to Cm carried on plasmids pNB100 and pNB108. Those transformed with pNB108 show all, or some, of the initial six colonies that have lost ApR thereby demonstrating Nemesis Symbiotic activity. In FIGS. 27A, B, E and F, arrow shows all colonies now Ap sensitive. If FIGS. 27C, D and G, arrow shows reduced AP resistance. In (H) single colonies were picked from the primary transformants and toothpicked onto LBCm16 and LBCm16Ap100 plates. Those transformed with pNB108 (colonies on rows 3-6, 8 and last three colonies on row 7) have lost ApR (i.e., they are all now Ap sensitive) thereby demonstrating Nemesis Symbiotic activity, in contrast to those transformed by pNB100 (colonies on rows 1, 2, or another plasmid lacking the blaTEM spacer sequence (first three colonies on row 7).

Figure 28:
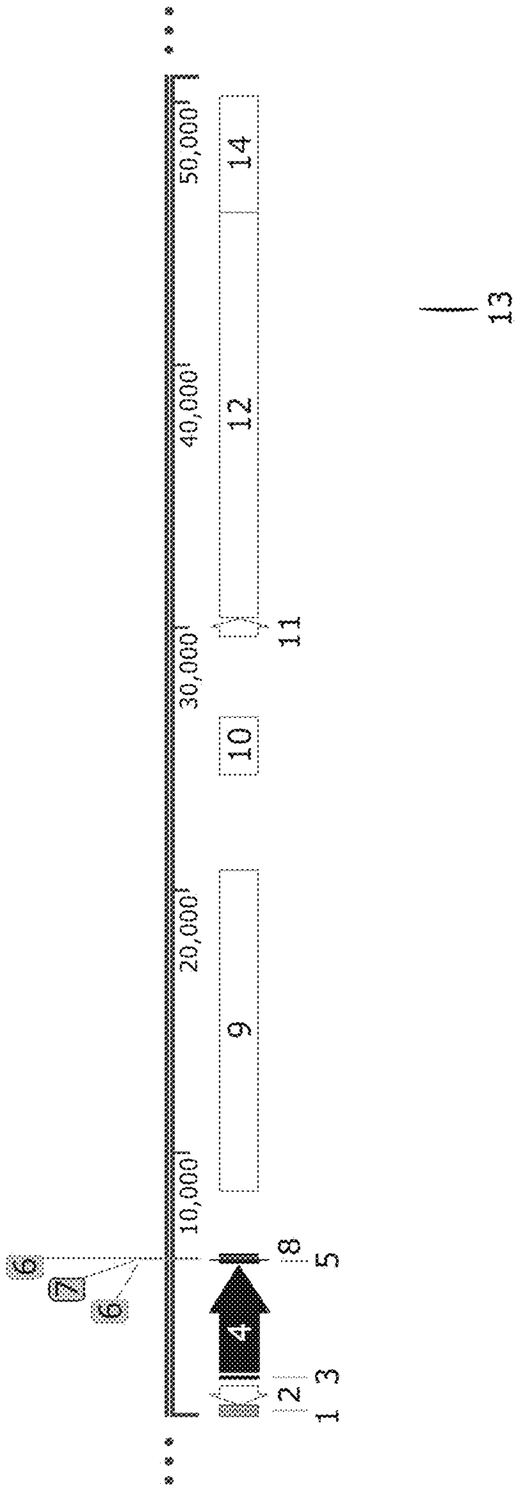

FIG. 28. Linear map of the Transmid cTNB00-X
Map shows: cos site (1), ornV (2), tracrRNA (3), cas9 (4), Leader (5), direct repeat (6), spacer for TEM-3 (7), trailer sequence (8), tra2 operon (9), Psr/Mrs operon (10), aphA gene (II), tra1 operon (12), oriT (13), control region (14).

FIG. 29. Photographs show results of NSA by plasmid transformation of cTNB000-X plasmid derivatives carrying six sgRNA cassettes (see Example 5).

Figure 29A:
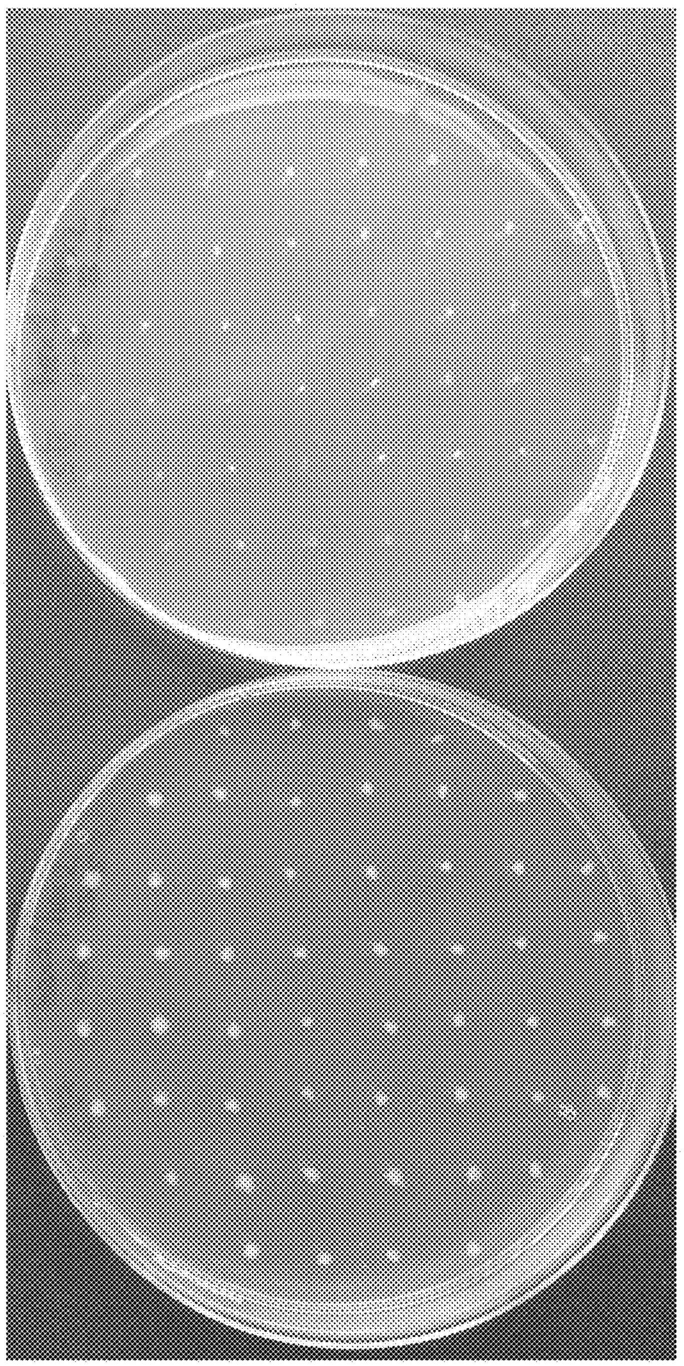
Figure 29B:
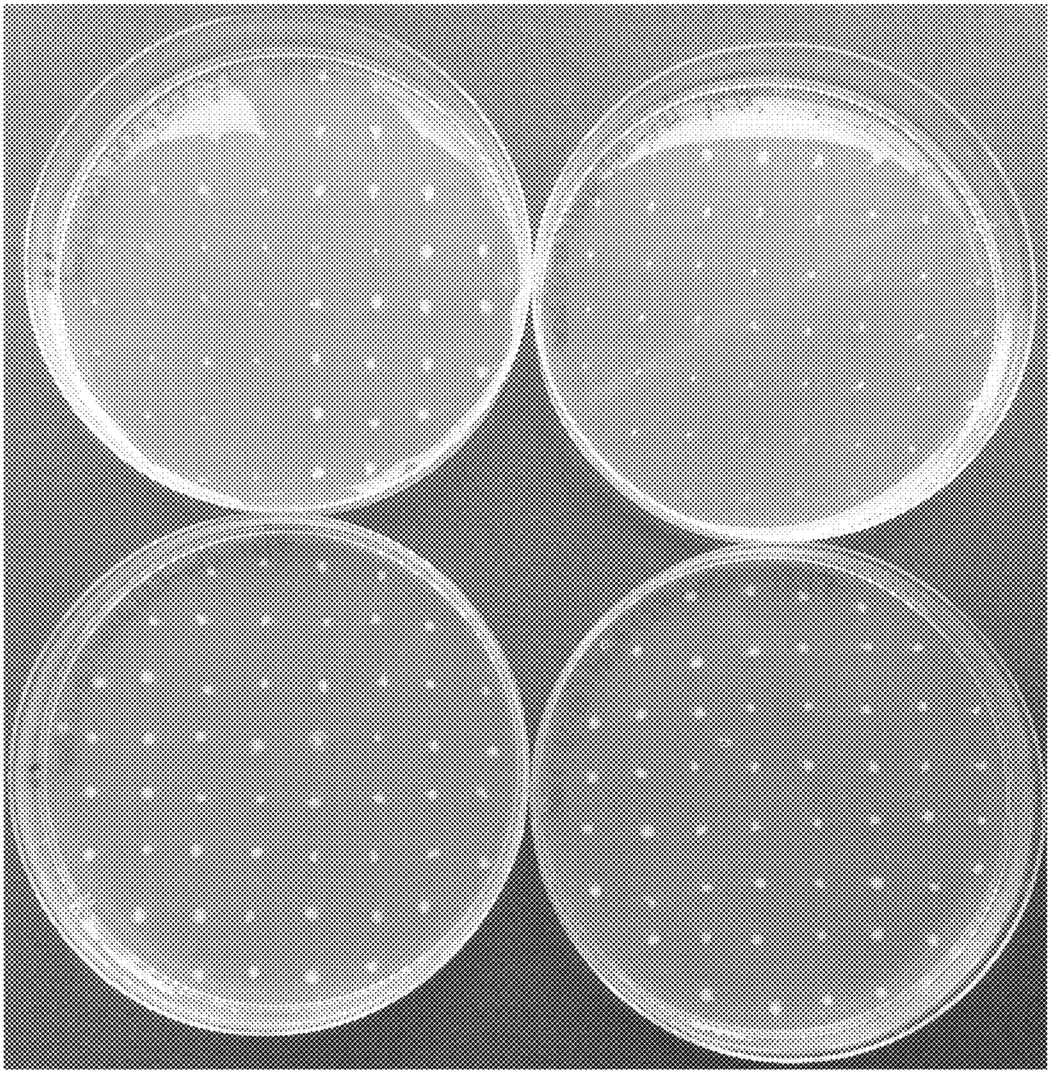
Figure 29C:
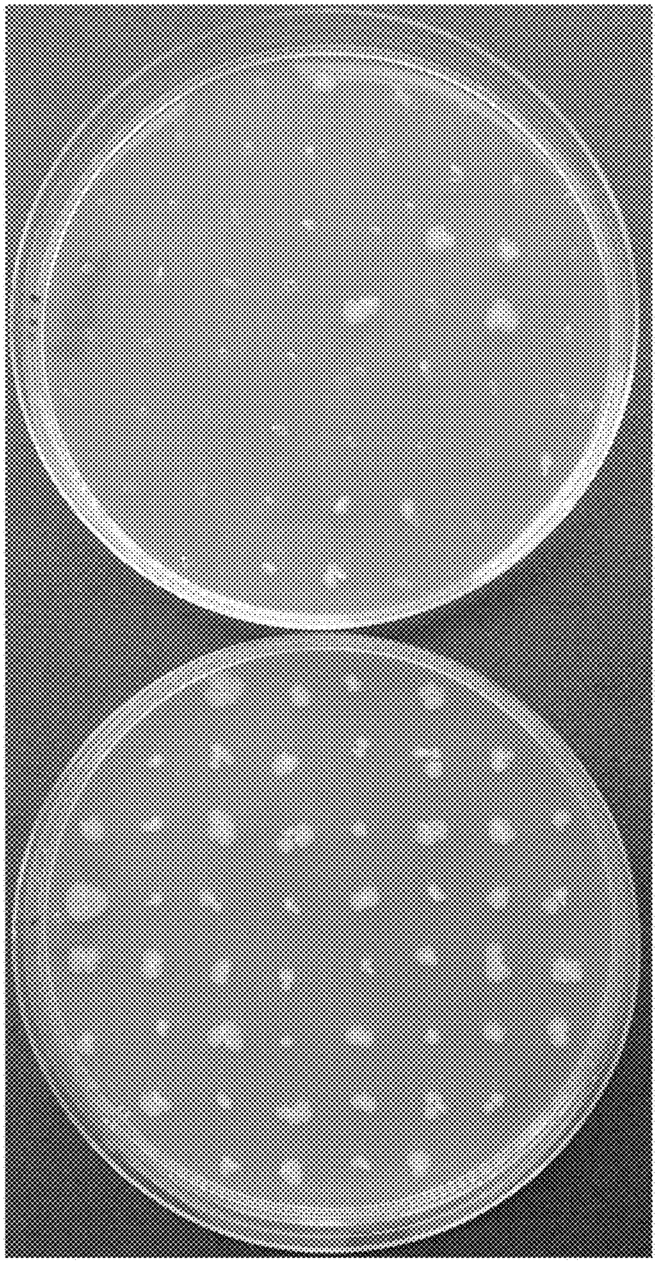

DH5α with plasmids carrying beta lactamase genes were transformed with cTNB000-X_sg01721034R carrying sgRNAs targeting VKONTC15, and selected on LB plates supplemented with chloramphenicol (Cm) 16 μg/mL. Then 26 single colonies were toothpicked onto LBCm16 plates, shown on the left, and on plates carrying both Cm and ampicillin (Ap), LBCm16Ap100 plates (Cm, 16 μg/mL Ap, 100 μg/mL) shown on the right. FIG. 29A shows: colonies 1-26 are of NBEc032 encoding VIM-1 (hex1) and are all ApS; colonies 27-52 are of NBEc036 encoding KPC-3 (hex2) and are all ApS. FIG. 29B top shows: colonies 1-26 are of NBEc033 encoding OXA-48 (hex3) and 25/26 colonies are ApS; colonies 27-52 are of NBEc0001 encoding TEM-3 (hex4) only 3/26 are ApS. FIG. 29B bottom shows: colonies 1-26 are of NBEc034 encoding NDM-1 (hex5) and all colonies are ApS; colonies 27-52 are of NBEc0035 encoding CTX-M-15 (hex6) are all ApS. FIG. 29C shows retesting the targeting of the TEM-3 gene. Here the primary transformant LBCm plates were grown overnight again and then tooth-picked: colonies 1-52 are of NBEc001 encoding TEM-3 (hex4) and 42/52 colonies are ApS.

DETAILED DESCRIPTION OF THE INVENTION

Further aspects and features of the invention are set out below.

The nucleic acid delivery vehicle of the invention, also herein referred to as a "Transmid", combines selected properties of bacterial viruses and bacterial plasmids to introduce selected nucleic acids of interest into microorganisms such as bacteria and facilitate subsequent dissemination of the selected nucleic acids to other microorganisms in the microbiome, for example, in a particular environment, such as in a human body or a part of the body. The deliverable nucleic acid component of a Transmid is packaged into bacteriophage coat proteins to allow delivery by infection. Infection leads to the release and replication of the deliverable nucleic acid component of the Transmid in the infected bacterial cell and its subsequent transmission to other bacteria by bacterial conjugation.

A Transmid may be used, for example, for the inactivation of antibiotic resistance and virulence genes in bacterial pathogens or for altering the population structure of the microbiome—in other words, microbiome engineering. Microbiome engineering may also be effected by Transmid delivery of desirable or beneficial genes to an existing microbiome in situ, for example, vaccines, therapeutics and nutraceuticals, in for example, the gastrointestinal tract. The Transmids of the present invention may be used in, for example, food and fermentation technology and in biochemical engineering and biofuel production.

The nucleic acid delivery vehicle described herein according to various aspects of the invention includes a conjugative, or is a mobilisable plasmid derivative, that may be packaged into a bacteriophage (phage) capsid or coat and so exploit the ability of the phage derivative to inject deliverable nucleic acid such as DNA into target bacterial cells for delivery of the deliverable nucleic acid. Following infection of target bacteria, for example bacterial pathogens in an infected individual, the deliverable nucleic acid is released from the phage particle and enters the bacterial cell and replicates.

Two particular types of Transmids can be defined: (i) conjugative Transmids, referred to herein as "c-Transmids"; and (ii) mobilisable Transmids, referred to herein as "m-Transmids".

A c-Transmid is self-transmissible as it includes a deliverable nucleic acid carrying all genetic functions that enable it to conjugate with recipient bacteria. These functions may include: (i) DNA mobilisation functions—an origin of transfer oriT and/or genes encoding a protein or proteins that form the relaxasome to introduce a nick at oriT; and (ii) other transfer, tra, functions including for example pili assembly and production, inner membrane proteins, periplasmic proteins, surface exclusion proteins and/or mating pair stabilisation (see review by Thomas & Nielsen *Nat. Rev. Microbiol.* 3, 711-21, 2005, which is hereby incorporated by reference in its entirety).

An m-Transmid includes a deliverable nucleic acid carrying genetic functions that enable it to be mobilised from donor to recipient cells, including for example nucleic acid (such as DNA) mobilisation functions. An m-Transmid requires functional complementation from other tra functions for example to be provided by a conjugative plasmid also resident in the donor bacterial cell.

Bacteria harbouring a deliverable nucleic acid from a c-Transmid, which is initially delivered by phage infection, may also serve as donors and by, bacterial plasmid conjugation, transmit the deliverable nucleic acid to other bacteria (e.g. in a microbiome). Each bacterial cell that receives a deliverable nucleic acid from a c-Transmid may go on to transmit it to other new recipients (e.g. in the microbiome) in one or more subsequent rounds of bacterial conjugation. In this way, the selected nucleic acid of interest is spread within a bacterial population.

Bacteria harbouring deliverable nucleic acid from an m-Transmid, also initially delivered by phage infection, may also serve as donors and transmit the deliverable nucleic acid to other bacteria, including bacterial pathogens (e.g. in the microbiome). The selected nucleic acid of interest is also spread within the bacterial population. However, this requires that a co-resident conjugative plasmid is present in the bacteria to provide the required other tra functions.

Transmids may also be used to deliver deliverable nucleic acid initially by phage infection to non-pathogenic commensal bacteria present in the microbiome of an individual being treated. Again the commensal bacteria now carrying the deliverable nucleic acid serve as donors. By bacterial conjugation these bacteria can transmit the Transmid and hence spread the selected nucleotide sequences of interest to further recipient bacteria. Or commensal bacterial carrying the deliverable nucleic acid may be directly administered as a probiotic, for example to facilite the spread of the deliverable nucleic acid by bacterial conjugation.

Thus a single genetic construct, the deliverable nucleic acid from a Transmid, delivered initially by phage infection or by commensal bacteria, and spread by bacterial conjugation, can be used for both therapeutic and prophylactic applications.

Transmids of the invention in various aspects can offer one or more or all of the following additional advantages:

(i) The delivery vehicle preferably does not involve the use of lysogenic phage that can transduce host genes, including virulence genes. There are likely to be fewer regulatory hurdles to commercialise Transmids for use in pharmaceutical compositions or in bio-engineering; and/or (ii) Transmids are preferably not lytic phage capable of killing the host bacterial cell. There should be no or little selection for target bacteria that are resistant to phage delivery; and/or (iii) Following initial phage infection, subsequent spreading of the deliverable nucleic acid is by conjugation. The absence of any further need for phage infection means that there will be no or little immune response by a patient against a pharmaceutical composition comprising the Transmid; and/or (iv) A pharmaceutical composition comprising the Transmid is preferably cell-free. Therefore, delivery of the composition can be parenterally and by, for example, aerosol delivery for pulmonary infection; and/or (v) Transmids can be tailored or modified for the phage infection stage and/or the conjugation transmittal stage to a broad or narrow range of bacterial cells. The tailoring or modification may use appropriate genetic modules for phage infection and plasmid conjugation; and/or (vi) Transmids are ideal for use in a clinical delivery system, for example delivery of therapeutic and prophylactic genetic modules, but also offer applications in industrial microbiology and synthetic biology.

A Transmid of the invention may be thought of to comprise, and may be constructed from, the following three components: (i) a "Ship"—the Transmid vector backbone carrying functions required for replication, phage packaging and (for c-Transmids) conjugal transfer; (ii) a "Cargo"—the selected nucleic acid of interest to be delivered, which may be constructed on a non-mobilisable plasmid cloning vector for ease of construction and flexibility for the addition of selected nucleic acid of interest; and (iii) a "Dock"—functions that allow in vivo site-specific recombination to transfer the Cargo, the selected nucleotide sequences of interest, from a cloning vector to the Ship, the conjugative plasmid vector backbone.

A Transmid according to certain aspects of the invention may comprise features (or "genetic modules") as outlined below.

OriV and rep genes and copy number regulation—A plasmid DNA origin of vegetative replication oriV, in order to allow replication of the deliverable nucleic acid after delivery by phage infection to a bacterial cell or host. Typically plasmids recruit bacterial host replication machinery to initiate DNA replication from recognition sequences in oriV. Typically one or more plasmid-encoded replication proteins rep are required to assist in the recruitment of host replication machinery to oriV. Some plasmid Ori V and rep proteins for use in the present invention are able to interact with the host DNA replication machinery of a large range of bacterial species and are known as broad host range (BHR) plasmids.

Additional plasmid functions regulate the copy number of the plasmid and its stability through partitioning at cell division as well as a variety of other mechanisms, so-called "plasmid addiction" systems, described below. Replication and copy number regulation functions define plasmids into various so-called incompatibility classes where those that are incompatible share common mechanisms for replication, copy number control and stability. Such incompatibility classes include Inc C, J, N, P, Q and W. An exemplar is the incPα type plasmid RK2 (also known as RP4, R18, R68, RP1).

Other conjugative plasmids show a narrow host range in their ability to replicate in bacterial hosts. An exemplar is the F plasmid of *E. coli* so named as the Fertility Factor or F factor—the first plasmid discovered by Lederberg.

Thus the choice of the Ori V and rep genes used in the present invention can be tailored to suit the required use. For example, if a Transmid is required that is capable of replication in a broad range of bacterial species, for example members of the Gram negative family the Enterobacteriaciae that include, along with many harmless symbionts, pathogens such as *Salmonella, E. coli, Yersinia pestis,*

*Klebsiella, Shigella, Proteus, Enterobacter, Serratia* and *Citrobacter*, then a Transmid incorporating features from a BHR plasmid RK2 is a suitable choice. RK2 was first identified in *Pseudomonas aeruginosa*—a member of the family Pseudomondaceae and is able to replicate in most genera of Gram negative bacteria Enterobacteriaciae. Alternatively, if a Transmid is required that is capable of replication in only a narrow range of bacterial species, then a Transmid incorporating features from a narrow host range conjugative plasmid might be more suitable—for example, a plasmid based upon the F factor for use in *E. coli.* tra operons—Genes encoding pili assembly and production, inner membrane proteins, periplasmic proteins, surface exclusion proteins and/or mating pair stabilisation may also be included in the deliverable nucleic acid. These genes may be obtained from, for example, a broad host range conjugative plasmid such as RK2, or a narrow host range conjugative plasmid such as the F factor.

oriT and relaxase gene(s)—A plasmid origin of transfer oriT is required in order to allow conjugal transfer of the deliverable nucleic acid from a donor to a recipient bacterial cell. The oriT serves as a recognition sequence for a relaxase—a single-strand DNA transesterase enzyme responsible for site- and strand-specific nicks in double-stranded DNA. The nick produced by the relaxase at oriT initiates plasmid rolling circle replication ("RCR") to generate a single-stranded DNA (ssDNA) that is transferred from a donor to a recipient during bacterial conjugation. Relaxases are so named since the single-stranded DNA nick they catalyse leads to relaxation of helical tension.

Bacteriophage packaging signal(s)—For successful packaging into a phage capsid or protein coat, the deliverable nucleic acid comprises a phage packaging signal sequence. Packaging of the deliverable nucleic acid to form a Transmid may be in vitro, or in vivo using a helper phage. For in vivo packaging, a bacterial strain carrying a helper phage derivative may be used that expresses all the components required for phage assembly, but itself lacks the phage packaging signal sequence and so is, itself, unable to be packaged; thus only phage derivatives carrying the deliverable nucleic acid will be produced.

The host range for infection by Transmids may be manipulated in different ways. One way is by choice of the genetic module carrying the phage packaging signal sequence(s), such that for in vivo packaging, different types of helper phage may be used in order to infect a range of different bacterial species including pathogens.

Another way to manipulate host range is by alteration of phage specificities for infection: such specificities are carried on phage tail fibre proteins since phage infect a range of bacteria by a specific interaction between a tail fibre protein and a cell surface receptor or membrane protein. Some such receptors are present in a range of bacterial species, others are common only to one or a few species. In the case of *E. coli* bacteriophage lambda, this is the maltose permease protein that transports the sugar maltose into the bacterial cell. In the case of another, bacteriophage Mu, the receptor is LPS. Thus a genetic module encoding the tail fibre protein may also be exchanged to suit a range of different phages capable of infecting different bacteria including pathogens.

For in vitro packaging, a well-established method may be used to package plasmid DNA into bacteriophage coat proteins by exploiting the phage lambda system, as developed by Collins and Hohn, 1978 (*Proc. Natl. Acad. Sci. USA* 75 (9): 4242-4246, which is hereby incorporated by reference in its entirety). The method uses cosmids, a plasmid gene-cloning vector that is packageable in vitro into bacteriophage lambda heads as it carries ~200 base pairs (bp) long lambda Cos sequences required for packaging. Cos sequences comprise a cosN site where DNA is nicked at each strand, 12 bp apart, by terminase—a phage lambda encoded endonuclease. This leads to linearisation of the circular cosmid with two "cohesive" or "sticky" ends of 12 bp. (The DNA should be linear and in the size range of 37-50 kilobase pairs (kbp) to fit into a phage head.) The cosB site holds the terminase while it is nicking and separating the strands. The cosQ site of next cosmid (as rolling circle replication often results in linear concatemers) is held by the terminase after the previous cosmid has been packaged, to prevent degradation by cellular DNases.

Packaging may involve a concatemer of multiple genome lengths that may be achieved in vitro prior to packaging. It is possible to use derivatives of cosmids, known as fosmids, which have been developed that allow replication in a broad range of bacterial hosts. This allows cloning of large amounts of DNA into the vector in *E. coli*, taking advantage of the bacteriophage lambda in vitro packaging system, for subsequent delivery to other bacteria by conjugation for functional studies (for example Aakvik et al., *FEMS Microbiol. Lett.* 296, 149-58, 2009, which is hereby incorporated by reference in its entirety). Here the functions for conjugation are provided by another plasmid in the bacterial cell or from plasmid functions introduced to the chromosome. In essence it is a shuttle system to allow introduction of large sections of DNA to less well-studied bacterial systems than *E. coli.*

Selectable marker gene—The inclusion of the suitable selectable marker gene in a deliverable nucleic acid allows testing for successful phage delivery as well as successful delivery by bacterial conjugation. Suitable selectable marker genes include antibiotic resistance marker genes. For clinical applications, after development of a Transmid, it may be desirable to remove antibiotic resistance marker genes.

A selection gene providing a selective advantage for the transmittal of a deliverable nucleic acid—In order to increase the efficiency of transmittal or spreading of a deliverable nucleic acid such as through the microbiome, including, if desired, a population of microbial pathogens, the deliverable nucleic acid may, according to various aspects of the invention, further comprise a selection nucleotide sequence that may for example encode a gene conferring a growth advantage to the microorganism acquiring the deliverable nucleic acid—for example, thereby giving a selective advantage over non-infected siblings. Additionally or alternatively, the selection nucleotide sequence may encode a bacteriocin, which are proteinaceous toxins produced by bacteria to kill or inhibit growth of other bacteria, and the corresponding immunity polypeptide may be used to protect bacterial cells carrying the deliverable nucleic acid (see review by Cotter et al., *Nature Reviews Microbiology* 11: 95, 2013, which is hereby incorporated by reference in its entirety).

Genes ensuring maintenance of a deliverable nucleic acid in bacteria—The deliverable nucleic acid may also carry genetic functions that ensure it is not lost from its bacterial cell host. These genetic functions may include, for example a toxin/antitoxin (TA) pair such as a plasmid addiction system (reviewed by Goeders & Melderen, Toxins 6, 2014, which is hereby incorporated by reference in its entirety) that lead to post-segregational killing of cells that have lost a plasmid. Cessation of expression of the antitoxin that neutralises the effect of a toxin or killer function allows the lingering plasmid-encoded toxin to kill the bacterial cell. Such TA systems are widespread in bacteria and not only for ensuring plasmid segregation. Thus a deliverable nucleic acid carrying a TA addiction system will ensure its inheritance by daughter cells following cell division by post-segregational killing of cells that have lost the deliverable nucleic acid.

The "Dock"—The Transmid vector backbone or "Dock" is typically capable of being packaged in bacteriophage coat proteins (or "caspid"), replicating following infection, and conjugating to recipient cells. The Dock can be used as the basis for the addition of the other genetic modules, such as the "Cargo". The Dock may employ a Cre-lox system, which is a site-specific recombination system derived from bacteriophage P1 that has been used experimentally, primarily in eukaryotic systems. The Cre recombinase is a single enzyme that, without requiring any other proteins, recombines a pair of 34 bp target sequences called LoxP sequences. The presence of a lox site in the Ship allows for selection for transfer of the Cargo from the cloning vector in vivo in a Cre-mediated sequence-specific recombination reaction. Thus the deliverable nucleic acids may be constructed in a suitable non-mobilisable cloning vector to be flanked by lox sites. The cloning vector used would also encode the Cre recombinase in this example. A plasmid construct carrying the Cargo could be transformed into an *E. coli* or other bacterial host carrying the Ship. Successful site-specific recombination events in the transformant, where the Cargo is transferred from the non-mobilisable cloning vector to the Ship, are selected for by subsequent mating of this transformant with a bacterial recipient with suitable selection for the transfer of the Cargo.

Genes encoding transposition of the Cargo (the selected nucleotide sequences of interest)—The Cargo present within the Transmid may also be placed within a transposable genetic element that allows its efficient transposition from the Transmid to the bacterial chromosome. For example, if the Transmid is introduced to a bacterial cell in which it is unable to replicate, or in which a resident incompatible plasmid prevents its stable establishment, or in which endogenous host defense mechanisms such as restriction endonucleases degrade it, the delivery of the selected nucleic acid of interest will still be successful if they escape the Transmid and insert into the chromosome.

Features of m-Transmids—An m-Transmid may share many of the genetic modules of c-Transmids, but does not require the relatively large Tra operon(s) present in c-Transmids. The m-Transmid can thus accommodate a larger selected nucleic acid of interest than a c-Transmid, whilst still being packaged in phage coat proteins.

Following infection by an m-Transmid, infected bacterial cells may serve as donors and transmit the deliverable nucleic acid component of the m-Transmid to different bacteria if the different bacteria have a co-resident conjugative plasmid present to provide the required tra functions. For the deliverable nucleic acid to be transmitted further from the different bacteria to other bacteria by conjugation, those other bacteria should either themselves have co-resident conjugative plasmid present to provide the required tra functions for conjugation, or alternatively the co-resident conjugative plasmid present in the different bacteria could be co-transferred with the deliverable nucleic acid into the other bacteria.

The requirement for a co-resident conjugative plasmid provides a tool to restrict or control the spread or transmittal of deliverable nucleic acid from an m-Transmid if required. For example, if an m-Transmid infects an *Escherichia coli* strain harbouring a conjugative plasmid that is capable of conjugation only with other *E. coli* cells, then the ability to transmit the deliverable nucleic acid component of the m-Transmid by conjugation will be limited to *E. coli.*

By way of illustration: the plasmid pRK2013 (Ditta et al., *Proc. Natl. Acad. Sci. U.S.A.* 77, 7347-7351, 1980, which is hereby incorporated by reference in its entirety) is a helper plasmid containing tra and mob genes for mobilisation of non-self-transmissible plasmids. If pRK2013 is present in a bacterial cell infected by an m-Transmid, the deliverable nucleic acid component of the m-Transmid can be transmitted by conjugation to a broad range of different bacterial species as recipients. However, once the deliverable nucleic acid is transmitted to such recipients, it will not be transmitted by conjugation to further bacteria unless a conjugative plasmid is already present in those further bacteria.

The "Cargo"—Several options for the selected nucleic acid of interest within the deliverable nucleic acid of the present invention are envisaged, as noted above.

One application of the Transmid delivery system is for delivery of a selected nucleic acid of interest to interfere with antibiotic resistance genes, and/or replicons carrying such genes, in microorganisms such as bacteria in order to disable antibiotic resistance in the microorganisms.

Antibiotics, originally isolated from microorganisms such as *Streptomyces*, are a powerful way to treat infectious disease. However, very quickly bacteria acquired anti-microbial resistance (AMR) to antibiotics in response to selection pressure. One common route to AMR has been the acquisition of resistance genes evolved in the original antibiotic-producing microorganisms, via horizontal transmission on plasmid vectors. Such plasmids have in some instances acquired multiple antibiotic resistance genes carried by transposable elements and integrons. Host-encoded mutations that modify the bacterial protein target or prevent entry of the antibiotic have also occurred.

Resistance to antibiotics by microorganisms such as bacterial pathogens is one of our most serious health threats. Infections from resistant bacteria, for example, are now not uncommon, and some pathogens have even become resistant to multiple types or classes of antibiotics. The loss of effective antibiotics undermines our ability to fight infectious diseases and manage the infectious complications common in vulnerable patients, for example those undergoing chemotherapy for cancer, dialysis for renal failure, and surgery, especially organ transplantation, for which the ability to treat secondary infections is critical.

Many achievements of modern medicine are put at risk by AMR. Without effective antibiotics for care and prevention of infections, the success of treatments such as organ transplantation, cancer chemotherapy and major surgery would be compromised.

Resistance mechanisms fall into four classes:

(1) enzymes that degrade antibiotics, including beta-lactamases that break the beta-lactam ring of the penicillin family of antibiotics;

(2) enzymes that modify antibiotics include aminoglycoside phosphotransferases that phosphorylate aminoglycoside antibiotics such as kanamycin; chloramphenicol acetyltransferase (CAT) that acetylate chloramphenicol;

(3) efflux pumps that actively export antibiotics from cytoplasm out of the cell, such as the tetracycline efflux pump that is expressed in the presence of tetracycline, plus other pumps, conferring multidrug resistance, that are capable of exporting a range of antibiotics; and (4) mutations that change the protein target of the antibiotic such that it is no longer inactivated by it; for example, beta-lactams are bactericidal because they inhibit penicillin-binding proteins (PBPs) that are required for peptidoglycan biosynthesis and bacterial cell wall integrity and PBP mutants with reduced binding to beta-lactams will not be inhibited.

Several approaches are currently being used or developed to address the problem of antibiotic resistance, including new antibiotics, direct inhibition of resistance enzymes, and non-antibiotic bactericides. For example, infection by bacteriophage was developed in the 1920's and although largely discontinued with the discovery of antibiotics, has been retained in certain countries. Current approaches use virulent, lytic bacteriophage that kill bacteria, including antibiotic resistant bacteria, but this opens the way for selection of bacterial variants that are resistant to bacteriophage infection. To obviate this, preparations containing a mixture of different strains of bacteriophage are being used. Another disadvantage of the use of such lytic bacteriophage in patients suffering from sepsis is that cell lysis and death by lytic bacteriophage can release endotoxins from the cell into the blood and can cause endotoxin shock (see review by Nobrega et al., 2015; supra).

The present invention provides in various aspects an alternative mechanism for tackling antibiotic resistance in microorgansims such as bacteria.

In one aspect, the selected nucleic acid of interest according to the invention may be or include a recombinant polynucleotide comprising a clustered regularly interspaced short palindromic repeat (CRISPR) array nucleic acid sequence having or transcribing an RNA guide molecule with a spacer sequence sufficiently complementary to a target sequence of an antibiotic resistance gene in a microorganism (such as a bacterium) for the antibiotic resistance gene to be inactivated in the presence of a CRISPR associated (Cas) DNA-binding polypeptide or a functional equivalent or a modified version thereof, thereby sensitising the microorganism to the antibiotic.

An aim of various aspects of the invention is inactivation of DNA carrying a gene encoding an antibiotic resistance enzyme using a CRISPR/Cas system. An advantage of the invention is that one or more existing antibiotics can be used to treat infectious disease, as microorganisms become re-sensitised to the antibiotics or are prevented from acquiring antibiotic resistance.

The target sequence of an antibiotic resistance gene may be a sequence flanking the gene itself which, if disrupted, inactivates the antibiotic resistance gene. For example, if the antibiotic resistance gene is located on a plasmid, the invention may encompass a target sequence in the plasmid.

In contrast to prior art approaches of inactivating antibiotic resistance enzymes, these aspects of the present invention will not require new drug development and the concomitant regulatory approval required for each new drug. Rather, the invention provides a tool that can be applied to target and inactivate relevant antibiotic resistance genes directly rather than the gene products. For example, a gene encoding an antibiotic resistance enzyme, or a gene encoding a protein regulating the uptake and export of an antibiotic by altering the membrane permeability and efflux pump expression, respectively, can be targeted.

By way of background to various aspects of the invention, the CRISPR/Cas system is an RNA-mediated genome defense pathway that is part of a natural bacterial and archaeal immune system against nucleic acid invaders, analogous to the eukaryotic RNAi pathway. Natural CRISPR systems contain a combination of Cas genes as well as non-coding RNA elements capable of programming the specificity of the CRISPR-mediated nucleic acid cleavage. Three types (I-III) of CRISPR systems have been identified thus far in a wide range of bacterial and archaeal hosts. Each CRISPR locus is composed of a series of short DNA direct repeats separated by non-repetitive spacer sequences. The spacer sequences, in nature, typically originate from foreign genetic elements such as bacteriophage and plasmids. As used herein, the series of repeats plus non-repetitive spacer sequences is known as a CRISPR array. The CRISPR array is transcribed and hybridised with repeat complementary tracrRNA followed by cleavage within the direct repeats and processed into short mature dual tracrRNA:crRNAs containing individual spacer sequences, which direct Cas nucleases to a target site (also known as a "protospacer"). For example, the Type II CRISPR/Cas9 system carries out a targeted DNA double-strand break ("DSB") in four steps. Firstly, two RNAs, the pre-crRNA array and tracrRNA, are transcribed from the CRISPR locus. Secondly, tracrRNA hybridises to the repeat regions of the pre-crRNA and mediates the processing of pre-crRNA into mature crRNAs (also referred to herein as "RNA guide molecules gRNA") containing individual or monomer spacer sequences. Thirdly, the mature crRNA:tracrRNA complex directs Cas9 protein in the form of a ribonucleoprotein to the target DNA via base-pairing between the spacer on the crRNA and the target site on the target DNA. Finally, Cas9 mediates cleavage of target DNA and creates a DSB.

In aspects of the present invention, as elaborated herein, modified CRISPR constructs may be used to target antibiotic resistance genes. The deliverable nucleic acid of the invention using such a construct is also referred to herein as an "assassin construct" which is used to effect inactivation of such genes.

The main focus of using CRISPR technology to date has been for use as a DNA editing tool for reverse genetics, primarily in eukaryotes. WO2007/025097 describes the use of CRISPR technology for modulating resistance in a cell against an invading target nucleic acid or a transcription product thereof, especially against invading bacteriophages. Methods for downregulating prokaryotic gene expression using CRISPR technology to target mRNA transcribed by the genes have been suggested for example in WO2010/075424. WO2012/164565 describes a CRISPR system from Lactoccocus and use of the system for modulating resistance of a cell against an invading target nucleic acid or a transcription product thereof. None of the prior art systems describe a nucleic acid delivery vehicle (also referred to herein as a "Transmid") as defined herein or its use for tacking antibiotic resistance in microorganisms.

According to aspects of the invention, the RNA guide molecule may mediate binding of the Cas DNA-binding polypeptide or its functional equivalent or its modified version to the antibiotic resistance gene. This mirrors the natural system described above.

The Cas DNA-binding polypeptide or its functional equivalent or its modified version of various aspects of the invention may also be capable of binding to RNA or other nucleic acid molecules. In other words, the requirement for the Cas DNA-binding polypeptide or its functional equivalent or its modified version to be capable of binding DNA does in some aspects of the invention does not exclude the polypeptide or its functional equivalent or its modified version being capable of binding RNA or other nucleic acid molecules. In these aspects, the Cas DNA-binding polypeptide or its functional equivalent or its modified version may be referred to as a Cas nucleic acid-binding polypeptide or its functional equivalent or its modified version.

For certain applications, the microorganism such as a bacterium may have a natural endogenous, or introduced engineered, Cas DNA-binding polypeptide or functional equivalent or modified version. This means that the deliverable nucleic acid or recombinant polynucleotide of these aspects of the invention is not required to encode the Cas DNA-binding polypeptide or functional equivalent or modified version. Alternatively, the deliverable nucleic acid or recombinant polynucleotide of these aspects of the invention may further comprise a nucleic acid sequence which encodes the Cas DNA-binding polypeptide or its functional equivalent or modified version. In another aspect, the deliverable nucleic acid or recombinant polynucleotide of the invention does not encode the Cas DNA-binding polypeptide or its functional equivalent or modified version but may be used in conjunction with a separate polynucleotide which does. Other means for introducing the Cas DNA-binding polypeptide or its functional equivalent or its modified version into the microorganism may be used.

An exemplar Cas DNA-binding polypeptide is Cas9 or a functional equivalent thereof or a modified version thereof.

In the deliverable nucleic acid or recombinant polynucleotide according to various aspects of the invention, the CRISPR array nucleic acid sequence may have or transcribe additional RNA guide molecules each comprising a spacer sequence sufficiently complementary to a target sequence of the antibiotic resistance gene or one or more additional antibiotic resistance genes. The or each RNA guide molecule may be transcribed from its own promoter sequence. Alternatively, a set of a number of RNA guide molecules may be transcribed from one promoter sequence and optionally in combination with one or more other such sets. For example, a set of four RNA guide molecules may be transcribed from one promoter sequence, for example in combination with one or more other such sets of guide molecules.

Having multiple RNA guide molecules allows different antibiotic resistance (or other types of) genes in a microorganism to be targeted and inactivated simultaneously.

The deliverable nucleic acid or recombinant polynucleotide according to various aspects of the invention may additionally or alternatively be designed to include an RNA guide molecule (such as a further RNA guide molecule) targeting a gene involved in pathogenicity or other aspects of microbial metabolism. For example, certain pathogens form biofilms that make it difficult for antibiotics to gain access to them. One or more genes involved in bacterial metabolism for biofilm production may be targeted.

Figure 1:
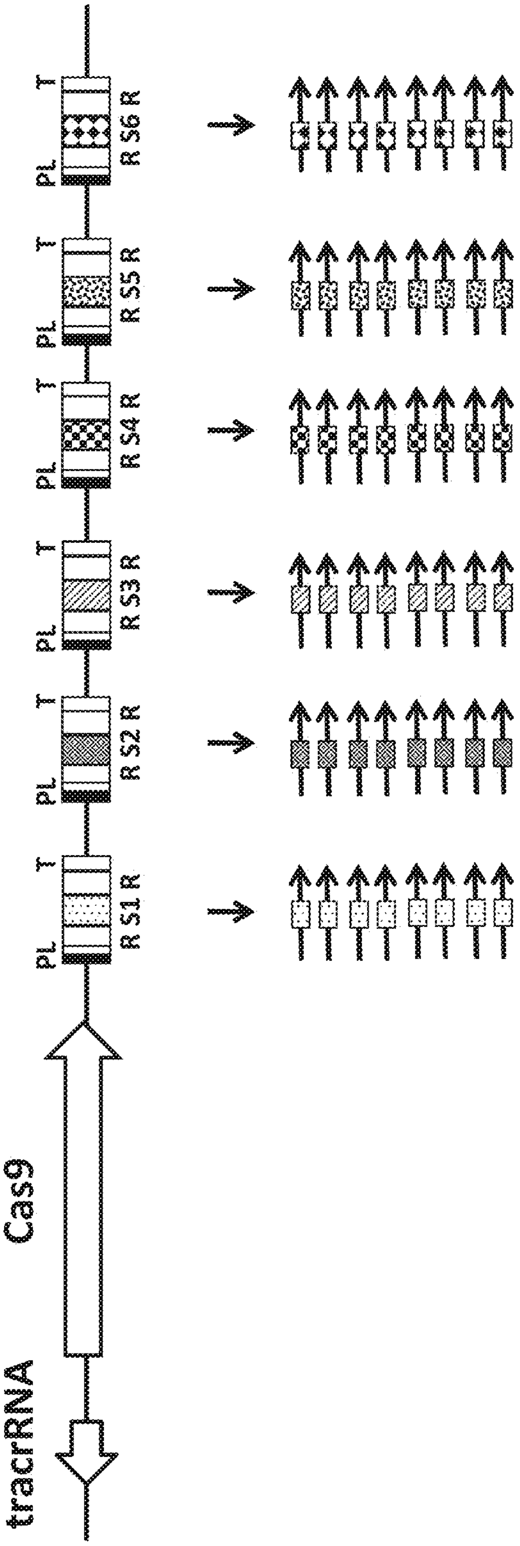
FIG. 1. Structure of CRISPR locus: This figure shows a CRISPR locus containing six spacers targeting six different regions. Each crRNA is transcribed monocistronically from the same promoters denoted P to control the transcription level identical for each target. Each crRNA transcript starts with a leader sequence L and terminates with a terminator sequence T. Transcripts of each pre-crRNA are shown as arrows and boxes containing different spacer sequences are indicated by unique shading.

Spacer sequence distal from a promoter are typically less efficiently transcribed. Ideally, multiple RNA guide molecules to different targets should be more or less equally represented. Thus, one promoter transcribing each RNA guide molecule (see for example FIG. 1) may be used (instead of relying on a long polycistronic RNA guide molecule [or precursor crRNA] transcription).

For example, there are many resistance genes encoding beta-lactamases (bla genes) giving resistance to a large range of different beta-lactam antibiotics. DNA constructs expressing multiple RNA guide molecules, which may each be individually transcribed from their own such promoters, may be used to target a number of different bla genes.

Thus in aspects of the invention, the CRISPR array nucleic acid sequence may have or transcribe one or more RNA guide molecules each comprising a spacer sequence sufficiently complementary to a target sequence of one or more beta-lactamase genes.

For example, the one or more RNA guide molecules may target one or more or all of the genes selected from the group consisting of: NDM, VIM, IMP, KPC, OXA, TEM, SHV, CTX, OKP, LEN, GES, MIR, ACT, ACC, CMY, LAT, and FOX.

In particular, the one or more RNA guide molecules may comprise a spacer sequence sufficiently complementary to target sequences of the beta lactam family of antibiotic resistance genes, including one or more or all of the following: a first spacer sequence sufficiently complementary to target sequences for NDM-1, -2, -10; a second spacer sufficiently complementary to target sequences for VIM-1, -2, -4, -12, -19, -26, -27-33, 34; a third spacer sufficiently complementary to target sequences for IMP-32, -38, -48; a fourth spacer sufficiently complementary to target sequences for KPC-1, -2, -3, -4, -6, -7, -8, -11, -12, -14, -15, -16, -17; a fifth spacer sufficiently complementary to target sequences for OXA-48; a sixth spacer sufficiently complementary to target sequences for TEM-1, -1B, -3, -139, -162, -183, -192, -197, -198, -209, a seventh spacer sufficiently complementary to target sequences for SHV and its variants; and an eighth spacer sufficiently complementary to target sequences for CTX and its variants (see Tables 1 and 2 below).

Table 1 shows a set of spacer sequences that encode 20 guide RNA molecules targeted against 117 different bla genes identified in the NCBI ARDB database for *Klebsiella pneumoniae* beta lactamase genes found in the ARDB database. Beta lactamase gene sequences are collected from the ARDB database with the keyword *Klebsiella pneumoniae*. Redundant sequences were removed and unique sequences used for multiple sequence alignment using web program Clustal Omega. One canonical sequence was chosen from each cluster and the 20 nt spacer sequences predicted by the web program Jack Lin's CRISPR/Cas9 gRNA finder were collected. The spacer sequence is chosen to maximise the ratio of the proto-spacer sequence found in the sequences belonging to the same branch. Thus each of the example spacer sequences shown in the $4^{th}$ column has the capability to disrupt the genes in the third column. Beta lactamase genes used in this analysis are: SHV-a=1, 2, 2a, 5, 5a, 11, 12, 14, 26, 27, 28, 31, 33, 38, 43, 44, 48, 55, 56, 60, 61, 62, 71, 73, 74, 75, 76, 77, 78, 79, 80, 81, 82, 85, 89, 92, 98, 99, 101, 103, 106, 107, 108, 109, CTXM-b=1, 3, 10, 12, 15, 22, 32, 54, 60, 62, 68, CTXM-c=13, 14, 16, 18, 19, 24, 26, CTXM-d=2, 35, 59, CTXM-e=26, 63, TEM-f=1, 1b, 3, ESBL, 139, KPC-g=1, 2, 3, 4, OKP-h=A11, A12, A16, A17, B13, B-SB613, 6, LEN-i=2, 17, 18, 19, 20, 21, 22, 24, GES-j=1, 3, 4, 5, VIM-a=1, 2, 4, 12, 19, IMP-b=4, 8, CMY-a=2, 4, 25, 31, 36, LAT-b=1, 2, CMY-c=1, 8b, 10, 19, FOX-d=1, 5, 7, OXA-a=1, 30, 47, OXA-2, OXA-9, OXA-b=10, 17. Beta lactam antibiotics are classified into four classes, penams, cephems, carbapenems and monobactams. One antibiotic name is listed as an example under each class. The beta lactamase, which can open the beta lactam ring is indicated by R. For example, carbapenem is inactivated by KPC. If it is desired to re-sensitise bacteria to carbapenem, the spacer sequence of SEQ ID NO: 11 (see Table 1 below) should be employed into spacer array to inactivate KPC genes. Note that the spacer sequence for CMY-a can also be employed for LAT-b cleavage. The example of spacer sequences are shown from 5' to 3' direction.

TABLE 1

| CI | Gene type | gene | Example of Required Spacers 5' to 3' | PAM | P | C-e | C-n | C-I | C-II | C-III | Cb | Mb |
|---|---|---|---|---|---|---|---|---|---|---|---|---|
| A | bl2be_shv2 | SHV-a | CCGCGTAGGCATGATAGAAA (SEQ ID NO: 5) | TGG | R | R | R | | | | | R |
| A | bl2be_ctxm | CTXM-b | ACGTTAAACACCGCCATTCC (SEQ ID NO: 6) | KGG | R | | | R | R | R | | R |
| A | bl2be_ctxm | CTXM-c | GCGCTGGAGAAAAGCAGCGG (SEQ ID NO: 7) | RGG | R | | | R | R | R | | R |
| A | bl2be_ctxm | CTXM-d | AAGCTGATTGCCCATCTGGG (SEQ ID NO: 8) | TGG | R | | | R | R | R | | R |
| A | bl2be_ctxm | CTXM-e | ACGCTCAACACCGCGATCCC (SEQ ID NO: 9) | CGG | R | | | R | R | R | | R |
| A | bl2_tem | TEM-f | AACTACTTACTCTAGCTTCC (SEQ ID NO: 10) | CGG | R | | | R | R | | | R |
| A | bl2_kpc | KPC-g | TTGTTGCTGAAGGAGTTGGG (SEQ ID NO: 11) | CGG | R | R | R | R | R | R | R | |
| A | bl2a_okp | OKP-h | AGCGAAAAACACCTTGCCGA (SEQ ID NO: 12) | CGG | R | | | | | | | |
| A | bl2_len | LEN-i | CTGGGAAACGGCACTGAATG (SEQ ID NO: 13) | AGG | R | | | | | | | |
| A | bls_ges | GES-j | TGGGTTGTTGGAGAGAAAAC (SEQ ID NO: 14) | TGG | R | R | R | R | R | R | | |
| B | bl3_vim | VIM-a | AAACACAGCGGCACTTCTCG (SEQ ID NO: 15) | CGG | R | R | R | R | R | R | R | |
| B | bl3_imp | IMP-b | AAAATTGAAGTTTTTTATCC (SEQ ID NO: 16) | MGG | R | R | R | R | R | R | R | |
| C | bl1_ampC | | TGGCAGCCGCAGTGGAAGCC (SEQ ID NO: 17) | KGG | | R | R | R | R | R | R | |
| C | bl1_acc | ACC-1 | TCACAGCTACTTGAAGGTTC (SEQ ID NO: 18) | CGG | R | R | R | R | R | R | R | |
| C | bl1_cmy2 | CMY-a | ATCAAAACTGGCAGCCGCAA (SEQ ID NO: 19) | TGG | | R | R | R | R | R | R | |
| C | bl1_cmy2 | LAT-b | ATCAAAACTGGCAGCCGCAA (SEQ ID NO: 19) | TGG | | R | R | R | R | R | R | |
| C | bl1_mox | CMY-c | CAGTACTCCAACCCCAGCAT (SEQ ID NO: 20) | AGG | | R | R | R | R | R | R | |
| C | bl1_fox | FOX-d | TCACCTGGCCGCAAATAGTC (SEQ ID NO: 21) | TGG | | R | R | R | R | R | R | |
| D | bl2d_oxa1 | OXA-a | ACAACGGATTAACAGAAGCA (SEQ ID NO: 22) | TGG | R | | | | | | | |
| D | bl2d_oxa2 | OXA-2 | AGAACATCAGCGCTTGGTCA (SEQ ID NO: 23) | AGG | R | | | | | | | |
| D | bl2d_oxa9 | OXA-9 | ATAACGGCTTGACCCAGTCA (SEQ ID NO: 24) | TGG | R | | | | | | | |
| D | bl2d_oxa10 | OXA-b | GGCAACCAGAATATCAGTGG (SEQ ID NO: 25) | TGG | R | | | | | | | |

Key to Table 1

| | | | |
|---|---|---|---|
| PAM | protospacer adjacent motif | | |
| CI | beta lactamase class A, B, C or D | | |
| P | Penams | | for example amoxicillin |
| C-e | Cephems: | e_Cephalosporin | |
| C-n | Cephems: | n_Cephalosporin | |
| C-I | Cephems | Cephalosporin I | for example Cefazolin |
| C-II | Cephems | Cephalosporin II | for example Cephamycin |
| C-III | Cephems | Cephalosporin III | for example Ceftazidime |
| Cb | Carbapenem | | for example Ertapenem |
| Mb | Monobactam | | for example Aztreonam |

Table 2 shows a set of spacer sequences that encode 17 guide RNA molecules targeted against 154 different bla genes identified in the CARD database for *Klebsiella pneumoniae*. Candidate spacer sequences were identified to disrupt all the *Klebsiella pneumoniae* beta lactamase genes found in the CARD database. Table 2 was created with the same method explained in Table 1 above, and the same key to Table 1 applies.

TABLE 2

| CI | Gene type | gene | Example of Required Spacers 5' to 3' | PAM | P | C-e | C-n | C-I | C-II | C-III | Cb | Mb |
|---|---|---|---|---|---|---|---|---|---|---|---|---|
| A | bl2be_shv2 | SHV-a | GGATGCCGGTGACGAACAGC (SEQ ID NO: 26) | TGG | R | R | R | | | | | R |
| A | bl2be_ctxm | CTXM-b | GCTACAGTACAGCGATAACG (SEQ ID NO: 27) | TGG | R | | | R | R | R | | R |
| A | bl2be_ctxm | CTXM-c | GACGTTGCGTCAGCTTACGC (SEQ ID NO: 28) | TGG | R | | | R | R | R | | R |
| A | bl2_tem | TEM-f | AACTACTTACTCTAGCTTCC (SEQ ID NO: 10) | CGG | R | | | R | R | | | R |
| A | bl2_kpc | KPC-g | TTGTTGCTGAAGGAGTTGGG (SEQ ID NO: 11) | CGG | R | R | R | R | R | R | R | |
| A | bl2a_okp | OKP-h | AGCGAAAAACACCTTGCCGA (SEQ ID NO: 12) | CGG | R | | | | | | | |
| A | bl2_len | LEN-i | ACCTTTAAAGTGCTGCTGTG (SEQ ID NO: 29) | CGG | R | | | | | | | |
| A | bls_ges | GES-j | TGGGTTGTTGGAGAGAAAAC (SEQ ID NO: 14) | TGG | R | R | R | R | R | R | | |
| B | bl3_vim | VIM-a | AAACACAGCGGCACTTCTCG (SEQ ID NO: 15) | CGG | R | R | R | R | R | R | R | |
| B | bl3_imp | IMP-b | AAAATTGAAGTTTTTTATCC (SEQ ID NO: 16) | AGG | R | R | R | R | R | R | R | |
| B | bl3_ndm | NDM-c | GGTTTGATCGTCAGGGATGG (SEQ ID NO: 30) | CGG | R | R | R | R | R | R | R | |
| C | bl1_ampC | ACT-3 | GTGGATTAACGTTCCGAAAG (SEQ ID NO: 31) | CGG | | R | R | R | R | R | R | |
| C | bl1_cmy2 | CMY-a | CAGCGACAGCAAAGTGGCAT (SEQ ID NO: 32) | TGG | | R | R | R | R | R | R | |
| C | bl1_fox | FOX-d | CTTGCCACCTACAGTGCGGG (SEQ ID NO: 33) | TGG | | R | R | R | R | R | R | |
| D | bl2d_oxa1 | OXA-1 | CCCCCAAAGGAATGGAGATC (SEQ ID NO: 34) | TGG | R | | | | | | | |
| D | bl2d_oxa | OXA-a | CACCAAGTCTTTAAGTGGGA (SEQ ID NO: 35) | TGG | R | | | | | | | |
| D | bl2d_oxa9 | OXA-9 | ATAACGGCTTGACCCAGTCA (SEQ ID NO: 24) | TGG | R | | | | | | | |

The antibiotic resistance gene to be inactivated may be located on a chromosome, or on an extrachromosomal replicating DNA molecule known as a replicon and including plasmids and bacteriophage.

The CRISPR/Cas system used according to various aspects of the invention generates a DSB in the target sequence. Where the target sequence is located on a chromosome or a replicon such as a bacterial chromosome or plasmid, then a DSB can lead to degradation and hence loss of the chromosome or replicon suffering such a DSB. If the target sequence is located on a bacterial chromosome then the cell may die directly as a consequence of the DSB. Additionally, some plasmids (including natural plasmids) carry killing functions that only become toxic if the cell loses the plasmid, which is a natural mechanism to ensure faithful inheritance of plasmids in dividing cells. If a plasmid carrying the target sequence of the antibiotic resistance gene also carries such a killing function, and the plasmid is lost as a result of the DSB generated, the cell may die.

In the event that cell death caused by such DSB increases selection pressure for resistance against the deliverable nucleic acid or recombinant polynucleotide according to various aspects of the present invention, this may be mitigated by, for example, employing a modified Cas DNA-binding polypeptide which seals the target site after generating a deletion to inactivate the target sequence of the antibiotic resistance gene, rather than generate a DSB.

Thus the Cas DNA-binding polypeptide according to various aspects of the invention may in certain aspects be substituted by a modified Cas DNA-binding polypeptide comprising a recombinase catalytic domain, wherein the modified Cas DNA-binding polypeptide does not generate DSBs but creates a deletion and reseals a site in the target sequence.

Figure 2:
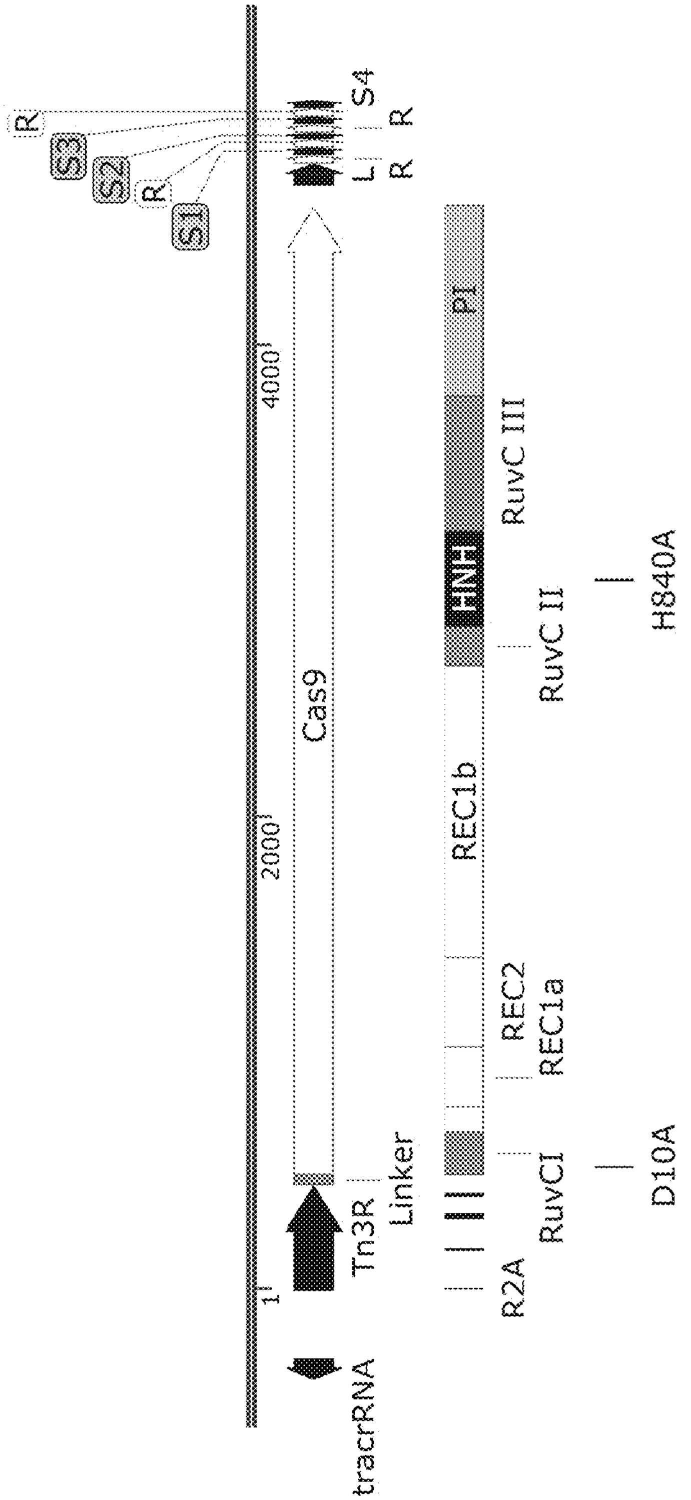
FIG. 2. Map of a modified Cas DNA-binding polypeptide, Cas9R. A genetic fusion between Cas9 and Tn3 resolvase. Resolvase and Cas9 are indicated by arrows. The direction of the arrowhead represents the transcription polarity. Functional domain names of Cas9 are shown in the boxes below Cas9 open arrow. This Cas9 is the endonuclease activity deficient mutant dCas9, with amino acid substitutions D10A in RuvCI domain, H840A in HNH domain (as described by Tsai et al. [2014, Nature Biotechnology 32: 569-576], which is hereby incorporated by reference in its entirety). A mutant Tn3 resolvase (as described by Proudfoot et al. [2011 PloS ONE 6(4): e19537], which is hereby incorporated by reference in its entirety) is fused to the N-terminus of this dCas9 via a 12 mer polypeptide linker. Positions of some of these substituted amino acid residues reducing the specificity of the recombination site are indicated by short vertical bars in the N terminal domain, residues 1-148, of the resolvase. The full list of these substitutions is: R2A, E56K, G101S, D102Y, M1031, Q105L, V107F, E132A, L135R. In the Cas9 regions of the fusion: RuvCI, II, III, HNH and PI (PAM interaction) domains are nuclease domains, REC1a and REC1b are recognition domains of repeat and anti-repeat RNA, respectively. REC2 domain does not have any contact to the protospacer-gRNA heteroduplex. Four CRISPR spacer sequences S1, S2, S3 and S4 are arrayed under the expression of one CRISPR leader sequence and are required to bring about the Cas9R-mediated recombination event by the mutant Tn3 resolvase leading to the deletion and religation of the target sequence. Tn3R=Tn3 Resolvase, R=Direct repeat, L=Leader sequence.
Figure 3:
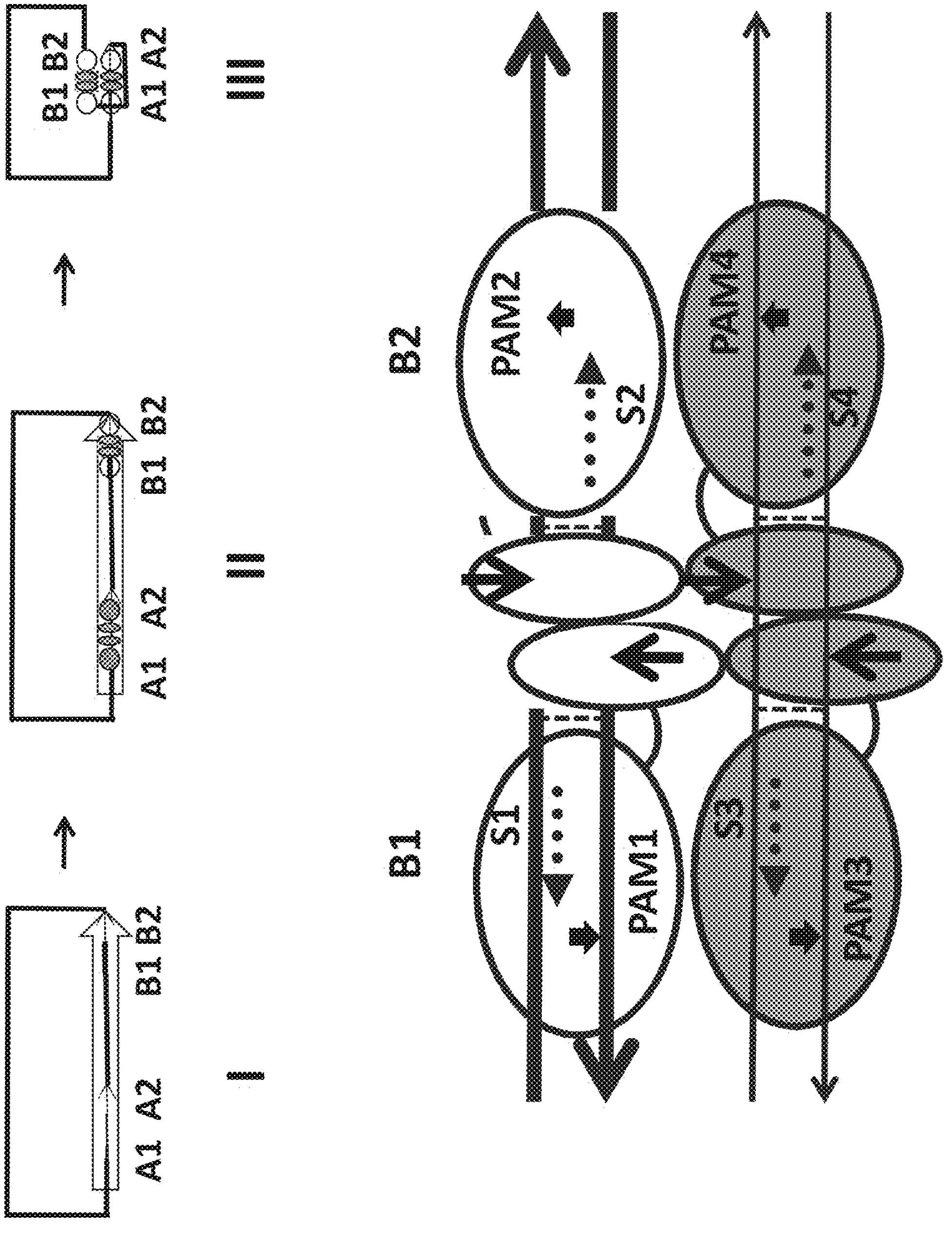
FIG. 3. Schematic showing site-specific positioning of resolvase by gRNA directed Cas9. The open arrow in step I is the target antibiotic resistance gene on the plasmid for inactivation. Each recombination site A (A1, A2) and B (B1, B2) are recognised by gRNA independently and correctly positioned resolvases are dimerised in close proximity (step II). Dimers in each recombination site A1+A2 and B1+B2 are tetramerised to form a synapse (step III). The synaptic complex (III) is enlarged, gRNAs are presented as dotted arrows designated S1, S2, S3 and S4. Large ovals represent dCas9, longitudinal ovals are resolvases connected via linker peptides. White and grey longitudinal ovals are resolvase catalytic domains dimerising on the recombination site B and A, respectively. The vertical arrows indicate the cleavage position on the recombination sites by resolvase. The thin horizontal parallel arrows represent DNA containing the recombination site A1+A2 and the thick horizontal parallel arrows represent DNA containing the recombination sites B1+B2. The arrowhead shows the 3' end of the DNA sequence. Short black block arrows are locations of each of the PAM sequences.
Figure 4:
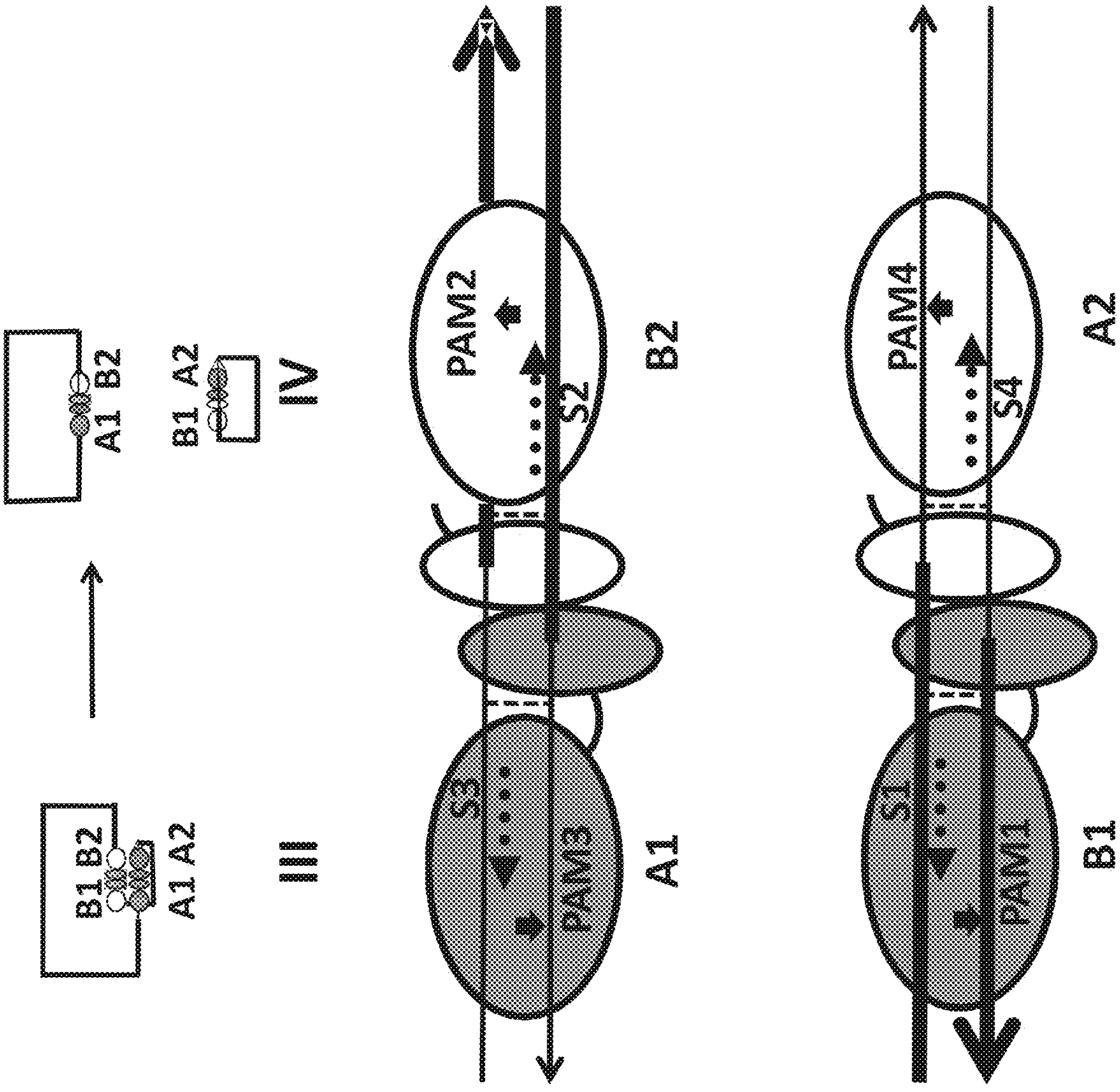
FIG. 4. Schematic showing exchanging half site of the recombination site A1+A2 and B1+B2 followed by strand resolution and sealing break point. Half-site of recombination A1 and B1 are exchanged and ligated and resolved. The region of the target antibiotic gene is resolved as a circular DNA, while the rest of the chromosomal or plasmid replicon is re-circularised (step IV). Short black block arrows are locations of each PAM sequences after resolution.

The modified Cas DNA-binding polypeptide may for example be a modified Cas9 protein comprising a recombinase catalytic domain (see for example FIGS. 2, 3 and 4).

The deliverable nucleic acid or recombinant polynucleotide according to various aspects of the invention may further comprise a nucleotide sequence which encodes a gene conferring a selective advantage to the microorganism, for example thereby increasing the efficiency of delivery of the CRISPR/Cas system to the target microorganism. For example, the gene may confer a growth advantage over non-infected siblings, or genes encoding a bacteriocin—these are protein toxins produced by bacteria to kill or inhibit growth of other bacteria—and corresponding immunity polypeptide may be used.

The selective advantage to the microorganism may include or be one which prevents or diminishes the effect of loss of a replicon due to a DSB caused by Cas DNA-binding polypeptide. For example, the nucleotide sequence which encodes a gene conferring a selective advantage to the microorganism may encode an antitoxin that neutralises the effect of a toxin or killer function carried by a replicon on which the target sequence is located. Also, the nucleotide sequence which encodes a gene conferring a selective advantage to the microorganism may encode one or more proteins that are encoded by a replicon subject to degradation due to a DSB caused by Cas DNA-binding polypeptide.

A composition of the invention comprising a nucleic acid delivery vehicle and/or deliverable nucleic acid for inactivating an antibiotic resistance gene may be a pharmaceutical composition, a non-pathogenic microorganism such as a commensal bacterium for example in a probiotic formulation, or a dietary supplement.

Microorganisms such as bacteria targeted by various aspects of the invention may be on a body surface, localised (for example, contained within an organ, at a site of a surgical wound or other wound, within an abscess), or may be systemic. Included is the treatment of bacterial infections that are amenable to therapy by topical application of the nucleic acid delivery vehicle of the invention.

The present invention also encompasses coating of surfaces other than body surfaces with the delivery vehicle or composition of the present invention, for example wound dressings or medical device surfaces.

In the present invention, an advantage of using a Transmid that comprises a deliverable nucleic acid or recombinant polynucleotide of the invention is that it may serve as a "Trojan horse" that, following Transmid delivery by phage infection, or following plasmid conjugation, results in the insertion of the "assassin construct" into the target bacteria or other microorganism.

The assassin constructs then begin the process of degradation of the antibiotic resistance genes. If a DSB created by the Cas DNA-binding protein of the invention destroys a replicon carrying such an antibiotic resistant gene then a microorganism harbouring the antibiotic resistance gene may be killed directly by an assassin construct. If the microorganism survives the DSB, the resistance gene will be inactivated, and a patient may then be treated with the antibiotic(s) to which the microorganism has now become sensitised.

Importantly, there should be no or reduced direct selection pressure acting against this event if and until patients are subsequently treated with antibiotics. Thus there should be little or no direct selection against Transmid delivery in the pathogenic bacteria or other microorganisms and therefore no or less establishment of an "evolutionary arms race"—sometimes a significant limiting feature of the known use of bacteriophage directly as bactericidal agents.

In the event that DSB-induced killing of a microorganism increases selection pressure for resistance to a bacteriophage or conjugative plasmid delivery agent, the problem could be mitigated by, for example, using a modified Cas DNA polypeptide as defined herein.

This present invention provides potential agents for oral, topical and probiotic, dietary supplement delivery as well as an epidemiological tool to silently inactivate antibiotic resistance genes in pathogenic bacteria or other microorganisms. Patients scheduled for surgery, or other treatment in hospital, may well be treated with Transmids carrying CRISPR/Cas9 (or other) assassin constructs targeted against antibiotic resistance genes prophylactically in advance of hospital admission. In this way, pathogens present in their microbiome can be directly killed or purged of antibiotic resistance genes in anticipation of any post-operative infection that might occur requiring treatment with antibiotics.

Thus this present invention provides an epidemiological tool to silently inactivate antibiotic resistance genes in pathogenic bacteria.

To effect exemplification of aspects of the invention, a set of CRISPR/Cas9 "assassin" constructs targeted against selected antibiotics may be constructed.

Definitions

Unless defined otherwise, all technical and scientific terms used herein have the same meaning as commonly understood by one of ordinary skill in the art to which this invention is related.

Furthermore, unless otherwise required by context, singular terms shall include pluralities and plural terms shall include the singular.

Generally, nomenclatures utilized in connection with, and techniques of, cell and tissue culture, molecular biology, and protein and oligo- or polynucleotide chemistry and hybridization described herein are those well known and commonly used in the art.

Standard techniques are typically used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g. Sambrook & Russell, 2015, supra. The nomenclatures utilised in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

The term "and/or" as used herein is to be taken as specific disclosure of each of the two specified features or components with or without the other. For example "A and/or B" is to be taken as specific disclosure of each of (i) A, (ii) B and (iii) A and B, just as if each is set out individually.

The term "a" or "an" can refer to one of or a plurality of the elements it modifies (e.g., "a reagent" can mean one or more reagents) unless it is contextually clear either one of the elements or more than one of the elements is described.

The term "about" as used herein in connection with any and all values (including lower and upper ends of numerical ranges) means any value having an acceptable range of deviation of up to ±10% (and values there between, e.g., ±0.5%, ±1%, ±1.5%, ±2%, ±2.5%, ±3%, ±3.5%, ±4%, ±4.5%, ±5%, ±5.5%, ±6%, ±6.5%, ±7%, ±7.5%, ±8%, ±8.5%, ±9%, ±9.5%). The use of the term "about" at the beginning of a string of values modifies each of the values (i.e. "about 1, 2 and 3" refers to about 1, about 2 and about 3). For example, a weight of "about 100 grams" can include weights between 90 grams and 110 grams. Further, when a listing of values is described herein (e.g. about 50%, 60%, 70%, 80%, 85% or 86%) the listing includes all intermediate and fractional values thereof (e.g., 54%, 85.4%).

As used herein, a "pharmaceutical composition" refers to a preparation of one or more of the active agents (such the recombinant polynucleotide or the delivery vehicle or the deliverable nucleic acid as described herein) with other chemical components such as physiologically suitable carriers and excipients. The purpose of a pharmaceutical composition is to facilitate administration of the active agent to an organism.

Compositions of the present invention may, if desired, be presented in a pack, dispenser device or kit, each of which may contain one or more unit dosage forms containing the active agent(s). The pack, dispenser device or kit may be accompanied by instructions for administration.

Compositions of the present invention for administration topically can be in a form suitable for topical use such as, for example, an aerosol, cream, ointment, lotion or dusting powder.

Compositions provided herein may be formulated for administration by inhalation. For example, the compositions may be in a form as an aerosol, a mist or a powder. Thus compositions described herein may be delivered in the form of an aerosol spray presentation from pressurised packs or a nebuliser, with the use of a suitable propellant such as for example dichlorodifluoromethane, trichlorofluoromethane, dichlorotetrafluoroethane, carbon dioxide or other suitable gas. Where using a pressurised aerosol, a dosage unit may be determined by providing a valve to deliver a metered amount.

As used herein, the term "antibiotic" refers to a classical antibiotic that is produced by a microorganism that is antagonistic to the growth of other microorganisms and also encompasses more generally an antimicrobial agent that is capable of killing or inhibiting the growth of a microorganism, including chemically synthesised versions and variants of naturally occurring antibiotics.

The term "sufficiently complementary" means that the sequence identity of the spacer sequence and the target sequence is such that the RNA guide molecule comprising the spacer sequence is able to hybridise, preferably specifically and selectively, with the target sequence, thereby allowing for inactivation of the antibiotic resistance gene comprising the target sequence via the CRISPR/Cas system described herein. For example, the spacer sequence may have at least 60%, 65%, 70%, 75%, 80%, 85%, 90%, 95%, 96%, 97%, 98%, 99% or 100% sequence identity over its entire length with the target sequence.

The term "functional equivalent" as used herein refers to a polypeptide which is capable of the same activity as a Cas DNA-binding polypeptide (or, as used herein, a Cas nucleic acid-binding polypeptide). The "functional equivalent" may have the same qualitative biological property as the Cas DNA-binding polypeptide. "Functional equivalents" include, but are not limited to, fragments or derivatives of a native Cas DNA-binding polypeptide and its fragments, provided that the equivalents have a biological activity in common with a corresponding native sequence polypeptide. Although structural identity is not necessarily required for common biological activity, in one aspect the functional equivalent may have at least 50%, 55%, 60% 65%, 70%, 75%, 80%, 85%, 90%, 95%, 96%, 97%, 98%, 99% or 100% sequence identity over its entire length with a Cas DNA-binding polypeptide, for example Cas9 (Ferretti et al, 2001, *PNAS,* 98 *No.* 8: 4658-4663, Gene ID: 901176, Cas9 GI: 15675041).

The term "Cas DNA-binding polypeptide" encompasses a full-length Cas polypeptide, an enzymatically active fragment of a Cas polypeptide, and enzymatically active derivatives of a Cas polypeptide or fragment thereof. Suitable derivatives of a Cas polypeptide or a fragment thereof include but are not limited to mutants, fusions, covalent modifications of a Cas protein or a fragment thereof.

The term "modified" Cas DNA-binding polypeptide encompasses Cas DNA-binding polypeptides as defined above except that the DSB catalytic function of the polypeptide is replaced by a DNA sealing function due for example to the presence of a recombinase catalytic domain. Further features of such modified Cas DNA-binding polypeptides are described herein.

Sequence identity between nucleotide or amino acid sequences can be determined by comparing an alignment of the sequences. When an equivalent position in the compared sequences is occupied by the same base or amino acid, then the molecules are identical at that position. Scoring an alignment as a percentage of identity is a function of the number of identical amino acids or bases at positions shared by the compared sequences. When comparing sequences, optimal alignments may require gaps to be introduced into one or more of the sequences to take into consideration possible insertions and deletions in the sequences. Sequence comparison methods may employ gap penalties so that, for the same number of identical molecules in sequences being compared, a sequence alignment with as few gaps as possible, reflecting higher relatedness between the two compared sequences, will achieve a higher score than one with many gaps. Calculation of maximum percent identity involves the production of an optimal alignment, taking into consideration gap penalties.

Suitable computer programs for carrying out sequence comparisons are widely available in the commercial and public sector. Examples include MatGat (Campanella et al., 2003, BMC Bioinformatics 4: 29, incorporated by reference in its entirety; program available from http://bitincka.com/ledion/matgat), Gap (Needleman & Wunsch, 1970*, J. Mol. Biol.* 48: 443-453, incorporated by reference in its entirety), FASTA (Altschul et al., 1990*, J. Mol. Biol.* 215: 403-410, incorporated by reference in its entirety; program available from http://www.ebi.ac.uk/fasta), Clustal W2.0 and X 2.0 (Larkin et al., 2007*, Bioinformatics* 23: 2947-2948, incorporated by reference in its entirety; program available from http://www.ebi.ac.uk/tools/clustalw2) and EMBOSS Pairwise Alignment Algorithms (Needleman & Wunsch, 1970, supra; Kruskal, 1983, In: Time warps, string edits and macromolecules: the theory and practice of sequence comparison, Sankoff & Kruskal (eds), pp 1-44, Addison Wesley, incorporated by reference in its entirety; programs available from http://www.ebi.ac.uk/tools/emboss/align). All programs may be run using default parameters.

For example, sequence comparisons may be undertaken using the "needle" method of the EMBOSS Pairwise Alignment Algorithms, which determines an optimum alignment (including gaps) of two sequences when considered over their entire length and provides a percentage identity score. Default parameters for amino acid sequence comparisons ("Protein Molecule" option) may be Gap Extend penalty: 0.5, Gap Open penalty: 10.0, Matrix: Blosum 62. Default parameters for nucleotide sequence comparisons ("DNA Molecule" option) may be Gap Extend penalty: 0.5, Gap Open penalty: 10.0, Matrix: DNAfull.

In one aspect of the invention, a sequence comparison may be performed over the full length of the reference sequence.

As used herein, the term "gene" or "genetic module" refers to a DNA sequence from which a polypeptide is encoded or a non-coding, functional RNA is transcribed.

The term "antibiotic resistance gene" encompasses a gene, or the encoding portion thereof, which encodes a product or transcribes a functional RNA that confers antibiotic resistance. For example, the antibiotic resistance gene may be a gene or the encoding portion thereof which contributes to any of the four resistance mechanisms described above. The antibiotic resistance gene may for example encode (1) an enzyme which degrades an antibiotic, (2) an enzyme which modifies an antibiotic, (3) a pump such as an efflux pump, or (4) a mutated target which suppresses the effect of the antibiotic.

The terms "polynucleotide" and "nucleic acid" each refer to a polymeric form of nucleotide of any length, for example RNA (such as mRNA) or DNA. The term also includes, particularly for oligonucleotide markers, the known types of modifications, for example, labels which are known in the art, methylation, "caps", substitution of one or more of the naturally occurring nucleotides with an analog, internucleotide modifications, such as, for example, those with unchanged linkages, e.g., methyl phosphates, phosphotriesters, phosphoamidates, carbamates, etc. and with charged linkages.

The term "polypeptide" as used herein refers to a polymer of amino acids. The term does not refer to a specific length of the polymer, so peptides, oligopeptides and proteins are included within the definition of polypeptide. The term "polypeptide" may include post-expression modifications, for example, glycosylations, acetylations, phosphorylations and the like. Included within the definition of "polypeptide" are, for example, polypeptides containing one or more analogues of an amino acid (including, for example, unnatural amino acids), polypeptides with substituted linkages, as well as other modifications known in the art both naturally occurring and non-naturally occurring.

The term "microorganism" encompasses prokaryotes such as bacteria and archaea (for example, those belonging to the Euryarchaeota and Crenarchaeota). Bacteria include both Gram positive and Gram negative bacteria. Some species of clinically significant, pathogenic fungi are included in the definition of microorganisms, for example members of the genus *Candida, Asperglltus, Cryptococcus, Histoplasma, Pneumocystis* and *Stachybotrys.*

EXAMPLES

The present invention is illustrated by the following non-limiting examples.

Example 1

Exemplification of the Construction of a c-Transmid-Mediated Delivery System to Deliver Selected Nucleic Acids of Interest into Bacteria Example 1 describes the construction of a conjugative Transmid (c-Transmid) delivery system as a proof-of-concept for the delivery of selected nucleic acid(s) of interest—hereafter termed the "Cargo"—to strains of *Escherichia coli* and other bacteria. Delivery is by infection in a bacteriophage lambda phage coat protein, and/or by transmission to other bacteria by conjugation. There is a possibility of transposition of the Cargo to the bacterial chromosome.

The c-Transmid delivery system is constructed from two components: (i) the "Ship", carrying functions required for replication, phage packaging and conjugal transfer; and (ii) the plasmid Cargo shuttle cloning vector that carries the Cargo plus the "docking" machinery (the "Dock")—the Cre-lox system, that delivers the Cargo to the Ship.

The c-Transmid c-TNB001, the delivery vehicle exemplified here, carries a number of genetic functions isolated from various plasmid sources that enable it to: (i) conjugate, (ii) mobilise Transmid DNA, (iii) replicate, (iv) be packageable into the lambda phage head, (v) allow the Cargo to be introduced to the c-Transmid by Cre-lox-mediated in vivo recombination—giving c-TBN001::Cargo, and (vi) allow the transfer of the Cargo into host chromosome (Xsome) by Tn7 transposase-mediated in vivo transposition—giving Xsome::Cargo.

The functional genes employed in the c-Transmid Ship construct are shown in bold letters in FIG. 5:

a. Thus, c-TNB001 carries conjugative functions—the Tra1 and Tra2 operons, and mobilisation functions—the origin of transfer oriT and mobilisation proteins traI, traJ, traK, traA of the broad host range (BHR) conjugative plasmid RK2, in addition to the RK2 Ctl region encoding korA and korB (reviewed by Bingle & Thomas, *Current Opinion in Microbiology* 2001, 4:194-200, which is hereby incorporated by reference in its entirety). The Transmid also carries the aphA gene encoding aminoglycoside 3'-phosphotransferase gene from RK2 and conferring kanamycin (Km) resistance (KmR).
b. The c-Transmid, c-TNB001, carries the narrow host range vegetative replication origin of the F plasmid, ori2 (also known as oriS) plus the gene encoding the replication protein, repE; these genetic modules are isolated from the BAC (bacterial artificial chromosome) vector pBeloBAC11 (available from New England Biolabs) together with the cos site of bacteriophage lambda. c-TNB001 also carries, from pBeloBAC11, the SopA and SopB-encoded functions for active partitioning. These functions act at SopC to ensure that each daughter cell inherits a copy of the c-Transmid at cell division.
c. Also present in c-TNB001 are the tnsA, tnsB, tnsC, tnsD genes, encoding the four transposition proteins of the bacterial transposon Tn7 that bring about site-specific transposition to the chromosomally located Tn7 attachment site, attTn7, that is present in *E. coli* (Lichtenstein & Brenner *Nature* 297, 601-3, 1982, hereby incorporated by reference in its entirety; Lichtenstein & Brenner *Mol. Gen. Genet.* 183, 380-7, 1981, hereby incorporated by reference in its entirety) and many species of the family of Enterobacteriaceae (reviewed in Crépin, Harel & Dozois, *Appl. Environ. Microbiol.* 78, 6001-8 (2012), hereby incorporated by reference in its entirety).

d. Additionally, c-TNB001 also carries the terminal inverted repeats (TIR) of Tn7 required for interaction with TnsA,B,C,D proteins to effect transposition of DNA sequences lying between them to attTn7.

e. These TIRs flank a lox site to allow Cre-lox-mediated in vivo recombination to deliver Cargo. The structure of c-TNB001 is shown in FIG. 6.

The c-Transmid Ship in this example is large and not easy to directly clone Cargo into by in vitro genetic manipulation. Instead such genetic manipulation is more readily performed in a small non-mobilisable plasmid cloning vector such as pACYC184 (available in *E. coli* K12 strain ER2420 from New England Biolabs). A derivative of this plasmid, pNB300, is described (FIGS. 18-20) with the following features:

a. pNB300 (like pACYC184) is non-mobilisable and so cannot be transferred by plasmid conjugation.

b. The plasmid retains the cat gene encoding chloramphenicol acetyl transferase and conferring chlorampheniol resistance (CmR) as a selectable drug marker.

c. The cre gene encoding the Cre recombinase, plus cloning sites flanked by lox sites.

d. The F plasmid-derived ccdB killer gene regulated by the lac promotor (Bernard, Gabant, Bahassi & Couturier *Gene* 148:71-4, 1994). This marker provides a negative-selection against undesired single reciprocal Ore-lox recombination events where the entire pNB300 (including ccdB) recombines into the c-Transmid.

e. The lox sites also flank the dhfr gene from Tn7 (Fling & Richards *Nucl. Acid. Res.* 11:5147, 1983, hereby incorporated by reference in its entirety) encoding a dihydrofolate reductase that is resistant to inhibition by the antibiotic trimethoprim (Tp); this marker allows selection for transfer of the Cargo from pNB300::: Cargo to cTNB001 by a double reciprocal Cre-lox recombination event (see FIG. 13. It also subsequently allows selection for transposition of the Cargo to attTn7 in recipients where the c-Transmid cannot replicate.

Thus the overall scheme for the construction of a c-Transmid carrying the selected nucleic acids of interest—the Cargo—is as follows:

1. The selected nucleic acids of interest, the Cargo, is cloned into a site between the lox sites and adjacent to the dhfr gene in the Cargo shuttle vector pNB300 by in vitro genetic manipulation, followed by transformation of DH5α (F-endA1 glnV44 thi-1 recA1 relA1 gyrA96 deoR nupGϕ80dlacZΔM15 Δ(lacZYA-argF)U169, hsdR17(rK-mK+), λ−) competent cells (available from New England Biolabs) with selection for CmR; plasmid DNA isolated from such cells are checked for integrity of the desired recombinant plasmid, pNB300:: Cargo by DNA sequence analysis.
2. The recombinant plasmid, pNB300::Cargo, is then transformed into DH5α competent cells also carrying the c-Transmid, c-TNB001 with selection for CmR (pNB300::Cargo encoded) and KmR (c-TNB001 encoded).
3. As the DH5α transformant now carries both pNB300:: Cargo and c-TNB001, Cre-lox recombination between the lox sites flanking the Cargo and the lox target site in the Transmid may occur to recombine the Cargo into the c-Transmid. To select for this event, the DH5α (c-TNB001) (pNB300::Cargo) donor is then mated with a recipient *E coli* strain carrying resistance to streptomycin (SmR) and plated on Mueller-Hinton (MH) plates supplemented with kanamycin 50 μg/mL (Km50), streptomycin 50 μg/mL (Sm50) and trimethoprim 50 μg/mL (Tp50) and IPTG. Thus:
   a. Sm50 selects for recipient strain and against the donor, Km50 selects for conjugal transfer of the c-Transmid to the recipient;
   b. Tp50 selects for Cre-lox-mediated transfer of the Cargo from pNB300::Cargo to c-TNB001 by double reciprocal recombination to give c-TNB001::Cargo;
   c. Addition of IPTG allows against transfer of undesired recombinants resulting from Cre-lox-mediated just a single reciprocal Cre-lox recombination event, where the entire pNB300 recombines into the c-Transmid (cTNB001::pNB300::Cargo). This is because if the pNB300 plasmid backbone is transferred, then IPTG induces expression of the toxic ccdB gene.
4. The resulting exconjugant carrying just c-TNB001:: Cargo may then screened for the predicted loss of CmR (present on pNB300) for confirmation.
5. The c-TNB001::Cargo, so constructed, is now ready for delivery to target bacteria either by phage infection and/or bacterial conjugation. For phage delivery, c-TNB001::Cargo DNA may be prepared from the ex-conjugant and packaged in vitro.
6. Following infection target bacteria with lambda-packaged c-TNB001::Cargo, cells carrying c-TNB001:: Cargo may be selected for KmR or TpR.
7. Such cells may be mated with other bacteria in a given microbiome.
8. And transposition of the Cargo to attTn7 may be tested by mating a donor carrying c-TNB001::Cargo to a recipient bacterial species where the c-Transmid cannot replicate.

9, For each of steps 6-8 above, the functionality of the Cargo, the selected nucleic acids of interest may be tested in the new recipient using the appropriate assay.

The following describes the construction of the two components: (i) the c-Transmid c-TNB001 and the Cargo shuttle vector pNB300.

Example 1.1 Construction of a c-Transmid, c-TNB001

The scheme for the construction of the c-Transmid, c-TNB001 is shown in FIG. 7: it is constructed by combining sequence elements from the cosmid pBeloBAC11 (template A), the large conjugative plasmid RK2 (template B), and a derivative of plasmid pGRG36 carrying the Tn7 elements but with the addition of a lox site between the Tn7 TIRs giving pGRG36::lox (template C). The overall strategy for construction (i) to divide the entire construct into 13 segments where each segment is generated as 13 PCR amplicons. (ii) Then overlapping sets of neighbouring such amplicons are combined together by Gibson assembly (Gibson D G, et.al. Nature Methods 2009; 6: 343-345, hereby incorporated by reference in its entirety) and cloned into a derivative of pBeloBAC11 to generate four plasmids designated I, II, III, IV. (iii) Since unique restriction sites are introduced with the appropriate PCR primers during the amplification of the segments, the four Gibson-assembled plasmid constructs, I, II, III, IV, comprising neighbouring segments may then be digested with the appropriate unique restriction enzymes; (iv) this enables ligation of each Gibson-assembled set of composite segments from each of the four plasmids to produce the entire c-Transmid structure.

The first step is the construction of the plasmid derivative pGRG36::lox from pGRG36 as follows: the DNA cassette containing two inverted lox sites loxN (8 base core sequence mutant) and lox71 (left arm mutant) are inserted at PacI and EagI sites on pGR36 and designated pGR36::lox. The sequence of this lox cassette are as provided in the legend to FIG. 7 above.

1. The three plasmid templates (A,B,C) are now used for PCR amplification of the 13 amplicons. Table 3 summarises the primers and their annealing sites on the template plasmids (TP) pBeloBAC11, RK2, and pGRG36::lox (A,B,C respectively). Tm is given in ° C. The primer sequences used in the design of this c-Transmid construction and the annealing sites on each plasmid are shown. The restriction enzyme recognition sites, which are used later to ligate the assembled construct to get the final Transmid construct, are shown in capital letters and underlined. CCTCGAGGCGCGCC (SEQ ID NO: 36) in BAC3 contains the AbsI (CCTCGAGG) and AscI (GGCGCGCC) recognition sites, ggcGCGCC in BAC4 is the AscI recognition site, GCGATCGCACGCGTTTAATTAACCTAGG (SEQ ID NO: 37) in tra2_1.for contains the AsiSI (GCGATCGC), MluI (ACGCGT), PacI (TTAATTAA) and AvrII (CCTAGG) recognition sites, GGCGCGCCTCGAGG (SEQ ID NO: 38) in tra2_3.rev contains the AscI (GGCGCGCC) and the AbsI (CCTCGAGG) recognition sites, GCGATCGC in tra1A_1.for is the AsiSI recognition site, ACGCGT in tra1A_2.rev and tra1B_1.for is the MluI recognition site, TTAATTAA in tra1B_3.rev and tns_1.for is the PacI recognition site and CCTAGG in tns_2.rev is the AvrII recognition site. The primer annealing locations and genetic organisation of c-TNB001 are shown in FIG. 8.

TABLE 3

Primers used in the design of c-TNB001.

| Primer | Sequence 5' to 3' | TP | Coordinate | Tm |
|---|---|---|---|---|
| BAC1 | ttccattgttcattccacggacaaaaac (SEQ ID NO: 39) | A | 7422 . . . 7449 | 60 |
| BAC2 | gcctgaaaaaacttcccttggggtt (SEQ ID NO: 40) | A | 2439 . . . 2463 | 61 |
| BAC3 | accgtcggttcgagcggtaaCCTCGAGGCGCGCCggcgtttaagggcaccaat (SEQ ID NO: 41) | A | 731 . . . 749 | 55 |
| BAC4 | ggataagtggataaccccaagggaagtttttcaggcGCGCCatcgtgtgtaagcagaatatataagtgc (SEO ID NO: 42) | A | 2411 . . . 2475 | 67 |
| BAC5 | aggcgtagcaaccaggcg (SEQ ID NO: 43) | A | 717 . . . 734 | 61 |
| BAC6 | ggttacgacgacatgtcaatacttgc (SEQ ID NO: 44) | A | 6840 . . . 6865 | 59 |
| tra2_1F | ttttgtccgtaaaatgaacaatggaaGCGATCGCACGCGTTTAATTAACCTAGGtcaccctccttgcgggattgcc (SEQ ID NO: 45) | B | 17670 . . . 17691 | 63 |
| tra2_1R | atcagcacgacgacgctggtgtagtagcccacggccacg (SEQ ID NO: 46) | B | 21651 . . . 21689 | 75 |
| tra2_2F | tcgtggccgtgggctactacaccagcgtcgtcgtgc (SEQ ID NO: 47) | B | 21650 . . . 21685 | 75 |
| tra2_2R | gcaacttcgccatgcggatgcggtccaggtcctcgtt (SEQ ID NO: 48) | B | 25653 . . . 25689 | 74 |
| tra2_3F | cgcaacgaggacctggaccgcatccgcatggcgaagtt (SEQ ID NO: 49) | B | 25650 . . . 25687 | 75 |
| tra2_3R | aacgccGGCGCGCCTCGAGGttaccgctcgaaccgacggtaggcgtcgct (SEQ ID NO: 50) | B | 29846 . . . 29875 | 64 |
| tra1A_1F | aatgcctgtcaagggcaagtattgacatgtcgtcgtaaccGCGATCGCcatcgtggcgttgacaacgtgcctgg (SEQ ID NO: 51) | B | 38324 . . . 38349 | 67 |
| tra1A_1R | accatgcgtggggcggccaccaatggcttgccgacttcg (SEQ ID NO: 52) | B | 42297 . . . 42335 | 78 |
| tra1A_2F | gcgaagtcggcaagccattggtggccgccccacgcatggt (SEQ ID NO: 53) | B | 42296 . . . 42335 | 79 |
| tra1A_2R | ttattggtgcccttaaacgcctggttgctacgcctACGCGTgggtagggggatatatgcaatttgaacg (SEQ ID NO: 54) | B | 46030 . . . 46057 | 61 |

TABLE 3-continued

Primers used in the design of c-TNB001.

| Primer | Sequence 5' to 3' | TP | Coordinate | Tm |
|---|---|---|---|---|
| tra1B_1F | aatgcctgtcaagggcaagtattgacatgtcgtcgtaac cACGCGTtcaccaggtcagaaccggcct (SEO ID NO: 55) | B | 46058 . . . 46078 | 63 |
| tra1B_1R | tgggccgactggctcaaggccgaggcgatgaagggcg (SEQ ID NO: 56) | B | 49541 . . . 49577 | 78 |
| tra1B_2F | cgtcgcccttcatcgcctcggccttgagccagtcg (SEQ ID NO: 57) | B | 49538 . . . 49571 | 75 |
| tra1B_2R | gcaaaaacaagcccggcaacgccgggctttttcatctgc gcctctgcgattcataac (SEQ ID NO: 58) | B | 53021 . . . 53077 | 76 |
| tra1B_3F | cgcagatgaaaaagcccggcgttgccgggcttgtttttg c (SEQ ID NO: 59) | B | 53038 . . . 53077 | 74 |
| tra1B_3R | ggcagttattggtgcccttaaacgcctggttgctacgcc tTTAATTAAtttagcggctaaaggtgttgacgtgcgaga aatgtt (SEQ ID NO: 60) | B | 59421 . . . 59456 | 60 |
| tns_1F | aatgcctgtcaagggcaagtattgacatgtcgtcgtaac cTTAATTAAtgtgggcggacaaaatagttggg (SEQ ID NO: 61) | C | 12045 . . . 12067 | 61 |
| tns_1R | taattcaggcacgtatgtgggtaggctgtaatcttcttg atcatccg (SEQ ID NO: 62) | C | 4290 . . . 4336 | 68 |
| tns_2F | tcaagaagattacagcctacccacatacgtgcctgaatt atttcagg (SEQ ID NO: 63) | C | 4297 . . . 4343 | 67 |
| tns_2R | ggcagttattggtgcccttaaacgcctggttgctacgcc tCCTAGGagtaaatcgagtccatttccg (SEQ ID NO: 64) | C | 7680 . . . 7701 | 56 |

Thus the amplicons 1, 2 and 3 are separately amplified from template A; amplicons 4, 5, 6, 7, 8, 9, 10 and 11 are separately amplified from template B and amplicons 12 and 13 are separately amplified from template C. The genes contained in each of these amplicons are shown in FIG. 8.

2. Plasmids I-IV are assembled as follows:
   a. amplicons 1, 2, 4, 5, 6 are Gibson-assembled to give plasmid construct I;
   b. amplicons 3, 7, 8 are Gibson-assembled to give construct II, and;
   c. amplicons 3, 9, 10, 11 are Gibson-assembled to give construct III, and;
   d. amplicons 3, 12, 13 are Gibson-assembled to give construct IV.
3. Since plasmids I-IV all carry vector backbone sequences from pBeloBAC11 that allow replication and selection of CmR, the Gibson-assembled plasmids 1-IV are transformed into DH5α and plasmid DNA isolated and is subjected to DNA sequence analysis to confirm the integrity of the construct.
4. The next step is the assembly of c-TNB001 from components of plasmids 1-IV: FIG. 7 shows the positions of the relevant restriction enzyme sites: a, b, c, d, e, f—where a=AscI, b=AbsI, c=AvrII, d=PacI, e=MluI, f=AsiSI. Relevant restriction fragments are cloned into plasmid I that already bears fragments 4, 5, 6 in the plasmid pBeloBAC11 vector backbone 1, 2 (1+2+4+5+6).
   a. First Plasmid III is digested with both MluI and PacI (e+d) and fragment 9+10+11 is isolated from a gel following separation by agarose gel electrophoresis and the fragment is cloned into a MluI/PacI double digest of plasmid I to give plasmid 1+2+4+5+6+9+10+11.
   b. Next Plasmid II is digested with both AsiSI and MluI (f+e) and fragment 7+8 is isolated from a gel following separation by agarose gel electrophoresis and the fragment is cloned into AsiSI/MluI double digest of plasmid carrying 1+2+4+5+6+9+10+11 to give 1+2+4+5+6+7+8+9+10+11.
   c. Then plasmid IV is digested with AvrII and PacI (c+d) and fragment 12+13 is isolated from a gel following separation by agarose gel electrophoresis and the fragment is cloned into AvrII/PacI double digest of plasmid carrying 1+2+4+5+6+7+8+9+10+11 to give 1+2+4+5+6+7+8+9+10+11+12+13.
   d. Finally 1+2+4+5+6+7+8+9+10+11+12+13 is digested with AscI (a) and recircularised to remove the unneeded region of pBeloBac11 including chloramphenicol resistant gene.
   e. The resulting plasmid 1+2+4+5+6+7+8+9+10+11+12+13-Delta-AscI-fragment is the c-Transmid c-TNB001.

Example 1.2 Construction of pNB300, the Plasmid Cargo Shuttle Cloning Vector

The total size of this Cargo vector pNB300 is 4851 bp (FIG. 14). It replicates from the p15A ori employed from pACYC184. It contains two inverted lox sites, lox71 and loxN, between which the dihydrofolate reductase gene, dhfr, is located, which is used as a selectable maker for a Cre-mediated recombination event. The Cargo can be cloned at unique restriction sites NotI and XhoI. Cre is constitutively expressed from this Cargo vector. ccdB gene is under the regulation of lac operator, which will be a negative selection of the Cre-recombinant. See FIGS. 15 and 16 for more detailed description. The primer sequences used in this Cargo plasmid vector construction and the annealing sites on each plasmid are shown in Table 4. Template plasmid denoted A is described in the figure legend of FIG. 15. Tm is given in ° C.

spacer sequence(s) targeted against any chosen bacterial gene(s). The CRISPR-Cas9 activity was first tested by addition of a single beta-lactamase spacer sequence, to generate the plasmid pNB102 (pNB100::TEM), and shown to inactivate exemplar beta lactamase gene targets from the TEM family both by delivery by plasmid transformation and by delivery by M13mp18::NB102—a derivative of bacteriophage M13 carrying the CRISPR-Cas9::TEM cassette: M13 is a non-virulent single-stranded (ss) DNA phage.

TABLE 4

Primers used in the design of the Cargo vector, pNB300.

| Primer | Sequence 5' to 3' | Template plasmid | Coordinate | Tm |
|---|---|---|---|---|
| P2F | ctttaGCGGCCGCccggtagagttttaatttaatgcta attaaaatgttatgagttc (SEQ ID NO: 65) | pFE872 | 1 . . . 57 | 60 |
| P2R | aaaacctttaGCGATCGCtcgaacacttcacgaacaat gaaatggt (SEQ ID NO: 66) | pFE872 | 864 . . . 899 | 60 |
| P3F | CGACGACCGGGTCGAATTTG (SEQ ID NO: 67) | A | 3759 . . . 3778 | 59 |
| P3R | ACATGAGAATTACAACTTATATCGTATGGGGCT (SEQ ID NO: 68) | A | 1536 . . . 1586 | 60 |
| P4F | TGAAGTCAGCCCCATACGATATAAGTTGTAATTCTCAT GTATCGCCATCTTCCAGCAGG (SEQ ID NO: 69) | pCAG-Cre_GFP | 2747 . . . 2765 | 60 |
| P4R | CGGTTTGCGTATTGGGCGCTTGCCGCAGGGGGACG (SEQ ID NO: 70) | pCAG-Cre_GFP | 1549 . . . 1563 | 60 |
| P5F | ATTTCACACAGGAAACAGCTatgCAGTTTAAGGTTTAC ACCTATAAAAGAGAGAG (SEQ ID NO: 71) | pCR Blunt II-TOPO | 585 . . . 617 | 59 |
| P5R | GAATGGCAGAAATTCGAAAGCAAATTCGACCCGGTCG TCGGTAGCTGACATTCATCCGGGG (SEQ ID NO: 72) | pCR Blunt II-TOPO | 970 . . . 990 | 60 |
| P6F | GCAGCCGTCCCCCTGCGGCAAGCGCCCAATACGCAAAC CG (SEQ ID NO: 73) | pCR Blunt II-TOPO | 1 . . . 18 | 60 |
| P6R | GTGTAAACCTTAAACTGcatAGCTGTTTCCTGTGTGAA ATTGTTATCC (SEQ ID NO: 74) | pCR Blunt II-TOPO | 189 . . . 219 | 61 |

Example 2

Exemplification of Use of the c-Transmid c-TNB001: Delivery of Cargo Resulting in Inactivation of Antibiotic Resistance Genes in *Escherichia coli*

Example 2 demonstrates the application of c-Transmids for delivery of the Cargo, resulting in inactivation of antibiotic resistance genes. The Cargo is a selected nucleotide of interest encoding a CRISPR-Cas9 construct with 8 spacer sequences encoding guide RNAs (gRNAs) targeting antibiotic resistance genes from 8 different families of beta-lactamases (bla): the blaVIM (V), blaOXA (O), blaNDM (N), blaCTX-M (C), blaKPC (K), blaIMP (I), blaSHX (S) and blaTEM (T) families, hereafter termed the VONCKIST gene families. Inactivation of such antibiotic resistance genes allows for resurrection of antibiotic sensitivity in bacterial strains, including pathogenic strains of *Escherichia coli* and *Klebsiella pneumoniae*. The steps involved in this exemplification are summarised below:

Example 2.1

A generally applicable DNA cassette on plasmid pNB100 was constructed that carries the CRISPR-Cas9 system and allows the construction of plasmid derivatives carrying

Example 2.2

Spacers were added to pNB100 to generate the derivative plasmid pNB108 (pNB100::NIVKOSTC, where NIVKOSTC denotes the order of the spacers targeting blaNDM, blaIMP, blaVIM, blaKPC, blaOXA, blaSHV, blaTEM, blaCTX-M beta lactamase gene families) capable of targeting selected beta lactamase resistance genes from VONCKIST families for inactivation.

Example 2.3

Eight plasmids were constructed encoding one beta-lactamase from each of the eight VONCKIST beta-lactamase gene families, where seven such beta lactamases were isolated from clinical isolates, pathogenic strains of *Escherichia coli* and *Klebsiella pneumoniae* plus one beta lactamase (blaTEM-3) from a non-pathogenic laboratory strain of *Escherichia coli.*

Example 2.4

Non-pathogenic laboratory strains of *E. coli* carrying plasmids encoding one of each of the eight VONCKIST beta-lactamases were transformed with the derivative plasmids carrying spacer sequences capable of targeting selected families of beta lactamase resistance genes and tested for their capacity to inactivate the VONCKIST beta lactamase genes.

Example 2.5

The CRISPR-Cas9-NIVKOSTC cassette, carrying all eight spacers, the Cargo is added into the c-Transmid, c-TNB001, by Cre/lox-mediated recombination (docking) and the resulting c-Transmid with Cargo, c-TNB001::CRISPR-Cas9-NIVKOSTC is packaged into an infectious bacteriophage lambda particle giving lambda(c-TNB001::CRISPR-Cas9-NIVKOSTC) and tested for delivery to *E. coli* cells by lambda(c-Transmid::VONCKIST) infection.

Example 2.6 c-TNB001::CRISPR-Cas9-NIVKOSTC is tested for conjugal transfer to bacterial recipients *E. coli* and *K. pneumoniae.*

Example 2.7 c-TNB001::CRISPR-Cas9-NIVKOSTC is tested for the ability to inactivate each of the eight VONCKIST beta-lactamases following lambda(c-Transmid::VONCKIST) infection of non-pathogenic laboratory strains of *E. coli* carrying plasmids encoding one of each of the eight VONCKIST beta-lactamases.

Example 2.8 c-TNB001::CRISPR-Cas9-NIVKOSTC is tested for the ability to inactivate each of the eight VONCKIST beta-lactamases c-Transmid::VONCKIST following conjugation from a donor strain to non-pathogenic laboratory recipient strains of *E. coli* carrying plasmids encoding one of each of the eight VONCKIST beta-lactamases.

The steps summarised above are described in further detail below:

Example 2.1 Construction of Generally Applicable CRISPR-Cas9 Plasmids

A generally applicable DNA cassette on plasmid pNB100 was constructed that carries the CRISPR-Cas9 system and allows the construction of plasmid derivatives carrying spacer sequence(s) targeted against any chosen bacterial gene(s). The CRISPR-Cas9 activity was confirmed using a derivative of pNB100, pNB102, carrying a spacer sequence targeted against members of the TEM family of beta-lactamases such as TEM-3 and TEM-1—the beta lactamase genes of the bacterial transposons Tn3 and Tn1, respectively, with delivery by plasmid transformation; and also by delivery by M13mp18::NB102—a derivative of bacteriophage M13, a non-virulent single-stranded (ss) DNA phage.

Example 2.1.1 Construction of pNB100 pNB100 is a vector to express the CRISPR-Cas9 system in *E. coli* and other bacterial species with the appropriate unique restriction site, Bsa I, to clone any desired spacer sequence between two direct repeats in the CRISPR locus. The backbone of the vector is derived from pACYC184 (purified from *E. coli* K12 strain ER2420 purchased from New England Biolabs) and the CRISPR-cas9 locus was inserted into Eco RV site of the vector. Three regions of the CRISPR-cas9 locus were amplified by PCR from the genomic DNA of *Streptococcus pyogenes* strain SF370, purchased from the ATCC, and assembled by Gibson assembly (Gibson et al., 2009, supra) along with the pACYC184 vector in the reaction. The sequence of the final construct was verified by Sanger sequencing.

The Amplified Sequence of the Three Regions and Amplicon Image on the Gel

The following sequences are the three regions amplified by PCR. Underlined sequences are template-specific primer sequences, bold letters are overlapping sequences used for Gibson assembly.

1. Fragment 1, tracrRNA-cas9: amplicon length=4758 bp

Forward primer is from 854170 to 854193 and reverse primer is from 858867 to 858848 on *S. pyogenes* SF370 genomic DNA.

(SEQ ID NO: 75)

ATGCCGGTACTGCCGGGCCTCTTGCGGGATCCAGAAGTCTTTTTCTTGCA

CTGTTTCCTTTTCTTTATGATAGTTTACGAAATCATCCTGTGGAGCTTAG

TAGGTTTAGCAAGATGGCAGCGCCTAAATGTAGAATGATAAAAGGATTAA

GAGATTAATTTCCCTAAAAATGATAAAACAAGCGTTTTGAAAGCGCTTGT

TTTTTTGGTTTGCAGTCAGAGTAGAATAGAAGTATCAAAAAAAGCACCGA

CTCGGTGCCACTTTTTCAAGTTGATAACGGACTAGCCTTATTTTAACTTG

CTATGCTGTTTTGAATGGTTCCAACAAGATTATTTTATAACTTTTATAAC

AAATAATCAAGGAGAAATTCAAAGAAATTTATCAGCCATAAAACAATACT

TAATACTATAGAATGATAACAAAATAAACTACTTTTTAAAAGAATTTTGT

GTTATAATCTATTTATTATTAAGTATTGGGTAATATTTTTTGAAGAGATA

TTTTGAAAAAGAAAAATTAAAGCATATTAAACTAATTTCGGAGGTCATTA

AAACTATTATTGAAATCATCAAACTCATTATGGATTTAATTTAAACTTTT

TATTTTAGGAGGCAAAAATGGATAAGAAATACTCAATAGGCTTAGATATC

GGCACAAATAGCGTCGGATGGGCGGTGATCACTGATGAATATAAGGTTCC

GTCTAAAAAGTTCAAGGTTCTGGGAAATACAGACCGCCACAGTATCAAAA

AAAATCTTATAGGGGCTCTTTTATTTGACAGTGGAGAGACAGCGGAAGCG

ACTCGTCTCAAACGGACAGCTCGTAGAAGGTATACACGTCGGAAGAATCG

TATTTGTTATCTACAGGAGATTTTTTCAAATGAGATGGCGAAAGTAGATG

ATAGTTTCTTTCATCGACTTGAAGAGTCTTTTTTGGTGGAAGAAGACAAG

AAGCATGAACGTCATCCTATTTTTGGAAATATAGTAGATGAAGTTGCTTA

TCATGAGAAATATCCAACTATCTATCATCTGCGAAAAAAATTGGTAGATT

CTACTGATAAAGCGGATTTGCGCTTAATCTATTTGGCCTTAGCGCATATG

ATTAAGTTTCGTGGTCATTTTTTGATTGAGGGAGATTTAAATCCTGATAA

TAGTGATGTGGACAAACTATTTATCCAGTTGGTACAAACCTACAATCAAT

TATTTGAAGAAAACCCTATTAACGCAAGTGGAGTAGATGCTAAAGCGATT

CTTTCTGCACGATTGAGTAAATCAAGACGATTAGAAAATCTCATTGCTCA

GCTCCCCGGTGAGAAGAAAAATGGCTTATTTGGGAATCTCATTGCTTTGT

CATTGGGTTTGACCCCTAATTTTAAATCAAATTTTGATTTGGCAGAAGAT

GCTAAATTACAGCTTTCAAAAGATACTTACGATGATGATTTAGATAATTT

ATTGGCGCAAATTGGAGATCAATATGCTGATTTGTTTTTGGCAGCTAAGA

-continued

ATTTATCAGATGCTATTTTACTTTCAGATATCCTAAGAGTAAATACTGAA
ATAACTAAGGCTCCCCTATCAGCTTCAATGATTAAACGCTACGATGAACA
TCATCAAGACTTGACTCTTTTAAAAGCTTTAGTTCGACAACAACTTCCAG
AAAAGTATAAAGAAATCTTTTTTGATCAATCAAAAAACGGATATGCAGGT
TATATTGATGGGGGAGCTAGCCAAGAAGAATTTTATAAATTTATCAAACC
AATTTTAGAAAAAATGGATGGTACTGAGGAATTATTGGTGAAACTAAATC
GTGAAGATTTGCTGCGCAAGCAACGGACCTTTGACAACGGCTCTATTCCC
CATCAAATTCACTTGGGTGAGCTGCATGCTATTTTGAGAAGACAAGAAGA
CTTTTATCCATTTTTAAAAGACAATCGTGAGAAGATTGAAAAAATCTTGA
CTTTTCGAATTCCTTATTATGTTGGTCCATTGGCGCGTGGCAATAGTCGT
TTTGCATGGATGACTCGGAAGTCTGAAGAAACAATTACCCCATGGAATTT
TGAAGAAGTTGTCGATAAAGGTGCTTCAGCTCAATCATTTATTGAACGCA
TGACAAACTTTGATAAAAATCTTCCAAATGAAAAAGTACTACCAAAACAT
AGTTTGCTTTATGAGTATTTTACGGTTTATAACGAATTGACAAAGGTCAA
ATATGTTACTGAAGGAATGCGAAAACCAGCATTTCTTTCAGGTGAACAGA
AGAAAGCCATTGTTGATTTACTCTTCAAAACAAATCGAAAAGTAACCGTT
AAGCAATTAAAAGAAGATTATTTCAAAAAAATAGAATGTTTTGATAGTGT
TGAAATTTCAGGAGTTGAAGATAGATTTAATGCTTCATTAGGTACCTACC
ATGATTTGCTAAAAATTATTAAAGATAAAGATTTTTTGGATAATGAAGAA
AATGAAGATATCTTAGAGGATATTGTTTTAACATTGACCTTATTTGAAGA
TAGGGAGATGATTGAGGAAAGACTTAAAACATATGCTCACCTCTTTGATG
ATAAGGTGATGAAACAGCTTAAACGTCGCCGTTATACTGGTTGGGGACGT
TTGTCTCGAAAATTGATTAATGGTATTAGGGATAAGCAATCTGGCAAAAC
AATATTAGATTTTTTGAAATCAGATGGTTTTGCCAATCGCAATTTTATGC
AGCTGATCCATGATGATAGTTTGACATTTAAAGAAGACATTCAAAAAGCA
CAAGTGTCTGGACAAGGCGATAGTTTACATGAACATATTGCAAATTTAGC
TGGTAGCCCTGCTATTAAAAAAGGTATTTTACAGACTGTAAAAGTTGTTG
ATGAATTGGTCAAAGTAATGGGGCGGCATAAGCCAGAAAATATCGTTATT
GAAATGGCACGTGAAAATCAGACAACTCAAAAGGGCCAGAAAAATTCGCG
AGAGCGTATGAAACGAATCGAAGAAGGTATCAAAGAATTAGGAAGTCAGA
TTCTTAAAGAGCATCCTGTTGAAAATACTCAATTGCAAAATGAAAAGCTC
TATCTCTATTATCTCCAAAATGGAAGAGACATGTATGTGGACCAAGAATT
AGATATTAATCGTTTAAGTGATTATGATGTCGATCACATTGTTCCACAAA
GTTTCCTTAAAGACGATTCAATAGACAATAAGGTCTTAACGCGTTCTGAT
AAAAATCGTGGTAAATCGGATAACGTTCCAAGTGAAGAAGTAGTCAAAAA
GATGAAAAACTATTGGAGACAACTTCTAAACGCCAAGTTAATCACTCAAC
GTAAGTTTGATAATTTAACGAAAGCTGAACGTGGAGGTTTGAGTGAACTT
GATAAAGCTGGTTTTATCAAACGCCAATTGGTTGAAACTCGCCAAATCAC
TAAGCATGTGGCACAAATTTTGGATAGTCGCATGAATACTAAATACGATG
AAAATGATAAACTTATTCGAGAGGTTAAAGTGATTACCTTAAAATCTAAA

-continued

TTAGTTTCTGACTTCCGAAAAGATTTCCAATTCTATAAAGTACGTGAGAT
TAACAATTACCATCATGCCCATGATGCGTATCTAAATGCCGTCGTTGGAA
CTGCTTTGATTAAGAAATATCCAAAACTTGAATCGGAGTTTGTCTATGGT
GATTATAAAGTTTATGATGTTCGTAAAATGATTGCTAAGTCTGAGCAAGA
AATAGGCAAAGCAACCGCAAAATATTTCTTTTACTCTAATATCATGAACT
TCTTCAAAACAGAAATTACACTTGCAAATGGAGAGATTCGCAAACGCCCT
CTAATCGAAACTAATGGGGAAACTGGAGAAATTGTCTGGGATAAAGGGCG
AGATTTTGCCACAGTGCGCAAAGTATTGTCCATGCCCCAAGTCAATATTG
TCAAGAAAACAGAAGTACAGACAGGCGGATTCTCCAAGGAGTCAATTTTA
CCAAAAAGAAATTCGGACAAGCTTATTGCTCGTAAAAAAGACTGGGATCC
AAAAAAATATGGTGGTTTTGATAGTCCAACGGTAGCTTATTCAGTCCTAG
TGGTTGCTAAGGTGGAAAAAGGGAAATCGAAGAAGTTAAAATCCGTTAAA
GAGTTACTAGGGATCACAATTATGGAAAGAAGTTCCTTTGAAAAAAATCC
GATTGACTTTTTAGAAGCTAAAGGATATAAGGAAGTTAAAAAAGACTTAA
TCATTAAACTACCTAAATATAGTCTTTTTGAGTTAGAAAACGGTCGTAAA
CGGATGCTGGCTAGTGCCGGAGAATTACAAAAAGGAAATGAGCTGGCTCT
GCCAAGCAAATATGTGAATTTTTTATATTTAGCTAGTCATTATGAAAAGT
TGAAGGGTAGTCCAGAAGATAACGAACAAAAACAATTGTTTGTGGAGCAG
CATAAGCATTATTTAGATGAGATTATTGAGCAAATCAGTGAATTTTCTAA
GCGTGTTATTTTAGCAGATGCCAATTTAGATAAAGTTCTTAGTGCATATA
ACAAACATAGAGACAAACCAATACGTGAACAAGCAGAAAATATTATTCAT
TTATTTACGTTGACGAATCTTGGAGCTCCCGCTGCTTTTAAATATTTTGA
TACAACAATTGATCGTAAACGATATACGTCTACAAAAGAAGTTTTAGATG
CCACTCTTATCCATCAATCCATCACTGGTCTTTATGAAACACGCATTGAT
TTGAGTCAGCTAGGAGGTGACTGATGGCCACGTGAACTATATGATTTTCC
GCAGTATA.

2. Fragment 2, Leader and first direct repeat: amplicon length=276 bp

Forward primer is from 860648 to 860671 and reverse primer is from 860862 to 860806 on *S. pyogenes* genomic DNA.

(SEQ ID NO: 76)
ATTGATTTGAGTCAGCTAGGAGGTGACTGATGGCCACGTGAACTATATGA
TTTTCCGCAGTATATTTTAGATGAAGATTATTTCTTAATAACTAAAAATA
TGGTATAATACTCTTAATAAATGCAGTAATACAGGGGCTTTTCAAGACTG
AAGTCTAGCTGAGACAAATAGTGCGATTACGAAATTTTTTAGACAAAAAT
AGTCTACGAGGTTTTAGAGCTATGCTGTTTTGAATGGTCCCAAAACTGAG
ACCAGTCTCGGACGTCCAAAGGTCTC.

3. Fragment 3, Second direct repeat: amplicon length=452 bp

Forward primer is from 861221 to 861276 and reverse primer is from 861613 to 861594 on *S. pyogenes* genomic DNA. Decamer sequence from 861246-861255 GGTCTCCATT, which contains BsaI recognition sequence on the genomic DNA, was substituted with GGTCCCAAAA to destroy BsaI recognition sequence and convert the 7th truncated direct repeat in the CRISPR array on the genome to the canonical 2nd direct repeat sequence in this vector.

(SEQ ID NO: 77)

GAGACCAGTCTCGGACGTCCAAAGGTCTCGTTTTAGAGCTATGCTGTTTT

GAATGGTCCCAAAACAACATTGCCGATGATAACTTGAGAAAGAGGGTTAA

TACCAGCAGTCGGATACCTTCCTATTCTTTCTGTTAAAGCGTTTTCATGT

TATAATAGGCAAAAGAAGAGTAGTGTGATGGAACAAACATTTTTTATGAT

TAAGCCATATGGGGTTAAGCAAGGGGAGGTAGTTGGAGAGGTTTTACGGT

GGATTGAACGCCTAAGATTTACGTTTAAGCGATTCGAGCTAAGACAAGCT

AGTTCGAAATACTTGGCTAAGCACGACGAGGCCTTGGTGATAAACCTTTT

GATCCTAAACTTAAAGCTTACATGACAAGTGGTCCTGTTTTAATTGGGAT

AATTCTTGGGGACTAAGGTGGTATCGTCCATTCCGACAGCATCGCCAGTC

AC.

PCR conditions to generate the three fragments are provided in Table 5.

TABLE 5

| | Fragment 1 | Fragment 2 | Fragment 3 |
|---|---|---|---|
| 5X Q5 Reaction Buffer | 1x | 1x | 1x |
| 10 mM dNTPs | 200 μM | 200 μM | 200 μM |
| 10 μM Forward Primer | 0.5 μM | 0.5 μM | 0.5 μM |

TABLE 5-continued

| | Fragment 1 | Fragment 2 | Fragment 3 |
|---|---|---|---|
| 10 μM Reverse Primer | 0.5 μM | 0.5 μM | 0.5 μM |
| *S. pyogenes* DNA 50-100 ng/ul | 1 ng/μl | 1 ng/μl | 1 ng/μl |
| Q5 High-Fidelity DNA Polymerase 2U/μL(NEB) | 0.04 U/μl | 0.02 U/μl | 0.02 U/μl |
| Thermocycling condition | | | |
| Initial Denaturation | 98° C._60 sec | 98° C._60 sec | 98° C._60 sec |
| 35 Cycles | 98° C._10 sec | 98° C._10 sec | 98° C._10 sec |
| | 64° C._30 sec | 62° C._30 sec | 62° C._30 sec |
| | 72° C._240 sec | 72° C._30 sec | 72° C._30 sec |
| Final Extension | 72° C._120 sec | 72° C._120 sec | 72° C._120 sec |
| Hold | 4° C. | 4° C. | 4° C. |

Assembly of pNB100 from Three PCR Amplicons, tracrRNA-Cas9, Leader and First Direct Repeat, Second Direct Repeat; Plus pACYC184 Digested with EcoRV We employed a Gibson assembly kit from New England Biolabs (E5510) and followed the protocol provided by the manufacturer to assemble the above three PCR amplicons along with pACYC184. The component of each fragment in the assembling reaction is shown in Table 6.

TABLE 6

| | |
|---|---|
| 0.1 pmol/μL Fragment 1 | 0.2 pmol |
| 0.2 pmol/μL Fragment 2 | 0.2 pmol |
| 0.2 pmol/μL Fragment 3 | 0.2 pmol |
| 0.01 pmol/μL pACYC184 | 0.04 pmol |
| Fragments 1::Fragment 2:Fragment 3:vector | 5:5:5:1 |
| Gibson Assembly Master Mix (2X) | 1x |
| Incubation | 50° C. for 1 hr |

2 μL of the assembly reaction was transformed to DH5α competent cells (purchased from New England Biolabs) followed by selection on chloramphenicol (35 μg/mL) LB plates. The recombinants were screened by PCR using the three primer sets used for obtaining the initial three fragments. The plasmid templates giving three desired amplicons were isolated from the candidate clones and were subjected to sequence analysis.

The sequence of the final construct of pNB100

(SEQ ID NO: 78)

*GAATTCCGGATGAGCATTCATCAGGCGGGCAAGAATGTGAATAAAGGCCGGATAAAACTTGTGCTTATTTTTCTTTACGG*

*TCTTTAAAAAGGCCGTAATATCCAGCTGAACGGTCTGGTTATAGGTACATTGAGCAACTGACTGAAATGCCTCAAAATGT*

*TCTTTACGATGCCATTGGGATATATCAACGGTGGTATATCCAGTGATTTTTTTCTCCATTTTAGCTTCCTTAGCTCCTGA*

*AAATCTCGATAACTCAAAAAATACGCCCGGTAGTGATCTTATTTCATTATGGTGAAAGTTGGAACCTCTTACGTGCCGAT*

*CAACGTCTCATTTTCGCCAAAAGTTGGCCCAGGGCTTCCCGGTATCAACAGGGACACCAGGATTTATTTATTCTGCGAAG*

*TGATCTTCCGTCACAGGTATTTATTCGGCGCAAAGTGCGTCGGGTGATGCTGCCAACTTACTGATTTAGTGTATGATGGT*

*GTTTTTGAGGTGCTCCAGTGGCTTCTGTTTCTATCAGCTGTCCCTCCTGTTCAGCTACTGACGGGGTGGTGCGTAACGGC*

*AAAAGCACCGCCGGACATCAGCGCTAGCGGAGTGTATACTGGCTTACTATGTTGGCACTGATGAGGGTGTCAGTGAAGTG*

*CTTCATGTGGCAGGAGAAAAAAGGCTGCACCGGTGCGTCAGCAGAATATGTGATACAGGATATATTCCGCTTCCTCGCTC*

*ACTGACTCGCTACGCTCGGTCGTTCGACTGCGGCGAGCGGAAATGGCTTACGAACGGGGCGGAGATTTCCTGGAAGATGC*

*CAGGAAGATACTTAACAGGGAAGTGAGAGGGCCGCGGCAAAGCCGTTTTTCCATAGGCTCCGCCCCCCTGACAAGCATCA*

*CGAAATCTGACGCTCAAATCAGTGGTGGCGAAACCCGACAGGACTATAAAGATACCAGGCGTTTCCCCCTGGCGGCTCCC*

*TCGTGCGCTCTCCTGTTCCTGCCTTTCGGTTTACCGGTGTCATTCCGCTGTTATGGCCGCGTTTGTCTCATTCCACGCCT*

-continued

*GACACTCAGTTCCGGGTAGGCAGTTCGCTCCAAGCTGGACTGTATGCACGAACCCCCCGTTCAGTCCGACCGCTGCGCCT*

*TATCCGGTAACTATCGTCTTGAGTCCAACCCGGAAAGACATGCAAAAGCACCACTGGCAGCAGCCACTGGTAATTGATTT*

*AGAGGAGTTAGTCTTGAAGTCATGCGCCGGTTAAGGCTAAACTGAAAGGACAAGTTTTGGTGACTGCGCTCCTCCAAGCC*

*AGTTACCTCGGTTCAAAGAGTTGGTAGCTCAGAGAACCTTCGAAAAACCGCCCTGCAAGGCGGTTTTTTCGTTTTCAGAG*

*CAAGAGATTACGCGCAGACCAAAACGATCTCAAGAAGATCATCTTATTAATCAGATAAAATATT*TCTAGA*TTTCAGTGCA*

*ATTTATCTCTTCAAATGTAGCACCTGAAGTCAGCCCCATACGATATAAGTTGTAATTCTCATGTTTGACAGCTTATCATC*

*GATAAGCTTTAATGCGGTAGTTTATCACAGTTAAATTGCTAACGCAGTCAGGCACCGTGTATGAAATCTAACAATGCGCT*

*CATCGTCATCCTCGGCACCGTCACCCTGGATGCTGTAGGCATAGGCTTGGTTATGCCGGTACTGCCGGGCCTCTTGCGGG*

*AT*CCAGAAGTCTTTTTCTTGCACTGTTTCCTTTTCTTTATGATAGTTTACGAAATCATCCTGTGGAGCTTAGTAGGTTTA

GCAAGATGGCAGCGCCTAAATGTAGAATGATAAAAGGATTAAGAGATTAATTTCCCTAAAAATGATAAAACAAGCGTTTT

GAAAGCGCTTGTTTTTTTGGTTTGCAGTCAGAGTAGAATAGAAGTATCAAAAAAAGCACCGACTCGGTGCCACTTTTTCA

AGTTGATAACGGACTAGCCTTATTTTAACTTGCTATGCTGTTTTGAATGGTTCCAACAAGATTATTTT*ATAACTTTTATA*

*ACAAATAATCAAGGAGAAATTCAAAGAAATTTATCAGCCATAAAAC*AATACTTAATACTATAGAATGATAACAAAATAAA

CTACTTTTTAAAAGAATTTTGTGTTATAATCTATTTATTATTAAGTATTGGGTAATATTTTTTGAAGAGATATTTTGAAA

AAGAAAAAATTAAAGCATATTAAACTAATTTCGGAGGTCATTAAAACTATTATTGAAATCATCAAACTCATTATGGATTTA

ATTTAAACTTTTTATTTTAGGAGGCAAAAATGGATAAGAAATACTCAATAGGCTTAGATATCGGCACAAATAGCGTCGGA

TGGGCGGTGATCACTGATGAATATAAGGTTCCGTCTAAAAAGTTCAAGGTTCTGGGAAATACAGACCGCCACAGTATCAA

AAAAAATCTTATAGGGGCTCTTTTATTTGACAGTGGAGAGACAGCGGAAGCGACTCGTCTCAAACGGACAGCTCGTAGAA

GGTATACACGTCGGAAGAATCGTATTTGTTATCTACAGGAGATTTTTTCAAATGAGATGGCGAAAGTAGATGATAGTTTC

TTTCATCGACTTGAAGAGTCTTTTTTGGTGGAAGAAGACAAGAAGCATGAACGTCATCCTATTTTTGGAAATATAGTAGA

TGAAGTTGCTTATCATGAGAAATATCCAACTATCTATCATCTGCGAAAAAAATTGGTAGATTCTACTGATAAAGCGGATT

TGCGCTTAATCTATTTGGCCTTAGCGCATATGATTAAGTTTCGTGGTCATTTTTTGATTGAGGGAGATTTAAATCCTGAT

AATAGTGATGTGGACAAACTATTTATCCAGTTGGTACAAACCTACAATCAATTATTTGAAGAAAACCCTATTAACGCAAG

TGGAGTAGATGCTAAAGCGATTCTTTCTGCACGATTGAGTAAATCAAGACGATTAGAAAATCTCATTGCTCAGCTCCCCG

GTGAGAAGAAAAATGGCTTATTTGGGAATCTCATTGCTTTGTCATTGGGTTTGACCCCTAATTTTAAATCAAATTTTGAT

TTGGCAGAAGATGCTAAATTACAGCTTTCAAAAGATACTTACGATGATGATTTAGATAATTTATTGGCGCAAATTGGAGA

TCAATATGCTGATTTGTTTTTGGCAGCTAAGAATTTATCAGATGCTATTTTACTTTCAGATATCCTAAGAGTAAATACTG

AAATAACTAAGGCTCCCCTATCAGCTTCAATGATTAAACGCTACGATGAACATCATCAAGACTTGACTCTTTTAAAAGCT

TTAGTTCGACAACAACTTCCAGAAAAGTATAAAGAAATCTTTTTTGATCAATCAAAAAACGGATATGCAGGTTATATTGA

TGGGGGAGCTAGCCAAGAAGAATTTTATAAATTTATCAAACCAATTTTAGAAAAAATGGATGGTACTGAGGAATTATTGG

TGAAACTAAATCGTGAAGATTTGCTGCGCAAGCAACGGACCTTTGACAACGGCTCTATTCCCCATCAAATTCACTTGGGT

GAGCTGCATGCTATTTTGAGAAGACAAGAAGACTTTTATCCATTTTTAAAAGACAATCGTGAGAAGATTGAAAAAATCTT

GACTTTTCGAATTCCTTATTATGTTGGTCCATTGGCGCGTGGCAATAGTCGTTTTGCATGGATGACTCGGAAGTCTGAAG

AAACAATTACCCCATGGAATTTTGAAGAAGTTGTCGATAAAGGTGCTTCAGCTCAATCATTTATTGAACGCATGACAAAC

TTTGATAAAAATCTTCCAAATGAAAAAGTACTACCAAAACATAGTTTGCTTTATGAGTATTTTACGGTTTATAACGAATT

GACAAAGGTCAAATATGTTACTGAAGGAATGCGAAAACCAGCATTTCTTTCAGGTGAACAGAAGAAAGCCATTGTTGATT

TACTCTTCAAAACAAATCGAAAAGTAACCGTTAAGCAATTAAAAGAAGATTATTTCAAAAAAATAGAATGTTTTGATAGT

GTTGAAATTTCAGGAGTTGAAGATAGATTTAATGCTTCATTAGGTACCTACCATGATTTGCTAAAAATTATTAAAGATAA

AGATTTTTTGGATAATGAAGAAAATGAAGATATCTTAGAGGATATTGTTTTAACATTGACCTTATTTGAAGATAGGGAGA

TGATTGAGGAAAGACTTAAAACATATGCTCACCTCTTTGATGATAAGGTGATGAAACAGCTTAAACGTCGCCGTTATACT

-continued

GGTTGGGGACGTTTGTCTCGAAAATTGATTAATGGTATTAGGGATAAGCAATCTGGCAAAACAATATTAGATTTTTTGAA

ATCAGATGGTTTTGCCAATCGCAATTTTATGCAGCTGATCCATGATGATAGTTTGACATTTAAAGAAGACATTCAAAAAG

CACAAGTGTCTGGACAAGGCGATAGTTTACATGAACATATTGCAAATTTAGCTGGTAGCCCTGCTATTAAAAAAGGTATT

TTACAGACTGTAAAAGTTGTTGATGAATTGGTCAAAGTAATGGGGCGGCATAAGCCAGAAAATATCGTTATTGAAATGGC

ACGTGAAAATCAGACAACTCAAAAGGGCCAGAAAAATTCGCGAGAGCGTATGAAACGAATCGAAGAAGGTATCAAAGAAT

TAGGAAGTCAGATTCTTAAAGAGCATCCTGTTGAAAATACTCAATTGCAAAATGAAAAGCTCTATCTCTATTATCTCCAA

AATGGAAGAGACATGTATGTGGACCAAGAATTAGATATTAATCGTTTAAGTGATTATGATGTCGATCACATTGTTCCACA

AAGTTTCCTTAAAGACGATTCAATAGACAATAAGGTCTTAACGCGTTCTGATAAAAATCGTGGTAAATCGGATAACGTTC

CAAGTGAAGAAGTAGTCAAAAAGATGAAAAACTATTGGAGACAACTTCTAAACGCCAAGTTAATCACTCAACGTAAGTTT

GATAATTTAACGAAAGCTGAACGTGGAGGTTTGAGTGAACTTGATAAAGCTGGTTTTATCAAACGCCAATTGGTTGAAAC

TCGCCAAATCACTAAGCATGTGGCACAAATTTTGGATAGTCGCATGAATACTAAATACGATGAAAATGATAAACTTATTC

GAGAGGTTAAAGTGATTACCTTAAAATCTAAATTAGTTTCTGACTTCCGAAAAGATTTCCAATTCTATAAAGTACGTGAG

ATTAACAATTACCATCATGCCCATGATGCGTATCTAAATGCCGTCGTTGGAACTGCTTTGATTAAGAAATATCCAAAACT

TGAATCGGAGTTTGTCTATGGTGATTATAAAGTTTATGATGTTCGTAAAATGATTGCTAAGTCTGAGCAAGAAATAGGCA

AAGCAACCGCAAAATATTTCTTTTACTCTAATATCATGAACTTCTTCAAAACAGAAATTACACTTGCAAATGGAGAGATT

CGCAAACGCCCTCTAATCGAAACTAATGGGGAAACTGGAGAAATTGTCTGGGATAAAGGGCGAGATTTTGCCACAGTGCG

CAAAGTATTGTCCATGCCCCAAGTCAATATTGTCAAGAAAACAGAAGTACAGACAGGCGGATTCTCCAAGGAGTCAATTT

TACCAAAAAGAAATTCGGACAAGCTTATTGCTCGTAAAAAAGACTGGGATCCAAAAAAATATGGTGGTTTTGATAGTCCA

ACGGTAGCTTATTCAGTCCTAGTGGTTGCTAAGGTGGAAAAAGGGAAATCGAAGAAGTTAAAATCCGTTAAAGAGTTACT

AGGGATCACAATTATGGAAAGAAGTTCCTTTGAAAAAAATCCGATTGACTTTTTAGAAGCTAAAGGATATAAGGAAGTTA

AAAAAGACTTAATCATTAAACTACCTAAATATAGTCTTTTTGAGTTAGAAAACGGTCGTAAACGGATGCTGGCTAGTGCC

GGAGAATTACAAAAAGGAAATGAGCTGGCTCTGCCAAGCAAATATGTGAATTTTTTATATTTAGCTAGTCATTATGAAAA

GTTGAAGGGTAGTCCAGAAGATAACGAACAAAAACAATTGTTTGTGGAGCAGCATAAGCATTATTTAGATGAGATTATTG

AGCAAATCAGTGAATTTTCTAAGCGTGTTATTTTAGCAGATGCCAATTTAGATAAAGTTCTTAGTGCATATAACAAACAT

AGAGACAAACCAATACGTGAACAAGCAGAAAATATTATTCATTTATTTACGTTGACGAATCTTGGAGCTCCCGCTGCTTT

TAAATATTTTGATACAACAATTGATCGTAAACGATATACGTCTACAAAAGAAGTTTTAGATGCCACTCTTATCCATCAAT

CCATCACTGGTCTTTATGAAACACGCATTGATTTGAGTCAGCTAGGAGGTGACTGATGGCCACGTGAACTATATGATTTT

CCGCAGTATATTTTAGATGAAGATTATTTCTTAATAACTAAAAATATGGTATAATACTCTT*AATAAATGCAGTAATACAG*

*GGGCTTTTCAAGACTGAAGTCTAGCTGAGACAAATAGTGCGATTACGAAATTTTTTAGACAAAAAATAGTCTACGAG*GTTT

TAGAGCTATGCTATTTTGAATGGTCCCAAAAC*TGAGACC*AGTCTCG*GACGTC*CAAA*GGTCTC*GTTTTAGAGCTATGCTGT

TTTGAATGGTCCCAAAACAACATTGCCGATGATAACTTGAGAAAGAGGGTTAATACCAGCAGTCGGATACCTTCCTATTC

TTTCTGTTAAAGCGTTTTCATGTTATAATAGGCAAAAGAAGAGTAGTGTGATGGAACATACATTTTTTATGATTAAGCCA

TATGGGGTTAAGCAAGGGGAGGTAGTTGGAGAGGTTTTACGGTGGATTGAACGCCTAAGATTTACGTTTAAGCGATTCGA

GCTAAGACAAGCTAGTTCGAAATACTTGGCTAAGCACGACGAGGCCTTGGTGATAAACCTTTTGATCCTAAACTTAAAGC

TTACATGACAAGTGGTCCTGTTTTAATTGGGATAATTCTTGGGGACTAAGGTGGT*ATCGTCCATTCCGACAGCATCGCCA*

*GTCACTATGGCGTGCTGCTAGCGCTATATGCGTTGATGCAATTTCTATGCGCACCCGTTCTCGGAGCACTGTCCGACCGC*

*TTTGGCCGCCGCCCAGTCCTGCTCGCTTCGCTACTTGGAGCCACTATCGACTACGCGATCATGGCGACCACACCCGTCCT*

*GTGGATCCTCTACGCCGGACGCATCGTGGCCGGCATCACCGGCGCCACAGGTGCGGTTGCTGGCGCCTATATCGCCGACA*

*TCACCGATGGGGAAGATCGGGCTCGCCACTTCGGGCTCATGAGCGCTTGTTTCGGCGTGGGTATGGTGGCAGGCCCCGTG*

*GCCGGGGGACTGTTGGGCGCCATCTCCTTGCATGCACCATTCCTTGCGGCGGCGGTGCTCAACGGCCTCAACCTACTACT*

*GGGCTGCTTCCTAATGCAGGAGTCGCATAAGGGAGAGC* *GTCGAC* *CGATGCCCTTGAGAGCCTTCAACCCAGTCAGCTCCT*

-continued

*TCCGGTGGGCGCGGGGCATGACTATCGTCGCCGCACTTATGACTGTCTTCTTTATCATGCAACTCGTAGGACAGGTGCCG*

*GCAGCGCTCTGGGTCATTTTCGGCGAGGACCGCTTTCGCTGGAGCGCGACGATGATCGGCCTGTCGCTTGCGGTATTCGG*

*AATCTTGCACGCCCTCGCTCAAGCCTTCGTCACTGGTCCCGCCACCAAACGTTTCGGCGAGAAGCAGGCCATTATCGCCG*

*GCATGGCGGCCGACGCGCTGGGCTACGTCTTGCTGGCGTTCGCGACGCGAGGCTGGATGGCCTTCCCCATTATGATTCTT*

*CTCGCTTCCGGCGGCATCGGGATGCCCGCGTTGCAGGCCATGCTGTCCAGGCAGGTAGATGACGACCATCAGGGACAGCT*

*TCAAGGATCGCTCGCGGCTCTTACCAGCCTAACTTCGATCATTGGACCGCTGATCGTCACGGCGATTTATGCCGCCTCGG*

*CGAGCACATGGAACGGGTTGGCATGGATTGTAGGCGCCGCCCTATACCTTGTCTGCCTCCCCGCGTTGCGTCGCGGTGCA*

*TGGAGCCGGGCCACCTCGACCTGAATGGAAGCCGGCGGCACCTCGCTAACGGATTCACCACTCCAAGAATTGGAGCCAAT*

*CAATTCTTGCGGAGAACTGTGAATGCGCAAACCAACCCTTGGCAGAACATATCCATCGCGTCCGCCATCTCCAGCAGCCG*

CACGCGGCGCATCTCGGGCAGCGTTGGGTCCTGGCCACGGGTGCGCATGATCGTGCTCCTGTCGTTGAGGACCCGGCTAG

*GCTGGCGGGGTTGCCTTACTGGTTAGCAGAATGAATCACCGATACGCGAGCGAACGTGAAGCGACTGCTGCTGCAAAACG*

*TCTGCGACCTGAGCAACAACATGAATGGTCTTCGGTTTCCGTGTTTCGTAAAGTCTGGAAACGCGGAAGTCCCCTACGTG*

*CTGCTGAAGTTGCCCGCAACAGAGAGTGGAACCAACCGGTGATACCACGATACTATGACTGAGAGTCAACGCCATGAGCG*

*GCCTCATTTCTTATTCTGAGTTACAACAGTCCGCACCGCTGTCCGGTAGCTCCTTCCGGTGGGCGCGGGGCATGACTATC*

*GTCGCCGCACTTATGACTGTCTTCTTTATCATGCAACTCGTAGGACAGGTGCCGGCAGCGCCCAACAGTCCCCCGGCCAC*

*GGGGCCTGCCACCATACCCACGCCGAAACAAGCGCCCTGCACCATTATGTTCCGGATCTGCATCGCAGGATGCTGCTGGC*

*TACCCTGTGGAACACCTACATCTGTATTAACGAAGCGCTAACCGTTTTTATCAGGCTCTGGGAGGCAGAATAAATGATCA*

*TATCGTCAATTATTACCTCCACGGGGAGAGCCTGAGCAAACTGGCCTCAGGCATTTGAGAAGCACACGGTCACACTGCTT*

*CCGGTAGTCAATAAACCGGTAAACCAGCAATAGACATAAGCGGCTATTTAACGACCCTGCCCTGAACCGACGACCGGGTC*

*GAATTTGCTTTCGAATTTCTGCCATTCATCCGCTTATTATCACTTATTCAGGCGTAGCACCAGGCGTTTAAGGGCACCAA*

*TAACTGCCTTAAAAAAATTACGCCCCGCCCTGCCACTCATCGCAGTACTGTTGTAATTCATTAAGCATTCTGCCGACATG*

*GAAGCCATCACAGACGGCATGATGAACCTGAATCGCCAGCGGCATCAGCACCTTGTCGCCTTGCGTATAATATTTGCCCA*

*TGGTGAAAACGGGGGCGAAGAAGTTGTCCATATTGGCCACGTTTAAATCAAAACTGGTGAAACTCACCCAGGGATTGGCT*

*GAGACGAAAAACATATTCTCAATAAACCCTTTAGGGAAATAGGCCAGGTTTTCACCGTAACACGCCACATCTTGCGAATA*

*TATGTGTAGAAACTGCCGGAAATCGTCGTGGTATTCACTCCAGAGCGATGAAAACGTTTCAGTTTGCTCATGGAAAACGG*

*TGTAACAAGGGTGAACACTATCCCATATCACCAGCTCACCGTCTTTCATTGCCATACG*.

The total number of nucleotides is 9578 bp. The backbone vector pACYC184 sequence is italicised, sequence positions are numbered from G of EcoRI site (GAATTC) underlined. tracrRNA is located at nucleotide No. from 1889 to 1974 indicated bold letters, Cas9 initiation and termination codons are indicated by bold three letters, starting at nucleotide No. 2270 and ending at 6376 followed by leader sequence 6462-6556 indicated by italicised bold letters, first and second direct repeat sequences are underlined, between which spacer cloning region (30 mer) is located. This spacer cloning region contains two inverted BsaI sites indicated by bold italicised letters 5'-GAGACC-3' and 5'-GGTCTC-3' for creating 5' four bases protruding spacer cloning sites 5'-GTTT-3' and 5'-TTTT-3', respectively and one unique AatII (5'-GACGTC-3') site also indicated by bold italicised to reduce self-ligation in the event of incomplete BsaI digestion. Note the transition and transversion base changes G6573A, A6779T that were detected by Sanger sequencing and are shown in bold letters, respectively. However, these point mutations do not affect the CRISPR-Cas9 activity, which will be shown in the later section. The two unique sites, Sal I (GTCGAC) and Xba I (TCTAGA) highlighted in bold italicised letters are utilised to isolate the CRISPR-Cas9 construct for cloning into M13mp18.

A plasmid map of pNB100 is shown in FIG. 22.

The desired spacer sequence can be cloned in the clockwise direction between BsaI sites. This vector contains the p15A origin at 1393-848 and cat (chloramphenicol resistant) gene at 219-9137. Cutting positions of each restriction enzyme, indicated in the parentheses, refer to the position of the 5' cutting sites on the top strand within the recognition sequence.

Example 2.1.2 Construction of pNB102

Selection of Spacer Sequence from the Target Sequence

We can use Guide RNA Target Design Tool (see; https://wwws.blueheronbio.com/external/tools/gRNASrc.jsp) from BlueHeron to select spacer sequence from the target. This program simply returns the 20 nt spacer sequence with the appropriate PAM (protospacer adjacent motif) sequence in the 3' end and GC content. It does not consider secondary structure stability and sequence specificity. Secondary structure prediction and specificity search is performed manually.

We choose the actual spacer sequence from the candidate sequences obtained in the above program, which should meet the following two criteria: 1) low tendency to form stable secondary structure of crRNA, 2) no target DNA on the host genomic DNA. It may be very difficult to find a unique sequence to satisfy criterion No. 2. Considering mismatched target data from FIG. 3 E in Jinek et al., *Science* 337, 816 (2012; hereby incorporated by reference in its entirety), criterion No. 2 is relaxed to allow a matched sequence up to the 12th nucleotide position in the target sequence (the first nucleotide position is counted from just next to the PAM sequence). In other words, when the first 12 mer protospacer sequence of the target sequence is completely matched to the 12 mer sequence of crRNA spacer sequence in the 3' end, but the rest of the sequence is not matched, it is assumed that target dsDNA is not cleaved. The specificity check of the protospacer sequence along the *E. coli* K12 genome sequence is performed by BLAST. The bla sequence is searched against the subject sequence *Escherichia coli* str. substr. MG1655 (http://www.ncbi.nlm.nih.gov/nucleotide/556503834?report=genbank&log$=nuclalign&blast_rank=1&RID=JUYB76FX014), and each of any matched chromosomal sequence is mapped against the bla sequence for counting the seed sequence from the canonical PAM (NGG) sequence. Secondary structures can be predicted by mFold. (http://mfold.rna.albany.edu/?q=mfold/RNA-Folding-Form) to choose the sequence whose Delta G is large as possible, preferably to be positive for crRNA spacer secondary structure. Table 7 shows the way to select the appropriate spacer sequences from the bla sequence.

TABLE 7

Candidate anti-protospacer sequence.

| Location | anti-protospacer seq | MG1655 Off targ | pCas9 Off targ | pBR322 Off targ | PAM | GC | ΔG |
|---|---|---|---|---|---|---|---|
| 83-102(F) | TAGATAACTACGATACGGGA (SEQ ID NO: 79) | CGGGA | None | None | GGG | 0.48 | -0.40 |
| 83-102(F) | TAGATAACTACGATACGGGA (SEQ ID NO: 79) | 5 | | | GGG | 0.48 | +0.50 |
| 442-461(F) | GATCGTTGTCAGAAGTAAGT (SEQ ID NO: 80) | AGTAAGT | AGTAAGT | None | TGG | 0.43 | -0.80 |
| 442-461(F) | GATCGTTGTCAGAAGTAAGT (SEQ ID NO: 80) | 7 | 7 | | TGG | 0.43 | -0.50 |
| 647-666(F) | ACTTTAAAAGTGCTCATCAT (SEQ ID NO: 81) | TCAT | ATCAT | None | TGG | 0.35 | -1.30 |
| 647-666(F) | ACTTTAAAAGTGCTCATCAT (SEQ ID NO: 81) | 4 | 5 | | TGG | 0.35 | -1.30 |
| 767-786(F) | TTTACTTTCACCAGCGTTTC (SEQ ID NO: 82) | GCGTTTC | TTTC | None | TGG | 0.43 | +1.30 |
| 767-786(F) | TTTACTTTCACCAGCGTTTC (SEQ ID NO: 82) | 7 | 4 | | TGG | 0.43 | +2.20 |
| 231-250(RC) | ATTAATAGACTGGATGGAGG (SEQ ID NO: 83) | GATGGAGG | GAGG | GAGG | CGG | 0.48 | +0.00 |
| 231-250(RC) | ATTAATAGACTGGATGGAGG (SEQ ID NO: 83) | 8 | 4 | 4 | CGG | 0.48 | +0.90 |
| 234-253(RC) | ACAATTAATAGACTGGATGG (SEQ ID NO: 84) | GATGG | None | None | AGG | 0.39 | -0.30 |
| 234-253(RC) | ACAATTAATAGACTGGATGG (SEQ ID NO: 84) | 5 | | | AGG | 0.39 | +0.20 |
| 237-256(RC) | GCAACAATTAATAGACTGGA (SEQ ID NO: 85) | GACTGGA | CTGGA | CTGGA | TGG | 0.39 | -0.20 |

TABLE 7-continued

Candidate anti-protospacer sequence.

| Location | anti-protospacer seq | MG1655 Off targ | pCas9 Off targ | pBR322 Off targ | PAM | GC | ΔG |
|---|---|---|---|---|---|---|---|
| 237-256(RC) | GCAACAATTAATAGACTGGA (SEQ ID NO: 85) | 7 | 5 | 5 | TGG | 0.39 | -0.20 |
| 241-260(RC) | CCCGGCAACAATTAATAGAC (SEQ ID NO: 86) | AATAGAC | AGAC | None | TGG | 0.48 | +1.80 |
| 241-260(RC) | CCCGGCAACAATTAATAGAC (SEQ ID NO: 86) | 7 | 4 | | TGG | 0.48 | +2.60 |
| 259-278(RC) | AACTACTTACTCTAGCTTCC (SEQ ID NO: 10) | AGCTTCC | GCTTCC | None | CGG | 0.48 | +0.60 |
| 259-278(RC) | AACTACTTACTCTAGCTTCC (SEQ ID NO: 10) | 7 | 6 | | CGG | 0.48 | +1.60 |
| 284-303(RC) | ACGTTGCGCAAACTATTAAC (SEQ ID NO: 87) | TATTAAC | None | TAAC | TGG | 0.43 | -1.90 |
| 284-303(RC) | ACGTTGCGCAAACTATTAAC (SEQ ID NO: 87) | 7 | | 4 | TGG | 0.43 | -1.90 |
| 375-394(RC) | TGTAACTCGCCTTGATCGTT (SEQ ID NO: 88) | TCGTT | CGTT | CGTT | GGG | 0.52 | -0.50 |
| 375-394(RC) | TGTAACTCGCCTTGATCGTT (SEQ ID NO: 88) | 5 | 4 | 4 | GGG | 0.52 | +0.10 |
| 376-395(RC) | ATGTAACTCGCCTTGATCGT (SEQ ID NO: 89) | TTGATCGT | TCGT | None | TGG | 0.48 | -0.50 |
| 376-395(RC) | ATGTAACTCGCCTTGATCGT (SEQ ID NO: 89) | 8 | 4 | | TGG | 0.48 | +0.10 |
| 443-462(RC) | AACTTACTTCTGACAACGAT (SEQ ID NO: 90) | CAACGAT | None | None | CGG | 0.43 | +0.40 |
| 443-462(RC) | AACTTACTTCTGACAACGAT (SEQ ID NO: 90) | 7 | | | CGG | 0.43 | +0.40 |
| 528-547(RC) | AGTCACAGAAAAGCATCTTA (SEQ ID NO: 91) | GCATCTTA | None | None | CGG | 0.43 | -0.50 |
| 528-547(RC) | AGTCACAGAAAAGCATCTTA (SEQ ID NO: 91) | 8 | | | CGG | 0.43 | +0.50 |
| 638-657(RC) | ACTTTTAAAGTTCTGCTATG (SEQ ID NO: 92) | GCTATG | None | None | TGG | 0.35 | -0.70 |
| 638-657(RC) | ACTTTTAAAGTTCTGCTATG (SEQ ID NO: 92) | 6 | | | TGG | 0.35 | +0.10 |

All the target sequence from the bla gene was obtained using Guide RNA Target Design Tool (https://wwws.blueheronbio.com/external/tools/gRNASrc.jsp) from BlueHeron. There are 98 target candidate sequences returned. Bacterial off-target chromosomal short similar sequences are mapped against the bla gene followed by counting the seed sequence from the canonical PAM sequence. Choose the sequences whose seed sequence number is less than eight and whose Gibbs free energy is relatively large. The summary of the property of the selected target sequences is shown in Table 7. Table 7 also shows nucleotide length of the seed sequence of the off-target sequences on pCas9 and pBR322.

Oligo Cassette Sequence for Spacer Sequence

The following four spacer sequences are crRNA generating cassettes targeting beta-lactamase on pBR322 in *E. coli* as a host strain, which meet the above two criteria. crRNA CR05 cleaves phosphodiester bond between 762nd base C and 763rd base C, CR30 cleaves phosphodiester bond between 198th base G and 199th base A, CR70 cleaves phosphodiester bonds between 575th base T and 576th base A and CR90 cleaves phosphodiester bonds between 221st base T and 222nd base A on the beta-lactamase gene.

Adaptors for Single Targets on the Beta-Lactamase Gene.

CR05
(SEQ ID NO: 93)
5'-AAACTAGATAACTACGATACGGGAg

(SEQ ID NO: 94)
atctattgatgctatgccctcAAAA-5'

CR30
(SEQ ID NO: 95)
5'-AAACACTTTAAAAGTGCTCATCATg

(SEQ ID NO: 96)
tgaaattttcacgagtagtacAAAA-5'
DraI

CR70
(SEQ ID NO: 97)
5'-AAACACGTTGCGCAAACTATTAACg

(SEQ ID NO: 98)
tgcaacgcgtttgataattgcAAAA-5'
AclI

CR90
(SEQ ID NO: 99)
5'-AAACACTTTTAAAGTTCTGCTATGg

(SEQ ID NO: 100)
tgaaaatttcaagacgataccAAAA-5'
DraI

Adaptor for Dual Targets on the Beta-Lactamase Gene.

Internal direct repeat sequence is italicised and underlined.

CR30 + CR90
5'-**AAACACTTTAAAAGTGCTCATCAT*GTTTTAGAGCTATGCTGTTTTGAATGGTCCCAAAAC*ACTTTTAAAGTTCTGCTATGg** ←*[1]
*[2] → tgaaattttcacgagtagtacaaaatctcgatacgacaaaacttaccagggttttgtgaaaatttcaagacgataccAAAA
DraI CR30 DraI CR90

(*[1] = SEQ ID NO: 101)
(*[2] = SEQ ID NO: 102).

The 5' end of each oligo is phosphorylated and ready for cloning at BsaI sites.

Sites of six base cutter restriction endonucleses are underlined, which are useful to screen the recombinants. We can also employ one of the cassette oligos as a primer to screen the recombinants by PCR together with another unique primer for the plasmid vector.

The spacer sequence CR30 was added to pNB100 as follows: pNB100 was digested with BsaI and AatII followed by purification using Agencourt ampure beads. The spacer sequence CR30 was prepared as a double-stranded DNA cassette from two oligonucleotides by denaturation at 95° C. for 1 min and re-annealing at −1 degree every min to 30 C in the 1×T4 ligase buffer (50 mM Tris-HCl (pH 7.5 at 25° C.), 10 mM MgCl2, 1 mM ATP 10 mM DTT) plus 50 mM NaCl following the kinase reaction to add a phosphate moiety in the 5' terminus of each oligo. The annealed cassette contains 5' protruding four base compatible bases on both ends for the sites created on pNB102 by BsaI digestion. This CR30 cassette was ligated to pNB100 by T4 DNA ligase and transformed to DH5α competent cells (purchased from New England Biolabs). The transformants were selected on chloramphenicol LB plate and were screened by PCR with the bottom sequence of the CR30 cassette as a reverse primer and a forward primer CF1: 5'-acgttgacgaatcttggagc, which anneals at 6209-6228 region on the recombinant plasmid to generate 409 bp PCR amplicon. PCR positive clones were sequenced to confirm the CR30 spacer sequence and this recombinant clone is designated as pNB102 and used for TEM beta lactamase-gene inactivation experiments. The CR30 spacer anneals to the sense strand of beta lactamase-gene and cleaves the phosphodiester bonds between 188th and 189th nucleotide on the sense and antisense strand.

Example 2.1.3 Construction of M13mp18::NB102 pNB102 was digested with unique restriction sites Sail and XbaI to generate two fragments 6044 bp and 3524 bp. The fragment length was calculated from the 5' end of the restricted sites in the top strand within the restriction recognition sites. The 6044 bp fragments containing CRISPR locus with CR30 spacer sequence in the CRISPR array was separated from the 3524 bp fragment and purified on the preparative 1% agarose gel. M13 mp18 was digested with SalI-XbaI, followed by Agencourt ampure purification to remove the six bases SalI-XbaI fragment from the reaction. These two purified fragments were combined and ligated by T4 DNA ligase and transformed to DH5αF'lq competent cells (purchased from New England Biolabs). Transformed cells were plated along with freshly grown DH5αF'lq cells as a phage indicator and IPTG/X-gal solution as a blue-white colour indicator with molten top agar to LB plate. White plaques collected from the lawn were screened by PCR for the presence of the CR30 spacer sequence. The correct phage constructs obtained were purified by two times single plaque isolation. The entire sequence length of the final construct is 13288 bp. This spacer CR30 positive recombinant is designated as M13mp18::NB102 and was used for the bla-gene inactivation experiments mediated by M13 phage delivery.

Example 2.1.4 Delivery of CRISPR-Cas9 Constructs to Bacteria to Test "Nemesis Symbiotic Activity" (NSA)

Having constructed the CRISPR-Cas9 plasmid pNB100 and the derivative plasmid pNB102 carrying a spacer insertion targeted against the beta-lactamase (bla) genes encoded by the bacterial transposable elements Tn1 and Tn3, we then sought to demonstrate, using three delivery methods, (i) plasmid conjugation, (ii) plasmid DNA transformation, (iii) bacteriophage infection, that bacterial cells carrying copies of the CRISPR-Cas9 construct with bla-spacer insertion would be unable to grow in the presence of the beta-lactam antibiotic ampicillin.

Constructs that are able to inactivate target genes, including antibiotic resistant genes, via the CRISPR-Cas system, and which may form part of aspects the present invention, are also referred to herein as "Nemesis Symbiotics".

NSA Assay by Plasmid Conjugation: A Prophylaxis Experiment

We demonstrate here that Nemesis Symbiotics can prevent the spread of antibiotic resistance by inhibiting conjugal transfer of conjugative plasmids carrying antibiotic resistance genes from a donor cell to a recipient cell carrying the Nemesis Symbiotics. To do this we mated a recipient cell carrying the Nemesis Symbiotics with a donor cell carrying a conjugative plasmid, plus a multicopy mobilisable plasmid carrying the bla gene encoding ampicillin resistance. In a successful mating, the conjugative plasmid will transfer itself plus the mobilisable plasmid carrying ampicillin resistance to the recipient. Exconjugants may be selected for resistance to both chloramphenicol present on a non-mobilisable plasmid in the recipient and ampicillin received from the donor. Successful Nemesis Symbiotic activity will reduce the efficiency of transfer of ampicillin resistance.

The recipient cell DH5α (F-endA1 glnV44 thi-1 recA1 relA1 gyrA96 deoR nupG ϕ80dlacZAM15 Δ(lacZYA-argF) U169, hsdR17(rK− mK+), λ−) was purchased from New England Biolabs and transformed with the plasmids pNB100 or pNB102 or pACYC184, where plasmids encode chloramphenicol resistance and both pNB100 and pNB102 carry CRISPR-Cas9 but only pNB102 carries the spacer sequence targeted against the beta-lactamase gene. The plasmid pACYC184 is the non-mobilisable parent plasmid used for the construction of pNB100 and pNB102 as described above.

The donor strain JA200 (F+thr-1, leu-6, DE(trpE)5, recA, lacY, thi, gal, xyl, ara, mtl) also carrying plasmid pNT3 is described by Saka et al. *DNA Research* 12, 63-68 (2005; hereby incorporated by reference in its entirety). The plasmid pNT3 is a mobilisable plasmid carrying the TEM-1 bla gene of Tn1.

A single colony of the donor JA200 pNT3 was picked from a Luria-Bertani (LB) plate containing 100 μg/mL ampicillin and grown shaking at 37° C. overnight in 1 mL LB medium with 100 μg/mL ampicillin. A single colony each of the recipients, DH5α pNB100 and DH5α pNB102 was picked from a LB plate containing 35 μg/mL chloramphenicol and grown shaking at 37° C. overnight in 1 mL LB with 35 μg/mL chloramphenicol. To wash cells to remove antibiotics, 50 μL of cells were added to 1 mL LB in Eppendorf tubes and centrifuged 60 sec at 12500 rpm. Cells were resuspended in 50 μL LB. To set up the mating JA200 pNT3 was spotted onto an LB plate, then 2 μL of each DH5α carrying pNB100 and pNB102 were added to this spot. Separate 2 μL spottings of donor and recipients were also performed (i.e. not mated). Plates were incubated at 37° C. for 4 hours. Cells were removed resuspended in LB and 100 μL plated on LB plates containing both 100 μg/mL ampicillin and 35 μg/mL chloramphenicol (LB ApCm). 100 μL of 10,000 fold (10^-4) dilutions were also plated on LB plates and incubated at 37° C. overnight. The resultant colonies were counted as shown in Table 8.

TABLE 8

| Cells | LB ApCm plates | LB plates 10^−4 dilution | Nemesis Symbiotic activity |
|---|---|---|---|
| JA200 pNT3 × DH5α pNB100 | Confluent | Approx. 500 | Negative |
| JA200 pNT3 × DH5α pNB102 | 37 | Approx. 500 | Positive |
| JA200 pNT3 × DH5α pACYC184 | Confluent | Approx. 500 | Negative |
| JA200 pNT3 | 0 | Not done | Not applicable |
| DH5α pNB100 | 0 | Not done | Not applicable |
| DH5α pNB102 | 0 | Not done | Not applicable |
| DH5α pACYC184 | 0 | Not done | Not applicable |

Photographs in FIG. 23 show platings of the matings between: (A) JA200 pNT3×DH5α pNB100 (as expected lacking Nemesis Symbiotic activity); and (B) JA200 pNT3×DH5α pNB102 (showing Nemesis Symbiotic activity).

The 10^-4 dilution plated on LB plates, gave approximately 500 colonies a count of 5×10^7 cells per mL in the mated cell suspension and for the JA200 pNT3×DH5α pNB102 only 3.7×10^2 cells/mL were able to grown on the LB Ap100Cm35 plates. Thus assuming half the cells are recipients/ex-conjugants then: 3.7×10^2 cells/ml divided by 2.5×10^7 gives a mating efficiency for the recipient carrying pNB102 of 1.2×5×10^-5

The experiment demonstrated a significant reduction in CmRApR exconjugants in matings with DH5α carrying pNB102 versus pNB100×JA200 pNT3.

In order to measure the relative mating efficiencies more accurately, after a liquid mating cells were plated on LB plates to titre all cells, LB Ap100 plates to titre donors plus exconjugants, LB Cm plates to titre recipients plus exconjugants and LB Ap100Cm35 to titre exconjugants only.

For the liquid mating overnight cultures of 10 μL of JA200 pNT3 were mixed with 10 μL of recipients DH5α pNB100 or DH5α pNB102 200 μL of LB added and tubes incubated overnight at 37° C. Mating mixtures were diluted 10^-1, 10^-3, 10^-5 in LB and 50 μL of dilutions plated on LB, LB Ap100Cm35, LB Ap100 and LB Cm35 plates and plates incubated overnight at 37° C. Table 9 summarises the cell titres obtained.

TABLE 9

| Mated with JA200 pNT3 | LB All cells | LB Ap Cm Exconjugants | LB Cm recipients and exconjugants | LB Ap donors and exconjugants | mating effic/donor | mating effic/recipient |
|---|---|---|---|---|---|---|
| pNB100 | 4.14 × 10^8 | 2.80 × 10^7 | 1.40 × 10^8 | 2.64 × 10^8 | 1.06 × 10^−1 | 2.00 × 10^−1 |
| pNB102 | 5.16 × 10^8 | 7.20 × 10^3 | 1.78 × 10^8 | 3.82 × 10^8 | 1.88 × 10^−5 | 4.04 × 10^−5 |

The number of cells on LB Cm plus LB Ap plates should equal the number of cells on LB plates. For pNB100 1.40×10^8 (Cm plates) plus 2.64×10^8 (Ap plates)=4.04×10^8 which agrees very well with 4.14×10^8 on LB plates. For pNB102 1.78×10^8 (Cm plates) plus 3.82 10^8 (Ap plates)=5.6×10^8 which agrees very well with 5.16×10^8 on LB plates.

In conclusion, the data show that after overnight mating in liquid culture, there is a 5,000 fold reduction in mating efficiency per recipient comparing pNB102 with the spacer to pNB100 lacking the spacer.

NSA Assay by Plasmid Transformation

In this experiment, we demonstrate that introduction of Nemesis Symbiotics to recipient cells by DNA transformation inactivates antibiotic resistance in the transformants.

In order to obtain a tester strain, DH5α competent cells purchased from New England Biolabs were transformed with pBR322 (carrying the bla gene derived from Tn3) and selected on LB Ap100 plates. Competent cells of the derived strain DH5α pBR322 were then prepared using the CaCl2) protocol 25 (1.116) as described by Sambrook and Russell in Molecular Cloning: A Laboratory Manual (3rd Edition, 2001) and subsequently transformed with plasmids pNB100, pNB102 and pACYC184 with selection for CmR. Transformant colonies were then picked onto LB Cm35 and LB Ap100 plates. Primary transformants were replica toothpicked onto both LB Cm35 and LB Ap100 plates and incubated overnight at 37° C.

The results, depicted in FIG. 24, show that all colonies toothpicked from DH5α pBR322 transformed by pNB100 (lacking the bla gene target spacer sequence) remain resistant to ampicillin. In contrast all colonies toothpicked from DH5α pBR322 transformed by pNB102 have lost ampicillin resistance, so demonstrating Nemesis Symbiotic activity.

The experiments above do not give a value for the fraction of primary transformants where NSA has inactivated the bla gene. To address this, single colonies from the primary transformants were picked into 1 mL LB and diluted 10^3 in LB. Then 100 μL plated onto plates as follows, and results scored. The results showed that following transformation of DH5α pBR322 with pNB102 fewer than 10^6 cells retain ApR. Nemesis Symbiotic activity is very efficient.

NSA Assay by Bacteriophage M13 Infection

In this experiment, we demonstrate that introduction of Nemesis Symbiotics to recipient cells by bacteriophage infection inactivate antibiotic resistance in the transformants. We chose the male-specific filamentous phage M13 as the delivery agent for the Nemesis Symbiotic construct. An M13 derivative M13mp18::NB102 carrying and the Cas9 CRISPR plus bla gene target spacer region of pNB102 was used to deliver the Nemesis Symbiotic by infection of an F+ strain, JA200, carrying ampicillin resistance on the plasmid pNT3. 0.2 mL of a fresh culture of this strain was added to 3 mL of LB top agar (Luria broth with 0.7% agar) and poured onto an LB plate. Then 2 μL of phage stocks of M13mp18::NB102 (10^8 pfu/mL) and as a control M13mp18 were spotted onto the lawn and the plate was incubated 8 hours at 37° C. Plaques were picked into 1.5 mL LB and grown shaking o/n at 37° C. A control strain DH5α lacking ampicillin resistance was also cultured overnight from a single colony picked into 1.5 mL LB.

Nitrocefin Assay for Beta Lactamase Activity was Performed:

1 mL of the culture of cells was centrifuged for 60 sec at 12,500 rpm in microfuge then 2 μL of stock nitrocefin (10 mg/mL in DMSO) was added to 1 mL of cell supernatant and absorbance of the degradation product of nitrocefin was measured at 482 nm in a spectrophotometer several time points after addition of nitrocefin. Table 9 summarises the results.

TABLE 9

| Strain | 30 sec | 60 sec | 2 min | 5 min |
|---|---|---|---|---|
| JA200 pNT3 infected by M13mp8 | 0.5 | 0.64 | 0.73 | 0.79 |
| JA200 pNT3 infected by M13mp8::NB102 | 0.08 | 0.09 | 0.11 | 0.15 |
| DH5α | 0.09 | 0.07 | 0.06 | 0.05 |

The experiments reported above provide the proof-of-concept that, in the model organism, *Escherichia coli*, DNA constructs carrying the Cas9 CRISPR region plus a spacer region with sequences directed against a target region of the beta-lactamase gene can inactivate ampicillin resistance when delivered by naked DNA transformation and bacteriophage infection as well as prevent transfer of ampicillin resistance by plasmid conjugation. It is apparent that Nemesis Symbiotics of the invention can be applied to pathogenic bacteria and for other antibiotic resistance genes.

Example 2.2 Construction of Plasmids Targeting Multiple Beta Lactamase Gene Families The following experiments describe some proof-of-concept experiments performed to demonstrate that the CRISPR-Cas9 system can be used in a single construct to inactivate a large number of different beta-lactamase genes that may be found amongst microbial pathogens as well as amongst the non-pathogenic members of the microbiome.

In these exemplifications, plasmids were constructed that carry the CRISPR-Cas9 system plus derivatives carrying spacer sequences, flanked by direct repeats, targeted against up to eight of the VONCKIST beta-lactamase families of resistance genes: SHV, CTX-M, TEM, KPC, VIM, IMP, NDM and OXA.

For each of these eight families of beta-lactamase genes, a single spacer was designed that targets a number of gene members of that family. These are: SHV-a=1, 1a, 2, 2a, 5, 5a, 11, 12, 14, 18, 20, 21, 22, 23, 26, 27, 28, 31, 32, 33, 38, 43, 44, 48, 52, 55, 56, 60, 61, 62, 71, 73, 74, 75, 76, 77, 78, 79, 80, 81, 82, 85, 89, 92, 98, 99, 100, 101, 103, 106, 107, 108, 109, 110, 111, 121, 136, 134, 137, 140, 143, 144, 147, 148, 149, 150, 151, 152, 153, 154, 155, 157, 158, 159, 160, 161, 162, 163, 164, 165, 168, 172, 173, 178, 179; CTXM-b=1, 3, 10, 12, 15, 19, 22, 32, 52, 54, 59, 60, 62, 68, 71, 80, 81, 99, 141, 147; TEM-c=1, 1B, 3, 139, 162, 183, 192, 197, 198, 209; KPC-d=1, 2, 3, 4, 6, 7, 8, 11, 12, 14, 15, 16, 17; VIM-e=1, 2, 4, 19, 26, 27, 33, 34; IMP-f=4, 8, 32, 38; and NDM-g=1, 9, 10.

Table 11 shows the eight spacer sequences that were designed to target the eight beta-lactamase families of resistance genes: SHV, CTX-M, TEM, KPC, VIM, IMP, NDM and OXA-48: a set of spacer sequences that encode 8 guide RNA molecules targeted against the class A genes, SHV-a, CTX-M-b, TEM-c, KPC-d; the class B genes VIM-e, IMP-f, NDM-g and the class D gene, OXA-48 where SHV-a=1, 1a, 2, 2a, 5, 5a, 11, 12, 14, 18, 20, 21, 22, 23, 26, 27, 28, 31, 32, 33, 38, 43, 44, 48, 52, 55, 56, 60, 61, 62, 71, 73, 74, 75, 76, 77, 78, 79, 80, 81, 82, 85, 89, 92, 98, 99, 100, 101, 103, 106, 107, 108, 109, 110, 111, 121, 136, 134, 137, 140, 143, 144, 147, 148, 149, 150, 151, 152, 153, 154, 155, 157, 158, 159, 160, 161, 162, 163, 164, 165, 168, 172, 173, 178, 179; CTXM-b=1, 3, 10, 12, 15, 19, 22, 32, 52, 54, 59, 60, 62, 68, 71, 80, 81, 99, 141, 147; TEM-c=1, 1B, 3, 139, 162, 183, 192, 197, 198, 209; KPC-d=1, 2, 3, 4, 6, 7, 8, 11, 12, 14, 15, 16, 17; VIM-e=1, 2, 4, 19, 26, 27, 33, 34; IMP-f=4, 8, 32, 38; and NDM-g=1, 9, 10 (see Example 2).

TABLE 11

| | Gene type | gene | Example of Required Spacers 5' to 3' | PAM | P | C-e | C-n | C-I | C-II | C-III | Cb | Mb |
|---|---|---|---|---|---|---|---|---|---|---|---|---|
| | bl2be_shv2 | SHV-a | CTGGGAAACGGAACTGAATG (SEQ ID NO: 103) | AGG | R | R | R | | | | | R |
| A | bl2be_ctxm | CTXM-b | ACGTTAAACACCGCCATTCC (SEQ ID NO: 6) | GGG | R | | | R | R | R | | R |
| A | bl2_tem | TEM-f | AACTACTTACTCTAGCTTCC (SEQ ID NO: 10) | CGG | R | | | R | R | | | R |
| A | bl2_kpc | KPC-g | TTGTTGCTGAAGGAGTTGGG (SEQ ID NO: 11) | CGG | R | R | R | R | R | R | R | |
| B | bl3_vim | VIM-a | AAACACAGCGGCACTTCTCG (SEQ ID NO: 15) | CGG | R | R | R | R | R | R | R | |
| B | bl3_imp | IMP-b | GGCTAGTTAAAAATAAAATTG AAGTTTTTTATCC (SEQ ID NO: 104) | AGG | R | R | R | R | R | R | R | |
| B | bl3_ndm | NDM-c | GGTTTGATCGTCAGGGATGG (SEQ ID NO: 30) | CGG | R | R | R | R | R | R | R | |
| D | bl2_oxa | COKA-48 | ATAACGGCTTGACCCAGTCA (SEQ ID NO: 24) | TGG | R | | | | | | | |

Key to Table

| | | | |
|---|---|---|---|
| PAM | protospacer adjacent motif | | |
| Cl | beta lactamase class A, B, C or D | | |
| P | Penams | | for example amoxicillin |
| C-e | Cephems: | e_Cephalosporin | |
| C-n | Cephems: | n_Cephalosporin | |
| C-I | Cephems | Cephalosporin I | for example Cefazolin |
| C-II | Cephems | Cephalosporin II | for example Cephamycin |
| C-III | Cephems | Cephalosporin III | for example Ceftazidime |
| Cb | Carbapenem | | for example Ertapenem |
| Mb | Monobactam | | for example Aztreonam |

The primer sequences used in the construction of the plasmids are listed Table 12.

TABLE 12

Sequences of oligonucleotides used in the construction of plasmids pNB108.

| Primer | Sequence 5' to 3' |
|---|---|
| NB026 | GGGCTGGCAAGCCACGTTTGGTGGGTCTCgAAACGGTTTGATCGTCAGGGATGG (SEQ ID NO: 105) |
| NB027 | ggataaaaaacttcaattttatttttaactagccGTTTTGGGACCATTCAAAACAGCATAGCTCTAAAACccatccctgacgatcaaacc (SEQ ID NO: 106) |
| NB028 | GGCTAGTTAAAAATAAAATTGAAGTTTTTTATCCGTTTTAGAGCTATGCTGTTTTGAATGGTCCCAAAACAAACACAGCGGCACTTCTCG (SEQ ID NO: 107) |
| NB029 | cccaactccttcagcaacaaGTTTTGGGACCATTCAAAACAGCATAGCTCTAAAACcgagaagtgccgctgtgttt (SEQ ID NO: 108) |

TABLE 12-continued

Sequences of oligonucleotides used in the construction of plasmids pNB108.

| Primer | Sequence 5' to 3' |
|---|---|
| NB030 | TTGTTGCTGAAGGAGTTGGGGTTTTAGAGCTATGCTGTTTTGAATGGTCCCAAAACGTCCATCCCACTTAAAGACT (SEQ ID NO: 109) |
| NB031 | cattcagttccgtttcccagGTTTTGGGACCATTCAAAACAGCATAGCTCTAAAACagtctttaagtgggatggac (SEQ ID NO: 110) |
| NB032 | CTGGGAAACGGAACTGAATGGTTTTAGAGCTATGCTGTTTTGAATGGTCCCAAAACAACTACTTACTCTAGCTTCC (SEQ ID NO: 111) |
| NB033 | CCGGGAGCTGCATGTGTCAGAGGggtctccaaaaCggaatggcggtgtttaacgtGTTTTGGGACCATTCAAAACAGCATAGCTCTAAAACggaagctagagtaagtagtt (SEQ ID NO: 112) |
| NB034 | CCGGGAGCTGCATGTGTCAGAGGggtctccaaaaCcccaactccttcagcaacaaGTTTTGGGACCATTCAAAACAGCATAGCTCTAAAACcgagaagtgccgctgtgttt (SEQ ID NO: 113) |
| NB035 | GGGCTGGCAAGCCACGTTTGGTGGCTCTTCAAACGTCCATCCCACTTAAAGACT (SEQ ID NO: 114) |
| NB036 | CCGGGAGCTGCATGTGTCAGAGGgctcttcaaaaCggaatggcggtgtttaacgtGTTTTGGGACCATTCAAAACAGCATAGCTCTAAAACGGAAGCTAGAGTAAGTAGTT (SEQ ID NO: 115) |

A plasmid derivative of pNB100, pNB108 (FIG. 25), a generally applicable DNA cassette, is described in the Examples that carries the CRISPR-Cas9 system plus derivatives carrying spacer sequences, flanked by direct repeats, targeted against eight beta-lactamase families of antibiotic resistance genes in bacteria and are expressed off one promotor: blaNDM, blaIMP, blaVIM and blaKPC, blaOXA-48, blaSHV, blaTEM and blaCTX-M (NIVKOSTC).

Construction of pNB108

The tetramer spacer concatemer A (a+b+c+d) and B (e+f+g+h) shown in FIG. 26A was subcloned in vector pCR Blunt II-TOPO and designated pCR Blunt II-TOPO_SpacerA and pCR Blunt II-TOPO_SpacerB, respectively. Then the concatenated spacer array sequences A and B were amplified from the subcloned vector pCR Blunt II-TOPO_SpacerA and pCR Blunt II-TOPO_SpacerB with the primer set NB026 and NB029, NB030 and NB033, respectively. At the 3' end of amplicon of spacer A and 5' end of amplicon of spacer B are 20 bases of overlapped sequence from the KPC spacer sequence. These two amplicons were gel purified and used for PCR-based pairwise cycle extension reaction in the absence of the primer. The extended material was re-amplified with primer set NB037 (5'-GGGCTGGCAAGCCACGTTTGGTG-3'; SEQ ID NO: 116) and NB038 (5'-CCGGGAGCTGCATGTGTCAGAGG-3'; SEQ ID NO: 117) to generate the full 8 spacer array concatemer. This eight-spacer concatemer was cloned into pCR Blunt II-TOPO vector and confirmed by sequence analysis.

BsaI digestion of this pCR Blunt II-TOPO subclone removes the full 8 spacer array concatemer as a subclone from the pCR Blunt II-TOPO vector, which contains 5' protruding four base compatible bases on both ends for the sites created on pNB100 by BsaI digestion. Then pNB100 was digested with BsaI followed by agarose gel purification. The eight-spacer concatemer cassette, released from the pCR Blunt II-TOPO was ligated into pNB100 by T4 DNA ligase and transformed to DH5α competent cells (purchased from New England Biolabs). The transformants were selected on chloramphenicol LB plates and were screened by PCR with the reverse primer NB021: 5'-GGTGACTGATGGCCACGT (SEQ ID NO: 118) and a forward primer NB020: 5'-CCAACTACCTCCCCTTGCTTAAC (SEQ ID NO: 119), which anneal at the 6368-6385 region and 7203-7225 region, respectively on the recombinant plasmid to generate 858 bp PCR amplicon. PCR-positive clones were sequenced to confirm the eight-spacer concatemer sequence and this recombinant clone is designated as pNB108 and used to demonstrate CRISPR-Cas9-mediated inactivation of targeted beta lactamase genes following DNA delivery to bacterial strains carrying such genes. A plasmid map of pNB108 is shown in FIG. 25.

Schematic Representation of the Structure of Concatenated Spacer Arrays

Spacer sequences were determined to maximise the coverage of the target beta-lactamase gene family. Each unit oligo contains the direct repeat flanking the appropriate spacer sequence at each end. Concatenation reactions are performed between pairwise oligos, i.e. the nearest neighbour unit oligos are concatenated first to generate two unit length oligo, then two unit length oligos are concatenated to generate four unit length of oligo etc.

The schematic structure of tetramer and octamer spacer structures are shown in FIG. 26. S: spacer, R: direct repeat, A and B contain BsaI site to create ligation compatible sites for cloning into pNB100. In this example, we employed spacer sequence S1 targeting NDM, S2 targeting IMP, S3 targeting VIM, S4 targeting KPC, S5 targeting OXA, S6 targeting SHV, S7 targeting TEM and S8 targeting CTX-M.

Spacer Concatenation Reaction

Each oligo has overlapped sequence in the 3' and 5' end to anneal to the nearest neighbour oligo except the first and the last oligo. The first and the last oligo have the overlapping sequence to the second and the penultimate oligo in the 5' end only. In order to concatenate four spacers, four oligos are synthesised. In other words, oligo No. 1 consists spacer 1 and 2 in the 5' and 3' ends. Oligo No. 2 contains reverse complement of spacer 2 and 3 in the 3' and 5' ends. Oligo No. 3 contains spacer 3 and 4 in the 5' and 3' ends. Oligo No. 4 contains reverse complement of spacer 4 in the 3' end. Thus the oligo No. 2 can link oligo No. 1 and oligo No. 3, oligo 4 anneals to 3' end of oligo No. 3. Oligo No. 1 and oligo No. 2, oligo No. 3 and oligo No. 4 are concatenated in a separate tube using the PCR reaction conditions shown in Tables 13 and 14.

TABLE 13

| Component | A1 | A2 | B1 | B2 | x4 |
|---|---|---|---|---|---|
| Nuclease-Free water | 33.5 μL | 33.5 μL | 33.5 μL | 33.5 μL | 134 |
| 5X Q5 Reaction Buffer | 10 μL | 10 μL | 10 μL | 10 μL | 40 |
| 10 mM dNTPs | 1 μL | 1 μL | 1 μL | 1 μL | 4 |
| Q5 High-Fidelity DNA Polymerase | 0.5 μL | 0.5 μL | 0.5 μL | 0.5 μL | 2 |
| 10 μM Forward Primer NB026 | 2.5 μL | | | | |
| 10 μM Reverse Primer NB027 | 2.5 μL | | | | |
| 10 μM Forward Primer NB028 | | 2.5 μL | | | |
| 10 μM Reverse Primer NB034 | | 2.5 μL | | | |
| 10 μM Forward Primer NB035 | | | 2.5 μL | | |
| 10 μM Reverse Primer NB031 | | | 2.5 μL | | |
| 10 μM Forward Primer NB032 | | | | 2.5 μL | |
| 10 μM Reverse Primer NB036 | | | | 2.5 μL | |

TABLE 14

Cycle conditions.

| STEP | TEMP | TIME |
|---|---|---|
| Initial Denat. | 98° C. | 60 sec |
| 35 cycles | 98° C. | 10 sec |
| | 55° C. | 10 sec |
| | 72° C. | 20 sec |
| Final Extension | 72° C. | 2 minutes |
| Hold | 4° C. | |

In this example, NB026 and NB027, NB028 and NB034, NB035 and NB031, NB032 and NB036 are concatenated. Each concatenated product A1, A2, B1 and B2 was gel purified and set up the second concatenation reaction using the purified A1 and A2, B1 and B2 dimer product in the PCR conditions shown in Tables 15 and 16.

TABLE 15

| Component | A | B | x2 |
|---|---|---|---|
| Nuclease-Free water | 35.75 μL | 35.75 μL | 71.5 |
| 10X PCR Buffer | 5 μL | 5 μL | 10 |
| 10 mM dNTPs | 1 μL | 1 μL | 2 |
| QIAGEN Hot Start Taq | 0.25 μL | 0.25 μL | 0.5 |
| Gel extracted A1 | 4 μL | | |
| Gel extracted A2 | 4 μL | | |
| Gel extracted B1 | | 4 μL | |
| Gel extracted B2 | | 4 μL | |

TABLE 16

Cycle conditions.

| STEP | TEMP | TIME |
|---|---|---|
| Initial Denat. | 95° C. | 15 min |
| 35 Cycles | 94° C. | 30 sec |
| | A: 55° C. | 30 sec |
| | 72° C. | 30 sec |
| Final Extension | 72° C. | 10 min |

These extention products were amplified by NB037 and NB038 with Q5 DNA polymerase. The final amplicons were cloned to pCR Blunt II TOPO vector and the concatemer sequences were confirmed.

In case of eight spacer concatenation, spacer concatemer A and spacer concatemer B on pCR Blunt II TOPO vector were amplified with primer pairs NB026 and NB029, NB030 and NB033, respectively and amplicons were gel purified. Purified spacer A and B were utilised as a long primer in the cycle extension reactions shown in Tables 17 and 18.

TABLE 17

| Component | A |
|---|---|
| Nuclease-Free water | 35.75 μL |
| 10X PCR Buffer | 5 μL |
| 10 mM dNTPs | 1 μL |
| QIAGEN Hot Start Taq | 0.25 μL |
| Gel extracted A | 4 μL |
| Gel extracted B | 4 μL |

TABLE 18

Cycle conditions

| STEP | TEMP | TIME |
|---|---|---|
| Initial Denat. | 95° C. | 15 min |
| 25 Cycles | 94° C. | 30 sec |
| | 55° C. | 30 sec |
| | 72° C. | 30 sec |
| Final Extension | 72° C. | 10 min |
| Hold | 4° C. | o/n |

These extension products were amplified by NB037 and NB038 with Q5 DNA polymerase. The final amplicons were cloned into pCR Blunt II TOPO vector and the concatemer sequences were confirmed.

Example 2.3 Construction of Eight Plasmids Encoding One Beta-Lactamase from Each of the Eight VONCKIST Beta-Lactamase Gene Families The NSA assay described in Example 2.1 showed that DNA transformation of an *E. coli* strain, DH5α, also carrying the TEM-3 beta lactamase gene on the plasmid pBR322, with plasmid pNB102 converts the transformant to ampicillin sensitivity (ApS). Here, the plasmid pNB102 encodes resistance to chloramphenicol and the DH5α (pBR322) transformants now carrying pNB102 were selected on LB Cm plates and then screened for ApS (see FIG. 28). Here, the plasmid pNB102, in expressing the CRISPR-Cas9 system with the spacer sequence encoding the gRNA targeting the TEM-3 gene, inactivated the TEM-3 gene. In contrast, in a negative control experiment, when DH5α (pBR322) was transformed with the parental plasmid pNB100 carrying the expressing the CRISPR-Cas9 system but lacking the gRNA targeting the TEM-3 gene, no conversion to ApS occurred.

For exemplification purposes an equivalent experiment is described where plasmid derivatives of pBR322, or pNT3 (for blaVIM-1) or pCR Blunt II-TOPO (for blaIPM-1) were constructed where the TEM-3 is replaced by representative genes from the other 7 different families of beta-lactamases: blaVIM, blaOXA, blaNDM, blaCTX-M, blaKPC, blaIMP, blaSHV and blaCTX-M. Such genes are obtained from suitable bacterial strains carrying such genes. This allows a direct comparison to the proof of concept experiments described in Example 2.1 in isogenic genetic backgrounds.

A set of *E. coli* and *K. pneumoniae* strains carrying representative genes from these seven different families of beta-lactam antibiotics were purchased from Culture Collections, Public Health England, Porton Down, Salisbury, SP4 0JG, UK. These are: NCTC13368, a *K. pneumoniae* strain carrying the SHV-18 gene; NCTC13353 an *E. coli* strain carrying the CTX-M-15 gene; NCTC13438 a *K. pneumoniae* strain carrying the KPC-3 gene; NCTC13440 a *K. pneumoniae* strain carrying the VIM-1 gene; NCTC13476 an *E. coli* strain carrying the IMP-1 gene; NCTC13443 a *K. pneumoniae* strain carrying the NDM-1 gene and NCTC13442 a *K. pneumoniae* strain carrying the OXA-48 gene. All seven genes encode beta lactamases that are also able to degrade and inactivate the penam class of antibiotics (see FIGS. 2 and 3). All strains were tested and, as expected, found to be resistant to the penam class antibiotic, ampicillin.

Beta lactamase coding sequences were amplified from the cell with appropriate forward and reverse primer set shown in Table 19.

TABLE 19

| Strain | NCTC No. | Resistance gene | Forward primer 5' to 3' | Reverse primer 5' to 3' |
|---|---|---|---|---|
| NBKp001 | 13443 | NDM-1 | attgaaaaaggaagagtATG GAATTGCCCAATATTATGCA CCC (SEQ ID NO: 120) | agtcccgctaGGTCTCaAC CGTCAGCGCAGCTTGTCGG (SEQ ID NO: 121) |
| NBKp002 | 13442 | CIYA-48 | attgaaaaaggaagagtATG CGTGTATTAGCCTTATCGGC TG (SEQ ID NO: 122) | agtcccgctaGGTCTCaAC CGCTAGGGAATAATTTTT CCTGTTTGAGCACTTCT (SEQ ID NO: 123) |
| NBKp003 | 13368 | SHV-18 | attgaaaaaggaagagtATG CGTTATTTTCGCCTGTGTAT TATCTCC (SEQ ID NO: 124) | agtcccgctaGGTCTCaAC CGTTAGCGTTGCCAGTGCT CGA (SEQ ID NO: 125) |
| NBKp004 | 13440 | VIM-1 | aatattgaaaaaggaagagt GGAAGAGCggcttgttatga ctgtttttttgtacagtct (SEQ ID NO: 126) | gagtaaacttggtctgaca gCGAAGAGCctactcggcg actgagcgat (SEQ ID NO: 127) |
| NBKp005 | 13438 | KPC-3 | attgaaaaaggaagagtATG TCACTGTATCGCCGTCTAGT TCT (SEQ ID NO: 128) | agtcccgctaGGTCTCaAC CGTTACTGCCCGTTGACGC C (SEQ ID NO: 129) |
| NBKp018 | 13476 | IMP-1 | attgaaaaaggaagagtATG AGCAAGTTATCTGTATTCTT TATATTTTTGTTTTGTAGCA (SEQ ID NO: 130) | agtcccgctaGGTCTCaAC CGTTAGTTGCTTAGTTTTG ATGGTTTTTTACTTTCGTT TAAC (SEQ ID NO: 131) |
| NBKp019 | 13353 | CTX-M-15 | attgaaaaaggaagagtATG GTTAAAAAATCACTGCGCCA GTTC (SEQ ID NO: 132) | agtcccgctaGGTCTCaAC CGTTACAAACCGTCGGTGA CGATTTTAG (SEQ ID NO: 133) |

For the following bla genes, each forward primer contains a 17 base sequence to restore the beta-lactamase promoter on pBR322, and each reverse primer contains a BsaI site (for NDM-1, OXA-48, SHV-18, KPC-3, and CTX-M15) to create 5'-ACCG four base protruding 5' end. After amplifying each beta lactamase gene with high fidelity DNA polymerase such as Q5 DNA polymerase, the amplicon was digested with the appropriate restriction enzyme located in the reverse primer, described above. The digested amplicons were ligated using T4 ligase between the SspI and BsaI sites on the plasmid pBR322 (purchased from New England Biolabs), after removal of the TEM-3 fragment. SspI creates a blunt end and BsaI creates a 5'-CGGT protruding end. The reverse complement of the coding sequences of the each amplicons after restriction digestion are shown below. The 5' protruding end is underlined and 3' end of the promotor sequence is in bold small letters. The reverse complement CAT of the methionine initiating codons ATG of these seven genes, also shown in bold, yields a precise fusion of the coding region of the seven other beta-lactamases to the translational signal sequences of the TEM-3 beta-lactamase of pBR322. The IMP-1 gene was amplified and cloned to pCR Blunt II-TOPO to give pNB014. The VIM-1 gene was amplified with its promoter region and assembled by the Gibson assembly kit (NEB) with two fragments amplified from pNT3 with primer pairs 5'-tcataacaagccGCTCTTC-Cactcttcctttttcaatattattgaagcatttatcagg (SEQ ID NO: 134) and 5'-acgggctgtctgattcaggttatttccgatgg (SEQ ID NO: 135) and primer pairs 5'-acctgaatcagacagcccgtaaggt-gaacagcgggcag (SEQ ID NO: 136) and 5'-gtcgccgagtagGCTCTTCGctgtcagaccaagtttactcatatatactt-tagattgattt (SEQ ID NO: 137) to give pNB013.

NDM-1

(SEQ ID NO: 138)

ACCGTCAGCGCAGCTTGTCGGCCATGCGGGCCGTATGAGTGATTGCGGCGCGGCTATCGGGGGCGGA

ATGGCTCATCACGATCATGCTGGCCTTGGGGAACGCCGCACCAAACGCGCGCGCTGACGCGGCGTAG

TGCTCAGTGTCGGCATCACCGAGATTGCCGAGCGACTTGGCCTTGCTGTCCTTGATCAGGCAGCCAC

CAAAAGCGATGTCGGTGCCGTCGATCCCAACGGTGATATTGTCACTGGTGTGGCCGGGGCCGGGGTA

AAATACCTTGAGCGGGCCAAAGTTGGGCGCGGTTGCTGGTTCGACCCAGCCATTGGCGGCGAAAGTC

AGGCTGTGTTGCGCCGCAACCATCCCCTCTTGCGGGGCAAGCTGGTTCGACAACGCATTGGCATAAG

TCGCAATCCCCGCCGCATGCAGCGCGTCCATACCGCCCATCTTGTCCTGATGCGCGTGAGTCACCAC

CGCCAGCGCGACCGGCAGGTTGATCTCCTGCTTGATCCAGTTGAGGATCTGGGCGGTCTGGTCATCG

GTCCAGGCGGTATCGACCACCAGCACGCGGCCGCCATCCCTGACGATCAAACCGTTGGAAGCGACTG

CCCCGAAACCCGGCATGTCGAGATAGGAAGTGTGCTGCCAGACATTCGGTGCGAGCTGGCGGAAAAC

CAGATCGCCAAACCGTTGGTCGCCAGTTTCCATTTGCTGGCCAATCGTCGGGCGGATTTCACCGGGC

ATGCACCCGCTCAGCATCAATGCAGCGGCTAATGCGGTGCTCAGCTTCGCGACCGGGTGCATAATAT

TGGGCAATTCCATactcttcctttttcaat

OXA-48

(SEQ ID NO: 139)

ACCGCTAGGGAATAATTTTTTCCTGTTTGAGCACTTCTTTTGTGATGGCTTGGCGCAGCCCTAAACC

ATCCGATGTGGGCATATCCATATTCATCGCAAAAAACCACACATTATCATCAAGTTCAACCCAACCG

ACCCACCAGCCAATCTTAGGTTCGATTCTAGTCGAGTATCCAGTTTTAGCCCGAATAATATAGTCAC

CATTGGCTTCGGTCAGCATGGCTTGTTTGACAATACGCTGGCTGCGCTCCGATACGTGTAACTTATT

GTGATACAGCTTTCTTAAAAAGCTGATTTGCTCCGTGGCCGAAATTCGAATACCACCGTCGAGCCAG

AAACTGTCTACATTGCCCGAAATGTCCTCATTACCATAATCGAAAGCATGTAGCATCTTGCTCATAC

GTGCCTCGCCAATTTGGCGGGCAAATTCTTGATAAACAGGCACAACTGAATATTTCATCGCGGTGAT

TAGATTATGATCGCGATTCCAAGTGGCGATATCGCGCGTCTGTCCATCCCACTTAAAGACTTGGTGT

TCATCCTTAACCACGCCCAAATCGAGGGCGATCAAGCTATTGGGAATTTTAAAGGTAGATGCGGGTA

AAAATGCTTGGTTCGCCCGTTTAAGATTATTGGTAAATCCTTGCTGCTTATTCTCATTCCAGAGCAC

AACTACGCCCTGTGATTTATGTTCAGTAAAGTGAGCATTCCAACTTTTGTTTTCTTGCCATTCCTTT

GCTACCGCAGGCATTCCGATAATCGATGCCACCAAAAACACAGCCGATAAGGCTAATACACGCATac tcttcctttttcaat

-continued

SHV-18
(SEQ ID NO: 140)
<u>ACCG</u>TTAGCGTTGCCAGTGCTCGATCAGCGCCGCGCCGATCCCGGCGATTTGCTGATTTCGCTCGGC

CATGCTCGCCGGCGTATCCCGCAGATAAATCACCACAATCCGCTCTGCTTTGTTATTCGGGCCAAGC

AGGGCGACAATCCCGCGCGCACCCCGTTTGGCAGCTCCGGTCTTATCGGCGATAAACCAGCCCGCCG

GCAGCACGGAGCGGATCAACGGTCCGGCGACCCGATCGTCCACCATCCACTGCAGCAGCTGCCGTTG

CGAACGGGCGCTCAGACGCTGGCTGGTCAGCAGCTTGCGCAGGGTCGCGGCCATGCTGGCCGGGGTA

GTGGTGTCGCGGGCGTCGCCGGGAAGCGCCTCATTCAGTTCCGTTTCCCAGCGGTCAAGGCGGGTGA

CGTTGTCGCCGATCTGGCGCAAAAAGGCAGTCAATCCTGCGGGGCCGCCGACGGTGGCCAGCAGCAG

ATTGGCGGCGCTGTTATCGCTCATGGTAATGGCGGCGGCACAGAGTTCGCCGACCGTCATGCCGTCG

GCAAGGTGTTTTTCGCTGACCGGCGAGTAGTCCACCAGATCCTGCTGGCGATAGTGGATCTTTCGCT

CCAGCTGTTCGTCACCGGCATCCACCCGCGCCAGCACTGCGCCGCAGAGCACTACTTTAAAGGTGCT

CATCATGGGAAAGCGTTCATCGGCGCGCCAGGCGGTCAGCGTGCGGCCGCTGGCCAGATCCATTTCT

ATCATGCCTACGCTGCCCGACAGCTGGCTTTCGCTTAGTTTAATTTGCTCAAGCGGCTGCGGGCTGG

CGTGTACCGCCAGCGGCAGGGTGGCTAACAGGGAGATAATACACAGGCGAAAATAACGCATactctt cctttttcaat

VIM-1
(SEQ ID NO: 141)
ACCGCTACTCGGCGACTGAGCGATTTTTGTGTGCTTTGACAACGTTCGCTGTGTGCTGGAGCAAGTC

TAGACCGCCCGGTAGACCGTGCCCGGGAATGACGACCTCTGCTTCCGGGTAGTGTTTTTGAATCCGC

TCAACGGAGGTGGGCCATTCAGCCAGATCGGCATCGGCCACGTTCCCCGCAGACGTGCTTGACAACT

CATGAACGGCACAACCACCGTATAGCACGTTCGCTGACGGGACGTATACAACCAGATTGTCGGTCGA

ATGCGCAGCACCAGGATAGAAGAGCTCTACTGGACCGAAGCGCACTGCGTCCCCGCTCGATGAGAGT

CCTTCTAGAGAATGCGTGGGAATCTCGTTCCCCTCTGCCTCGGCTAGCCGGCGTGTCGACGGTGATG

CGTACGTTGCCACCCCAGCCGCCCGAAGGACATCAACGCCGCCGACGCGGTCGTCATGAAAGTGCGT

GGAGACTGCACGCGTTACGGGAAGTCCAATTTGCTTTTCAATCTCCGCGAGAAGTGCCGCTGTGTTT

TTCGCACCCCACGCTGTATCAATCAAAAGCAACTCATCACCATCACGGACAATGAGACCATTGGACG

GGTAGACCGCGCCATCAAACGACTGCGTTGCGATATGCGACCAAACACCATCGGCAATCGGTAAAG

TCGGACCTCTCCGACCGGAATTTCGTTGACTGTCGGATACTCACCACTCGGCTCCCCGGAATGGGCT

AACGGACTTGCGACAGCCATGACAGACGCGGTCATGTAGACCAATAAACTACTAATAACTTTTAACA

Tactcttcctttttcaat

KPC-3
(SEQ ID NO: 142)
AQQQTTACTGCCCGTTGACGCCCAATCCCTCGAGCGCGAGTCTAGCCGCAGCGGCGATGACGGCCTC

GCTGTACTTGTCATCCTTGTTAGGCGCCCGGGTGTAGACGGCCAACACAATAGGTGCGCGCCCAGTG

GGCCAGACGACGGCATAGTCATTTGCCGTGCCATACACTCCGCAGGTTCCGGTTTTGTCTCCGACTG

CCCAGTCTGCCGGCACCGCCGCGCGGATGCGGTGGTTGCCGGTCGTGTTTCCCTTTAGCCAATCAAC

AAACTGCTGCCGCTGCGGCGCAGCCAGTGCAGAGCCCAGTGTCAGTTTTTGTAAGCTTTCCGTCACG

GCGCGCGGCGATGAGGTATCGCGCGCATCGCCTGGGATGGCGGAGTTCAGCTCCAGCTCCCAGCGGT

CCAGACGGAACGTGGTATCGCCGATAGAGCGCATGAAGGCCGTCAGCCCGGCCGGGCCGCCCAACTC

CTTCAGCAACAAATTGGCGGCGGCGTTATCACTGTATTGCACGGCGGCCGCGGACAGCTCCGCCACC

GTCATGCCTGTTGTCAGATATTTTTCCGAGATGGGTGACCACGGAACCAGCGCATTTTTGCCGTAAC

GGATGGGTGTGTCCAGCAAGCCGGCCTGCTGCTGGCTGCGAGCCAGCACAGCGGCAGCAAGAAAGCC

-continued

CTTGAATGAGCTGCACAGTGGGAAGCGCTCCTCAGCGCGGTAACTTACAGTTGCGCCTGAGCCGGTA

TCCATCGCGTACACACCGATGGAGCCGCCAAAGTCCTGTTCGAGTTTAGCGAATGGTTCCGCGACGA

GGTTGGTCAGCGCGGTGGCAGAAAAGCCAGCCAGCGGCCATGAGAGACAAGACAGCAGAACTAGACG

GCGATACAGTGACATactcttccttttcaat

IMP-1
(SEQ ID NO: 143)
<u>ACCG</u>TTAGTTGCTTGGTTTTGATGGTTTTTTACTTTCGTTTAACCCTTTAACCGCCTGCTCTAATGT

AAGTTTCAAGAGTGATGCGTCTCCAACTTCACTGTGACTTGGAACAACCAGTTTTGCCTTACCATAT

TTGGACTTTAATAATTTGGCGGACTTTGGCCAAGCTTCTATATTTGCGTCACCCAAATTGCCTAAAC

CGTACGGTTTAATAAAACAACCACCGAATAATATTTTCCTTTCAGGCAGCCAAACCACTACGTTATC

TGGAGTGTGTCCCGGGCCTGGATAAAAAACTTCAATTTTATTTTTAACTAGCCAATAGTTAACTCCG

CTAAATGAATTTGTAGCTTGAACCTTGCCGTCTTTTTTAAGCAGTTCATTTGTTAATTCAGATGCAT

ACGTGGGGATAGATCGAGAATTAAGCCACTCTATTCCGCCCGTGCTGTCGCTATGAAAATGAGAGGA

AATACTGCCTTTTATTTTATAGCCACGCTCCACAAACCAAGTGACTAACTTTTCAGTATCTTTAGCC

GTAAATGGAGTGTCAATTAGATAAGCCTCAGCATTTACAAGAACCACCAAACCATGTTTAGGAACAA

CGCCCCACCCGTTAACTTCTTCAAACGAAGTATGAACATAAACGCCTTCATCAAGCTTTTCAATTTT

TAAATCTGGTAAAGACTCTGCTGCGGTAGCAATGCTACAAAACAAAAATATAAAGAATACAGATAAC

TTGCTCATactcttccttttcaat

CTX-M-15
(SEQ ID NO: 144)
<u>ACCG</u>TTACAAACCGTCGGTGACGATTTTAGCCGCCGACGCTAATACATCGCGACGGCTTTCTGCCTT

AGGTTGAGGCTGGGTGAAGTAAGTGACCAGAATCAGCGGCGCACGATCTTTTGGCCAGATCACCGCG

ATATCGTTGGTGGTGCCATAGCCACCGCTGCCGGTTTTATCCCCCACAACCCAGGAAGCAGGCAGTC

CAGCCTGAATGCTCGCTGCACCGGTGGTATTGCCTTTCATCCATGTCACCAGCTGCGCCCGTTGGCT

GTCGCCCAATGCTTTACCCAGCGTCAGATTCCGCAGAGTTTGCGCCATTGCCCGAGGTGAAGTGGTA

TCACGCGGATCGCCCGGAATGGCGGTGTTTAACGTCGGCTCGGTACGGTCGAGACGGAACGTTTCGT

CTCCCAGCTGTCGGGCGAACGCGGTGACGCTAGCCGGGCCGCCAACGTGAGCAATCAGCTTATTCAT

CGCCACGTTATCGCTGTACTGTAGCGCGGCCGCGCTAAGCTCAGCCAGTGACATCGTCCCATTGACG

TGCTTTTCCGCAATCGGATTATAGTTAACAAGGTCAGATTTTTTGATCTCAACTCGCTGATTTAACA

GATTCGGTTCGCTTTCACTTTTCTTCAGCACCGCGGCCGCGGCCATCACTTTACTGGTGCTGCACAT

CGCAAAGCGCTCATCAGCACGATAAAGTATTTGCGAATTATCTGCTGTGTTAATCAATGCCACACCC

AGTCTGCCTCCCGACTGCCGCTCTAATTCGGCAAGTTTTTGCTGTACGTCCGCCGTTTGCGCATACA

GCGGCACACTTCCTAACAACAGCGTGACGGTTGCCGTCGCCATCAGCGTGAACTGGCGCAGTGATTT

TTTAACCATactcttccttttcaat

Then DH5α competent cells purchased from New England Biolabs were transformed with these ligations followed by selection for the desired recombinants on LB Ampicillin (100 μg/mL) plates.

Plasmid DNA samples were isolated from these transformants and submitted to DNA sequence analysis to confirm that the correct sequence for each of the seven different beta lactamases genes was present in each construct giving the plasmids:

These pBR322 derivative plasmids so derived were named:

i. pNB010 carrying the SHV-18 gene;
ii. pNB011 carrying the CTX-M-15 gene;
iii. pNB012 carrying the KPC-3 gene;
iv. pNB015 carrying the NDM-1 gene;
v. pNB016 carrying the OXA-48 gene; in addition to, as described,
vi. pBR322 carrying the TEM-3 gene The pNT3 derivative plasmid so derived was named:

i. pNB013 carrying the VIM-1 gene;

These pCR Blunt II-TOPO derivative plasmid so derived was named:

i. pNB014 carrying the IMP-1 gene;

Example 2.4 Testing Nemesis Symbiotic Activity Against the Eight VONCKIST Family Beta-Lactamases Nemesis Symbiotic Activity (NSA) Assay by Plasmid Transformation Eight recipient *E. coli* strains, DH5α, each carrying one of these eight VONCKIST beta lactamase genes on the plasmids pNB010-016 or pBR322, encoding TEM-3, was subsequently transformed with the plasmid pNB108 carrying spacers targeting the eight bla VONCKIST genes and selected for chloramphenicol resistance to select for acquisition of these Nemesis Symbiotic plasmids, along with the negative control pNB100 as well as with transformation of DH5α (pBR322) by pNB102 as the positive control, and then tested for conversion to ampicillin sensitivity essentially as described in Example 2.1 (see FIG. 27). Following transformation with pNB108, or the negative control plasmid pNB100 lacking the VONCKIST spacer sequences of the bacterial strains carrying the VONCKIST beta lactamase genes, colonies were picked and screened for loss of ampicillin resistance (ApR) as an indication of Nemesis Symbiotic activity present in pNB108 but not pNB100. The results show that the single eight spacer construct present in pNB108 is able to inactivate ApR of all 8 VONCKIST beta lactamase genes.

Example 2.5 Construction of Lambda(c-TNB001::CRISPR-Cas9-NIVKOSTC) and Delivery by Phage Infection The Cas9/CRISPR::NIVKOSTC cassette, carrying all eight spacers, the Cargo, is added into the c-Transmid, c-TNB001, by Cre/lox-mediated recombination (docking). An amplicon encoding tracrRNA Cas9 and VONCKIST CRISPR spacers from the plasmid pNB108 is digested with NotI and XhoI and the 5,335 bp fragment is cloned into the NotI and XhoI site on pNB300 giving pNB301 (FIG. 11). The total size of pNB301 is 10,179 bp. Then, after validation of pNB301 by DNA sequence analysis, pNB301 is transformed into DH5α carrying c-TNB001 with CmR selection and then mated with a recipient *E coli* strain carrying resistance to streptomycin (SmR) and plated on Mueller-Hinton (MH) plates supplemented with kanamycin 50 μg/mL (Km50), streptomycin 50 μg/mL (Sm50) and trimethoprim 50 μg/mL (Tp50) and IPTG (50 μL of 0.1 M) in order to select for the correct Cre-lox docking reaction, as described above, and then screened for the expected loss of CmR50, giving the c-Transmid with Cargo, c-TNB001::CRISPR-Cas9-NIVKOSTC (FIGS. 21 and 22). Then c-TNB001::NIVKOSTC is packaged into an infectious bacteriophage lambda particle giving lambda(c-TNB001::CRISPR-Cas9-NIVKOSTC) (FIG. 19). To do this, the c-Transmid, c-TNB001::NIVKOSTC, is isolated from the cells selected in FIG. 20 using a large construct plasmid preparation kit such as QIAGEN large construct kit (cat No. 12462). The Transmid is a template for rolling circle amplification (RCA) by phi21 DNA polymerase from the primer f (5'-gacatgaggt*t*g*c [SEQ ID NO: 3], where asterisks indicate phosphorothioate linkages) annealing at the cos site. In the presence of reverse (r) primer (5'-atgGCGAT*C*G*C [SEQ ID NO: 4], where asterisks indicate phosphorothioate linkages), which anneals downstream of the cos site on the polymerised DNA, concatemeric or mature double stranded DNA is accumulated in the RCA reaction. The reaction can be cleaned by membrane dialysis such as Genomic Tube-O-dialyzer (G-Biosciences, cat No. 786-142-45MC). This dialysed double-stranded DNA can be used as a substrate for in vitro packaging to package the c-Transmid into the lambda phage using a packaging kit such as MaxPlax Lambda Packaging Extracts (epicentre Cat. No. MP5105).

The resulting packaged lambda(c-TNB001::CRISPR-Cas9-NIVKOSTC) is then tested for infectivity to an *E. coli* recipient with Tp50 or Km50 selection. Efficiency of successful delivery of c-TNB001::CRISPR-Cas9-NIVKOSTC following lambda packaging is measured over a range of multiplicities of infection (moi).

Example 2.6. Conjugal Transfer of (c-TNB001::CRISPR-Cas9-NIVKOSTC)

Following delivery of c-TNB001::CRISPR-Cas9-NIVKOSTC by phage lambda infection, this recombinant c-Transmid is tested for conjugal transfer to bacterial recipients *E. coli* and *K. pneumoniae* in a mating to a recipient carrying for example SmR to select for exconjugants. In matings with *E. coli*, c-TNB001::CRISPR-Cas9-NIVKOSTC would be expected to replicate stably and exconjugants can be selected for KmR encoded by the c-Transmid. In matings with *K. pneumoniae*, the ori2/repA system of c-TNB001::CRISPR-Cas9-NIVKOSTC may not permit stable replication and exconjugants may be selected following transposition events where the CRISPR-Cas9-NIVKOSTC Cargo has jumped to the chromosomal attTn7 site (FIG. 21). Such transposition events to the attTn7 site may be selected for with the Cargo-encoded TpR marker and screened for loss of the c-Transmid on LBKm50 plates, since the KmR marker would be lost with the c-Transmid.

Example 2.7 Testing CRISPR-Cas9 Plus VONCKIST Spacers in the c-Transmid Following Bacteriophage Delivery The c-Transmid::VONCKIST is tested for the ability to inactivate each of the eight VONCKIST beta-lactamases following lambda(c-Transmid::VONCKIST) infection of non-pathogenic laboratory strains of *E. coli* carrying plasmids encoding one of each of the eight VONCKIST beta-lactamases. Thus following selection for delivery of the c-Transmid carrying the CRISPR/Ca9 system plus VON- CKIST spacers, they are then tested for sensitivity to ampicillin as described above. The results obtained with the c-Transmid::VONCKIST are compared to that obtained in a control experiment using an equivalent c-Transmid also carrying the Cas9 gene and tracr but lacking the VONCKIST spacers and derived from pNB100 in the same way that the Cas9-VONCKIST region was obtained from pNB108.

Example 2.8

The c-Transmid::VONCKIST is tested for the ability to inactivate each of the eight VONCKIST beta-lactamases c-Transmid::VONCKIST following conjugation from a donor strain to non-pathogenic laboratory recipient strains of *E. coli* carrying plasmids encoding one of each of the eight VONCKIST beta-lactamases. Thus following selection for delivery of the c-Transmid carrying the CRISPR/Ca9 system plus VONCKIST spacers, they are then tested for sensitivity to ampicillin as described above. In this experiment the c-Transmid::VONCKIST is first used to infect DH5α by phage delivery, then, following selection for cells successfully carrying the c-Transmid::VONCKIST DNA, these cells are used as donors to mate with a recipient carrying one or other of the eight different VONCKIST beta lactamase genes followed by selection for transconjugants with KnR and ApR. Nemesis Symbiotic activity may be measured by comparing the mating efficiency of this mating compared to a control mating experiment using an equivalent c-Transmid also carrying the Cas9 gene and tracr but lacking the VONCKIST spacers as described above.

Example 3

Exemplification of Use of the c-Transmid c-TNB00::VONCKIST: Delivery of Cargo Resulting in Inactivation of Antibiotic Resistance Genes in the Multi-Drug Resistant *Escherichia coli* ST131 Clone Example 3 demonstrates the application of c-Transmids for delivery of the Cargo resulting in inactivation of antibiotic resistance genes in a pathogenic strain. The Cargo is a selected nucleotide of interest encoding a CRISPR-Cas9 construct with spacer sequences encoding guide RNAs (gRNAs) targeting beta lactamase antibiotic resistance genes. Inactivation of such antibiotic resistance genes allows for resurrection of antibiotic sensitivity in bacterial strains, including pathogenic strains of *Escherichia coli* and *Klebsiella pneumoniae.*

For exemplification a multi-drug resistant (MDR) uropathogenic *Escherichia coli* (UPEC) strain such as the strain ST131 may be selected (Schembri et al., 2015, Pathogens 4:422-430, hereby incorporated by reference in its entirety). UPEC, cause 80% of all UTIs and such MDR UPECs have spread worldwide. ST131 has emerged recently and has spread globally and is associated with urinary tract infections (UTI) and bloodstream infections both nosocomially and in the community. The type 1 fimbrae fimH30 is allele is responsible for pathogenecity.

The steps involved in this exemplification are given below:

- Infectious phage protein coats carrying the recombinant c-Transmid::VONCKIST, prepared as described in Example 2, is first tested for Nemesis Symbiotic activity following infection of ST131 in vitro, using equivalent methods to that described in Example 2. Thus infected cells are examined for inactivation of beta lactamases they carried by screening for loss of resistance to beta lactam antibiotics. Such infection may result in the death of the cell, where the generation of a double-strand DNA break by the Cas9/tracr RNA/gRNA complex leads to the elimination of a plasmid carrying a post-segregational killing mechanism in addition to the beta lactamase gene target. This experiment demonstrates Nemesis Symbiotic activity by phage infection.
- Nemesis Symbiotic activity by bacterial conjugation similarly is demonstrated by mating a donor *E. coli* strain with the recipient ST131 with selection for exconjugants and again screening for loss of resistance to beta lactam antibiotics in the exconjugants. Again, it may be that a double-strand DNA break results in death of the recipient and this is seen as a failure to obtain exconjugants compared to a control strain lacking the VONCKIST spacers.
- Successful demonstration in vitro leads to pre-clinical demonstration in a suitable animal model system.

Example 4

Construction of a c-Transmid Packaged in a Bacteriophage Lambda Capsid and Expressing the Cas9 Gene tracrRNA and gRNA-TEM3 Resulting in Inactivation of the TEM-3 Antibiotic Resistance Genes in *Escherichia coli.*

The following proof-of-concept experiments describe the construction of a conjugative Transmid, cTNB000-X, expressing the Cas9 gene tracrRNA and gRNA-TEM3, that was packaged in vivo, in a bacteriophage lambda lysogen helper strain, that allowed delivery to *E. coli* by infection followed by spread by bacterial conjugation with consequent inactivation of the TEM-3 beta-lactamse gene, resulting in conversion of the bacteria from ampicillin resistant to ampicillin sensitive.

For the purposes of this proof-of-concept, it was not necessary to use the cre-lox recombination system to combine the "Ship" and "Cargo" as described in Example 1 as this is only needed for ease of construction of conjugative Transmid derivatives carrying new cargo sequences to be delivered to target bacteria. The conjugative Transmid described below also does not have the tnsA, tnsB, tnsC, tnsD genes, encoding the four transposition proteins of the bacterial transposon Tn7 that bring about site-specific transposition to the chromosomally located Tn7 attachment site, attTn7, that is present in *E. coli.*

This conjugative Transmid described below also retains the RK2 ori V and genes encoding vegetative replication as well as the plasmid partition functions, in place of the equivalent such functions that are isolated from the F plasmid described in Example 1.

Example 4.1 Construction of *E. coli* Helper Strain Carrying a Bacteriophage Lambda Lysogen Able to Package Transmids An *E. coli* helper strain carrying a bacteriophage lambda lysogen was constructed in order to be able to perform inducible in vivo packaging of Transmid DNA following the introduction of the Transmid to the helper strain by DNA transformation or by conjugation. However in order to avoid the packaging of the lambda phage itself, it was necessary to generate a mutation in the lambda DNA to mutate the packaging signal. Thus the lambda lysogen developed contains three pertinent features: (i) it carries a temperature sensitive mutation in the Cl repressor gene, the Cl857 mutation. Growth of the helper strain at the restrictive temperature, >37° C., results in the Cl857 repressor protein disassociating from the operator sequences regulating transcription of the lambda PL and PR promotors, so resulting in entry into the lytic cycle to express all of the proteins required for the production of phage; (ii) it carries the amber nonsense mutation Sam7 in the lambda S gene. The S gene encodes a small membrane protein, a holin, that, makes holes in the bacterial membrane allowing the product of the lambda R gene, an endolysin to escape through the S holes and cleave the cell wall, leading to lysis and release of packaged phage. The Sam7 amber mutation results in premature termination of translation of this protein resulting in a non-functional gene product; (iii) it carries a disruptive insertion mutation in the cos sequence, a cis-essential sequence required for packaging the bacteriophage lamda DNA into the assembled head before the tail assembles to produce the mature virion.

Phage DNA purchased from Promega (Cat No. D1501) carrying Cl857 and Sam7 mutations was heated to melt the cohesive ends which were filled-in to make the end blunt using Quick Blunting Kit (Cat No. E1201) purchased from NEB followed by the protocol provided by the manufacturer. The blunt-ended DNA reaction was purified by Agencourt AMPure XP (Cat No. A63880) beads purchased from Beckman Coulter using the protocol provided by the manufacturer. The resulting blunt-ended DNA, which was nucleotide free, was treated with 1 unit of T7 DNA polymerase in NEBuffer 2.1 (50 mM NaCl, 10 mM Tris-HCl, 10 mM $MgCl_2$, 100 μg/mL BSA, pH 7.9 at 25° C.) in the presence of 2.5 mM dGTP at 12° C. for 30 min followed by the addition of 10 mM EDTA and the polymerase was inactivated at 75° C. for 20 min. This T7 DNA polymerase mediated chew-back reaction created asymmetric 5' overhangs in the cos sites as follows:

(SEQ ID NO: 145)
Cos site 5'-GGGCGGCGACCT↓GGGCGGCG (SEQ ID NO: 146)
GCCGCTGGA↑CCCGCCGCTGGA.

In order to make the cos sites inactive, the right and left cos site ends were separated by inserting a chloramphenicol (Cm) acetyl transferase, cat, gene encoding Cm resistance, which was prepared by PCR from pACYC184 as a template with the primer pairs NB183 and NB184 shown 5'-3' below:

NB183
(SEQ ID NO: 147)
TACCGGGAAGGGTCTCGACCTACTTTTGGCGAAAATGAGACGTTGATC

NB184
(SEQ ID NO: 148)
ttaacgacccGCTCTTCACCCGACGACCGGGTCGAATTTGC.

The NB183 primer contains underlined BsaI sites (GGTCTC). The NB184 primer contains underlined SapI site (GCTCTTC). The amplicon of the chloramphenicol gene was digested with both restriction enzymes created 5' overhang, 5'-ACCT and 5'-CCC which are complementary to the chewed-back cos sites.

Chewed-back lambda DNA and the Bsa I-Sap I-digested cat gene were ligated using the conditions shown in Table 20.

TABLE 20

| | | |
|---|---|---|
| Water | | 62.6 μL |
| 10x T4 Ligase Buffer | | 9 μL |
| Cm/SapI-BsaI fragment | 28.5 ng/uL | 30 ng (1.1 μL) |
| Lambda/fill-in chewed-back A1 | 10 ng/uL | 162.8 ng (16.3 μL) |
| T4 DNA ligase | 400 U/μL | 1 |
| Vol μL | | 90 μL |

Ligation reactions were incubated at 16° C. for 12 hrs. The ligation reactions were drop-dialysed by Type_VS Millipore membrane (mean pore size=0.025 μM, Cat No. VSWP02500) according to the protocol provided by the manufacturer. The resulting ligation mixtures were used to transform strain DH10B (MegaX DH10B T1R electrocomp cells Cat No. C6400-03 Genotype: F– mcrA Δ(mrr-hs-dRMS-mcrBC), ϕ80lacZΔM15 ΔlacX74 recA1 endA1 araD139 Δ(ara, leu)7697 galU galK λ– rpsL nupG tonA) by electroporation, and transformants resistant to 25 μg of kanamycin/mL were selected at 30° C. and screened for an inability to grow at 42° C.—when cells are expected to die at the end of the induced lambda lytic cycle.

Example 4.2 Construction of cTNB001-X a Conjugative Transmid Expressing the Cas9 Gene tracrRNA and gRNA-TEM3 Spacer for Packaging in a Bacteriophage Lambda Capsid A prototype conjugative Transmid (c-Transmid), cTNB000-X was constructed based on the plasmid RK2 plus the Cas9 gene tracrRNA and gRNA-TEM3 spacer and bacteriophage lambda cos site. This construction was performed in two stages.

In stage one, PCR products from selected regions of the plasmids pACYC184, pBeloBAC11, RK2 and pNB102 were joined together by Gibson assembly to produce cTNB000-X, a plasmid based on pACYC184 and carrying oriV of RK2, the bacteriophage lambda cos site, and, taken from pNB102, cas9 plus tracrRNA plus the TEM-3 spacer.

In stage 2, the plasmid cTNB001-X was constructed by cloning the 6,226 bp Avr II-Eco RI restriction fragment of cTNB000-X into the 44,786 Avr II-Eco RI restriction fragment of RK2 DNA.

The resulting plasmid, cTNB001-X was then packaged into a bacteriophage lambda capsid and tested for delivery both by infection of *E. coli*, and spreading by conjugation, as well as for inactivation of the TEM-3 beta-lactamase gene.

Example 4.2.1 Construction of cTNB000-X a Plasmid Based on pACYC184 Carrying oriV of RK2, the Bacteriophage Lambda Cos Site, and Cas9 Plus tracrRNA The following oligonucleotides were synthesised by Biomers for the production of the PCR products to be used in the assembly of cTNB000-X:

NB159
(SEQ ID NO: 149)
ATTTTTTCGGACCGCCTAGGTGATCTTCTTGAGATCGTTTTGGTCTGC

-continued

NB160
(SEQ ID NO: 150)
GGCAACCTCATGTCGAATTCTGTGAATGCGCAAACCAACC

NB161
(SEQ ID NO: 151)
GGTTGGTTTGCGCATTCACAGAATTCGACATGAGGTTGCCCCGTATTCAG

NB162
(SEQ ID NO: 152)
CCTCACCCCAAAAATGGCAGTAGCGATGAGCTCGGACTTCCAT

NB163
(SEQ ID NO: 153)
GAAGTCCGAGCTCATCGCTACTGCCATTTTTGGGGTGAGG

NB164
(SEQ ID NO: 154)
GATACTTCTATTCTACTCTGAGATCTAGCGTGGACTCAAGG

NB165
(SEQ ID NO: 155)
CTTGAGTCCACGCTAGATCTCAGAGTAGAATAGAAGTATCAAAAAAAGCA

CCG

NB166
(SEQ ID NO: 156)
GGACCAACATAATAAGGGATTCGAAAAGTCAAGATT

NB167
(SEQ ID NO: 157)
CGAATCCCTTATTATGTTGGTCCATTGGCGC

NB128
(SEQ ID NO: 158)
ATACTGCGGAAAATCATATAGTCGGACCGGCCATCAGTCACCTCCTAG

NB129
(SEQ ID NO: 159)
AGGAGGTGACTGATGGCCGGTCCGACTATATGATTTTCCGCAGT

NB168
(SEQ ID NO: 160)
AAACGATCTCAAGAAGATCACCTAGGCGGTCCGAAAAAAATGTATGTTCCA

TCACACTACTCTTCT.

Then using the DNA template and primer combinations below, six PCR reactions were performed in 50 μL reaction volumes containing 0.5 μM each of forward and reverse primers, 200 μM dNTPs, in 1× Q5 reaction buffer plus 0.5 μL Q5 High Fidelity DNA polymerase: the Q5 buffer and enzyme were purchased from New England Biolabs (catalogue no. M0149S). PCR cycles were as follows: 98° C. for 30 sec., followed by 35 cycles of 98° C. for 10 sec., 54° C. for 10 sec., 72° C. for 60 sec. followed by 72° C. for 10 min. and then held at 4° C. overnight. Table 21 shows the expected products.

TABLE 21

| Fragment | Template | Product | Forward | Tm | Reverse | Tm | bp |
|---|---|---|---|---|---|---|---|
| 1 | pACYC184 | Vector | NB159 | 60 | NB160 | 59 | 2842 |
| 2 | pBeloBAC11 | cos | NB161 | 61 | NB162 | 60 | 462 |
| 3 | RK2 | oriV | NB163 | 59 | NB164 | 59 | 927 |
| 4 | pNB102 | tracr + 5'cas9 | NB165 | 59 | NB166 | 59 | 1782 |
| 5 | pNB102 | 3'cas9 | NB167 | 60 | NB128 | 60 | 2802 |
| 6 | pNB102 | tracr + 5'cas9 | NB129 | 61 | NB168 | 59 | 448 |

Then PCR products were fractionated by agarose (1.2%) gel electrophoresis and DNA fragments cut from the gel and purified using a Qiagen Qiaquick gel extraction kit (catalogue number 28704), as instructed by the manufacturer.

Then using a Gibson assembly kit purchased from New England Biolabs (Catalogue No: E5520S) the six gel purified PCR fragments were mixed together in equimolar ratios 0.05 pico moles each in a total reaction volume of 20 μL including 10 μL NEBuilder HiFi DNA Assembly Master Mix provided with the Gibson assembly kit. Then each end of the double stranded DNA fragments were degraded by 5' to 3' exonuclease to create 3' overhangs. Each of the overhang ends was annealed with appropriate ends. High fidelity DNA polymerase filled-in the gap and the nick was sealed by the DNA ligase and incubated at 50° C. for 60 min to allow assembly of the DNA fragments.

Then 2 μL of the assembly was used to transform competent DH5α *E. coli* cells purchased from New England Biolabs according to the manufacturer's instructions. Then cells were plated on LB plates containing 16 μg/mL chloramphenicol (LBCm16) and incubated overnight at 37° C.

To validate the correct construction of the Transmid, 33 colonies were screened by PCR using primer NB137 and NB138 (see Table below) to amplify the cos, oriV and 5' ends of cas9 gene. Then six plasmid DNAs were isolated from six independent PCR positive clones. Using these purified plasmid templates, a further eight regions were amplified by PCR with the primer sets given below.

NB129
(SEQ ID NO: 159)
AGGAGGTGACTGATGGCCggtccgACTATATGATTTTCCGCAGT

NB137
(SEQ ID NO: 161)
Gacatgaggttgccccgtattca

NB138
(SEQ ID NO: 162)
CTCAATCGTGCAGAAAGAATCGCTTTAG

NB165
(SEQ ID NO: 155)
cttgagtccacgctagatctCAGAGTAGAATAGAAGTATCAAAAAAAGCA

CCG

NB166
(SEQ ID NO: 156)
GGACCAACATAATAAGGgATTCGAAAAGTCAAGATT

NB168
(SEQ ID NO: 160)
AAACGATCTCAAGAAGATCAcctaggcggtccgAAAAAAATGTATGTTCCA

TCACACTACTCTTCT

NB169
(SEQ ID NO: 163)
ccagtgagtcggccgcAGTCCAGTTACGCTG

NB170
(SEQ ID NO: 164)
ctgctatggagtcgacGTATGATTTAAATGGTCAGTGATG

NB171
(SEQ ID NO: 165)
pACTTTTGGCGAAAATGAGACGTTGATC

NB172
(SEQ ID NO: 166)
pGACGACCGGGTCGAATTTGC

NB173
(SEQ ID NO: 167)
TCAGAATAAGAAATGAGGCCGCTCATG

-continued

NB174
(SEQ ID NO: 168)
ggatcaccggaaaggacccg

NB175
(SEQ ID NO: 169)
ttatttgacgtggtttgatggcctc

NB176
(SEQ ID NO: 170)
ggctcgatttcggccgg

NB177
(SEQ ID NO: 171)
gcccctcaagtgtcaaggatcg

NB178
(SEQ ID NO: 172)
CGGACAAGCTTATTGCTCGTAAAAAAGAC

NB179
(SEQ ID NO: 173)
CGCTTTAACAGAAAGAATAGGAAGGTATCCG

NB180
(SEQ ID NO: 174)
CAGCAGTCGGATACCTTCCTATTCTTTC

NB181
(SEQ ID NO: 175)
CCTGTTCCTGCCTTTCGGTTT.

The amplicon size and the forward and the reverse primers that anneal to the appropriate regions on the plasmid are shown in Table 22.

TABLE 22

| For/Rev | Amplicon bp | For | Rev |
|---|---|---|---|
| NB173/174 | 601 | pACYC184 | cos |
| NB175/176 | 795 | cos | oriV |
| NB177/138 | 1635 | oriV | 5'cas |
| NB178/179 | 1109 | 3'cas | Tail |
| NB180/181 | 535 | Tail | pACYC184 (P15A ori) |
| NB165/166 | 1782 | 5'cas | 5'cas |
| NB129/168 | 448 | crispr | crispr |
| NB137/138 | 2354 | cos | 5'cas |

The length of each amplicon from all six plasmid templates was confirmed by size fractionation on a 1.2% agarose gel. cos, oriV and the newly created RsrII, AvrII sites were confirmed by dideoxy sequencing performed by Source Bioscience (William James House, Cowley Road, Cambridge CB4 0WU, United Kingdom).

Sequence analysis identified 4 plasmid DNAs carrying the desired construction and these were designated cTNB000-X.

Example 4.2.2 Construction of cTNB001-X a Conjugative Transmid Carrying RK2 Functions Required for Conjugation Plus the Cas9 Gene tracrRNA and gRNA-TEM3 Spacer The plasmid cTNB001-X was constructed by cloning the 6,226 bp Avr II-Eco RI restriction fragment of cTNB000-X into the 44,786 Avr II-Eco RI restriction fragment of RK2 DNA. First 1 μg of RK2 plasmid DNA was digested with Avr II and Eco RI purchased from New England Biolabs (catalogue numbers: R0174 and R0101, respectively) followed by treatment with shrimp alkaline phosphatase (rSAP) also from New England Biolabs (catalogue number: M0371) to prevent re-circularisation of the plasmid vector without insert following ligation as well as religation of the RK2 DNA fragment to be deleted. Similarly 2 μg of cTNB000-X plasmid DNA was digested with Avr II and Eco RI and the 6,226 bp fragment isolated from a 0.7% agarose gel following fractionation by electrophoresis as described above. Then DNAs were mixed in a molar ratio of 10:1 insert:RK2 vector using 43.2 ng RK2 vector DNA with 60 ng cTNB000/EcoRI-AvrII 6,226 fragment, with 400 units of T4 DNA ligase, in a 90 μL reaction volume overnight at 16° C.

The ligation product was dialysed by drop dialysis (Silhavy, T., Berman, M. and Enquist, L. Experiments with Gene Fusions, Cold Spring Harbor, N.Y. Press (1984)) to remove salts and used for transformation of *E. coli* strain DH10B (F-mcrA Δ(mrr-hsdRS-mcrBC) φ80lacZ ΔM15 ΔlacX74 recA1 endA1 araD139 Δ(ara, leu)7697 galU galK λ-rpsL nupG tonA) by electroporation.

Transformants were selected on kanamycin plate. Chloramphenicol and ampicillin sensitivities were also checked as the desired construct should contain the aphA gene, encoding kanamycin resistance as the only antibiotic marker. The TEM-3 spacer region was confirmed by PCR.

The DNA sequence of the 51,012 bp Transmid cTNB001-X is given below and FIG. 28 gives a genetic map:

(SEQ ID NO: 176)
AATTCGACATGAGGTTGCCCCGTATTCAGTGTCGCTGATTTGTATTGTCTGAAGTTGTTTTTACGTT

AAGTTGATGCAGATCAATTAATACGATACCTGCGTCATAATTGATTATTTGACGTGGTTTGATGGCC

TCCACGCACGTTGTGATATGTAGATGATAATCATTATCACTTTACGGGTCCTTTCCGGTGATCCGAC

AGGTTACGGGGCGGCGACCTCGCGGGTTTTCGCTATTTATGAAAATTTTCCGGTTTAAGGCGTTTCC

GTTCTTCTTCGTCATAACTTAATGTTTTTATTTAAAATACCCTCTGAAAAGAAAGGAAACGACAGGT

GCTGAAAGCGAGCTTTTTGGCCTCTGTCGTTTCCTTTCTCTGTTTTTGTCCGTGGAATGAACAATGG

AAGTCCGAGCTCATCGCTACTGCCATTTTTGGGGTGAGGCCGTTCGCGGCCGAGGGGCGCAGCCCCT

GGGGGGATGGGAGGCCCGCGTTAGCGGGCCGGGAGGGTTCGAGAAGGGGGGGCACCCCCCTTCGGCG

TGCGCGGTCACGCGCCAGGGCGCAGCCCTGGTTAAAAACAAGGTTTATAAATATTGGTTTAAAAGCA

GGTTAAAAGACAGGTTAGCGGTGGCCGAAAAACGGGCGGAAACCCTTGCAAATGCTGGATTTTCTGC

CTGTGGACAGCCCCTCAAATGTCAATAGGTGCGCCCCTCATCTGTCATCACTCTGCCCCTCAAGTGT

CAAGGATCGCGCCCCTCATCTGTCAGTAGTCGCGCCCCTCAAGTGTCAATACCGCAGGGCACTTATC

-continued

CCCAGGCTTGTCCACATCATCTGTGGGAAACTCGCGTAAAATCAGGCGTTTTCGCCGATTTGCGAGG
CTGGCCAGCTCCACGTCGCCGGCCGAAATCGAGCCTGCCCCTCATCTGTCAACGCCGCGCCGGGTGA
GTCGGCCCCTCAAGTGTCAACGTCCGCCCCTCATCTGTCAGTGAGGGCCAAGTTTTCCGCGTGGTAT
CCACAACGCCGGCGGCCGCGGTGTCTCGCACACGGCTTCGACGGCGTTTCTGGCGCGTTTGCAGGGC
CATAGACGGCCGCCAGCCCAGCGGCGAGGGCAACCAGCCCGGTGAGCGTCGGAAAGGCGCTGGAAGC
CCCGTAGCGACGCGGAGAGGGGCGAGACAAGCCAAGGGCGCAGGCTCGATGCGCAGCACGACATAGC
CGGTTCTCGCAAGGACGAGAATTTCCCTGCGGTGCCCCTCAAGTGTCAATGAAAGTTTCCAACGCGA
GCCATTCGCGAGAGCCTTGAGTCCACGCTAGATCTCAGAGTAGAATAGAAGTATCAAAAAAAGCACC
GACTCGGTGCCACTTTTTCAAGTTGATAACGGACTAGCCTTATTTTAACTTGCTATGCTGTTTTGAA
TGGTTCCAACAAGATTATTTTATAACTTTTATAACAAATAATCAAGGAGAAATTCAAAGAAATTTAT
CAGCCATAAAACAATACTTAATACTATAGAATGATAACAAAATAAACTACTTTTTAAAAGAATTTTG
TGTTATAATCTATTTATTATTAAGTATTGGGTAATATTTTTTGAAGAGATATTTTGAAAAAGAAAAA
TTAAAGCATATTAAACTAATTTCGGAGGTCATTAAAACTATTATTGAAATCATCAAACTCATTATGG
ATTTAATTTAAACTTTTTATTTTAGGAGGCAAAAATGGATAAGAAATACTCAATAGGCTTAGATATC
GGCACAAATAGCGTCGGATGGGCGGTGATCACTGATGAATATAAGGTTCCGTCTAAAAAGTTCAAGG
TTCTGGGAAATACAGACCGCCACAGTATCAAAAAAAATCTTATAGGGGCTCTTTTATTTGACAGTGG
AGAGACAGCGGAAGCGACTCGTCTCAAACGGACAGCTCGTAGAAGGTATACACGTCGGAAGAATCGT
ATTTGTTATCTACAGGAGATTTTTTCAAATGAGATGGCGAAAGTAGATGATAGTTTCTTTCATCGAC
TTGAAGAGTCTTTTTTGGTGGAAGAAGACAAGAAGCATGAACGTCATCCTATTTTTGGAAATATAGT
AGATGAAGTTGCTTATCATGAGAAATATCCAACTATCTATCATCTGCGAAAAAAATTGGTAGATTCT
ACTGATAAAGCGGATTTGCGCTTAATCTATTTGGCCTTAGCGCATATGATTAAGTTTCGTGGTCATT
TTTTGATTGAGGGAGATTTAAATCCTGATAATAGTGATGTGGACAAACTATTTATCCAGTTGGTACA
AACCTACAATCAATTATTTGAAGAAAACCCTATTAACGCAAGTGGAGTAGATGCTAAAGCGATTCTT
TCTGCACGATTGAGTAAATCAAGACGATTAGAAAATCTCATTGCTCAGCTCCCCGGTGAGAAGAAAA
ATGGCTTATTTGGGAATCTCATTGCTTTGTCATTGGGTTTGACCCCTAATTTTAAATCAAATTTTGA
TTTGGCAGAAGATGCTAAATTACAGCTTTCAAAAGATACTTACGATGATGATTTAGATAATTTATTG
GCGCAAATTGGAGATCAATATGCTGATTTGTTTTTGGCAGCTAAGAATTTATCAGATGCTATTTTAC
TTTCAGATATCCTAAGAGTAAATACTGAAATAACTAAGGCTCCCCTATCAGCTTCAATGATTAAACG
CTACGATGAACATCATCAAGACTTGACTCTTTTAAAAGCTTTAGTTCGACAACAACTTCCAGAAAAG
TATAAAGAAATCTTTTTTGATCAATCAAAAAACGGATATGCAGGTTATATTGATGGGGGAGCTAGCC
AAGAAGAATTTTATAAATTTATCAAACCAATTTTAGAAAAAATGGATGGTACTGAGGAATTATTGGT
GAAACTAAATCGTGAAGATTTGCTGCGCAAGCAACGGACCTTTGACAACGGCTCTATTCCCCATCAA
ATTCACTTGGGTGAGCTGCATGCTATTTTGAGAAGACAAGAAGACTTTTATCCATTTTTAAAAGACA
ATCGTGAGAAGATTGAAAAAATCTTGACTTTTCGAATCCCTTATTATGTTGGTCCATTGGCGCGTGG
CAATAGTCGTTTTGCATGGATGACTCGGAAGTCTGAAGAAACAATTACCCCATGGAATTTTGAAGAA
GTTGTCGATAAAGGTGCTTCAGCTCAATCATTTATTGAACGCATGACAAACTTTGATAAAAATCTTC
CAAATGAAAAAGTACTACCAAAACATAGTTTGCTTTATGAGTATTTTACGGTTTATAACGAATTGAC
AAAGGTCAAATATGTTACTGAAGGAATGCGAAAACCAGCATTTCTTTCAGGTGAACAGAAGAAAGCC
ATTGTTGATTTACTCTTCAAAACAAATCGAAAAGTAACCGTTAAGCAATTAAAAGAAGATTATTTCA
AAAAAATAGAATGTTTTGATAGTGTTGAAATTTCAGGAGTTGAAGATAGATTTAATGCTTCATTAGG

-continued

TACCTACCATGATTTGCTAAAAATTATTAAAGATAAAGATTTTTTGGATAATGAAGAAAATGAAGAT
ATCTTAGAGGATATTGTTTTAACATTGACCTTATTTGAAGATAGGGAGATGATTGAGGAAAGACTTA
AAACATATGCTCACCTCTTTGATGATAAGGTGATGAAACAGCTTAAACGTCGCCGTTATACTGGTTG
GGGACGTTTGTCTCGAAAATTGATTAATGGTATTAGGGATAAGCAATCTGGCAAAACAATATTAGAT
TTTTTGAAATCAGATGGTTTTGCCAATCGCAATTTTATGCAGCTGATCCATGATGATAGTTTGACAT
TTAAAGAAGACATTCAAAAAGCACAAGTGTCTGGACAAGGCGATAGTTTACATGAACATATTGCAAA
TTTAGCTGGTAGCCCTGCTATTAAAAAAGGTATTTTACAGACTGTAAAAGTTGTTGATGAATTGGTC
AAAGTAATGGGGCGGCATAAGCCAGAAAATATCGTTATTGAAATGGCACGTGAAAATCAGACAACTC
AAAAGGGCCAGAAAAATTCGCGAGAGCGTATGAAACGAATCGAAGAAGGTATCAAAGAATTAGGAAG
TCAGATTCTTAAAGAGCATCCTGTTGAAAATACTCAATTGCAAAATGAAAAGCTCTATCTCTATTAT
CTCCAAAATGGAAGAGACATGTATGTGGACCAAGAATTAGATATTAATCGTTTAAGTGATTATGATG
TCGATCACATTGTTCCACAAAGTTTCCTTAAAGACGATTCAATAGACAATAAGGTCTTAACGCGTTC
TGATAAAAATCGTGGTAAATCGGATAACGTTCCAAGTGAAGAAGTAGTCAAAAAGATGAAAAACTAT
TGGAGACAACTTCTAAACGCCAAGTTAATCACTCAACGTAAGTTTGATAATTTAACGAAAGCTGAAC
GTGGAGGTTTGAGTGAACTTGATAAAGCTGGTTTTATCAAACGCCAATTGGTTGAAACTCGCCAAAT
CACTAAGCATGTGGCACAAATTTTGGATAGTCGCATGAATACTAAATACGATGAAAATGATAAACTT
ATTCGAGAGGTTAAAGTGATTACCTTAAAATCTAAATTAGTTTCTGACTTCCGAAAAGATTTCCAAT
TCTATAAAGTACGTGAGATTAACAATTACCATCATGCCCATGATGCGTATCTAAATGCCGTCGTTGG
AACTGCTTTGATTAAGAAATATCCAAAACTTGAATCGGAGTTTGTCTATGGTGATTATAAAGTTTAT
GATGTTCGTAAAATGATTGCTAAGTCTGAGCAAGAAATAGGCAAAGCAACCGCAAAATATTTCTTTT
ACTCTAATATCATGAACTTCTTCAAAACAGAAATTACACTTGCAAATGGAGAGATTCGCAAACGCCC
TCTAATCGAAACTAATGGGGAAACTGGAGAAATTGTCTGGGATAAAGGGCGAGATTTTGCCACAGTG
CGCAAAGTATTGTCCATGCCCCAAGTCAATATTGTCAAGAAAACAGAAGTACAGACAGGCGGATTCT
CCAAGGAGTCAATTTTACCAAAAAGAAATTCGGACAAGCTTATTGCTCGTAAAAAAGACTGGGATCC
AAAAAAATATGGTGGTTTTGATAGTCCAACGGTAGCTTATTCAGTCCTAGTGGTTGCTAAGGTGGAA
AAAGGGAAATCGAAGAAGTTAAAATCCGTTAAAGAGTTACTAGGGATCACAATTATGGAAAGAAGTT
CCTTTGAAAAAAATCCGATTGACTTTTTAGAAGCTAAAGGATATAAGGAAGTTAAAAAAGACTTAAT
CATTAAACTACCTAAATATAGTCTTTTTGAGTTAGAAAACGGTCGTAAACGGATGCTGGCTAGTGCC
GGAGAATTACAAAAAGGAAATGAGCTGGCTCTGCCAAGCAAATATGTGAATTTTTTATATTTAGCTA
GTCATTATGAAAAGTTGAAGGGTAGTCCAGAAGATAACGAACAAAAACAATTGTTTGTGGAGCAGCA
TAAGCATTATTTAGATGAGATTATTGAGCAAATCAGTGAATTTTCTAAGCGTGTTATTTTAGCAGAT
GCCAATTTAGATAAAGTTCTTAGTGCATATAACAAACATAGAGACAAACCAATACGTGAACAAGCAG
AAAATATTATTCATTTATTTACGTTGACGAATCTTGGAGCTCCCGCTGCTTTTAAATATTTTGATAC
AACAATTGATCGTAAACGATATACGTCTACAAAAGAAGTTTTAGATGCCACTCTTATCCATCAATCC
ATCACTGGTCTTTATGAAACACGCATTGATTTGAGTCAGCTAGGAGGTGACTGATGGCCGGTCCGAC
TATATGATTTTCCGCAGTATATTTTAGATGAAGATTATTTCTTAATAACTAAAAATATGGTATAATA
CTCTTAATAAATGCAGTAATACAGGGGCTTTTCAAGACTGAAGTCTAGCTGAGACAAATAGTGCGAT
TACGAAATTTTTTAGACAAAAATAGTCTACGAGGTTTTAGAGCTATGCTATTTTGAATGGTCCCAAA
ACACTTTAAAAGTGCTCATCATGTTTTAGAGCTATGCTGTTTTGAATGGTCCCAAAACAACATTGCC
GATGATAACTTGAGAAAGAGGGTTAATACCAGCAGTCGGATACCTTCCTATTCTTTCTGTTAAAGCG
TTTTCATGTTATAATAGGCAAAAGAAGAGTAGTGTGATGGAACATACATTTTTTCGGACCGCCTAGG

-continued

AGTGCGGTTGGAACGTTGGCCCAGCCAGATACTCCCGATCACGAGCAGGACGCCGATGATTTGAAGC
GCACTCAGCGTCTGATCCAAGAACAACCATCCTAGCAACACGGCGGTCCCCGGGCTGAGAAAGCCCA
GTAAGGAAACAACTGTAGGTTCGAGTCGCGAGATCCCCCGGAACCAAAGGAAGTAGGTTAAACCCGC
TCCGATCAGGCCGAGCCACGCCAGGCCGAGAACATTGGTTCCTTGTAGGCATCGGGATTGGCGGATC
AAACACTAAAGCTACTGGAACGAGCAGAAGTCCTCCGGCCGCCAGTTGCCAGGCCGTAAAGGTGAGC
AGAGGCACGGGAGGTTGCCACTTGCGGGTCAGCACGGTTCCGAACGCCATGGAAACCGCCCCCGCCA
GGCCCGCTGCGACGCCGACAGGATCTAGCGCTGCGTTTGGTGTCAACACCAACAGCGCCACGCCCGC
AGTTCCGCAAATAGCCCCCAGGACCGCCATCAATCGTATCGGGCTACCTAGCAGAGCGGCAGAGATG
AACACGACCATCAGCGGCTGCACAGCGCCTACCGTCGCCGCGACCCGCCCGGCAGGCGGTAGACCGA
AATAAACAACAAGCTCCAGAATAGCGAAATATTAAGTGCGCCGAGGATGAAGATGCGCATCCACCAG
ATTCCCGTTGGAATCTGTCGGACGATCATCACGAGCAATAAACCCGCCGGCAACGCCCGCAGCAGCA
TACCGGCGACCCCTCGGCCTCGCTGTTCGGGCTCCACGAAAACGCCGGACAGATGCGCCTTGTGAGC
GTCCTTGGGGCCGTCCTCCTGTTTGAAGACCGACAGCCCAATGATCTCGCCGTCGATGTAGGCGCCG
AATGCCACGGCATCTCGCAACCGTTCAGCGAACGCCTCCATGGGCTTTTTCTCCTCGTGCTCGTAAA
CGGACCCGAACATCTCTGGAGCTTTCTTCAGGGCCGACAATCGGATCTCGCGGAAATCCTGCACGTC
GGCCGCTCCAAGCCGTCGAATCTGAGCCTTAATCACAATTGTCAATTTTAATCCTCTGTTTATCGGC
AGTTCGTAGAGCGCGCCGTGCGCCCGAGCGATACTGAGCGAAGCAAGTGCGTCGAGCAGTGCCCGCT
TGTTCCTGAAATGCCAGTAAAGCGCTGGCTGCTGAACCCCCAGCCGGAACTGACCCCACAAGGCCCT
AGCGTTTGCAATGCACCAGGTCATCATTGACCCAGGCGTGTTCCACCAGGCCGCTGCCTCGCAACTC
TTCGCAGGCTTCGCCGACCTGCTCGCGCCACTTCTTCACGCGGGTGGAATCCGATCCGCACATGAGG
CGGAAGGTTTCCAGCTTGAGCGGGTACGGCTCCCGGTGCGAGCTGAAATAGTCGAACATCCGTCGGG
CCGTCGGCGACAGCTTGCGGTACTTCTCCCATATGAATTTCGTGTAGTGGTCGCCAGCAAACAGCAC
GACGATTTCCTCGTCGATCAGGACCTGGCAACGGGACGTTTTCTTGCCACGGTCCAGGACGCGGAAG
CGGTGCAGCAGCGACACCGATTCCAGGTGCCCAACGCGGTCGGACGTGAAGCCCATCGCCGTCGCCT
GTAGGCGCGACAGGCATTCCTCGGCCTTCGTGTAATACCGGCCATTGATCGACCAGCCCAGGTCCTG
GCAAAGCTCGTAGAACGTGAAGGTGATCGGCTCGCCGATAGGGGTGCGCTTCGCGTACTCCAACACC
TGCTGCCACACCAGTTCGTCATCGTCGGCCCGCAGCTCGACGCCGGTGTAGGTGATCTTCACGTCCT
TGTTGACGTGGAAAATGACCTTGTTTTGCAGCGCCTCGCGCGGGATTTTCTTGTTGCGCGTGGTGAA
CAGGGCAGAGCGGGCCGTGTCGTTTGGCATCGCTCGCATCGTGTCCGGCCACGGCGCAATATCGAAC
AAGGAAAGCTGCATTTCCTTGATCTGCTGCTTCGTGTGTTTCAGCAACGCGGCCTGCTTGGCCTCGC
TGACCTGTTTTGCCAGGTCCTCGCCGGCGGTTTTTCGCTTCTTGGTCGTCATAGTTCCTCGCGTGTC
GATGGTCATCGACTTCGCCAAACCTGCCGCCTCCTGTTCGAGACGACGCGAACGCTCCACGGCGGCC
GATGGCGCGGGCAGGGCAGGGGGAGCCAGTTGCACGCTGTCGCGCTCGATCTTGGCCGTAGCTTGCT
GGACCATCGAGCCGACGGACTGGAAGGTTTCGCGGGGCGCACGCATGACGGTGCGGCTTGCGATGGT
TTCGGCATCCTCGGCGGAAAACCCCGCGTCGATCAGTTCTTGCCTGTATGCCTTCCGGTCAAACGTC
CGATTCATTCACCCTCCTTGCGGGATTGCCCCGACTCACGCCGGGGCAATGTGCCCTTATTCCTGAT
TTGACCCGCCTGGTGCCTTGGTGTCCAGATAATCCACCTTATCGGCAATGAAGTCGGTCCCGTAGAC
CGTCTGGCCGTCCTTCTCGTACTTGGTATTCCGAATCTTGCCCTGCACGAATACCAGCGACCCCTTG
CCCAAATACTTGCCGTGGGCCTCGGCCTGAGAGCCAAAACACTTGATGCGGAAGAAGTCGGTGCGCT
CCTGCTTGTCGCCGGCATCGTTGCGCCACTCTTCATTAACCGCTATATCGAAAATTGCTTGCGGCTT

-continued

GTTAGAATTGCCATGACGTACCTCGGTGTCACGGGTAAGATTACCGATAAACTGGAACTGATTATGG

CTCATATCGAAAGTCTCCTTGAGAAAGGAGACTCTAGTTTAGCTAAACATTGGTTCCGCTGTCAAGA

ACTTTAGCGGCTAAAATTTTGCGGGCCGCGACCAAAGGTGCGAGGGGCGGCTTCCGCTGTGTACAAC

CAGATATTTTTCACCAACATCCTTCGTCTGCTCGATGAGCGGGGCATGACGAAACATGAGCTGTCGG

AGAGGGCAGGGGTTTCAATTTCGTTTTTATCAGACTTAACCAACGGTAAGGCCAACCCCTCGTTGAA

GGTGATGGAGGCCATTGCCGACGCCCTGGAAACTCCCCTACCTCTTCTCCTGGAGTCCACCGACCTT

GACCGCGAGGCACTCGCGGAGATTGCGGGTCATCCTTTCAAGAGCAGCGTGCCGCCCGGATACGAAC

GCATCAGTGTGGTTTTGCCGTCACATAAGGCGTTTATCGTAAAGAAATGGGGCGACGACACCCGAAA

AAAGCTGCGTGGAAGGCTCTGACGCCAAGGGTTAGGGCTTGCACTTCCTTCTTTAGCCGCTAAAACG

GCCCCTTCTCTGCGGGCCGTCGGCTCGCGCATCATATCGACATCCTCAACGGAAGCCGTGCCGCGAA

TGGCATCGGGCGGGTGCGCTTTGACAGTTGTTTTCTATCAGAACCCCTACGTCGTGCGGTTCGATTA

GCTGTTTGTCTTGCAGGCTAAACACTTTCGGTATATCGTTTGCCTGTGCGATAATGTTGCTAATGAT

TTGTTGCGTAGGGGTTACTGAAAAGTGAGCGGGAAAGAAGAGTTTCAGACCATCAAGGAGCGGGCCA

AGCGCAAGCTGGAACGCGACATGGGTGCGGACCTGTTGGCCGCGCTCAACGACCCGAAAACCGTTGA

AGTCATGCTCAACGCGGACGGCAAGGTGTGGCACGAACGCCTTGGCGAGCCGATGCGGTACATCTGC

GACATGCGGCCCAGCCAGTCGCAGGCGATTATAGAAACGGTGGCCGGATTCCACGGCAAAGAGGTCA

CGCGGCATTCGCCCATCCTGGAAGGCGAGTTCCCCTTGGATGGCAGCCGCTTTGCCGGCCAATTGCC

GCCGGTCGTGGCCGCGCCAACCTTTGCGATCCGCAAGCGCGCGGTCGCCATCTTCACGCTGGAACAG

TACGTCGAGGCGGGCATCATGACCCGCGAGCAATACGAGGTCATTAAAAGCGCCGTCGCGGCGCATC

GAAACATCCTCGTCATTGGCGGTACTGGCTCGGGCAAGACCACGCTCGTCAACGCGATCATCAATGA

AATGGTCGCCTTCAACCCGTCTGAGCGCGTCGTCATCATCGAGGACACCGGCGAAATCCAGTGCGCC

GCAGAGAACGCCGTCCAATACCACACCAGCATCGACGTCTCGATGACGCTGCTGCTCAAGACAACGC

TGCGTATGCGCCCCGACCGCATCCTGGTCGGTGAGGTACGTGGCCCCGAAGCCCTTGATCTGTTGAT

GGCCTGGAACACCGGGCATGAAGGAGGTGCCGCCACCCTGCACGCAAACAACCCCAAAGCGGGCCTG

AGCCGGCTCGCCATGCTTATCAGCATGCACCCGGATTCACCGAAACCCATTGAGCCGCTGATTGGCG

AGGCGGTTCATGTGGTCGTCCATATCGCCAGGACCCCTAGCGGCCGTCGAGTGCAAGAAATTCTCGA

AGTTCTTGGTTACGAGAACGGCCAGTACATCACCAAAACCCTGTAAGGAGTATTTCCAATGACAACG

GCTGTTCCGTTCCGTCTGACCATGAATCGCGGCATTTTGTTCTACCTTGCCGTGTTCTTCGTTCTCG

CTCTCGCGTTATCCGCGCATCCGGCGATGGCCTCGGAAGGCACCGGCGGCAGCTTGCCATATGAGAG

CTGGCTGACGAACCTGCGCAACTCCGTAACCGGCCCGGTGGCCTTCGCGCTGTCCATCATCGGCATC

GTCGTCGCCGGCGGCGTGCTGATCTTCGGCGGCGAACTCAACGCCTTCTTCCGAACCCTGATCTTCC

TGGTTCTGGTGATGGCGCTGCTGGTCGGCGCGCAGAACGTGATGAGCACCTTCTTCGGTCGTGGTGC

CGAAATCGCGGCCCTCGGCAACGGGGCGCTGCACCAGGTGCAAGTCGCGGCGGCGGATGCCGTGCGT

GCGGTAGCGGCTGGACGGCTCGCCTAATCATGGCTCTGCGCACGATCCCCATCCGTCGCGCAGGCAA

CCGAGAAAACCTGTTCATGGGTGGTGATCGTGAACTGGTGATGTTCTCGGGCCTGATGGCGTTTGCG

CTGATTTTCAGCGCCCAAGAGCTGCGGGCCACCGTGGTCGGTCTGATCCTGTGGTTCGGGGCGCTCT

ATGCGTTCCGAATCATGGCGAAGGCCGATCCGAAGATGCGGTTCGTGTACCTGCGTCACCGCCGGTA

CAAGCCGTATTACCCGGCCCGCTCGACCCCGTTCCGCGAGAACACCAATAGCCAAGGGAAGCAATAC

CGATGATCCAAGCAATTGCGATTGCAATCGCGGGCCTCGGCGCGCTTCTGTTGTTCATCCTCTTTGC

CCGCATCCGCGCGGTCGATGCCGAACTGAAACTGAAAAAGCATCGTTCCAAGGACGCCGGCCTGGCC

GATCTGCTCAACTACGCCGCTGTCGTCGATGACGGCGTAATCGTGGGCAAGAACGGCAGCTTTATGG

-continued

CTGCCTGGCTGTACAAGGGCGATGACAACGCAAGCAGCACCGACCAGCAGCGCGAAGTAGTGTCCGC

CCGCATCAACCAGGCCCTCGCGGGCCTGGGAAGTGGGTGGATGATCCATGTGGACGCCGTGCGGCGT

CCTGCTCCGAACTACGCGGAGCGGGGCCTGTCGGCGTTCCCTGACCGTCTGACGGCAGCGATTGAAG

AAGAGCGCCGGCGGCATTTCGAGAGCCTGGGAACGATGTACGAGGGCTATTTCGTCCTCACCTTGAC

CTGGTTCCCGCCGCTGCTCGCCCAGCGCAAGTTCGTCGAGCTGATGTTTGACGACGACGCGACCGCA

CCGGATCGCAAGGCGCGCACGCGGGGCCTCATCGACCAATTCAAGCGTGACGTGCGCAGCATCGAGT

CGCGCCTGTCGTCGGCCGTGTCGCTCACTCGCTTGAAGGGGCACAAGATCGTCAACGAGGACGGCAC

GACCGTCACGCATGACGACTTCCTGCGCTGGCTGCAATTCTGCGTGACGGGCCTGCACCATCCGGTG

CAGCTCCCCAGCAACCCGATGTACCTGGACGCCCTGGTCGGCGGACAGGAAATGTGGGGCGGGGTAG

TGCCCAAGGTCGGCCGCAAGTTCGTCCAGGTGGTCGCTCTCGAAGGCTTCCCCTTGGAGTCCTATCC

CGGCATCCTGACGGCGCTCGGCGAGCTGCCCTGCGAGTATCGGTGGTCGAGCCGGTTCATCTTCATG

GACCAGCACGAAGCCGTGAAGCACCTCGACAAGTTCCGCAAGAAGTGGCGGCAGAAGATTCGCGGCT

TCTTCGACCAGGTGTTCAACACGAACACCGGCCCGGTCGATCAGGACGCGCTTTCGATGGTGGCCGA

TGCTGAGGCGGCCATTGCCGAAGTCAACAGCGGCATCGTGGCCGTGGGCTACTACACCAGCGTCGTC

GTGCTGATGGATGAGGACCGCACGCGCCTGGAAGCTGCGGCCCGCGATGTTGAAAAGGCCGTCAACC

GGTTGGGCTTTGCCGCGCGCATCGAGTCCATCAACACCCTGGACGCCTTCCTTGGTAGTTTGCCGGG

CCACGGCGTGGAAAACGTCCGCCGGCCGCTCATCAACACGATGAACCTGGCCGACCTGCTGCCGACC

AGCACCATCTGGACCGGCAACGCGAACGCGCCATGCCCGATGTACCCGCCGCTGTCGCCGGCGCTCA

TGCACTGCGTCACGCAAGGATCAACGCCGTTCCGGCTGAACCTGCACGTGCGCGACCTCGGCCACAC

CTTTATGTTCGGGCCGACCGGCGCAGGTAAATCGACGCACCTGGCGATCCTCGCCGCGCAGCTCCGT

CGCTATGCCGGCATGTCGATCTTCGCCTTTGACAAGGGCATGTCGATGTACCCGCTGGCCGCCGGCA

TCCGTGCGGCCACGAAGGGCACCAGCGGCCTGCACTTCACCGTGGCGGCCGACGACGAACGCCTGGC

GTTCTGCCCGTTGCAGTTCCTGAGCACCAAGGGCGACCGTGCTTGGGCGATGGAGTGGATCGACACC

ATCCTGGCGTTGAACGGCGTCGAAACGACCCCGGCCCAGCGCAACGAAATCGGCAACGCGATCATGA

GCATGCACGCCAGCGGCGCGCGCACGCTCTCCGAGTTCAGCGTGACGATTCAGGATGAGGCGATCCG

CGAGGCGATCCGCCAGTACACCGTCGATGGCGCAATGGGCCATCTGCTCGACGCCGAAGAGGACGGC

TTGGCGCTGTCCGACTTTACAGTGTTCGAGATCGAAGAGCTGATGAACCTCGGCGAGAAATTCGCCC

TGCCTGTGTTGCTCTACCTGTTCCGCCGTATCGAGCGCGCCCTGACGGGCCAGCCGGCCGTCATCAT

CCTGGACGAAGCCTGGTTGATGCTCGGCCACCCGGCATTCCGCGCGAAGATCAGGGAATGGCTCAAG

GTGCTGCGTAAGGCCAACTGCCTTGTGCTGATGGCAACGCAGAGCCTGTCCGACGCCGCCAACAGCG

GCATCCTGGACGTGATCGTGGAATCGACCGCGACCAAGATTTTCCTGCCGAATATTTACGCCAGGGA

TGAGGACACGGCGGCCCTGTACCGCCGCATGGGCCTGAACGCTCGCCAGATCGAGATTCTGGCCCAG

GCCGTTCCCAAGCGTCAGTACTACTACGTGTCGGAAAACGGCCGCCGTCTCTACGACCTGGCACTTG

GCCCGCTCGCGCTCGCGTTCGTCGGCGCATCCGACAAGGAATCCGTCGCCATCATCAAGAACCTGGA

AGCCAAGTTCGGCGACCAGTGGGTGGATGAATGGCTGCGTGGCCGGGGCCTCGCCCTTGATGAATAC

CTGGAGGCAGCATGAGTTTTGCAGACACGATCAAGGGCTTGATCTTCAAGAAGAAGCCCGCAACGGC

CGCAGCAGCGGCGACGCCGGCCGCGACCGGCCCGCAAACCGACAACCCGTACCTGACGGCGCGGCGC

ACCTGGAACGACCACGTTGGTTCCGTTGTGTCGCAAAAGCAGACCTGGCAGGTTGTCGGCATCCTTT

CGCTGATGATCGTCCTCGCGGCGGTCGGCGGCATCATCCACATCGGCAGCCAGTCGAAGTTCGTGCC

CTATGTCTACGAGGTAGACAAGCTCGGGCAGACGGCCGCCGTGGGGCCGATGACCAGGGCGTCGAAA

-continued

GCCGATCCGCGTGTCATTCACGCCTCGGTGGCTGAGTTCGTCGGCGATGCTCGCCTGGTGACGCCGG

ACGTAGCTTTGCAGCGCAAGGCCGTCTACCGCCTCTATGCCAAGCTCGGGCCGAATGACCCGGCCAC

CGCCAAGATGAACGAATGGCTCAACGGCACCGCCGACGCCAGCCCGTTCGCTCGCGCGGCCGTCGAA

ACGGTCAGCACCGAAATCACTTCCGTAATCCCGCAGACGCCCGACACCTGGCAGGTCGATTGGGTCG

AGACGACGCGCGACAGGCAAGGCGTGGTGAAAGGCCAGCCCGTGCGCATGCGGGCCTTGGTGACGGT

CTACGTCGTCGAGCCGACGGCGGACACCAAGGAAGAACAACTGCGAAACAACCCGGCCGGGATCTAC

GTCCGGGACTTCTCCTGGTCGAGACTTCTGTGAGGCACTGAATTATGAAAAAGGAACTGTTTGCTTT

GGTCCTGGCCGCGTCCGTTAGCGTGCCTGCATTTGCCGCCGATCCCGGCGCGGACCTGACTGACCTC

TATTTTTCCGGCAAGAACCCGGAGCTGACCGCGCAAGAGCGGGCGGCCATCGCCATCGCCAAGAAGT

GGGAGGCGGGTACCGCCGGCATGCGGCCGGTGGCCGGCCCCGGTGGTTCGGTGCGCTTCCTGTTCGG

CGCGCAGCAGCCGAGCATCGTATGCGCCGTGCTGCAAGTGTGCGACGTGGCCCTGCAACCCGGCGAG

CAAGTCAACTCGATCAACCTGGGCGACACCGCCCGTTGGACGGTCGAGCCGGCCATTACCGGCAGCG

GCGCGAACGAAACCCAGCACCTCATCATCAAGCCGATGGATGTGGGCCTGGAAACCAGCCTGGTCGT

GACCACGGACCGCCGCAGCTACCACATGCGCCTGCGCTCGCATCGCACGCAGTACATGCCGCAGGTG

TCGTTCACCTACCCGGAAGATGCCCTTGCGAAGTGGGACGCCATCAAGAACCGCGAACAGCGGGATC

GCGTCGAGAAAACCATTCCGCAGACCGGCGAGTACCTGGGCAACCTGAGCTTCAACTACTCCGTCAG

CGGGTCCACGTCGTGGAAGCCGGTGCGCGTCTACAACGACGGCAAGAAAACCATCATCCAGATGCCG

CACTCGATGGAACAGACCGAAGCGCCGACGCTCCTGGTCGTTCGCAGGGAGGGCGGCCTGTTCTCCG

ACGATGAAACGGTGATGGTCAACTACCGGGTCCAGGGCGACCGCTACATCGTCGATACGATTTTCGA

CAAGGCCATCCTCATCGCGGGCGTGGGCAGCAGCCAGGACCGCGTGACCATTTCAAGGGGGAACTAA

ACCATGCGTAAGATTCTGACCGTCATCGCACTCGCGGCCACGTTGGCCGGCTGCGCGACCTCCAAGT

ACGGCAGCTTCGTCCAGGACGCGCCGGCCGCCTACAACCAGACCATTGCGACCGACGCGGTGAAGCA

GCTCGTCAAGCTCTACCCGCCGGCGCAAACCAAGCTGGAATTGCAGCAGGCTACGCCCGATCCGTTC

GGCATTGCCCTGGTCACTGACCTTCGCGCCCAGGGCTATGCTGTCATGGAGTACAAGCCCGACGGCA

ACGCGGCCGCAGCTCCGGCTGCTGCGTCCTCGGCCGCTGCGAAGCCGGCAACGCCGCAAGCCCAGGG

CGGCTATCCGCTGCGCTACGTGCTGGACCAATTCAGCGACAGCAACCTGTATCGCCTGACCGTCATG

GTCGGCTCTCAATCGCTCACGCGCGCCTACCTCGCCCAAAACAACACGATGGTCCCGGCCGGCGCAT

GGGTTCGGAAGGAGTAAGCCAATGAGCGAAGATCAAATGGCACCGGACGCATCGCCAGATGCGGTCA

AGCCGAAAAGCGGGGTTCGCCGCGTCAACAACATGCCGATGTACCTCATCGGCGGTGTGCTCGGCAT

CTTCCTGCTGGTGATGGCCCTGGTTGCTGCGGATCGCGCTGCGCAGCAGAACCAGCCGGGAGCTGCG

AAGGCTGAGAAGGCCGGCAGCACCAGCATGTTTGCCGACGAAATTGCCGGCAAACAGCAGGACGGCA

TCATCAAGGCCAAGCCGCTGGAGATTCCGCCGGAACAAACCGCCCAGCAACCGACGACGGAGCTGAC

GCCAGCCCCGGCGCAGGGAACGACTATCACGGTCGCACGGCCCGAGAACCTGGACCAGCCCCCGACG

CCGCCGCAGGGTGCGCGCAACGAGGACCTGGACCGCATCCGCATGGCGAAGTTGCAGATGCTGGAAG

AGGCGATCAAGGCCAAGACGACGGTGCGCATCGACGCGCCGCGCAGCCAGGGCAGCGCCGGCGGCGG

TGCTCCGCAGGGCCGCGAGGAAACCCTTGCGCGCATCCAGGAGCTGCGTCGGCAGGCTGAGAACGCC

CGCGCCACCGATCCGACCGCCGCCTATCAGGCCGCGCTTGCGCAGGCTCGCACGATGGGCGGCGCGG

CAGGGGGTGGCGGTATGGGCGGCTCGGGTGCGCCGACCCTCGTGCAGACCTCGAACCGCAGTGGTGG

CGGCGCTGGCTATGGGTCGTTCGACAACCGCAGCGAGGGCGACCGTTGGCGGCTCGACTCCCAGCCG

GAAGCACCTGCAACGCCCTATGTGCTGCGCGCTGGCTTCGTCGTTCCGGCTACGCTTATCTCGGGCA

TCAACTCCGATCTGCCAGGCCAAATCATGGCCCAGGTATCGCAGTCGGTGTACGACACGGCGACCGG

-continued

CAAGCACATGCTCATCCCCCAAGGCTCGCGCCTGGTGGGCAGCTACTCGAACGATGTGGCCTACGGG

CAGAAGCGCGTTCTGGTGGCATGGCAGCGCATCATCTTCCCCGACGGCAAGGCAATGGACATTGGGG

CCATGCCGGGCGGCGATAGCGCTGGGTATGCAGGCTTCAACGACAAGGTCAACAACCACTACTTCCG

CACCTTCGCATCGGCATTCCTCATGTCGGGCGTCGTTGCGGGCATCAGCTTGAGTCAGGACCGTGGC

AACAGCAACAGCGGTTACGGACGACAAGACGCGGGTTCCGCGATGAGTGAAGCGTTGGGTCAACAGC

TCGGCCAAGTAACGGCGCAGATGATCGCCAAAAACTTGAATATCGCGCCGACGCTGGAAATCCGTCC

GGGCTATCGCTTCAACGTCATTGTCACGAAAGACATGACGTTTTCTAAGCCCTACCAGGCGTTTGAC

TATTAACTCCAAGGAGTAACTTATGAAGAAGCTCGCTAAGAATGTTTTAGCCGCTAAAGTAGCTCTG

GTGCTGGCCCTCTCGGTCGGCACCTTGGCGGTCACGCCTGCGCAAGCGGGCATTCCGGTCATCGACG

GCACCAACCTGTCACAAACCACTGTCACCGCGATTCAGCAGGTTGCGCAGGTCCAGAAGCAAATCGA

GGAATACCGGACGCAGTTGCAGCAGTACGAAAACATGCTGCAAAACACGGTGGCCCCGGCCGCCTAC

GTGTGGGACCAGGCGCAGTCCACCATCAACGGCCTGATGAGCGCCGTTGATACCCTGAACTACTACA

AGAACCAGGCGGGCAGCATCGACGCTTACCTGGGCAAGTTCAAGGACGTGTCCTACTACAAGGGGTC

GCCGTGCTTCTCCCTGTCGGGCTGCTCGGAAAGCGAGCGCAAGGCGATGGAAGAGAACCGCCGCCTG

GCGTCCGAATCGCAGAAAAAGGCCAACGATGCGCTGTTCCGTGGCCTCGATCAGCAGCAGAGCAACC

TCAAGTCCGACGCCGCCACGCTGGAGCAATTGAAGGGCAAGGCGACGACGGCGCAGGGCCAGTTGGA

AGCCCTCGGCTACGCCAACCAGTTCGCCAGCCAGCAGGCCAACCAGCTCATGCAAATCCGTGGCCTT

CTGCTTGCGCAGCAGAACGCCATCGCCACGCAGATGCAGGCCCAGCAGGACCGGCAGGCCCAGCAGG

ACGCTGCGGGCGCGAAGCTGCGCGAGGGTTCGTACCGCGCAAGCCCGTCTAAGACCTGGTGAGGGGA

GGCGCGATGAAGAAATCCAACTTCATCGCAGTTGCCGCGCTGGCCGCCGTCATGGCGGCCAGCCTGG

CAGGCTGCGACAACAAGCCCGACACCGACAAGCTGACCTGCGCCGATCTGCCGAAGGTCACGGATGC

CGCTCAACGCGCGGAGCTGTTGAAGAAGTGCCCGCGCGGAGAACCGGGAGGCTTCAAGCCCAGCGAA

AAGAAAGAGTGGTGATGACGTATGAAAATCCAGACTAGAGCTGCCGCGCTCGCGGTCCTGATGCTGG

CCTTGATGCCGGTAGCGGCATACGCCCAAATCGACAATTCGGGCATCCTCGACAACGTATTGCAGCG

CTACCAGAACGCCGCGAGCGGCTGGGCCACTGTCGTCCAGAACGCCGCAACCTGGCTGTTCTGGACC

TTGACCGTGATTAGCATGGTCTGGACCTTCGGCATGATGGCACTGCGCAAGGCCGACATTGGCGAGT

TCTTCGCCGAGTTCGTGCGGTTCACCATCTTCACCGGCTTCTTCTGGTGGCTGCTGACCAACGGCCC

GAATTTCGCGTCGTCCATCTATGCGTCCCTGCGGCAGATTGCAGGCCAGGCAACGGGGTTGGGGCAG

GGGCTTTCGCCGTCCGGCATCGTCGATGTTGGCTTCGAGATTTTCTTCAAGGTGATGGACGAAACCT

CGTACTGGTCGCCGGTCGATAGCTTCGTCGGTGCCTCGTTGGCGGCCGCCATCCTCTGCATCCTGGC

CCTGGTCGGCGTGAATATGCTTCTGCTCCTGGCGTCCGGATGGATTCTTGCCTACGGCGGTGTGTTC

TTCCTGGGCTTCGGCGGCTCGCGCTGGACCTCGGACATGGCGATCAACTACTACAAGACCGTCCTCG

GGGTCGCCGCGCAGCTCTTCGCAATGGTGCTGCTCGTAGGCATCGGCAAGACCTTCCTCGATGACTA

CTACAGCCGCATGAGCGAAGGCATCAACTTCAAGGAACTTGGAGTGATGCTGATCGTCGGCCTGATC

CTGCTCGTTCTGGTCAACAAGGTGCCGCAGCTCATCGCCGGCATCATCACCGGCGCGAGCGTCGGCG

GTGCTGGTATCGGCCAGTTCGGCGCTGGCACGCTCGTCGGTGCGGCCGCGACGGCCGGCGCGGCAAT

CGCAACTGGCGGCGCATCTATCGCGGCCGGCGCTGCGGCGGCGGCCGGTGGCGCGCAGGCCATCATG

GCGGCCGCGTCGAAGGCCAGCGATAACGTCTCTGCCGGCACTGACATTCTGTCGAGCATGATGGGCG

GCGGCGGTGGCGGCGGCGGTGGTAGCGCCGGCACCAGCGGCGGCGACGGCGGCGGCTCGGGTGGCGG

CGGTGGCTCGGGCGGCGGTGAAACCCCGATGGCCTCGGCCGCCGGCGACAACAGCAGCGGCGCACGC

-continued

GGCGGCAGTTCGGGCGGCGGCTCGGGTGGTGGCCGTTCGTCTGGCGGTATCGGTGCCACGGCGGCCA

AGGGCGGCCGGATCGCGGCCGATACCGTCGCCAACCTGGCGAAAGGTGCCGGCTCGATTGCCAAGGC

CAAGGCCGGCGAAATGCGCGCATCGGCCCAGGAACGCATCGGCGATACCGTAGGCGGCAAGATCGCG

CAGGCAATTCGCGGCGCGGGTGCGGCGGCGCAGACCGCTGCAACCGTCGCCGATAGCAACAGCCAGG

CGCAGGAACAACCTGCACCGGCACCCGCACCGTCGTTCGACGACAACAGCCTTTCCGCAAGCAACAA

CAGGGAAGCGGCCGCCGACGCGGATTCCGAAGTGGCGAGCTTCGTCAACAAGCCCGCCCAATCCTGA

AACGACTCTTAGGAGCTACGACCATGCAACTGAAAAAAGCGTTCTCGTCGGCCGCCCTGGTGGTGGC

CTTGGGCCTCGGCGCAACTGGCTCGGCCAGCGCGCAAGACGTGCTGACGGGCGATACCCGCCTGGCC

TGCGAGGCCATTCTGTGCCTGTCCACGGGCAGCCGGCCCAGCGAGTGCAGCCCGTCGCTCTCGCGGT

ACTTCGGCATCCACAAGCGCAAGCTGTCGGACACGCTCAAGGCGCGGCTGAACTTCCTCAACCTCTG

CCCGGTATCGAACCAGACGCCGGAAATGCAGACGCTCGTTTCCTCGATTTCGCGCGGGGCCGGGCGC

TGCGATGCGTCCTCGCTGAACTCCGTGCTGCGTGAGTGGCGGAGCTGGGACGACCAGTTCTACATCG

GCAACCGCCTGCCGGACTACTGCGCGGCCTACACCGGCCATGCCTATACCGACTTCAACACGACCGC

GCCGCGCTACGTCGGCACGCCGGAAGAGGGCGGCTATTGGATCGAGGCGGCCGACTACGACCGCGCG

CTCAAGGAGTACGAGGCGAAGCTGAAAGAGCGGCAGCAGCAGTACGGTCGCTATGGCAGCGACGCCT

ACCGTCGGTTCGAGCGGTAAGGGGAGGGGATAGCGATGCCGTTTGCCAAGCTGCTGGCACGGAACGC

TCTGCCGGTGGTCGCCCTGGTGGCGGCCACTGGCTTCGGTGCGGCGGATGCGACCGCCGCACGGCTC

TTCCCCGATCTGTCGGAACAGATGGAAGAGCGCGTTGTGTGCTCGGTGTCTGCGGCCGCGAAGTACG

AGATTCCGGCCAACATTCTTCTCGCCATTCGGGAAAAGGAGGGCGGCAAGCCGGGCCAGTGGGTCAA

GAACACCAATGGCACCTATGACGTGGGCGAGCTGCAATTCAACACCGCCTACCTGGGCGACCTGGCG

AAGTATGGGATCACGGCCCAGGACGTTGCTGCGGCAGGCTGCTATCCCTATGACCTGGCGGCCTGGC

GGTTGCGCGGGCACATTCGCAACGACAGGGGCGATCTGTGGACACGCGCCGCTAACTATCACTCGCG

CACGCCGTCGAAGAACGCGATCTATCGCGCCGATCTGATGGTGAAGGCCGACAAGTGGGCGAAGTGG

CTGGATGCGCGTTTCGTCACCGTCAACTATGGCCCCAGCTCGCCGGCGCAGCCGGCAGGGAAGGGGA

CCACACTTGCGGCCGCTGATACGTCGGCAGCAGCGCCGGCCGAAGCGCAGCCGATGAAGCAAGGCCG

GATCACCCGCACCAGCCTCCGCAGCTCGGGTTACGTACCCCGGCAGCTCATCATCAACAACACGCCA

TAAGGAGGAACGGCCGTTTAGCGGCTAAAGCCTATGGGCATTCGCAACCTGACGCAGCGATACATGA

ACGGGGCCAGGGCCTACGCGGCCTGGGCGGCATCGCAGGCGAAAGCGCCGTTTGATCTTCTGGTACT

GGGCATCGGGCCTGTCATCGTCTTTGGCCTGGTCGCGCATACGCTGCTCGCGTTCCTGCCCACATGG

GCCATGTACGCCGCCGGCGCTCTGCTGGTCCTCGCGGCCCTGCCTTTGGCGCTGCACGTCCTCCGGG

AATACGCGCTGCGCTATGGGCGCAAATAGCGCCCTGCAGGGCGTTCTTACTCCAAGGGGGAGGGCAT

GAATACACGCGCCATGAACGACGCCAGCGGCCGGGCCTCGCTGCCTGCCATGGTGATCGCCGACGGC

ACCATTGAAGCCTTGAAGTGGCTCGCCTTGCTTCCCATGACCGGGGATCACGTCAACAAGTACCTGT

TCAACGGTACGCTGCCATATCTGTTCGAGGCGGGGCGCTTGGCCCTGCCTCTTTTCGTTTTCGTCCT

GGCGTACAACCTCGCCCGCCCGGGCGCGCTCGAGCGCGGTTTGTACGGGCGAGCGATGAAACGCCTG

TTGGCCTTCGGCCTGGTCGCCTCGGTCCCGTTCATTGCGTTGGGTGGAGTGGTGGGCGGATGGTGGC

CGCTGAACGTCATGTTCACGCTGTTGGCCGCAACCGCGATGCTCTACCTGGTCGAGCGCGGCCGCTC

GGTCGCTCCTATAGCGCTGTTCGTCGTGGCCGGCGGCCTGGTCGAGTTCTGTTGGCCGGCGCTGCTG

CTGGCCGCGTCTGTCTGGTTGTACCTCAAGCGCCCGACGTGGGCGGCCGCGTTGATGGCGCTGCTGT

CTTGCGCGTCCCTGTGGTACATCAATGGCAACCTTTGGGCGCTTGCTGTTGTGCCCCTGGTGATCGT

CGCCGCCGGCGTCGATCTTCGTGTCCCGCGCCTGCGCTGGGCCTTTTACACGTACTACCCGCTGCAT

-continued

CTTGCCGCTCTTTGGCTGATCCGCATTCCGATGCGCGAGGCGGGCTACTTGTTTTTCACCTGACCTT
TGAGATTCCAATATGCAATTGCTCAAGAAATGCACCATCGCGGCCCTGCCGCTGCTCGCCCTGTCCG
GCTGCGCACTGCTGAACATCCCCATGCCGACGCCGCCCGGTTCGACCCCGCCGGAAATGCTGACCGT
GCCAGTGGCGCAAATCTGCCGCGACGCTGACAAGAACCCTGTTCGGGCAACGGAGCTGTACGGCAAG
AAAGGGTTGTCGGCCACCGGCAAGGTGCAGGTGATTTCCGAAGGCTTCAAGCCTCGCTATCGGGTGC
TGCTGCCGCCTGGCAGCGCCTCGGTCCATGCTGGGACCGATAACCAGCTCGCCATCAAGTCGGTTTC
CACCGGCCAGACCACGCGCGTCACTGGCACCGTGAAGGACGTGTCCTACGACCATAACGGCTGCTCG
ATCTCGCTTGACGATGCGAAGTTCTACTGAGGGGAGGGCGGCGGATGCTGACACGGTTGAAGGGCTT
CCTTGCTCGTCGCCGCGAGTTGAAGGAACTGGATGTGTCCGTGGTGAGCCGGCCCCGGCCGGCTCCG
GCGGAATTGGTCCAGGTTGATGCACGCGAGGCCGTTTGGCGCGTGCCGGTGCCCGGCCAGGCCGACC
GCTTCATGTCGGCCAAGCCTGGCGCGATCAACGATGAAATGTTCGTGGTTCGGGTGGACACCGAAGC
GTTCTATCGGGCTTGGCTGCGCAGCAGCTCGACGGGCCGCGAAACGCGGTCGGACAACTGCCCGCTG
CGCTCGGAAATGCCGCAGGACTACAAGTTCAAGCACGCCGTCCAGGGCTTCGCGCACGGCAGGGAAA
ATCCTGTGCCGCTGGCCTTCGCCGGCGCGCACCAGGAGCGCCACCGGGTGGACATTGGTTTCAGCAA
CGGGGTCACGCGCTCGTTCTGGCTGATTGCCAACAAGGCTCCGTCGTTCCCGATCCAGGTCCACGGC
CGGGAGTCGGCCGAGCTGCTGAACAAGGTTTGCGGCCTCGATCCTGCGCCGCTGTCGTTCACGGAAC
TGTTCGCGCAGGCCCAACGCCAGGCTCCGCAGGTCGCCACACCGGCCCGGCCTGCGCCGGCAGCGGC
CACCCGGCCAGCTCCCAAGGTGCAGCCACGCCCCGGCCGAAGCGGCCCGCGCAAAGGCCGCGGACTC
TGACTACAACCGTGCGCAAGGCGCATTAGGGAGGATGTATGTATGTAATCGCCTGCGGCATCGTTGC
CGGCTTGGCGGCTGCGGTGGCCCTGTTGGGCTTCACGCCGATGATGGAGGCGCTTGCCGCCGGCGAA
CGCCGCAAGGCACTCGCGCAATGGACGCGGACGATGTTCCTGGTGCTGCTGCCTGTCGTGCTGATGT
GCGCGCCCATCGGGTCCAGCATTTACGACGCCGTGCAAGCGGACGCTGGCAAGCCCATCGCTTTCCA
CAACGGCCGGATCACGGTCGTCATGGCCCTGGTCGGCAGCTTGGCCGTTGTCCTGGTCGCGGCTGCG
CGTGCGGTGGTCAACCGCAAGCATGCCAGCTTCTGGTTCGTCGGCTGGGTGATGGCGTCGGTTTTGG
CCGGCGGCGTCGGCGCGATCGCCAGCGCGAAGCAACTGGCGTTCCTCGGCGAACATAGCGGCATGGT
GGCCTTCGGCTTCTTCCGCGACCAGGTGAAGGACATGCACTGCGATGCGGACGTGATCCTGGCCCGG
TGGGATGAAAAGGCGAACTCGCCGGTGGTCTACCGCTGCCCGAAGGCGTACCTGCTCAACAGGTTCG
CATCCGCGCCCTTCGTGCCCTGGCCGGACTACACCGAGGGGGAAAGCGAGGATCTAGGTAGGGCGCT
CGCAGCGGCCCTGCGGGACGCGAAAAGGTGAGAAAAGCCGGGCACTGCCCGGCTTTATTTTTGCTGC
TGCGCGTTCCAGGCCGCCCACACTCGTTTGACCTGGCTCGGGCTGCATCCGACCAGCTTGGCCGTCT
TGGCAATGCTCGATCCGCCGGAGCGAAGCGTGATGATGCGGTCGTGCATGCCGGCGTCACGTTTGCG
GCCGGTGTAGCGGCCGGCGGCCTTCGCCAACTGGACACCCTGACGTTGACGCTCGCGCCGATCCTCG
TAGTCGTCGCGGGCCATCTGCAAGGCGAGCTTCAAAAGCATGTCCTGGACGGATTCCAGAACGATTT
TCGCCACTCCGTTCGCCTCGGCGGCCAGCTCCGACAGGTCCACCACGCCAGGCACGGCCAGCTTGGC
CCCTTTGGCCCGGATCGACGCAACCAGGCGCTCGGCCTCGGCCAACGGCAAGCGGCTGATGCGGTCG
ATCTTCTCCGCAACGACGACTTCACCAGGTTGCAGGTCCGCGATCATGCGCAGCAGCTCGGGCCGGT
CGGCGCGTGCGCCGGACGCCTTCTCGCGGTAGATGCCGGCGACGTAGTACCCGGCGGCCCGCGTGGC
CGCTACAAGGCTCTCCTGGCGTTCAAGATTCTGCTCGTCCGTACTGGCGCGCAGGTAGATGCGGGCG
ACCTTCAACCTTCGTCCCTCCGGTTGTTGCTCTCGCGTCGCCATTTCCACGGCTCGACGGCGTGCGG
ATCGGACCAGAGGCCGACGCGCTTGCCTCGCGCCTCCTGTTCGAGCCGCAGCATTTCAGGGTCGGCC

-continued
GCGCGGCCGTGGAAGCGATAGGCCCACGCCATGCCCTGGTGAACCATCGCGGCGTTGACGTTGCGCG

GCTGCGGCGGCCGGCTGGCCAGCTCCATGTTGACCCACACGGTGCCCAGCGTGCGGCCGTAACGGTC

GGTGTCCTTCTCGTCGACCAGGACGTGCCGGCGGAACACCATGCCGGCCAGCGCCTGGCGCGCACGT

TCGCCGAAGGCTTGCCGCTTTTCCGGCGCGTCAATGTCCACCAGGCGCACGCGCACCGGCTGCTTGT

CTACCAGCACGTCGATGGTGTCGCCGTCGATGATGCGCACGACCTCGCCGCGCAGCTCGGCCCATGC

CGGCGAGGCAACGACCAGGACGGCCAGCGCGGCAGCGGCGCGCAGCATGGCGTAGCTTCGGCGCTTC

ATGCGTGGCCCCATTGCTGATGATCGGGGTACGCCAGGTGCAGCACTGCATCGAAATTGGCCTTGCA

GTAGCCGTCCAGCGCCACCCGCGAGCCGAACGCCGGCGAAAGGTACTCGACCAGGCCGGGCCGGTCG

CGGACCTCGCGCCCCAGGACGTGGATGCGCCGGCCGCGTGTGCCGTCGGGTCCAGGCACGAAGGCCA

GCGCCTCGATGTTGAAGTCGATGGATAGAAGTTGTCGGTAGTGCTTGGCCGCCCTCATCGCGTCCCC

CTTGGTCAAATTGGGTATACCCATTTGGGCCTAGTCTAGCCGGCATGGCGCATTACAGCAATACGCA

ATTTAAATGCGCCTAGCGCATTTTCCCGACCTTAATGCGCCTCGCGCTGTAGCCTCACGCCCACATA

TGTGCTAATGTGGTTACGTGTATTTTATGGAGGTTATCCAATGAGCCGCCTGACAATCGACATGACG

GACCAGCAGCACCAGAGCCTGAAAGCCCTGGCCGCCTTGCAGGGCAAGACCATTAAGCAATACGCCC

TCGAACGTCTGTTCCCCGGTGACGCTGATGCCGATCAGGCATGGCAGGAACTGAAAACCATGCTGGG

GAACCGCATCAACGATGGGCTTGCCGGCAAGGTGTCCACCAAGAGCGTCGGCGAAATTCTTGATGAA

GAACTCAGCGGGGATCGCGCTTGACGGCCTACATCCTCACGGCTGAGGCCGAAGCCGATCTACGCGG

CATCATCCGCTACACGCGCCGGGAGTGGGGCGCGGCGCAGGTGCGCCGCTATATCGCTAAGCTGGAA

CAGGGCATAGCCAGGCTTGCCGCCGGCGAAGGCCCGTTTAAGGACATGAGCGAACTCTTTCCCGCGC

TGCGGATGGCCCGCTGCGAACACCACTACGTTTTTTGCCTGCCGCGTGCGGGCGAACCCGCGTTGGT

CGTGGCGATCCTGCATGAGCGCATGGACCTCATGACGCGACTTGCCGACAGGCTCAAGGGCTGATTT

CAGCCGCTAAAAATCGCGCCACTCACAACGTCCTGATGGCGTACTTACCCAAAGAACAGCTAGGAGA

ATCATTTATGCTCAGCACACTTCCACAAGCTCATGCAACTTTCTTGAACCGCATCCGCGATGCGGTC

GCTTCCGATGTTCGCTTCCGCGCTCTTCTGATCGGCGGCTCTTACGTTCACGGAGGACTCGATGAGC

ACTCCGATTTGGATTTCGACATCGTTGTTGAGGACAACTGCTACGCAGATGTCTTGTCTACACGCAA

GGATTTTGCCGAGGCACTGCCCGGCTTCCTCAACGCGTTCACCGGCGAACATGTAGGAGAACCGCGC

CTTCTGATCTGCCTATATGGTCCGCCACTGCTACACATCGATTTGAAGTTTTCTCTTGCTTCCGATC

TCGACCAGCAAATCGAGCGGCGGGCGGTTCTGTTTGCTCGTGATCCGGCAGAGATCGAGAAGCGCAT

TGAGGCGGCAGCGGTGGCATGGCCAAACCGTCCCTCCGAGTGGTTCGAAGCACGTTGTCAGCGCCAG

TGATATAAGACGGTAATTCACCATTTGGATTGTCCGCTCCACCCAACATGTTGTTTCCTTAAGGTTC

TCACACCAGAAAGGACATCAACATGCTGAGCAGAGAGGACTTTTACATGATAAAGCAAATGCGCCAG

CAGGGCGCGTACATTGTCGATATTGCGACTCAGATTGGTTGCTCTGAACGGACGGTCAGACGCTACC

TCAAATACCCTGAACCGCCAGCCAGAAAGACCCGCCACAAAATGGTTAAGCTGAAACCGTTTATGGA

TTACATCGACATGCGCCTGGCAGAGAATGTCTGGAATAGTGAGGTTATCTTTGCGGAGATTAAGGCA

ATGGGTTATACGGGCGGACGTTCCATGCTGCGTTACTACATCCAGCCCAAACGTAAAATGCGTCCGT

CAAAAAGAACAGTTCGCTTCGAAACTCAGCCTAGATACCAGCTCCAGCACGACTGGGGCGAAGTTGA

GGTGGAGGTTGCCGGGCAACGGTGCAAAGTTAACTTTGCGGTTAATACGCTGGGGTTCTCCCGCCGC

TTCCATGTCTTCGCCGCACCAAAACAGGATGCTGAGCATACCTACGAATCACTGGTTCGCGCCTTCC

GCTACTTCGGTGGTTGTGTGAAAACGGTGCTGGTTGATAACCAGAAGGCTGCGGTGCTGAAGAATAA

CAACGGGAAAGTCGTGTTCAACTCCGGATTCCTGTTGCTGGCCGACCACTATAACTTCCTGCCACGG

GCATGCCGTCCACGCAGGGCCAGAACAAAAGGTAAGGTTGAGCGGATGGTGAAATACCTCAAGGAGA

-continued

ACTTCTTCGTTCGGTACCGCAGGTTCGACAGCTTCACTCATGTTAATCAACAACTGGAGCAATGGAT

AGCCGATGTGGCTGACAAACGGGAACTTCGCCAGTTCAAAGAAACGCCGGAACAGCGCTTCGCGCTG

GAGCAGGAACATCTGCAGCCGTTACCGGATACGGACTTCGATACCAGTTACTTCGACATCCGCCATG

TGTCCTGGGACAGCTATATCGAGGTTGGTGGTAATCGTTACAGCGTTCCCGAAGCGCTGTGTGGTCA

GCCGGTATCGATACGAATATCGCTGGATGACGAGTTGCGGATCTACAGTAATGAGAAACTGGTGGCC

TCACATCGCCTCTGTTCGGCATCGTCTGGCTGGCAGACAGTGCCGGAGCATCACGCCCCGCTCTGGC

AGCAGGTCAGTCAGGTGGAACATCGACCACTGAGTGCCTATGAGGAGCTGTTGTGATGCATGAGCTG

GAAGTCCTGCTGAGTCGCCTGAAAATGGAGCATCTGAGTTATCACGTTGAAAGCCTGCTGGAACAGG

CAGCTAAAAAAGAGCTGAACTACCGGGAGTTCCTGTGCATGGCGCTACAGCAGGAATGGAACGGCAG

GCATCAGCGCGGTATGGAGTCCAGGCTGAAGCAGGCTCGTCTGCCGTGGGTCAAAACGCTGGAGCAG

TTCGACTTTACCTTCCAGCCGGGCATCGACCGTAAGGTTGTCCGGGAACTGGCTGGTCTGGCGTTCG

TGGAGCGCAGCGAAAACGTGATCCTGCTGGGACCTCCTGGTGTCGGAAAAACTCATCTGGCCATAGC

TCTTGGCGTGAAAGCGGTGGATGCGGGACATCGGGTACTGTTTATGCCACTGGACAGACTGATCGCG

ACACTGATGAAAGCGAAACAGGAAAACCGGCTGGAGCGTCAGCTGCAGCAACTGAGTTATGCCCGGG

TGTTGATCCTGGATGAAATAGGCTATCTGCCGATGAACAGAGAGGAAGCCAGCCTGTTCTTCCGGCT

ACTGAACCGTCGATATGAAAAAGCGAGCATCATACTGACGTCAAACAAAGGGTTCGCAGACTGGGGA

GAAATGTTCGGAGATCACGTGCTGGCAACAGCGATACTGGATCGGTTGCTACATCACTCAACCACGC

TGAATATCAAAGGAGAGAGTTACCGGTTAAAAGAGAAACGTAAAGCTGGAGTGCTGACCAAAAACAC

AACGCCAATCAGTGATGATGAAATGGTGAAAAGCGGACAGCATCAGTAACGAAAGTATCTTAGCGGG

CATGAAAATGGCAAATAACGGTCAAACATCGTGGCGTTGACAACGTGCCTGGATCTGGCTACACTAT

GCGGCCACCAAGCTCGCCCGTGGAGTCTCTACGAAGCGATCGGCATGCTCGGTTTCCTTCCGTGAGC

AAGTGTTAGGACCTTTGCTCTACCGTCGCGCTGGAAAGGACCAGCGCGGAGTGAGGCGATTGGAAAC

CCTTCGACTGGGATGAAGAGCGCAGACCTAGCCACCACCATTGCGCTGCACGATGCGTTGTCTGTCA

GGGATGCCATCAAAGCATCTGCCTCCATCTATCTCGACCTCCGAGCCGCCGATCCGTCGTTGGAACC

GACAACGCATATGCCAGGTCTTCTGTACGACTTAATAGAACGTGCGGTACCAGGCACGCCTAACCGT

CAGTGAGATTGGATGAGTGAACGATATTGATCGAGAAGAGCCCTGCGCAGCCGCTGCCGTGCCCGAG

AGCATGGCGGCTCACGTGATGGGATACAAATGGGCGCGTGATAAGGTTGGTCAGTCCGGCTGCGCGG

TCTATCGGCTGCATAGCAAGTCAGGCGGCTCCGACTTGTTTCTGAAGCACGGCAAAGATGCTTTTGC

CGACGACGTGACTGATGAAATGGTGAGATTGCGTTGGCTGGCGGGGCACATTTCTGTGCCCTCCGTT

GTAAGCTTCGTTCGCACGCCCAATCAGGCATGGCTCCTGACAACAGCAATACATGGAAAAACGGCAT

ATCAAGTGCTGAAATCGGATTTCGGAGCCCGTCTCGTTGTTGTTGACGCATTGGCGGCGTTCATGCG

CCGACTGCATGCGATCCCAGTGAGCGAATGCTCCGTTCAACAGTGGACCACGCATGCAGGCTTGCCC

GAGCGCGGGAGTATCGAGGCGGGGGTTGTTGATGTCGATGACTTCGATAAGGAGCGCGAAGGGTGGA

CGGCCGAACAGGTTTGGGAGGCGATGCATCGCCTCCTACCGCTCGCGCCGGACCCAGTCGTGACGCA

CGGCGATTTTTCACTCGATAATCTACTTATCGTCGAAGGTAAGGTAGTCGGCTGCATCGACGTTGGG

CGGGCTGGTATTGCTGATCGATACCAAGACCTTGCCGTGTTATGGAACTGTCTTGAGGAGTTCGAAC

CTTCGCTTCAGGAGAGGCTTGTTGCGCAATATGGCATTGCCGATCCGGATAGGCGCAAGCTGCAATT

TCATCTCCTGCTGGACGAACTTTTCTAAGGCGATGCCCCCTCGACCTCGATCAGGGAGGCGTTCAGG

ACGACTCACAAAGAAAGCCGGGCAATGCCCGGCTTTTTCTGCTGCTACCTCCGTAGTCGTAAGGTCG

TTGCAGGTGCTCGGGTGCGGTACAACTCGCCGGTCGCCAGCTCAAGCGCGATCACGTCGTTGCCGTC

-continued

GTAGTTGACGATGATGCTGTTGGGCCGACTGTCCTCACGCTTCGCAGGGAGAGGCCAGCCTTCAATC

GAAGCCGGCGCAAGCTCGTAGTGCTTCCCGGTTTCGACGCTGCGCAGCGTCCAGGTCCTGCAACCGG

CCACGCCGGTCGCAGAAACCACGGCGAGCGAGCCGCGAAAATCGTGCGGGTACGCCTCGATGTTCAT

ACGCCTCCTAGATCGAGCGCGAGCGTTTCTGCTCGGCCTTGGCCGCCTGTTCCTGGGACACCTCGCC

GATGACCTTGCCCTGGCCCCGGCTGTAGGCGATTTCGTAGTTCTTGCCGACAACCGGCGGCTTCTCA

AAGATGCCCCGGCTGTGTTTCACGATCCCGCCTTCGCTGAACTGGTAGACGTTGCGCCCATCGTCGT

GCAGCACCTGGCCGACGTGCTTGTGCGGGTGGACGTTTTTGCTTGCGTCCTTCGCATCGCTCAACTG

GTGAATGCCTTTCGGTAGCCCCGCCTCGGGCAACACCTTCATGGTCAGCCATTCGCCGTTCACTACC

TGGTCCACCTGGCGGCTGCCGTTCATGACGGCGATCTTGACGCTGCCCTCGGGTTTCATGATGACGC

CAGGGCTTGCCGATGTGCGTGGTGCCCCGATCTGTACTTTGTTCATACGCTCTAGTTCTCCTTAGTA

GGTTCTCGCGCGGCGTTGCCGCTGTTCTTGCTGCTCGATGTCTTGCTGCTTGAGCTGCTGCACCTTC

TGCCGCTGGCCCTCGTCGAGAAGCACCTTGCCGACAGCACTTCTCACCTGGCGTTCAACCCCGTCCT

TGCCCAGGCTGCTGCGCTCGGACAGGTCGTTGAAATCGGTGTGCTTCTTCATGTTCGACAGGGCGGC

GAGCTGGCCATCGTTCAACAGCGATTCCTTGAGCTTGGCCGTGTCGGCCTCGCTCAACTGGACCTTG

CCGGCCGCCGCGTCCGCGAGGCGCTTTTCAGCGTGCAAATGGTTGCGGTAGTTCTCCGGGGTGATCG

GCGGCAGCTCCTTCGGGTAGGCGTTCTCGCCCGGCGCGAAGATTGGGAAGATGGCCTTGCCGCCGAC

CGCCTTGGCGGCCTCCTGTGCCTTCGTCCTGCCGGGATTCACGCCCTGGGTGATCTGCACCTGGCGG

TCGTCGTCGCCGGCGATCACAACGGGCTTGTCCGGGAATTTCGCGTGCAGGGCCTCGGCAACAGCCT

GTAGGTTGCCGGAATCGAACGCGGCGACAGTCGCGTGCCCCAGCGCTTCGGCCACTGTGGCGGCGGT

GGCATAGCCTTCGCCGATCACCAGCGCCGGCGCGGCCGCGAGCGCATCCATGCCACCGACGACATGG

AAGCATCCTTCCTTGCGGCTGTCCTTGGCGAAGCGCTTGGTGCCGTCCTCCTGGATGTACTGCATGG

TCCATTGCTTGCCGTCGGCGTCGTAGGCCGGGATGTAGGTTTTCTGGCCCTCCTGGTCGGTAAGGAC

GCCGGCGTGCACCTGTAGACCCTTGTCGCGCAGGTACGGCGTCGGTTCCGTGATGGGAACCAGGCTT

TGCGCCTGGCGGCCGATGCGCTGCGCCGTGGCTTCGTGCTGGCGTTCTTGTTCCTCGGCACGCGCGG

CCAGCTTGGCCGCCGCCTCGGCCTGCATCTTGGCCTTCTCGGCGGGGTCCAGGGCGTAGCCCTTGGC

CTTCCACTTCATTTCGACGCCGGTGCGGTTGTTTTTGATGTAACCGGCCGGGTGGCCGTCGAGGTGG

CCGACGTAGAAGCCCGACTTCTCGCCCTTCTTGTCGCCCTCGGTCTCGATGCGGTGCTTCTTGCCGT

CCATGATGGGGTGCTCGCCGCCTGGGGTGACGACGCAGCCCATGCTTTTCAGGGCCTCCGCGAACTC

ATCTTCGGGGGTGACGGCCGGGGATTGCTGGGTGGGCACGTTGTCCGGCAGCCAGCGTTGCAGCTTG

CCCATGTCGGCGTTCGGTCCGGCGTACCAGGACTTGGCCACCTTGTCCCACTGCGCGCCGGCCGCCT

TGGCAACCTGGCGCTCGCCGTAGGGCACGGCCAGGTAGACGCGCTCCTGGGCCGCGTTGGGGCGCTC

GGCCGTGGGTTGGGTAGGCTGGGCCTCGGCGCGGGCCTCTACGGCCGCTGTAGCGCCCTCGCGCGCC

CATTTGGCGAACGGGGCAGGGTCAACCCCTGCCGGAACGTACCAGGCGCGTTCCTGGCGGTCCCAGC

GCGCTCCAAGGGCCTTCACCTCGTCTTTCTCCTTGAACGGCACGTTCAAGTAGGCGCGCTCGGGCTT

GGCGGGGGCTTGAGCGGCCGCCGGCTGCTCGGCGGCGTTCATGGCCTGGGCCATTTCCTGCTGCTCG

CGCTCGTAGTCGGCGATCCGGCGCTGTAGGTCCTCGTCGTGCAGCATGGCCGTGCCCTCGGCGGCCT

TGCGCGCCTCCTTGGCGGCAACGCGGTCCTCGTCGGTGCTGTTGGGATCGCGGCGAACTCGCTCTTC

ATGGATGCGGGCGAACTTCGCGGCCTGCTCGTACTCGTTGGCCGTCGCGTAAGCGTCGATCACGGCC

AGGCGGTCGGCGAGCGCTTCGGCATTGGTCTGCGCGTCGGGGCCGGCGAAGTCGGCAAGCCATTGGT

GGCCGCCCCACGCATGGTTCGCATAGACGCCCCAAAACTCCGGCTCTCGGTCGCCGGCCGGCACCAC

GGACCGTTCGCCGTCGTGCTCGACCTCGACGTTGGCCTGGACCTGGACGCGGCCGGTCCAATCGGCA

-continued

GGCAGCTCAAAGCCCAGCGTGGTTTCGGTCAGCGCGGCCAGCGATTGGTTGCCTTCCGCCGGCTCCG

CGCCGGCGCGGTACATGCGCAGGGTCTGCGCGATCAGCTCGTCGGCCGGCGCAATGGCCGGTCGTGC

CACCTGGTCTTGCTGTTGCTCCATAGTTGCCCCCTGCGCAGGCTCGATGGCCTGCTGGGTCGTTTGT

TCTTGAATTTGCTTCTGCTCGAACGCCAGGACGAAATCCTGGATCTTCTCCGCGTCGGCGGCCGCGC

GGAAAATCTCTAGCGGGTCCTCTTGTAGCGCCTTGATCCACGATCCGACATAGGCCGCGTGCTGGCC

GGGGTCGTGGCCGATGCCCAGCTCGTCGCCCAGGATCATGCTGGCAATCTCGGCCCGCAGCTCTTCC

TTGGCGTACCCCTCGCTCCCGAAGGGATGCGCCAGGTCGCGGTCCAGCCGCGACGGGTGGCCGGTCC

AGTGCCCCAGCTCATGGAGCGCGGTTGCGTAGTAGTTGTCGGCGCTCGGGAACTGGCCTTTGTCGGG

CAGATGGATGCTGTCCGTGGACGGCCGATAAAACGCGCGGTCGTGCTCGCCGTGGCGGATGGTGGCA

CCTGACGCCGCAAGGATGTGCTCGGCCCGCTCGACGGCGCTCCAAGTCTGTTCCTTGCGTTCCAACG

GCGGCAGGCCGTCGATCTGCTCCGCATTGAACACGGTGGCGAAGAACACGCGCGGGCGTTCGAGCTG

CACCGTCACCTTGACCGGATCGCCGTTGGCATCGAGGACCGGCTTGCCGGTCTGCTCGTCGGTCTTG

GTCTGCTCTTCGCTGAACTTCCAATACTGGATCGGCGTGCCTTTCTCGCCGCGACGCACCTGTGCGC

CGGCGGCAGCGGCCTGCTTGTAGGTCATCCAGCGCGGGTCCGCATGGCCCTGGGCCATGAGCTGAAT

CGCGTTGATGCCCTTGTAACGCTTCCCGGTAGTCGGGTTGAGCGGGATGAAGGAGCCGGGCATGCCC

GGTTCCCACGGTTTTTGCCACGGCGCAGTGCCGGCTTTCAGTTGCTCAATGAGGCGTTCGGCAACCT

GCTCGTGGAACGGCTTTTTGACCTCTGCCATAGCCAATTACCTCCCGTCATTGGCGGCCGCGGTCGT

CGTGTCCTCGGGCACGGTCGCGTCCACCAGGTCAATGTCGCTCTCGGCGGCGTCCTGCTCGCTCAAG

GCGTCCTCGGGGAAGGCCCCGGCCTTCTCCGCTTCTTCCGGGTCGAACTCGACCTGGAAGCCGGGCG

TCATCGCATCGGCGAGCTTTTCACGCAGGGCGGCGGCGGCGTTCGCGGTATCGTCGAACGGCGCAAA

GTCGTCCTGCTGCACGGTCTTGGGATCATTCATCGCTTTCACTCCTGGTTGGTGCCGTTACGGCCTT

TGCTGTAGTCCGGCCTGCCTTTCAGGTCGGGGTATGTCTGCTTGCACGTCGGGAAGTTGCTGCACCC

CCACCAGAACATGCCGCGCTTCTTGCCAGGCCGACGGGAAAGGCCGTGGCCGCAGGCCATGCACTTG

TGCAGCTCGGAGACTTTCGGGGCCTCGCGCGGGACGGGCTTGCCGCCCTTGTCGTCGCACGCGAACT

TGCAGCCGTCGGCAAAGCCGGTGCAGCCCCAAAAGTATTCGTTCTTGTCCTTCTTCTTGAGGCGTCG

CAGCGGCTTGCCGCAGGACGGGCAAGGGTGCGTGTCGATCTTCATGTTGAGGCCGTTGTCTTTGATG

TTGGCGACCTCGGCGCCGATGTATTCCATCAGCTCGTTGACGAACGACAGCGTGTCGCGCTCGCCGG

CCTGGATGGCCTTCTGCTGCTCATGCCAGAGCGCGGTCATGTCGGGGAATCTGGCCGTGTCGGGCAG

TGCGTCGTACAGCTCTTCGCCGGTCGGCGTGGACACGATGTGCTTGCCCTTCTCCACCAGGTAGCCG

CGCTCGAAAAGCGTGGCGATGATGGAGTCTCGCGTTGCCGGCGTGCCGATCCCGCCGTGCTCGCCTT

GCTTGCCCTTGTCCTTTTCGATCAAGATTTTCCGCAGGCGGTCATCGCGGATGTATTTCGCAACGCG

GGTAAGGTCCGACAGCAGAGATTCCATCGTGTACAGCGGCTGCGGTTTCGTCTCCTGCTGCTCGGCC

TTCGCATCGGTGCAGGTGCCGGCCTGGCCGTCACGCAGCTTGCGCAGGTCCTGTTCAATGTCGTCGG

CATTGCCTTCCAGGTCCTCGTTGCCGGCGTCGTTCTTGTAGAGAATCTTCCAGCCCGGCGACGTGGT

GACGTTCGAGCGCACGCCGAAACGATGATCGCCGACCTGGGCAAGCACGTCGGTCTGGTCATACAGA

TGCTTCGGCCAGAACTGCGCGACGTAGGCGCGCGCGATCAGCAGGTAAATCTTCTGCTCGGCATCGG

TGAGCTTCGACAGGTCGGCCGTGCTTTCGGTCGGGATGATCGCGTGGTGCGCGGAAACCTTGGACGA

GTTGAAGGCGCGGCTCTTGATCGTCGGATTGGCGCGCTGCGCAGCAGCGGCCAGCATGGGGGCCGTC

TGTGCGATGGCCGCCAGCACGCCCGGCGCATCGCCGTGCTGTTCCTCGCTCAAGTATTCGCAGTCGG

AACGGTTGTAGGTGATGAGCTTGTGCTTCTCGCGCAGGGCCTGCGTAATGTCCTTCACCTGGTCCGG

-continued

CTTGAAGCCGAACTTGCGCGAGGCGTCCATTTGCAGTTTCAGCAGGTTGTAGGGCAGCGGCGCAGCC

GCTTCCTTCGCCTTGGTGGTCACGGACACGATGCGGGCGGGTTGGCCGCTCACGGCGGCCGCGATGC

CCTCGGCGTGCTCCTTGTTGCTGAGGCGGCCTTTCTCGTCCACCGGATCGCCGTCGGCGACCTGGTA

ACGGGCCGGGAACTGAATGCCCTCGACCTCGAACTGGCCGTTCACCAGGTAGTAGTAGGTTTTCTGG

TGGGCCGCGTTCTCGCGGCAACGGCGCACGACAAGGCCCAGGATCGGAGTCTGCACGCGCCCCACGC

TCAACAGCCCCTGATAGCCCTTCGCGCGTGCCGCAAGCGTGTACAGGCGCGTGATGTTGAAGCCGTA

TAGCTGGTCGCCGACGCTGCGGGCCTCGGCCGCAGCGGACAGGCCGGCGAACTCGCGGTTGTCGCGC

ATCGCGGCGAGCTGCCGGCGCACGATCTTCACGTTGTTGTCGTTGATAAGCAGCCGCTGCACCGGCA

GACGGCAGTTGGCGTATTCCAGGATTTCATCGACCAGAAGCTGGCCTTCGTCGTCCGGGTCGCCGGC

GTGAACCACGCTTTTCGCCTGCTTCAACAGGCTGAGGATGGTCTTGAACTGAGCTTTCGCACCGGCA

TCGCCGGACGGTTTCTTGCGCCAGGGAATATGGACGATGGGCAGGTCGGCCATGTTCCAGTTGGCGT

AGCGCTCGTCGTAGTCCTCCGGGTCTAGCAAGGCCAGCATGTGACCGTAGCACCAGGTCACGCGGTC

GGAGCCGCATTCGTAATAGCCGTCCTTGCGGCTGCCGCCGCCCAGGCCCTCGACGATGGCTTTTGCC

AGCTCCGGTTTTTCAGCGATTACAAGGCGTTCAAATTGCATATATCCCCCTACCCTCACCAGGTCAG

AACCGGCCTGATGACGGTGATGATTTGCGAACGATTGACAGGCCCGAAGTAGCGGCCGTCGAAAGAC

GTGTCGCTTACGTCGGACATAAGCAGAACCTCGGCGGTCCCCAGGGTGTAGCTGTCGGACTGATAAC

GAGGCAGCGGCCGTCCTGATGGATCGGCCTTGATGAGCGCGCTGTGAGGCAGCAGCCCGCCATTCAC

GCGCACGCCGGCGTCGGTGATGGCAACCTCGTCGCCTTTAGCGGCTAAAACTCGCTTCATCATGTAG

CCGTAGTCGCCGGGGCAGAAACCGCCGGCGATGTAGCCCCGCTCCTTGGCGTCCGAAAACACGCCGA

CTTGCGGCGGGCAGAACATGACGTAAGCCCCCTTCTCCACCGGCGCATTCGATTTCCAGTACAGGCC

GACCGGAATGCTTTTGGTGGTGTTGACCTTCGCGCCGGCGAGATAGGCCGCGCCGGCGAGCAACAAG

GCCGCGCCGCCTCCGATGGCGACGTACTTGGTGAGGCGCTGGAAGCGGCTCATATCGTGATCCCCTC

CCCTTCCTCGACGGTGGCCGTCTGGATCAGCTTGTCGCTGACCTTCGGAGCCGGTACGGCCGCGCGG

GCCTGGAATATCGGGTCTTTGAAGTAGAGCGGCTGCTTGCCGTAGATCGCGGGATAGCCGGCGACGT

ACACAACCATGTCGCCCGCCTCTTCAATGCTGCCGTCGGCGCTCTTCTTCGGCCCCGGCATGCGCAG

GCATTCATCGGGGGTCAGCAATGGCCGCTGCACTTCCTGGAAGGTCCGCGAGACGTTGCCCAACAGC

GCCGACGTGCGGCGGCCGCTCGTCGTGATCTGCTCCTTCACGATGGTCGTGGTGCCTGTCAGTTTTG

ACAGGTGCTCGGCCGTCTCCACGCGGTTCGGCGGGTAGGCGTTCTGCACGTGGCAGTTCGACGTGAT

GCTTTCGTCGTGGCCGTAGCCGGTTTCGCGGCTCTTGAGCTGGTTAATGTCCTGGCAGATGAGGTAG

CACTTGATGCCGTAGCCGGCGACGAAGGCAAGGGACTCTTGCAGGATTTCGAGCTTGCCCAGGCTGG

GGAACTCGTCGAGCATCATCAGCAGACGATGCTTGTAGTGCGCGACAGGACGGCCGTTCTCGAAGTC

CATCTTGTCGGCCAGCAGCCGGACGATCATGTTGACCATGACGCGCACCAGAGGCCGCAGACGGGCC

TTGTCGTTGGGCTGCGTCACGATGAACAGGCTTACCGGGTCGTCGTGGTGCATCAGTTGCTTGATGC

GGAAGTCGGACTTGCTGACGTTGCGGGCCACAACCGGGTCGCGGTACAGGGCCAGGTAGGACTTGGC

GGTGGACAGCACGGAACCGGATTCTTCCTCCGGGCGGTCCATCATGTCGCGGGCCGCAGAGCCGACC

GCAGGGTGGTTCTGCCCGTCAACGTGGCCGTAGGTGGTCATTTCCATCCAAAGCTCGCCCACGTCGC

GGTTCGGGTCGGCAAGCATGCCGTCCACCGACGGCAGGGTGGCCGGCGTACCCTCGTTCTTAGCCTT

GTAGAGCGCGTGCAGGATGACGCCGACAAGCAGCGCCTGGCTGGTTTTCTGCCAGTGCGATTCCAGG

CCCTTGCCGTCCGGATCGACGATCAGGGTGGCAAGGTTCTGCACGTCGCCAACCTCGTACTCGGTCC

CCAAGCGGATTTCATCGAGCGGGTTCCAGCACGCGCTACCCTGCGCGGATGCCGGCTCAAAGCGCAC

GACCTTGTTGCGGGCATGCTTCTTCCGCCAGCCGGCGGTCAGCGCCCACAACTCGCCTTTCAGGTCG

-continued

GTGATGACGGCGCTGTGCGCCCAGGAAAGCAGCGTCGGAACGACCAGGCCGACGCCCTTGCCGGAGC

GCGTCGGCGCGTAGGTCAAGACGTGCTCGGGGCCGTTGTGCCGCAGGTAGTGGAACTTGCCGTCCTT

GTCCTGCCAGCCGCCCACATAGACGCCGCTGGAAGTGGGCGGGTGTTTGCCTGACACCAGCTCGACG

ACGGTGCGCGGCCGGGGCAGCAGGCCGGCGGCCTGTATGTCCTTCTTGTCGGCCCAGCGGGCCGAAC

CGTGCAGATAGTCGTTCGCCTTGCCGGTGTTCGCCTTGACCATCTGCGTGACGGCCGTGCCCAGCAG

GCCCACGGTCGAAACGACCATACCCATGCTGGCCGCGCGCATGAAATCGTCGGGATATTGGCCGTAC

CACTTGCCGGCCCATTGAAGGATCGACCAGGGCGTGTAGACGTGGTTGATATTCCAGCCAAGTCCGG

CCTGATACTGGAAGGAATGGGCGAAATATTGCGTCGCGGTCTGCAAGCCTGCCCCAAGGGACAGGCC

GGCGAGGATGGGAACGGTCTTGCTGGCCTTCGGTTTTTTCGCCCGTATCTGTGGCCCCACGGCGTTG

TTTCGGTTCTTCATCTACTCCTACCTCGGGTAGTTTTAAGGGAGCCTCGCGGGGTCACGGTGACGGG

ATCACCGATGGCGAGGCGCTTCATGCGTTGCACCGTGGCCTTATCGACGGGCAGCACCAGAATCTCG

TCGTTTTCTTTCCTCAACAGGGCCAGCGCCTGGTCCTCGACGTTCCGGGTGCCTGCATAGGACAGCG

CACCAACATAATCAGTATATCGTGCATGCTTCGGTATATCGAAGCCGTTTAGCCGCTTTTGCTCGCG

CTCGGCAACATATTTCTCGGCCGCCGCGATCTGTTCGGGCTTTAGCCCTCTTCCTGGCCCAGAAACT

CCCCGTCGCAGTGCGTGAGCTGGTTCGGCTCCTTGCTGCTCCACGTGACCAGGAACATCACGCGGCA

ATAGCATTTCAGCTCCGCCGGCGATGCGAACCACACCGAGTTGGGACAGCGCTCGCAAACGGTTTTG

GCTTTGGGGCGGCGGCTTTCGTCCAATGCGTCCAACGTTGGGCTTGCGGAGTGCGACGGTTCCGCCG

GCGCTGACGGCGCGAGCGTCCCGTCGGTCGCCGTCGCCGCCTGTGGCGTTGAGGGTGGTTCTGGCTG

CGGCAGGTCGAATGCCTCCATCGCCGCCGCGATCTCTTCGTCCGTCATTTCGTTCGGGTTGCTCATG

TGCTTGCTCCTTCGTCAGTAGTTCTTGACGGCGGCGCTCAAGGGCGGCGTCGTCAAAGGTGATTGCC

AGACGGCCAGCGGCGGCCGCCTGCGCGATCCGCTCCTTGAACTCTGCTGTGCCGTTGACGGTGATCC

GGTCGCCGAAGCGCTCCATTGCCAGGCGCAGGGCGGCGTCCAGGCCGTCCGTGGTGGCCTCGCGCGA

GACTTGCAGGCGGTCGCCGTCGTCGCGGACGGCGCTGCTGCCGACGCGATAGATGATGGTTCCCTTC

TTCGTGATGTTGTCCGTCACGGCCGCATGGCCCGGCTTGGCCTCGCCGCTGCCCTGGATGGTGTTGC

CCTTGAGGTCGCTGCGGCCCTCGCGTGCGCGCAGCGCGGCCAGGGCCTTGTCGTCGCCCTTCATCGC

CTCGGCCTTGAGCCAGTCGGCCCACGCGCGGCGCTGCGTGCGCTCCTGGACCGCCTGACGGCCCTGC

CGGTACTCGCGGTTGATCTTGTCCAGGTCGGCGCGCAGAGCCTTGTGCGCCTGCGCGTACATCAGTC

GCTTTGCAATGCGCCCCTCGCCCAGCAGCTTGATAGCGGCGCGGCGCAGCCGGTTGCTGCGCATCGC

GGCTTCAATCAGGCGGTCACGACGCCGGCGCAGCGTGTCCAGCTCGCCCTTGCGCACGGCCCCCATT

TCCTGGCGTTCAGACTGATACCGGGCGTATAGCTCGGTGGTGTCGATGCGGGTCTTGAGCGGCTTCG

CTCGATACTCCCGCCGCCGGGGGGCTTCGCCGCCCTCGGCTGGCGTGAATGCCCCGAATCGGGCTTC

GAGCTTCGGCTTGGACAGGTCGCGCGAAACGGTGCTGGCCTTGACCGTCGTGCCGTCGCCGGCCTCG

AAGATGAAGCCGTTTCCGCGCTCGCGCAGCTTAAGCCCGTTTTCCCGCAGGACGCGGTGCAGGTCCT

CCCAGGATTGCGCCGCTTGCAGCTCCGGCAGGCATTCGCGCTTGATCCAGCCGACCAGGCTTTCCAC

GCCCGCGTGCCGCTCCATGTCGTTCGCGCGGTTCTCGGAAACGCGCTGCCGCGTTTCGTGATTGTCA

CGCTCAAGCCCGTAGTCCCGTTCGAGCGTCGCGCAGAGGTCAGCGAGGGCGCGGTAGGCCCGATACG

GCTCATGGATGGTGTTTCGGGTCGGGTGAATCTTGTTGATGGCGATATGGATGTGCAGGTTGTCGGT

GTCGTGATGCACGGCACTGACGCGCTGATGCTCGGCGAAGCCAAGCCCAGCGCAGATGCGGTCCTCA

ATCGCGCGCAACGTCTCCGCGTCGGGCTTCTCTCCCGCGCGGAAGCTAACCAGCAGGTGATAGGTCT

TGTCGGCCTCGGAACGGGTGTTGCCGTGCTGGGTCGCCATCACCTCGGCCATGACAGCGGGCAGGGT

-continued

GTTTGCCTCGCAGTTCGTGACGCGCACGTGACCCAGGCGCTCGGTCTTGCCTTGCTCGTCGGTGATG

TACTTCACCAGCTCCGCGAAGTCGCTCTTCTTGATGGAGCGCATGGGGACGTGCTTGGCAATCACGC

GCACCCCCCGGCCGTTTTAGCGGCTAAAAAAGTCATGGCTCTGCCCTCGGGCGGACCACGCCCATCA

TGACCTTGCCAAGCTCGTCCTGCTTCTCTTCGATCTTCGCCAGCAGGGCGAGGATCGTGGCATCACC

GAACCGCGCCGTGCGCGGGTCGTCGGTGAGCCAGAGTTTCAGCAGGCCGCCCAGGCGGCCCAGGTCG

CCATTGATGCGGGCCAGCTCGCGGACGTGCTCATAGTCCACGACGCCCGTGATTTTGTAGCCCTGGC

CGACGGCCAGCAGGTAGGCCGACAGGCTCATGCCGGCCGCCGCCGCCTTTTCCTCAATCGCTCTTCG

TTCGTCTGGAAGGCAGTACACCTTGATAGGTGGGCTGCCCTTCCTGGTTGGCTTGGTTTCATCAGCC

ATCCGCTTGCCCTCATCTGTTACGCCGGCGGTAGCCGGCCAGCCTCGCAGAGCAGGATTCCCGTTGA

GCACCGCCAGGTGCGAATAAGGGACAGTGAAGAAGGAACACCCGCTCGCGGGTGGGCCTACTTCACC

TATCCTGCCCGGCTGACGCCGTTGGATACACCAAGGAAAGTCTACACGAACCCTTTGGCAAAATCCT

GTATATCGTGCGAAAAAGGATGGATATACCGAAAAAATCGCTATAATGACCCCGAAGCAGGGTTATG

CAGCGGAAAAGCGCTGCTTCCCTGCTGTTTTGTGGAATATCTACCGACTGGAAACAGGCAAATGCAG

GAAATTACTGAACTGAGGGGACAGGCGAGAGACGATGCCAAAGAGCTACACCGACGAGCTGGCCGAG

TGGGTTGAATCCCGCGCGGCCAAGAAGCGCCGGCGTGATGAGGCTGCGGTTGCGTTCCTGGCGGTGA

GGGCGGATGTCGAGGCGGCGTTAGCGTCCGGCTATGCGCTCGTCACCATTTGGGAGCACATGCGGGA

AACGGGGAAGGTCAAGTTCTCCTACGAGACGTTCCGCTCGCACGCCAGGCGGCACATCAAGGCCAAG

CCCGCCGATGTGCCCGCACCGCAGGCCAAGGCTGCGGAACCCGCGCCGGCACCCAAGACGCCGGAGC

CACGGCGGCCGAAGCAGGGGGGCAAGGCTGAAAAGCCGGCCCCCGCTGCGGCCCCGACCGGCTTCAC

CTTCAACCCAACACCGGACAAAAAGGATCTACTGTAATGGCGAAAATTCACATGGTTTTGCAGGGCA

AGGGCGGGGTCGGCAAGTCGGCCATCGCCGCGATCATTGCGCAGTACAAGATGGACAAGGGGCAGAC

ACCCTTGTGCATCGACACCGACCCGGTGAACGCGACGTTCGAGGGCTACAAGGCCCTGAACGTCCGC

CGGCTGAACATCATGGCCGGCGACGAAATTAACTCGCGCAACTTCGACACCCTGGTCGAGCTGATTG

CGCCGACCAAGGATGACGTGGTGATCGACAACGGTGCCAGCTCGTTCGTGCCTCTGTCGCATTACCT

CATCAGCAACCAGGTGCCGGCTCTGCTGCAAGAAATGGGGCATGAGCTGGTCATCCATACCGTCGTC

ACCGGCGGCCAGGCTCTCCTGGACACGGTGAGCGGCTTCGCCCAGCTCGCCAGCCAGTTCCCGGCCG

AAGCGCTTTTCGTGGTCTGGCTGAACCCGTATTGGGGGCCTATCGAGCATGAGGGCAAGAGCTTTGA

GCAGATGAAGGCGTACACGGCCAACAAGGCCCGCGTGTCGTCCATCATCCAGATTCCGGCCCTCAAG

GAAGAAACCTACGGCCGCGATTTCAGCGACATGCTGCAAGAGCGGCTGACGTTCGACCAGGCGCTGG

CCGATGAATCGCTCACGATCATGACGCGGCAACGCCTCAAGATCGTGCGGCGCGGCCTGTTTGAACA

GCTCGACGCGGCGGCCGTGCTATGAGCGACCAGATTGAAGAGCTGATCCGGGAGATTGCGGCCAAGC

ACGGCATCGCCGTCGGCCGCGACGACCCGGTGCTGATCCTGCATACCATCAACGCCCGGCTCATGGC

CGACAGTGCGGCCAAGCAAGAGGAAATCCTTGCCGCGTTCAAGGAAGAGCTGGAAGGGATCGCCCAT

CGTTGGGGCGAGGACGCCAAGGCCAAAGCGGAGCGGATGCTGAACGCGGCCCTGGCGGCCAGCAAGG

ACGCAATGGCGAAGGTAATGAAGGACAGCGCCGCGCAGGCGGCCGAAGCGATCCGCAGGGAAATCGA

CGACGGCCTTGGCCGCCAGCTCGCGGCCAAGGTCGCGGACGCGCGGCGCGTGGCGATGATGAACATG

ATCGCCGGCGGCATGGTGTTGTTCGCGGCCGCCCTGGTGGTGTGGGCCTCGTTATGAATCGCAGAGG

CGCAGATGAAAAAGCCCGGCGTTGCCGGGCTTGTTTTTGCGTTAGCTGGGCTTGTTTGACAGGCCCA

AGCTCTGACTGCGCCCGCGCTCGCGCTCCTGGGCCTGTTTCTTCTCCTGCTCCTGCTTGCGCATCAG

GGCCTGGTGCCGTCGGGCTGCTTCACGCATCGAATCCCAGTCGCCGGCCAGCTCGGGATCGTCCGCG

CGCATCTTGCGCGTCGCCAGTTCCTCGATCTTGGGCGCGTGAATGCCCATGCCTTCCTTGATTTCGC

-continued

GCACCATGTCCAGCCGCGTGTGCAGGGTCTGCAAGCGGGCTTGCTGTTGGGCCTGCTGCTGCTGCCA

GGCGGCCTTTGTACGCGGCAGGGACAGCAAGCCGGGGGCATTGGACTGTAGCTGCTGCAAACGCGCC

TGCTGACGGTCTACGAGCTGTTCTAGGCGGTCCTCGATGCGCTCCACCTGGTCATGCTTTGCCTGCA

CGTAGAGCGCAAGGGTCTGCTGGTAGGTCTGCTCGATGGGCGCGGATTCTAAGAGGGCCTGCTGTTC

CGTCTCGGCCTCCTGGGCCGCCTGTAGCAAATCCTCGCCGCTGTTGCCGCTGGACTGCTTTACTGCC

GGGGACTGCTGTTGCCCTGCTCGCGCCGTCGTCGCAGTTCGGCTTGCCCCCACTCGATTGACTGCTT

CATTTCGAGCCGCAGCGATGCGATCTCGGATTGCGTCAACGGACGGGGCAGCGCGGAGGTGTCCGGC

TTCTCCTTGGGTGAGTCGGTCGATGCCATAGCCAAAGGTTTCCTTCCAAAATGCGTCCATTGCTGGA

CCGTGTTTCTCATTGATGCCCGCAAGCATCTTCGGCTTGACCGCCAGGTCAAGCGCGCCTTCATGGG

CGGTCATGACGGACGCCGCCATGACCTTGCCGCCGTTGTTCTCGATGTAGCCGCGTAATGAGGCAAT

GGTGCCGCCCATCGTCAGCGTGTCATCGACAACGATGTACTTCTGGCCGGGGATCACCTCCCCCTCG

AAAGTCGGGTTGAACGCCAGGCGATGATCTGAACCGGCTCCGGTTCGGGCGACCTTCTCCCGCTGCA

CAATGTCCGTTTCGACCTCAAGGCCAAGGCGGTCGGCCAGAACGACCGCCATCATGGCCGGAATCTT

GTTGTTCCCCGCCGCCTCGACGGCGAGGACTGGAACGATGCGGGGCTTGTCGTCGCCGATCAGCGTC

TTGAGCTGGGCAACAGTGTCGTCCGAAATCAGGCGCTCGACCAAATTAAGCGCCGCTTCCGCGTCGC

CCTGCTTCGCAGCCTGGTATTCAGGCTCGTTGGTCAAAGAACCAAGGTCGCCGTTGCGAACCACCTT

CGGGAAGTCTCCCCACGGTGCGCGCTCGGCTCTGCTGTAGCTGCTCAAGACGCCTCCCTTTTTAGCC

GCTAAAACTCTAACGAGTGCGCCCGCGACTCAACTTGACGCTTTCGGCACTTACCTGTGCCTTGCCA

CTTGCGTCATAGGTGATGCTTTTCGCACTCCCGATTTCAGGTACTTTATCGAAATCTGACCGGGCGT

GCATTACAAAGTTCTTCCCCACCTGTTGGTAAATGCTGCCGCTATCTGCGTGGACGATGCTGCCGTC

GTGGCGCTGCGACTTATCGGCCTTTTGGGCCATATAGATGTTGTAAATGCCAGGTTTCAGGGCCCCG

GCTTTATCTACCTTCGTGGTTCGTCCATGCGCCTTGGTTCTCGGTCTCGGACAATTCTTTCGCCCAT

TCATGACCAGGAGGCGGTGTTTCATTGGGTGACTCCTGACGGTTGCCTCTGGTGTTCAAACGTGTCC

TGGTCGCTTGCCGGCTAAAAAAAAAGCCGACCTCGGCAGTTCGAGGCCGGCTTTCCCTAGAGCCGGGC

GCGTCAAGGTTGTTCCATCTATTTTAGTGAACTGCGTTCGATTTATCAGTTACTTTCCTCCCGCTTT

GTGTTTCCTCCCACTCGTTTCCGCGTCTAGCCGACCCCTCAACATAGCGGCCTCTTCTTGGGCTGCC

TTTGCCTCTTGCCGCGCTTCGTCACGCTCGGCTTGCACCGTCGTAAAGCGCTCGGCCTGCCTGGCCG

CCTCTTGCGCCGCCAACTTCCTTTGCTCCTGGTGGGCCTCGGCGTCGGCCTGCGCCTTCGCTTTCAC

CGCTGCCAACTCCGTGCGCAAACTCTCCGCTTCGCGCCTGGTCGCGTCGCGCTCGCCGCGAAGCGCC

TGCATTTCCTGGTTGGCCGCGTCCAGGGTCTTGCGGCTCTCTTCTTTGAATGCGCGGGCGTCCTGGT

GAGCGTAGTCCAGCTCGGCGCGCAGCTCCTGCGCTCGACGCTCCACCTCGTCGGCCCGCTGCGTCGC

CAGCGCGGCCCGCTGCTCGGCTCCTGCCAGGGCGGTGCGTGCTTCGGCCAGGGCTTGCCGCTGGCGT

GCGGCCAGCTCGGCCGCCTCGGCGGCCTGCTGCTCTAGCAATGTAACGCGCGCCTGGGCTTCTTCCA

GCTCGCGGGCCTGCGCCTCGAAGGCGTCGGCCAGCTCCCCGCGCACGGCTTCCAACTCGTTGCGCTC

ACGATCCCAGCCGGCTTGCGCTGCCTGCAACGATTCATTGGCAAGGGCCTGGGCGGCTTGCCAGAGG

GCGGCCACGGCCTGGTTGCCGGCCTGCTGCACCGCGTCCGGCACCTGGACTGCCAGCGGGGCGGCCT

GCGCCGTGCGCTGGCGTCGCCATTCGCGCATGCCGGCGCTGGCGTCGTTCATGTTGACGCGGGCGGC

CTTACGCACTGCATCCACGGTCGGGAAGTTCTCCCGGTCGCCTTGCTCGAACAGCTCGTCCGCAGCC

GCAAAAATGCGGTCGCGCGTCTCTTTGTTCAGTTCCATGTTGGCTCCGGTAATTGGTAAGAATAATA

ATACTCTTACCTACCTTATCAGCGCAAGAGTTTAGCTGAACAGTTCTCGACTTAACGGCAGGTTTTT

-continued

TAGCGGCTGAAGGGCAGGCAAAAAAAGCCCCGCACGGTCGGCGGGGGCAAAGGGTCAGCGGGAAGGG

GATTAGCGGGCGTCGGGCTTCTTCATGCGTCGGGGCCGCGCTTCTTGGGATGGAGCACGACGAAGCG

CGCACGCGCATCGTCCTCGGCCCTATCGGCCCGCGTCGCGGTCAGGAACTTGTCGCGCGCTAGGTCC

TCCCTGGTGGGCACCAGGGGCATGAACTCGGCCTGCTCGATGTAGGTCCACTCCATGACCGCATCGC

AGTCGAGGCCGCGTTCCTTCACCGTCTCTTGCAGGTCGCGGTACGCCCGCTCGTTGAGCGGCTGGTA

ACGGGCCAATTGGTCGTAAATGGCTGTCGGCCATGAGCGGCCTTTCCTGTTGAGCCAGCAGCCGACG

ACGAAGCCGGCAATGCAGGCCCCTGGCACAACCAGGCCGACGCCGGGGGCAGGGGATGGCAGCAGCT

CGCCAACCAGGAACCCCGCCGCGATGATGCCGATGCCGGTCAACCAGCCCTTGAAACTATCCGGCCC

CGAAACACCCCTGCGCATTGCCTGGATGCTGCGCCGGATAGCTTGCAACATCAGGAGCCGTTTCTTT

TGTTCGTCAGTCATGGTCCGCCCTCACCAGTTGTTCGTATCGGTGTCGGACGAACTGAAATCGCAAG

AGCTGCCGGTATCGGTCCAGCCGCTGTCCGTGTCGCTGCTGCCGAAGCACGGCGAGGGGTCCGCGAA

CGCCGCAGACGGCGTATCCGGCCGCAGCGCATCGCCCAGCATGGCCCCGGTCAGCGAGCCGCCGGCC

AGGTAGCCCAGCATGGTGCTGTTGGTCGCCGCCGGCCACCAGGGCCGACGTGACGAAATCGCCGTCA

TTCCCTCTGGATTGTTCGCTGCTCGGCGGGGCAGTGCGCCGCGCCGGCGGCGTCGTGGATGGCTCGG

GTTGGCTGGCCTGCGACGGCCGGCGAAAGGTGCGCAGCAGCTCGTTATCGACCGGCTGCGGCGTCGG

GGCCGCCGCCTTGCGCTGCGGTCGGTGTTCCTTCTTCGGCTCGCGCAGCTTGAACAGCATGATCGCG

GAAACCAGCAGCAACGCCGCGCCTACGCCTCCCGCGATGTAGAACAGCATCGGATTCATTCTTCGGT

CCTCCTTGTAGCGGAACCGTTGTCTGTGCGGCGCGGGTGGCCCGCGCCGCTGTCTTTGGGGATCAGC

CCTCGATGAGCGCGACCAGTTTCACGTCGGCAAGGTTCGCCTCGAACTCCTGGCCGTCGTCCTCGTA

CTTCAACCAGGCATAGCCTTCCGCCGGCGGCCGACGGTTGAGGATAAGGCGGGCAGGGCGCTCGTCG

TGCTCGACCTGGACGATGGCCTTTTTCAGCTTGTCCGGGTCCGGCTCCTTCGCGCCCTTTTCCTTGG

CGTCCTTACCGTCCTGGTCGCCGTCCTCGCCGTCCTGGCCGTCGCCGGCCTCCGCGTCACGCTCGGC

ATCAGTCTGGCCGTTGAAGGCATCGACGGTGTTGGGATCGCGGCCCTTCTCGTCCAGGAACTCGCGC

AGCAGCTTGACCGTGCCGCGCGTGATTTCCTGGGTGTCGTCGTCAAGCCACGCCTCGACTTCCTCCG

GGCGCTTCTTGAAGGCCGTCACCAGCTCGTTCACCACGGTCACGTCGCGCACGCGGCCGGTGTTGAA

CGCATCGGCGATCTTCTCCGGCAGGTCCAGCAGCGTGACGTGCTGGGTGATGAACGCCGGCGACTTG

CCGATTTCCTTGGCGATATCGCCTTTCTTCTTGCCCTTCGCCAGCTCGCGGCCAATGAAGTCGGCAA

TTTCGCGCGGGGTCAGCTCGTTGCGTTGCAGGTTCTCGATAACCTGGTCGGCTTCGTTGTAGTCGTT

GTCGATGAACGCCGGGATGGACTTCTTGCCGGCCCACTTCGAGCCACGGTAGCGGCGGGCGCCGTGA

TTGATGATATAGCGGCCCGGCTGCTCCTGGTTCTCGCGCACCGAAATGGGTGACTTCACCCCGCGCT

CTTTGATCGTGGCACCGATTTCCGCGATGCTCTCCGGGGAAAAGCCGGGGTTGTCGGCCGTCCGCGG

CTGATGCGGATCTTCGTCGATCAGGTCCAGGTCCAGCTCGATAGGGCCGGAACCGCCCTGAGACGCC

GCAGGAGCGTCCAGGAGGCTCGACAGGTCGCCGATGCTATCCAACCCCAGGCCGGACGGCTGCGCCG

CGCCTGCGGCTTCCTGAGCGGCCGCAGCGGTGTTTTTCTTGGTGGTCTTGGCTTGAGCCGCAGTCAT

TGGGAAATCTCCATCTTCGTGAACACGTAATCAGCCAGGGCGCGAACCTCTTTCGATGCCTTGCGCG

CGGCCGTTTTCTTGATCTTCCAGACCGGCACACCGGATGCGAGGGCATCGGCGATGCTGCTGCGCAG

GCCAACGGTGGCCGGAATCATCATCTTGGGGTACGCGGCCAGCAGCTCGGCTTGGTGGCGCGCGTGG

CGCGGATTCCGCGCATCGACCTTGCTGGGCACCATGCCAAGGAATTGCAGCTTGGCGTTCTTCTGGC

GCACGTTCGCAATGGTCGTGACCATCTTCTTGATGCCCTGGATGCTGTACGCCTCAAGCTCGATGGG

GGACAGCACATAGTCGGCCGCGAAGAGGGCGGCCGCCAGGCCGACGCCAAGGGTCGGGGCCGTGTCG

ATCAGGCACACGTCGAAGCCTTGGTTCGCCAGGGCCTTGATGTTCGCCCCGAACAGCTCGCGGGCGT

-continued

```
CGTCCAGCGACAGCCGTTCGGCGTTCGCCAGTACCGGGTTGGACTCGATGAGGGCGAGGCGCGCGGC
CTGGCCGTCGCCGGCTGCGGGTGCGGTTTCGGTCCAGCCGCCGGCAGGGACAGCGCCGAACAGCTTG
CTTGCATGCAGGCCGGTAGCAAAGTCCTTGAGCGTGTAGGACGCATTGCCCTGGGGGTCCAGGTCGA
TCACGGCAACCCGCAAGCCGCGCTCGAAAAAGTCGAAGGCAAGATGCACAAGGGTCGAAGTCTTGCC
GACGCCGCCTTTCTGGTTGGCCGTGACCAAAGTTTTCATCGTTTGGTTTCCTGTTTTTTCTTGGCGT
CCGCTTCCCACTTCCGGACGATGTACGCCTGATGTTCCGGCAGAACCGCCGTTACCCGCGCGTACCC
CTCGGGCAAGTTCTTGTCCTCGAACGCGGCCCACACGCGATGCACCGCTTGCGACACTGCGCCCCTG
GTCAGTCCCAGCGACGTTGCGAACGTCGCCTGTGGCTTCCCATCGACTAAGACGCCCCGCGCTATCT
CGATGGTCTGCTGCCCCACTTCCAGCCCCTGGATCGCCTCCTGGAACTGGCTTTCGGTAAGCCGTTT
CTTCATGGATAACACCCATAATTTGCTCCGCGCCTTGGTTGAACATAGCGGTGACAGCCGCCAGCAC
ATGAGAGAAGTTTAGCTAAACATTTCTCGCACGTCAACACCTTTAGCCGCTAAAACTCGTCCTTGGC
GTAACAAAACAAAAGCCCGGAAACCGGGCTTTCGTCTCTTGCCGCTTATGGCTCTGCACCCGGCTCC
ATCACCAACAGGTCGCGCACGCGCTTCACTCGGTTGCGGATCGACACTGCCAGCCCAACAAAGCCGG
TTGCCGCCGCCGCCAGGATCGCGCCGATGATGCCGGCCACACCGGCCATCGCCCACCAGGTCGCCGC
CTTCCGGTTCCATTCCTGCTGGTACTGCTTCGCAATGCTGGACCTCGGCTCACCATAGGCTGACCGC
TCGATGGCGTATGCCGCTTCTCCCCTTGGCGTAAAACCCAGCGCCGCAGGCGGCATTGCCATGCTGC
CCGCCGCTTTCCCGACCACGACGCGCGCACCAGGCTTGCGGTCCAGACCTTCGGCCACGGCGAGCTG
CGCAAGGACATAATCAGCCGCCGACTTGGCTCCACGCGCCTCGATCAGCTCTTGCACTCGCGCGAAA
TCCTTGGCCTCCACGGCCGCCATGAATCGCGCACGCGGCGAAGGCTCCGCAGGGCCGGCGTCGTGAT
CGCCGCCGAGAATGCCCTTCACCAAGTTCGACGACACGAAAATCATGCTGACGGCTATCACCATCAT
GCAGACGGATCGCACGAACCCGCTG.
```

Functional conjugation ability was confirmed by the conjugation with the donor NBEcO63 (DH10B carrying cTNB001-X, and encoding kanamycin (Kin) resistance), to the recipient NBEcO36, containing the plasmid pNB012 encoding the KPC-3 gene, that is not a target for the TEM-3 gRNA but giving ampicillin (Ap) resistance. Ex-conjugants, showing transfer of cTNB001-X to NBEcO36, were selected for growth on LB plates containing 100 μg/mL ampicillin, 16 μg/mL chloramphenicol (LBAp100Cm16). TEM-3 spacer activity was confirmed by conjugation of the donor DH10B carrying cTNB001-X to the recipient NBEc001, which contains pBR322 encoding TEM-3 that is a target for the TEM-3 gRNA.

Thus from overnight cultures, 100 μL was inoculated into 900 μL LBAp100 or LBKm20 broth where appropriate, and grown shaking for 2 hours at 37° C. Then cells were washed to remove antibiotics here: 500 μL of cells centrifuged at 13,000 rpm, for 60 sec and re-suspended into 800 μl LB broth. Then 40 μL of the donor strain (NBEc063) was mixed with 16 μL of the recipients (NBEc001 or NBEc036) in an Eppendorf tube and then 7 μL of mating mixtures, NBEc 001×NBEc063 and NBEc036×NBEc063, were spotted onto an LB plate and incubated at 37° C., over-night. Then cells were removed from the plate with a sterile wooden stick and re-suspended in 500 μL LB broth, mixed well and then diluted 10^1-10^6 in LB and 100 μL plated out 100 μL of dilutions on LBAp100, LBKm20 and LBAp100Km20 plates and incubated overnight at 37° C.

The results shown in Table 23 show efficient conjugation of the cTNB001-X from the donor to the recipient carrying KPC-3 that is not a target for the TEM-3 gRNA. In contrast, as expected, the mating efficiency to the recipient carrying the target TEM-3 gene is reduced 1000 fold.

TABLE 23

| | A | B | C | D = A/B x100 | E = A/C x100 |
|---|---|---|---|---|---|
| Mating | cfu/mL<br>E<br>LBApKm | cfu/mL<br>R + E<br>LBAp | cfu/mL<br>D + E<br>LBKm | ME<br>R/(R + E) | ME<br>E/(D + E) |
| NBEc001x63 | 4.0 × 10^4 | 3.4 × 10^4 | 1.2 × 10^8 | 118% | 0.0328% |
| NBEc036x63 | 1.2 × 10^7 | 1.2 × 10^7 | 3.7 × 10^7 | 98% | 32% |

Key to Table:

cfu colony forming units

ME Mating Efficiency

TABLE 23-continued

| | A | B | C | D = A/B x100 | E = A/C x100 |
|---|---|---|---|---|---|

D Donor
R Recipient
E Ex-conjugant
Recipient Strains:
NBEc001 is DH5a carrying pBR322 encoding TEM-3 for ampicillin resistance (100 μg/mL)
NBEc036 is DH5a carrying pNB012 encoding KPC-3 for ampicillin resistance (100 μg/mL)
Donor Strain:
NBEc063 is DH10B carrying cTNB001 encoding aphA for kanamycin resistance (20 μg/mL).

Example 4.3 Time Course Studies on the Delivery of the Conjugative Transmid by Infection and Subsequent Spread by Conjugation In order to package the Transmid, cTNB001-X, in vivo, the strain NBEc063, carrying the Transmid was mated with the helper strain, NBEc062 (DH10B::lambda(Cl857 Sam7, cos::cat) (Cm resistant) at 30° C. and ex-conjugants selected on LBCm16Km20 plates also incubated over-night at 30° C. A single colony was picked from the LBCm16Km20 plate and inoculated in 1 mL LBCm16Km20 broth and grown overnight at 30° C. Then cells were diluted 50× in 50 mL of LBCm16Km20 and grown at 30° C. to OD600 0.5. Then cells were heat induced at 42° C. for 25 minutes. Then cells were incubated at 37° C. for 3-5 hours. Then cells were harvested by centrifugation at 6,000 r.p.m for 15 minutes and resuspended in 5 mL of lambda dilution buffer (20 mM Tris-HCl, pH 7.5, 100 mM NaCl, 10 mM MgCl2). The cells were lysed by the addition of 50 μL of chloroform and shaking for 10-15 min. at 37° C. Then after centrifugation at 13,000 r.p.m in a microcentrifuge in 2 mL aliquots for 5 min., the packaged Transmid particles were stored at 4° C.

To infect bacteria with the packaged Transmid particles, NBEc036 was inoculated into 1.5 mL LBAp100 and grown shaking o/n at 37° C. Then cells were washed mixing 200 μL of the over-night culture with 1 mL of LB followed by centrifugation at 12,000 r.p.m in a microcentrifuge for 60 sec. and then re-suspended in 1 mL LB. Then 5 mL of additional LB was added and cells were grown shaking at 37° C. to OD60 nm 0.5 (2.5×10^8 cfu/mL). Then 400 μL of 5× diluted packaged Transmid (80 μL of packaged Transmid particles in 320 μL fresh LB with 10 mM MgCl2) was mixed with 400 μL of freshly grown cells in LB in a 50 mL conical tube, and then incubated at 37° C. with shaking. At various time points, samples from the mixture were diluted and plated out (50 μL) on LB, LBAp100, LBKm20 and LBAp100Km20 plates.

The results shown in Table 24 show that after 4 h, all the cells have received the Transmid.

TABLE 24

| T | LB | LBKm | LBKmAp |
|---|---|---|---|
| 0 | 7 × 10^7 | <1.4 × 10^−8 | <1.4 × 10^−8 |
| 4 h | 5 × 10^7 | 5 × 10^7 | 6 × 10^7 |

TABLE 24-continued

| T | LB | LBKm | LBKmAp |
|---|---|---|---|
| 5 h | 6 × 10^7 | 6 × 10^7 | 5 × 10^7 |
| 24 h | 1 × 10^9 | 1 × 10^9 | 1 × 10^9 |

Example 5

Demonstration of Gene Cassettes Expressing Each Single-Guide RNA (sgRNA) from a Unique Promotor Plus Cas9 to Target the Members of the VONCKIST Families of Beta-Lactamases.

Inactivation, by Nemesis Symbiotics, of the genes, VIM-1, OXA-48, NDM-1, CTX-M-15, KPC-3, IMP-1, SHV-18 and TEM-3, representing the VONCKIST families of eight beta-lactamase genes are exemplified in Example 2 above and presents the DNA sequences of the spacer sequences that were used in the construction of the plasmid pNB108 (FIG. 25), encoding these spacer sequences plus tracrRNA and Cas9. In pNB108 these spacer RNAs are transcribed off a single promotor pair, with tracrRNA and are processed, in vivo, to produce the mature guide RNAs that complex with the Cas9 endonuclease to inactivate the target VONCKIST beta lactamases.

In the exemplification herein described, gene cassettes were constructed to express single guide RNAs (sgRNAs), each from a separate and unique promotor, with termination of transcription by a unique terminator, to target members of the VONCKIST families of beta-lactamases. Single guide RNAs are in essence a genetic fusion of elements of the spacer RNA and the tracrRNA that are found in the mature guide RNA following RNA processing (Jinek, M., Chylinski, K., Fonfara, I., Hauer, M., Doudna, J. A., and Charpentier, E. (2012). A programmable dual-RNA-guided DNA endonuclease in adaptive bacterial immunity. Science 337, 816-821). The advantage of the use of sgRNAs is that less RNA processing is required in vivo and the spacer and tracrRNAs moities are co-transcribed and hence equimolar and can form intra-molecular secondary structure. The use of unique promotors ensures high levels of transcription of each sgRNA.

The promotors and terminators used are given in Table 25.

TABLE 25

Promotors (P) and terminators (T) used in spacer constructs

| sgRNA | Target | Promoter P | Promoters* iGEM part No. | Terminator T | Terminator** |
|---|---|---|---|---|---|
| 01 | VIM-1 | P1 | BBa_M13110 | T1 | Glycoside hydrolase |
| 02 | OXA-48 | P2 | Bba_M13101 | T2 | Transposase |
| 03 | NDM-1 | P3 | BBa_I14018 | T3 | Heat shock protein |
| 04 | CTX-M-15_28 | P4 | BBa_M13104 | T4 | tdh |

TABLE 25-continued

Promotors (P) and terminators (T) used in spacer constructs

| sgRNA | Target | Promoter P | Promoters* iGEM part No. | Terminator T | Terminator** |
|---|---|---|---|---|---|
| 05 | CTX-M-8_14 | P5 | BBa_M13105 | T5 | Feredoxin-ion sulfur binding domain |
| 06 | KPC-3 | P6 | BBa_J54200 | T6 | Sulfatase |
| 07 | IMP-1 | P7 | BBa_I14033 | T7 | Sugar phosphatase |
| 08 | SHV-18_48 | P8 | BBa_M13102 | T8 | rph |
| 09 | TEM-3 | P9 | BBa_M13103 | T9 | pyrE |

Promoters* are constitutive *E.coli* sigma70 promoters employed from iGEM promoter catalogue.
Terminators** are employed from transcription terminator database (WebGesTer DB).

Nemesis Symbiotic activity for these sgRNA constructs was tested using the plasmid transformation assay as exemplified in Example 2.

The sgRNA genes were synthesised by BioCat GmbH (Neuenheimer Feld 584 69120 Heidelberg, Germany) and provided cloned into the EcoR V site on the plasmid vector pUC57 (GenBank accession number: Y14837).

The DNA sequences of these sgRNA gene cassettes are given below:

```
SG01 to target VIM-1
                                                     (SEQ ID NO: 177)
AGGAGGTGACTGATGGCCGGTCCGACTATATGATTTTCCGCAGTATTCTTTTTGATGCAATCCGCTT

TGCTTCTGACTATAATAGTCAGGGTAAGGGGTGCGAAAAACACAGCGGCACTTCTCGGTTTTAGAGC

TAGAAATAGCAAGTTAAAATAAGGCTAGTCCGTTATCACGTCGAAAGACGGGCACCGAGTCGGTGCT

TTTGGACTGGCATCCGTTGGGTGCTGGTCCGTATTCTTTAGAAAACTAATACTTTTCTACCGTTTGC

GATTATTCCCCCGATACTGGCTTTTACGGCTACTTTTGCGCGATGTCAGACTGCGATTTCCGTTTGA

ACTAAGACAGCGATGACTAATGCCACGACGATAGCTACCAAAGTAACCACTGCAAAGTCGATCGAGA

CCCTTGAGAGCCTTCAACCCGGTCTCTACTGCGGACCGATGGAAAAACGCCTGCTACG

SG02 to target OXA-48
                                                     (SEQ ID NO: 178)
AGGAGGTGACTGATGGCCGGTCCGACTATATGATGAAGACCACGATCCCGTCTAATGCGCTTCCCTG

TTTTTATGTTATTCTCTCTGTAAAGGTCGCGCGTCTGTCCATCCCACTTAAAGACTGCCCCAGAGCT

AGAAATAGCAAGTTGGGGTAAGGCTAGTCCGTTATCAACTTGAAAAAGTGGCACCGAGTCGGTGCTT

TAGCCGTGCTGTTTGCGCGGTTCTTCGGTCCATCCGTGACTGGGGCAATTTTGAATAATGGTCATGT

GAGGACATAGTAGTTTTCGGTACATACTGCGAATGACCTTGCCATTTAAGTCTCTGACGCGAAAGGT

AAGACCGAAATTACTCCTAAATAAACAAACACTTATAGTTCCGGTTAGTCGATCGAGACCCTTGAGA

GCCTTCAACCCGGTCTCTACTGACGTCTTCCGGACCGATGGAAAAACGCCTGCTACG

SG03 to target NDM-1
                                                     (SEQ ID NO: 179)
AGGAGGTGACTGATGGCCGGTCCGACTATATGATGAAGACCACGATTGTAAGTTTATACATAGGCGA

GTACTCTGTTATGGAGCTGGCGGAAAACCAGATCGCCAAACCGTGTTTTAGAGACAAGTTAAAATAA

GGCTAGTCCGTTATCAACTTGAAAAAGTGGCACCGAGTCGGTGCTTTAGGCCGCCTGGCGCGGCCTG

ACATCTCCAGCCGGAACGATTACCATTACCACGATGACCACTAAAACGACCGAGATTAAGGGTTTAC

CGAGTTCAGCCACTGCCACTATTAAGTGGAAATTACTTATTAAAGGCAGTTATAAATGGAAGGGAGG

GAGTTAGCCAACTTACAGCGGGAAATCGATCGAGACCCTTGAGAGCCTTCAACCCGGTCTCTACTGA

CGTCTTCCGGACCGATGGAAAAACGCCTGCTACG

SG04 to target CTX-M15
                                                     (SEQ ID NO: 180)
AGGAGGTGACTGATGGCCGGTCCGACTATATGATGAAGACCACGATTTGATAAATTCACTATTGACT

CTTCTCAGCGTCTTAATCTAAGCTATCGTACCGAGCCGACGTTAAACACCGCCATTCCGTTTTAGAG

CTAGAAATAGCAAGTTAAAATAAGGCTAGTCCGTAACTTGAAAAAGTGGCACCGAGTCGGTGCTTTA
```

-continued

```
AGGGCTGGTATTCCAGCCCTTTTATCTGAGGAAATCGTTTTAGGGTATGTCTTTTAAGTAAATGATT

GCAGACCTTTCTGCTGTTTTGAAATCTAGCAATGCGATTGATACTCCCGACAGACACCTTACGATGT

CCGCAACATCAAACATGACCACTGCTTTGAGTCACAATGCCATGTACTCGATCGAGACCCTTGAGAG

CCTTCAACCCGGTCTCTACTGACGTCTTCCGGACCGATGGAAAAACGCCTGCTACG

SG05 to target CTX-M8
                                                    (SEQ ID NO: 181)
AGGAGGTGACTGATGGCCGGTCCGACTATATGATGAAGACCACGATCCAACGTCCTGACTGGTATAA

TGAGCCAGTTCTTAAAATCGCATAAGGTAGCAAAAGCTGGCGGCGCTGGAGAAAAGCAGGTTTTAGA

GCTAGAAATAGCAAGTTAAAATAAGGCTAGTCCGTTATCACGCCGAAAGGCGGGCACCGAGTCGGTG

CTTTTTCCGGCGTTTCTCAACGCCGGAACAGTGCGCTTAGACGTAATCAACTTACACCATAAGGATT

TAGAGTTGACTACTTAGAAAGATGGACATTATTACAACAAGGCAATCAAGCAAAATAATTGCATCTA

AAAAGAAGGGTTGCAGGACTGACCATATTACTCGGTCAAGAATTTTAGCGTATTTCGATCGAGACCC

TTGAGAGCCTTCAACCCGGTCTCTACTGACGTCTTCCGGACCGATGGAAAAACGCCTGCTACG

SG06 to target CTX-M28
                                                    (SEQ ID NO: 182)
AGGAGGTGACTGATGGCCGGTCCGACTATATGATGAAGACCACGATGGTAAACCATATGAATTTTCT

ATTGATTGTGACAAAATAAACTTATTCCGCGCGGCCGCGCTACAGTACAGCGATAACGGTTTTAGAG

CTAGAAATAGCAAGTTAAAATAAGGCTAGTCCGTTATCAACTTGAGAAATCAAGTGGCACCGAGTCG

GTGCTTTAAATAAAGCCCTGAGTTTAACCGCTCGGGGCTTTTTGCGTTTTAGGTCAGATTTGTAAAA

TGATAATGGGGGAGAACGTTTTGAAGAAAACGTTTTCGGAGAGCGATAAAACCAAAAATAGCAGCAG

ACCATTTGCTCCCAATACTATCACAACGAGAATGATACGGAGCATTAAGGAAAACCGCAATACATTC

GATCGAGACCCTTGAGAGCCTTCAACCCGGTCTCTACTGACGTCTTCCGGACCGATGGAAAAACGCC

TGCTACG

SG07 to target KPC-3
                                                    (SEQ ID NO: 183)
AGGAGGTGACTGATGGCCGGTCCGACTATATGATGAAGACCACGATCCGTGACGGATCCTGGTGCAA

AACCTTTCGCGGTATGGCATGATAGCGCCCGCCGCCAATTTGTTGCTGAAGGAGTTGGGGTTTTAGA

GCTAGAAATAGCAAGTTAAAATAAGGCTAGTCCGTTATCAGCGGGAAACCGCGGCACCGAGTCGGTG

CTTTTCTGACGATAATGCCCGCTGATGATCACCCGGCGGGCATTATTCAGGCTGCTTAAACCAGACT

GGACGGAGTTGGAGGACAGTTACGACCGCCGCCGAGACTACCACCAAGACCACCGCCGAGACTCCCA

CCACCGAGACTCCCACCGCCAAGACTCCCACCGCCGAGACTCCCTCCGCCAAGGCCACCACCGAGAC

TAAGGCCACTTCGATCGAGACCCTTGAGAGCCTTCAACCCGGTCTCTACTGACGTCTTCCGGACCGA

TGGAAAAACGCCTGCTACG

SG08 to target IMP-1
                                                    (SEQ ID NO: 184)
AGGAGGTGACTGATGGCCGGTCCGACTATATGATGAAGACCACGATGGCACGTAAGAGGTTCCAACT

TTCACCATAATGAAATAAGATCACTACCGGGCGTATTTTTTGAGGGCTAGTTAAAAATAAAATTGAA

GTTTTTTATCCGGGGGAGAGCTAGAAATAGCAAGTTCCCCTAAGGCTAGTCCGTTATCAACTTGAAA

AAGTGGCACCGAGTCGGTGCTTTGGGCGGGCAAACAGCATAAACGCGTTTGCCCGCTTACTGATTAT

TACAGAAACCGCGACCATTTGGTATACTTAAAAGATAACTAACACTGTTTTATTTGAATAAGGCACC

ACAGAAACGCAAAGAAAATATACAACGGTGGAAATACATACATAAAAGATGCAAACGATTGTATGAC

GCATTATTCCTCAGAATTCGATCGAGACCCTTGAGAGCCTTCAACCCGGTCTCTACTGACGTCTTCC

GGACCGATGGAAAAACGCCTGCTACG
```

-continued

SG09 to target SHV-18

(SEQ ID NO: 185)

AGGAGGTGACTGATGGCCGGTCCGACTATATGATGAAGACCACGATTATTAACGTTTACAATTTAAA

TATTTGCTTATACAATCTTCCTGTTTTGCCTTGACCGCTGGGAAACGGAACTGAATGGTTTTAGAGC

TAGAAATAGCAAGTTAAAATAAGGCTAGTCCGTTATCAACTTGGAAACAAGTGGCACCGAGTCGGTG

CTTTAAGGCGACTGATGAGTCGCCTTTTTTTTGTCTGCCGTGAATAGGCGGACCATGACTCGTTTTG

GGGCGATTAGGATTAGGAAGAGAACTCCTCAGAGTCGGAGAATTATGAAAGTACAAAGTCTTATTAT

CCAAGGCTTTATCCGTCCCCCGTAATTGACAAATATGCCCGTGACAATGAGTTCGATCGAGACCCTT

GAGAGCCTTCAACCCGGTCTCTACTGACGTCTTCCGGACCGATGGAAAAACGCCTGCTACG

SG10 to target TEM-3

(SEQ ID NO: 186)

AGGAGGTGACTGATGGCCGGTCCGACTATATGATGAAGACCACGATAATTCACCTCGAAAGCAAGCT

GATAAACCGATACAATTAAAGGCTCCTTTAACTGGCGAACTACTTACTCTAGCTTCCGTTTTAGAGC

TAGAAATAGCAAGTTAAAATAAGGCTAGTCCGTTATCATGAAGAAATTCAGGCACCGAGTCGGTGCT

TTCGCCGGATGAAAAGTCATCCGGCGTCATATTACTCCAAGGATAACCCGAACGATAGGGACTTTTA

CTCCCACCACCGAGACTCCCACCGCCAAGACTCCCACCGCCAAGACTCCCACCGCCATGATTTGGAG

GACTCATGCCACTATGTGGATAAGGCCCGATATGAATATAGTTGGGAGAGCTTCGATCGAGACCCTT

GAGAGCCTTCAACCCGGTCTCTACTGACGTCTTCCGGACCGATGGAAAAACGCCTGCTACG

Sg08B to target IMP-1

(SEQ ID NO: 187)

AGGAGGTGACTGATGGCCggTccgACTATATGATgaagacCAcgattgatcggcacgtaagaggttc caactttcaccataatgaaataagatcactaccgggcgtattttttgagttatcgagattttcagga gctaaggaagctaaagaagttaacgggtggggcgttgttcctaaacaGggggAGAGCTAGAAATAGC AAGTTccccTAAGGCTAGTCCGTTATCAACTTGAAAAAGTGGCACCGAGTCGGTGCTTTagtcaaaa gcctccgaccggaggcttttgactacagaaaccgcgaccatttggtatacttaaaagataactaaca ctgttttatttgaataaggcaccacagaaacgcaaagaaaatatacaacggtggaaatacatacata aaagatgcaaacgattgtatgacgcattattcctcagaatcCGATCgagaccCTTGAGAGCCTTCAA CCCggtctcTACTGACgtcttccggAccgatggaaaaacgcctgctacg Sg09B to target SHV-18

(SEQ ID NO: 188)

AGGAGGTGACTGATGGCCggTccgACTATATGATgaagacCAcgattgtaagtttatacataggcga gtactctgttatggGCCTTGACCGCTGGGAAACGGAACTGAATGGTTTTAGAGCTAGAAATAGCAAG TTAAAATAAGGCTAGTCCGTTATCAACTTGAAAAAGTGcgtgCGAGTCGcacgTTTtcacactggct caccttcgggtgggcctttctgcgtttatagccgtgaataggcggaccatgactcgttttggggcga ttaggattaggaagagaactcctcagagtcggagaattatgaaagtacaaagtcttattatccaagg ctttatccgtcccccgtaattgacaaatatgcccgtgacaatgagtTCGATCgagaccCTTGAGAGC CTTCAACCCggtctcTACTGACgtcttccggAccgatggaaaaacgcctgctacg.

Example 5.1 Construction of Gene Cassettes Expressing sgRNAs that Target the VONCKIST Families of Beta-Lactamases The sgRNA cassettes were constructed in stages. In the first stage, single sgRNA genes were cloned into the vector pNB000-X and then in later stages, by concatenation, two, or three, or four, or six sgRNA genes were cloned into this vector.

Each monomeric sgRNA sequence synthesised by BioCat GmbH was amplified by the appropriate primer pairs followed by Rsr II digestion and cloned at the Rsr II sites located downstream of cas9 on cTNB000-X. The sequence at the left and right ends of sg01 is shown below.

Left (SEQ ID NO: 189)
5'-AGGAGGTGACTGATGGCCGGTCCGACTATATGATTTTCCGCAGTAT

...

right (SEQ ID NO: 190)
... TCGATCGAGACCCTTGAGAGCCTTCAACCCGGTCTCTACTGCGGAC

CGAT-3'.

Rsr II sites in the left and the right ends are underlined and two Bsa I sites at the right end are depicted by the capital bold letters. The part of the left and the right arm sequence of the rest of the sgxx, where xx=02, 03, 04, 05, 06, 07, 08, 08B, 09, 09B and 10, is shown below.

Left (SEQ ID NO: 191)
5'-AGGAGGTGACTGATGGCCGGTCCGACTATATGATgaagacCAcgat

...

right (SEQ ID NO: 192)
... TCGATCGAGACCCTTGAGAGCCTTCAACCCGGTCTCTACTGACgtc ttcGGACCGAT-3'.

Rsr II sites are underlined and Bsa I sites are depicted by the capital bold letters. Bbs I sites are depicted by the small bold letters.

Each sgxx amplicon, where xx=01, 02, 03, 04, 05, 06, 07, 08, 08B, 09, 09B and 10 was amplified by primer pair NB185 and NB186 (given below 5'-3').

(SEQ ID NO: 193)
NB185 Gacgttgtaaaacgacggccag (SEQ ID NO: 194)
NB186 Tcacacaggaaacagctatgaccatg.

The amplicons were purified by Agencourt AMPure XP beads and digested by Rsr II, The digested fragments were purified and ligated to the Rsr II-digested cTNB000-X vector. The single-stranded overhangs created by Rsr II digestion on the vector and inserts are 3'-GAC-5' and 5'-GTC-3', respectively. Although there were no vector self-ligation events, there were two orientations for the insert possible. These monomeric sgxx (where xx=01, 02, 03, 04, 05, 06, 07, 08, 08B, 09, 09B and 10) constructs were the starting materials for spacer concatenation. Two Bsa I sites are created in the 3' end of the sgxx insert. Below is the vector structure after cloning one Sgxx spacer sequence. The dots " . . . " on both ends represent the rest of the vector sequence, which is circular. The Bsa I sites are shown in lowercase.

5'-...[Sgxx]1_CGATCgagaccCTTGAGAGCCTTCAACCCggtctcT

ACTG*[1]_[Vector]...-3'

3'-...[Sgxx]1_GCTAGctctggGAACTCTCGGAAGTTGGGccagagA

TGAC*[2]_[Vector]...-5'

*[1]= SEQ ID NO: 195
*[2]= SEQ ID NO: 196.

Bsa I digestion linearises the vector containing asymmetric four base protruding 5' ends.

5'-...[Sgxx]1_ACTG_[Vector]...-3'

3'-...[Sgxx]1_GCTA_[Vector]...-5'

Each monomeric [Sgxx]2 (, where xx=01, 02, 03, 04, 05, 06, 07, 08, 08B, 09, 09B, 10) were amplified by primer pair NB185 and NB186 as before, followed by amplicon purification using Agencourt beads and digested by Bbs I. The Bbs I-digested fragments were gel purified, quantified and mixed in equimolar ratios and ligated to the mixed vector carrying the monomeric [Sgxx]1. The structure of the fragment containing the [Sgxx]2 digested with BbsI is as follows:

5'-CGAT-[Sgxx]2-CGATCgagacc*[1]...ggtctcT-3'

3'-[Sgxx]2-GCTAGctctgg*2...ccagagA_TGAC-5'

*[1]= SEQ ID NO: 197
*[2]= SEQ ID NO: 198.

After ligating [Sgxx]2 to the vector containing [Sgxx]1 gives the dimeric construct [Sgxx]1+[Sgxx]2 and two Bsa I sites (lower case) are restored and ready to ligate the third spacer structure [Sgxx]3 to construct trimeric spacer structure.

5'-...[Sgxx]1_CGAT-[Sgxx]2-CGATCgagacc*[3]...ggtctc

T_ACTG_[Vector]...-3'

3'-...[Sgxx]1_GCTA-[Sgxx]2-GCTAGctctgg*[4]...ccagag

A_TGAC_[Vector]...-5'

*[3]= SEQ ID NO: 197
*[4]= SEQ ID NO: 198.

Alternatively, when once dimeric constructs have been constructed, they can be amplified with the two primer pairs NB194 and NB189 (shown 5'-3' below):

(SEQ ID NO: 199)
NB194 catcggTccggaagacGTCAG (SEQ ID NO: 200)
NB189 GACTGATGGCCggTccgA.

Then fragments containing dimeric spacer construct can be prepared by Bbs I digestion. The structure of the fragment containing the dimeric spacer [Sgxx]3-[Sgxx]4 digested with BbsI is as follows:

```
5'-CGAT-[Sgxx]3-[Sgxx]4-CGATCgagacc*1...ggtctcT-3'

3'-[Sgxx]3-[Sgxx]4-GCTAGctctgg*2...ccagagA_TGAC-5'

*1= SEQ ID NO: 197
*2= SEQ ID NO: 198
```

Ligating [Sgxx]3-[Sgxx]4 to the vector containing [Sgxx] 1-[Sgxx]2 gives tetrameric construct [Sgxx]1-[Sgxx]2-[Sgxx]3-[Sgxx]4 and two Bsa I sites (lower case) are restored and ready to ligate the next spacer construct.

In this way, the spacer sequences encoding the sgRNA genes can be constructed in a combinatorial way using Bsa I digestion for the spacer cloned vector and BbsI digestion for the Sgxx monomeric, dimeric, trimeric, tetrameric etc amplicons. It is possible to collect 10! (ten factorial)=3,628,800 different orders of 10 spacers. The following examples are the exemplification of creating the subsets of concatenated sgxx spacer construct.

Example 5.1.1 Construction of Gene Cassettes Expressing a Single-Guide RNA (sgRNAs) that Target the VONCKIST Families of Beta-Lactamases The pUC57-derived plasmids provided by BioCat and encoding one or other of the sgRNA genes, sg01-sg10, sg8B and sg9B, were used as template to produce amplicons by PCR. These amplicons were digested with Rsr II and cloned into the vector cTNB000-X also previously digested with Rsr II to generate plasmids carrying each of the single sgRNA genes.

To produce the amplicons encoding the sgRNA amplicons, each pUC57 plasmid derivatives was used as template with primers NB185 and NB186:

PCR reactions were performed in 50 μL reaction volumes containing 0.5 μM each of forward and reverse primers, 200 μM dNTPs, in 1× Q5 reaction buffer plus 0.5 μL Q5 High Fidelity DNA polymerase: the Q5 buffer and enzyme were purchased from New England Biolabs (catalogue no. M0149S). PCR cycles were as follows: 98° C. for 60 sec., followed by 35 cycles of 98° C. for 10 sec, 55° C. for 10 sec 72° C. for 30 sec followed by 72° C. for 2 min., and then held at 4° C. overnight.

Then amplicon purification was performed with Ampure Agencourt beads as per manufacturer's instructions followed by digestion with Rsr II purchased from New England Biolabs.

The 8636 bp vector cTNB000-X, encoding resistance to chloramphenicol, was also digested with Rsr II, followed by DNA purification from 0.8% agarose gel after fractionation by electrophoresis.

PCR fragments were ligated into the RsrII-digested cTNB000-X and ligation products used to transform DH5α competent cells as described above, followed by selection on LBCm16 plates.

Colonies were screened for the presence of insert using PCR conditions described above with the primers NB189 and NB190, and PCR products analysed by 1.2% agarose gel electrophoresis.

```
                                   (SEQ ID NO: 200)
NB189 GACTGATGGCCggTccgA

                                   (SEQ ID NO: 201)
NB190 GGGTTGAAGGCTCTCAAGggtc.
```

Plasmid DNA was prepared from selected PCR-positive clones submitted to Source Bioscience for sequencing. Plasmids carrying the correct inserts of sgRNA genes are given in Table 26. Inserts were found present in two orientations relative to the vector, designated as Forward (F) and Reverse (R) where sgRNA transcription direction in the same transcription direction of cas9=Forward, and in opposite direction of cas9=Reverse.

TABLE 26

| Clone No. | Plasmid | Construct | Target |
|---|---|---|---|
| 01.1 | cTNB000-X_sg01R | cTNB000-X:: sgRNA(VIM-1)R | VIM-1 |
| 02.1 | cTNB000-X_sg02F | cTNB000-X:: sgRNA(OXA-48)F | OXA-48 |
| 03.2 | cTNB000-X_sg03F | cTNB000-X:: sgRNA(NDM-1)F | NDM-1 |
| 03.1 | cTNB000-X_sg03R | cTNB000-X:: sgRNA(NDM-1)R | NDM-1 |
| 04.1 | cTNB000-X_sg04F | cTNB000-X:: sgRNA(CTX-M-15)F | CTX-M-15 |
| 05.1 | cTNB000-X_sg05F | cTNB000-X:: sgRNA(CTX-M-8_14)F | CTX-M-8_14 |
| 06.1 | cTNB000-X_sg06R | cTNB000-X:: sgRNA(CTX-M-28)R | CTX-M-28 |
| 07.7 | cTNB000-X_sg07F | cTNB000-X:: sgRNA(KPC-3)F | KPC-3 |
| 07.3 | cTNB000-X_sg07R | cTNB000-X:: sgRNA(KPC-3)R | KPC-3 |
| 08.1 | cTNB000-X_sg08F | cTNB000-X:: sgRNA(IMP-1)F | IMP-1 |
| 08.2 | cTNB000-X_sg08R | cTNB000-X:: sgRNA(IMP-1)R | IMP-1 |
| 09.1 | cTNB000-X_sg09R | cTNB000-X:: sgRNA(SHV-18_48)R | SHV-18_48 |
| 10.2 | cTNB000-X_sg10F | cTNB000-X:: sgRNA(TEM-3)F | TEM-3 |

These plasmids were tested for Nemesis Symbiotic activity against their cognate beta-lactamase genes using the plasmid transformation assay as described in Example 5.3 below.

Example 5.1.2 Dimeric sgRNA Gene Concatenation: Gene Cassettes Expressing Two sgRNAs that Target the VONCKIST Families of Beta-Lactamases Plasmids cTNB000-X_sg01R, 02F, 03F were purified using Qiagen Spin Miniprep Kit (Cat No. 27104). Plasmids were digested by Bsa I and fractionated on 0.8% agarose gel to purify the digested fragments using NEB Monarch DNA Gel Extraction Kit (Cat No. T1020). Bbs I-digested monomeric amplicon sg04, sg07 and sg10 obtained in example 5.1.1 were fractionated on 1.2% agarose gel to purify the desired fragments using NEB Monarch DNA gel extraction kit. Three fragments sg04, sg07 and sg10 were mixed in equimolar ratios and ligated to each vector cTNB000-X_sg01R, 02F and 03F (Vector/insert=1/3 (molar ratio)) in 1× Quick ligation buffer purchased from NEB (Cat No. M2200). The ligation conditions are shown in Table 27.

TABLE 27

| | ng/uL | ng | A | B | C |
|---|---|---|---|---|---|
| Water | | | 3.1 | 2.1 | 2.9 |
| 2x Quick Lig. B. | | | 5 | 5 | 5 |
| T4 Ligase 2000 U/μL | | | 0.5 | 0.5 | 0.5 |
| sg04_07_10 | 6.5 | 3.25 | 0.5 | 0.5 | 0.5 |
| cTNB000-X_01R/BsaI | 17.4 | 25 | 1.4 | | |
| cTNB000-X_02F/BsaI | 12.9 | 25 | | 1.9 | |
| cTNB000-X_03F/BsaI | 16.2 | 25 | | | 1.5 |
| vol. | | | 10 | 10 | 10 |
| 25 C., 15 min | | | | | |

A is the ligation reaction between cTNB000-X_01R and the mixture of fragments sg04, sg07 and sg10. B is the ligation reaction between cTNB000-X_02F and the mixture of fragments sg04, sg07 and sg10. C is the ligation reaction between cTNB000-X_03F and the mixture of fragments sg04, sg07 and sg10. Ligation products were used to transform DH5α competent cells as described above, followed by selection on LBCm16 plates. Colonies were screened for the presence of dimeric insert using PCR conditions described above with the primers NB190 and NB129 (shown below 5'-3') for ligation condition A and NB195 and NB194 for ligation condition B and C and PCR products were analysed by 1.2% agarose gel electrophoresis.

(SEQ ID NO: 159)
NB129 AGGAGGTGACTGATGGCCggtccgACTATATGATTTTCCGCAGT (SEQ ID NO: 201)
NB190 GGGTTGAAGGCTCTCAAGggtc (SEQ ID NO: 199)
NB194 catcggTccggaagacGTCAG (SEQ ID NO: 202)
NB195 ggTccgACTATATGATgaagacCAcg.

Plasmid DNA was prepared from selected PCR-positive clones submitted to Source Bioscience for sequencing. Plasmids carrying the correct dimeric inserts of sgRNA genes are given in Table 28.

TABLE 28

| | |
|---|---|
| cTNB000-X_sg014R | cTNB000-X::sgRNA(VIM-1)R::sgRNA(CTX-M-15)R |
| cTNB000-X_sg017R | cTNB000-X::sgRNA(VIM-1)R::sgRNA(KPC-3)R |
| cTNB000-X_sg0110R | cTNB000-X::sgRNA(VIM-1)R::sgRNA(TEM-3)R |
| cTNB000-X_sg024F | cTNB000-X::sgRNA(OXA-48)F::sgRNA(CTX-M-15)F |
| cTNB000-X_sg0210F | cTNB000-X::sgRNA(OXA-48)F::sgRNA(TEM-3)F |
| cTNB000-X_sg034F | cTNB000-X::sgRNA(NDM-1)F::sgRNA(CTX-M-15)F |
| cTNB000-X_sg0310F | cTNB000-X::sgRNA(NDM-1)F::sgRNA(TEM-3)F |

These plasmids were tested for Nemesis Symbiotic activity against their cognate beta-lactamase genes using the plasmid transformation assay as described in Example 5.3 below.

Example 5.1.3 Construction of Gene Cassettes Expressing Four sgRNAs that Target the VONCKIST Families of Beta-Lactamases Plasmids cTNB000-X_sg017R was digested by BsaI and fractionated on 0.8% agarose gel to purify the digested fragments using NEB Monarch DNA Gel Extraction Kit (Cat No. T1020). Dimeric fragments sg024, sg0210, sg034 and sg0310 were amplified from plasmid cTNB-X_sg024F, cTNB000-X_sg034F and cTNB000-X_0310F as a template, respectively with primer pair NB194 and NB195 in a Q5 PCR reaction mentioned above. Amplicons were purified by Agencourt beads followed by digestion with BbsI. Digested dimeric fragments were fractionated on 1.2% agarose gel and the desired fragments were extracted using NEB Monarch DNA Gel Extraction Kit (Cat No. T1020). Four fragments sg024, sg0210, sg034 and sg0310 were mixed in equimolar ratios and ligated to the vector cTNB000-X_sg017R (Vector/insert=1/3 (molar ratio)) in 1× Quick ligation buffer purchased from NEB (Cat No. M2200). The ligation conditions are shown in Table 29.

TABLE 29

| | ng/μL | ng | ng | A |
|---|---|---|---|---|
| Water | | | | 2 |
| 2x Quick Lig. B. | | | | 5 |
| T4 Ligase 2000 U/μL | | | | 0.5 |
| sg(024)_(0210)_(034)_(0310) | 11.3 | 11.33 | 5.7 | 0.5 |
| cTNB000-X_017R/BsaI | 12.7 | 50 | 25 | 2.0 |
| vol. | | 20 | 10 | 10 |
| 25 C., 15 min | | | | |

Ligation products were used to transform DH5α competent cells as described above, followed by selection on LBCm16 plates. Colonies were screened for the presence of the tetrameric insert using PCR conditions described above with the primers NB190 and NB129 and PCR products were analysed by 1.2% agarose gel electrophoresis.

(SEQ ID NO: 159)
NB129 AGGAGGTGACTGATGGCCggtccgACTATATGATTTTCCGCAGT (SEQ ID NO: 201)
NB190 GGGTTGAAGGCTCTCAAGggtc.

Plasmid DNA was prepared from the selected PCR-positive clones submitted to Source Bioscience (William James House, Cowley Road, Cambridge CB4 0WU, United Kingdom) for sequencing. Plasmids carrying the correct tetrameric inserts of sgRNA genes are given in Table 30.

TABLE 30

| | |
|---|---|
| cTNB000-X_sg01724R | cTNB000-X::sgRNA(VIM-1)R::sgRNA(KPC-3)R::sgRNA(OXA-48)R::sgRNA(CTX-M-15)R |
| cTNB000-X_sg017210R | cTNB000-X::sgRNA(VIM-1)R::sgRNA(KPC-3)R::sgRNA(OXA-48)R::sgRNA(TEM-3)R |
| cTNB000-X_sg01734R | cTNB000-X::sgRNA(VIM-1)R::sgRNA(KPC-3)R::sgRNA(NDM-1)R::sgRNA(CTX-M-15)R |
| cTNB000-X_sg017310R | cTNB000-X::sgRNA(VIM-1)R::sgRNA(KPC-3)R::sgRNA(NDM-1)R::sgRNA(TEM-3)R |

These plasmids were tested for Nemesis Symbiotic activity against their cognate beta-lactamase genes using the plasmid transformation assay as described in Example 5.3 below.

Example 5.1.4 Construction of Gene Cassettes Expressing Six sgRNAs that Target the VONCKIST Families of Beta-Lactamases Plasmids containing tetrameric constructs cTNB000-X_sg01724R, sg017210R, sg01734R and sg017310 were digested by BsaI and fractionated on 0.8% agarose gel to purify the digested fragments using NEB Monarch DNA Gel Extraction Kit (Cat No. T1020).

Amplified dimeric constructs sg024, sg0210, sg034 and sg0310 digested by BbsI obtained in example 5.1.3 were used for ligation. Four fragments sg024, sg0210, sg034 and sg0310 were separately ligated to the vector cTNB000-X_sg017310R, cTNB000-X_sg01734R, cTNB000-X_sg017210R and cTNB000-X_sg01724R, respectively. The ligation conditions are shown in Table 31.

TABLE 31

| | ng/μL | ng | A | B | C | D |
|---|---|---|---|---|---|---|
| Water | | | 2.6 | 3.2 | 3.7 | 2.3 |
| 2x Quick Lig. B. | | | 5 | 5 | 5 | 5 |
| T4 Ligase 2000 U/μL | | | 0.5 | 0.5 | 0.5 | 0.5 |
| sg0310 | 10.44 | 5.22 | 0.5 | | | |
| sg0210 | 10.81 | 5.41 | | 0.5 | | |
| sg024 | 10.73 | 5.34 | | | 0.5 | |
| sg034 | 5.2 | | | | | 1 |
| 1.cTNB000-X_ 01724R/Bsal | 18.2 | 25 | 1.4 | | | |
| 2.cTNB000-X_ 01734R/Bsal | 32.6 | 25 | | 0.8 | | |
| 3.cTNB000-X_ 017310R/Bsal | 81.2 | 25 | | | 0.3 | |
| 4. cTNB000-X_ 017210R/Bsal | 20.3 | | | | | 1.2 |
| vol. | | 10 | 10 | 10 | 10 | 10 |
| 25 C., 15 min | | | | | | |

Ligation products were used to transform DH5α competent cells as described above, followed by selection on LBCm16 plates. Colonies were screened for the presence of the hexameric insert using PCR conditions described above with the primers NB190 and NB129 and PCR products were analysed by 1.2% agarose gel electrophoresis.

Plasmid DNA was prepared from selected PCR-positive clones submitted to Source Bioscience for sequencing. Plasmids carrying the correct hexameric inserts of sgRNA genes are given in Table 32.

```
CTXM8, 986 nt.
                                          (SEQ ID NO: 203)
Tggtttcttagacgtcaggtggcacttttcggggaaatgtgcgcggaacc

cctatttgtttatttttctaaatacattcaaatatgtatccgctcatgag

acaataaccctgataaatgcttcaataatattgaaaaaggaagagtatga

tgagacatcgcgttaagcggatgatgctaatgacaacggcctgtatttcg

ctgttgctggggagtgcgccgctgtatgcgcaggcgaacgacgttcagca

aaagctggcggcgctggagaaaagcagcgggggcggttgggagtggcgc

tgattgacaccgccgataacgcacagacgctctaccgcgccgatgagcgc

tttgccatgtgcagcaccagtaaggtgatggcggcagcggctgtgctcaa

gcaaagtgaaacgcaaaagaaggtgttgagtcagaaggttgagattaaat

cttcagacctgattaactacaatcccattactgaaaaacacgtcaacggc

acgatgacgctggcggaattgagcgccgcggcgttgcagtacagcgacaa

tacggccatgaacaagctgattgcccatcttgggggccggataaagtga

cggcgtttgcccgtgcgattggggataacaccttccggctcgatcgtact

gagccgacgctcaacaccgcgatccccggcgacccgcgcgataccaccac

gccattagcgatggcgcagacgcttcgcaatctgacgttgggcagtgcct

taggtgaaactcagcgtgcgcaactggtaacgtggctgaaaggcaatacc

accggcgctgccagcattcaggctgggctacccacatcgtgggttgtcgg

ggataaaaccggcagcggtgattatggtacgacgaatgacatcgccgtta

tctggccggaagggcgtgcgccgcttattctggtcacttacttcacccag

ccagagcagaagTAAggtctcgcggtatcattgcag.
```

TABLE 32

| | |
|---|---|
| cTNB000_sg01721034R | cTNB000-X::sgRNA(VIM-1)R::sgRNA(KPC-3)R::sgRNA(OXA-48)R::sgRNA(TEM-3)R::sgRNA(NDM-1)R::sgRNA(CTX-M-15)R |
| cTNB000_sg01724310R | cTNB000-X::sgRNA(VIM-1)R::sgRNA(KPC-3)R::sgRNA(OXA-48)R::sgRNA(CTX-M-15)R::sgRNA(NDM-1)R::sgRNA(TEM-3)R |
| cTNB000_sg01734210R | cTNB000-X::sgRNA(VIM-1)R::sgRNA(KPC-3)R::sgRNA(NDM-1)R::sgRNA(CTX-M-15)R::sgRNA(OXA-48)R::sgRNA(TEM-3)R |
| cTNB000_sg01731024R | cTNB000-X::sgRNA(VIM-1)R::sgRNA(KPC-3)R::sgRNA(NDM-1)R::sgRNA(TEM-3)R::sgRNA(OXA-48)R::sgRNA(CTX-M-15)R |

These plasmids were tested for Nemesis Symbiotic activity against their cognate beta-lactamase genes using the plasmid transformation assay as described in Example 5.3 below.

Example 5.2 Construction of pUC57Kan-CTX-M-8 Encoding the CTX-M8 Beta Lactamase Gene To complete the analysis with the sgRNA cassette targeting the CTX-M-8 gene, this gene was synthesised by BioCat GmbH (Neuenheimer Feld 584 69120 Heidelberg, Germany) and provided on their plasmid vector pUC57-Kan (GenBank accession number: JF826242.2) by insertion into the EcoR V site of this plasmid to give the plasmid pNB018 (pUC57-Kan::CTX-M-8).

The DNA sequence of the CTX-M-8 coding region plus flanking TEM-3 5' promotor and 3' terminator is given below (5'-3'):

The plasmid pNB018 was transformed into DH5α competent cells (purchased from New England Biolabs) and transformants selected on LBCm16 plates, to give the strain NBEc069.

Example 5.3 Plasmid Transformation Assays to Demonstrate Inactivation of Selected VONCKIST Families of Beta-Lactamases by Cas9 Plus sgRNA Expression Cassettes Gene cassettes expressing the sgRNA genes plus the Cas9 endonuclease were tested for Nemesis Symbiotic activity by the plasmid transformation assay using the nine recipient DH5α-derived *E. coli* strains (see Table 33) each carrying a plasmid encoding a representative VONCKIST beta lactamase gene, as described in Example 2, or Example 5.2 above for NBEc069.

TABLE 33

| DH5α derivative | Plasmid | Bla gene |
|---|---|---|
| NBEc032 | pNB013 | VIM-1 |
| NBEc033 | pNB016 | OXA-48 |
| NBEc034 | pNB015 | NDM-1 |
| NBEc035 | pNB011 | CTX-M-15 |
| NBEc069 | pNB018 | CTX-M-8 |
| NBEc036 | pNB012 | KPC-3 |
| NBEc037 | pNB014 | IMP-1 |
| NBEc038 | pNB10 | SHV-18 |
| NBEc001 | PBR322 | TEM-3 |

A modified quick transformation protocol was developed to introduce plasmids carrying the cTNB000-X plasmid derivatives carrying insertions of sgRNA expression cassettes. From overnight 2 mL cultures in LB plus 100 μg/mL ampicillin, 100 μL was used to inoculate 1 mL of LB and cells were grown shaking for 60-90 min. Then cells were centrifuged for 60 sec. in 1.4 mL Eppendorf tubes in a microcentrifuge (at room temperature) at 12,500 r.p.m. After removal of the supernatant, 1 mL of ice-cold 80 mM MgCl2, 20 mM CaCl2) was added and tubes were incubated on ice for 5 min. Then again cells were centrifuged for 60 sec. in 1.4 mL Eppendorf tubes (at room temperature) in a microcentrifuge at 12,500 r.p.m. After removal of the supernatant, 200 μL of ice-cold 100 mM CaCl2) was added. These were then split into 2 (or 4) chilled 1.4 mL Eppendorf tubes adding 100 (or 50 μL) of cells to each tube, followed by the addition of 0.3 μL of plasmid DNA. Tubes were incubated on ice for 20-30 min, then 42° C. for 90 sec. followed by 90 sec. on ice. Then 400 μL (or 200 μL) of LB was added, and the tubes were incubated in a shaking incubator at 37° C. for 60 min. Then 200 μL of cells were plated on LBCm16 plates and incubated overnight at 37° C. The following day colonies were picked from the primary transformant plates and replica-tooth-picked to LB plates containing 16 μg/ml chloramphenicol plus 100 μg/mL ampicillin (LBCm16Ap100) or LB plates containing 16 μg/ml chloramphenicol (LBCm16) and incubated overnight at 37° C. Growth of colonies was scored the following day.

All toothpicked cells should grow on LBCm16; failure to grow on the LBCm16Ap100 plates indicates the successful inactivation on the ampicillin resistance gene and indication of Nemesis Symbiotic activity.

The results of all Nemesis Symbiotic activity (NSA) assays performed, using the plasmid transformation assay are summarised in Table 34, where V, O, N, C15, C8, C28, K, I, S, T refer to the target beta lactamase genes: VIM-1, OXA-48, NDM-1, CTX-M-15, CTX-M-8, CTX-M-28, KPC-3, IMP-1 SHV-18, TEM-3 respectively. The positive, +, sign indicates successful inactivation of the designated beta lactamase gene in all colonies tested following testing the various strains NBEc032, NBEc033, NBEc034, NBEc035, NBEc069, NBEc036, NBEc 037, NBEc038, NBEc 001 carrying these genes, respectively. The positive sign in brackets (+) indicates that most but not all colonies showed inactivation of the designated beta lactamase gene and the negative sign, –, indicates that the designated beta lactamase gene has not been inactivated by that sgRNA gene (although alternative sgRNA gene sequences are being synthesised and tested to demonstrate inactivation of those beta lactamase genes). FIG. 29 shows examples of testing colonies of DH5α derivatives with plasmids carrying beta lactamse genes that were transformed with cTNB000-X_sg01721034R carrying sgRNAs targeting VKONTC15.

TABLE 34

| cTNB000-X::sg tested for NSA | | | | Bacterial strains carrying bla genes tested | | | | | | | | |
|---|---|---|---|---|---|---|---|---|---|---|---|---|
| Plasmid | Targets | Polarity | | V | O | N | C15 | C8 | K | I | S | T |
| Mono | | | | | | | | | | | | |
| sg01 | V | — | R | + | | | | | | | | |
| sg02 | O | F | — | | + | | | | | | | |
| sg03 | N | F | R | | | + | | | | | | |
| sg04 | C15 | F | — | | | | + | | | | | |
| sg05 | C8 | F | — | | | | | – | | | | |
| sg06 | C28 | — | R | | | | + | | | | | |
| sg07 | K | F | R | | | | | | + | | | |
| sg08 | I | F | R | | | | | | | – | | |
| sg08B | I | | | | | | | | | | | |
| sg09 | S | — | R | | | | | | | | – | |
| sg09B | S | F | — | | | | | | | | – | |
| sg10 | T | F | — | | | | | | | | | + |
| Di | | | | | | | | | | | | |
| sg014 | VC15 | — | R | + | | | + | | | | | |
| sg017 | VK | — | R | + | | | | | + | | | |
| sg0110 | VT | — | R | + | | | | | | | | + |
| sg024 | OC15 | F | — | | + | | | | + | | | |
| sg027 | OK | — | — | | | | | | | | | |
| sg0210 | OT | F | — | | + | | | | | | | + |
| sg034 | NC | F | — | | | + | + | | | | | |
| sg037 | NK | — | — | | | | | | | | | |
| sg0310 | NT | F | — | | | + | | | | | | + |
| Tri | | | | | | | | | | | | |
| sg0174 | VKC15 | — | R | | | | | | | | | |
| sg0177 | VKK | — | R | | | | | | | | | |
| sg01710 | VKT | — | R | + | + | | | | | | | + |

TABLE 34-continued

| cTNB000-X::sg tested for NSA | | | | Bacterial strains carrying bla genes tested | | | | | | | | |
|---|---|---|---|---|---|---|---|---|---|---|---|---|
| Plasmid | Targets | Polarity | | V | O | N | C15 | C8 | K | I | S | T |
| Tetra | | | | | | | | | | | | |
| sg01724 | VKOC15 | — | R | + | + | | + | | + | | | |
| sg017210 | VKOT | — | R | + | + | | | | + | | | + |
| sg01734 | VKNC15 | — | R | + | | + | + | | + | | | |
| sg017310 | VKNT | — | R | + | | + | | | + | | | + |
| sg024310 | OC15NT | F | — | | + | + | + | | | | | + |
| Hexa | | | | | | | | | | | | |
| sg01721034 | VKOTNC15 | — | R | + | + | + | + | | + | | | + |
| sg01724310 | VKOC15NT | — | R | + | + | (+) | (+) | | (+) | | | (+) |
| sg01734210 | VKNC15KT | — | R | + | + | + | (+) | | + | | | (+) |
| sg01731024 | VKNTOC15 | — | R | + | + | + | + | | + | | | + |
| Plasmid | Targets | Polarity | | V | O | N | C15 | C8 | K | I | S | T |

The experiments described above provide the proof-of-concept that, in the model organism, *Escherichia coli*, DNA constructs carrying the Cas9 CRISPR region plus a spacer region with sequences directed against a target region of the beta-lactamase gene can inactivate ampicillin resistance when delivered by naked DNA transformation and bacteriophage infection as well as prevent transfer of ampicillin resistance by plasmid conjugation. It is apparent that Nemesis Symbiotics of the invention can be applied to pathogenic bacteria and for other antibiotic resistance genes.

Although the present invention has been described with reference to preferred or exemplary embodiments, those skilled in the art will recognise that various modifications and variations to the same can be accomplished without departing from the spirit and scope of the present invention and that such modifications are clearly contemplated herein. No limitation with respect to the specific embodiments disclosed herein and set forth in the appended claims is intended nor should any be inferred.

All documents cited herein are incorporated by reference in their entirety.

The invention claimed is:

1. A pharmaceutical composition comprising a non-lytic nucleic acid delivery vehicle for delivering a deliverable nucleic acid into a bacterial cell, wherein the delivery vehicle comprises a deliverable nucleic acid packaged into one or more bacteriophage coat proteins, and the deliverable nucleic acid comprises:
  (a) a vegetative replication origin and one or more rep genes that allow vegetative nucleic acid replication of the deliverable nucleic acid;
  (b) a transmittal nucleic acid sequence comprising an origin of transfer and one or more tra genes encoding relaxasome functions required for plasmid mobilisation during conjugation;
  (c) one or more bacteriophage packaging signal sequences that allow packaging of the deliverable nucleic acid into the one or more bacteriophage coat proteins; and
  (d) a selected nucleic acid of interest, comprising a gene-inactivating nucleic acid sequence capable of inactivating an antibiotic resistance gene or virulence gene, wherein the gene-inactivating nucleic acid sequence comprises a clustered regularly interspaced short palindromic repeat (CRTSPRJ array nucleic acid sequence having or transcribing an RNA guide molecule with a spacer sequence sufficiently complementary to a target sequence of the antibiotic resistance gene or the virulence gene for the antibiotic resistance gene or the virulence gene to be inactivated in the presence of a CRISPR associated (Cas) DNA-binding polypeptide or a functional equivalent or a modified version thereof; and wherein either the transmittal nucleic acid sequence further comprises one or more tra genes encoding conjugation functions required for plasmid conjugation, or the bacterial cell comprises one or more tra genes encoding conjugation functions required for plasmid conjugation, such that the delivery vehicle is capable of infecting the bacterial cell to introduce the deliverable nucleic acid into the cell, following which the deliverable nucleic acid is capable of forming a plasmid in the cell and being transmitted to one or more different bacterial cells by conjugation and not by infection.

2. The pharmaceutical composition according to claim 1, wherein the deliverable nucleic acid further comprises genetic functions allowing transposition of the deliverable nucleic acid to a bacterial chromosome.

3. The pharmaceutical composition according to claim 1, wherein the deliverable nucleic acid further comprises a selection nucleic acid sequence that provides a selective advantage to the bacterial cell acquiring the deliverable nucleic acid.

4. The pharmaceutical composition according to claim 1, wherein the deliverable nucleic acid further comprises a selectable marker.

5. The pharmaceutical composition according to claim 1, formulated for administration via parenteral, oral, topical or inhalation methods.

6. The pharmaceutical composition according to claim 1, wherein the selected nucleic acid is an antibiotic resistance gene-inactivating nucleic acid sequence capable of inactivating one or more antibiotic resistance genes using a Cas9/CRISPR system for gene inactivation.

7. A method of treating an infection in a subject caused by an antibiotic-resistant bacterial cell comprising an antibiotic resistance gene, in which the method comprises the step of introducing into the bacterial cell a therapeutically effective amount of the pharmaceutical composition according to claim 6, thereby inactivating the antibiotic resistance gene and sensitising the bacterial cell to the antibiotic.

8. The method according to claim 7, in which the composition is administered parenterally, topically, orally, or by inhalation (for example, via aerosol delivery).

9. The method according to claim 7, in which the subject is a fish, a bird, a reptile or a mammal (such as a human).

10. The method according to claim 7, in which the deliverable nucleic acid is transferred from the antibiotic-resistant bacterial cell directly into another bacterial cell by plasmid conjugation.

11. The method according to claim 7, further comprising a step of simultaneously or subsequently administering to the subject an antibiotic to which the bacterial cell has become sensitised.

12. A method for modifying a bacterial cell in an industrial cell culture, comprising the step of infecting the bacterial cell with the nucleic acid delivery vehicle as defined in claim 1.

13. The method according to claim 12, wherein the selected nucleic acid is a biosynthetic gene or a gene encoding a pharmaceutically active protein.

14. A nucleic acid delivery vehicle as defined in claim 1.

15. A deliverable nucleic acid as defined in claim 1.

16. A method of inactivating antibiotic resistance in an antibiotic-resistant bacterial cell, the method comprising the step of introducing into the bacterial cell the nucleic acid delivery vehicle as defined in claim 14.

17. A method of making a nucleic acid delivery vehicle as defined in claim 1, comprising the steps of constructing the deliverable nucleic acid and then packaging the deliverable nucleic acid into the one or more bacteriophage coat proteins.

18. A method of making a probiotic composition for inactivating antibiotic resistance in a population of antibiotic-resistant bacterial cells, the method comprising the step of introducing into a probiotic bacterium the nucleic acid delivery vehicle as defined in claim 14, thereby producing a probiotic composition comprising a probiotic bacterium with deliverable nucleic acid capable of inactivating the antibiotic resistance.

19. A method of inactivating antibiotic resistance in an antibiotic-resistant bacterial cell, the method comprising the step of introducing into the bacterial cell the deliverable nucleic acid as defined in claim 15.

20. A method of making a probiotic composition for inactivating antibiotic resistance in a population of antibiotic-resistant bacterial cells, the method comprising the step of introducing into a probiotic bacterium the deliverable nucleic acid as defined in claim 15, thereby producing a probiotic composition comprising a probiotic bacterium with deliverable nucleic acid capable of inactivating the antibiotic resistance.

21. The pharmaceutical composition according to claim 1, wherein the bacterial cell is transformed with a plasmid comprising one or more conjugative nucleic acid sequences encoding conjugation functions required for plasmid conjugation.

22. The pharmaceutical composition according to claim 1, wherein the bacterial cell is selected from the group: *Pseudomonas, Salmonella, E. coli, Yersinia pestis, Klebsiella, Shigella, Proteus, Enterobacter, Serratia* and *Citrobacter.*

23. The pharmaceutical composition according to claim 1, wherein the bacterial cell is an *E. coli* cell.

* * * * *

UNITED STATES PATENT AND TRADEMARK OFFICE

CERTIFICATE OF CORRECTION

PATENT NO. : 11,166,994 B2
APPLICATION NO. : 15/752753
DATED : November 9, 2021
INVENTOR(S) : Lichtenstein et al.

It is certified that error appears in the above-identified patent and that said Letters Patent is hereby corrected as shown below:

In the Claims

Column 273, Claim 1, Line 41 should read:
short palindromic repeat (CRISPR) array nucleic acid Signed and Sealed this
Tenth Day of May, 2022

Katherine Kelly Vidal
*Director of the United States Patent and Trademark Office*